United States Patent
Choe et al.

(10) Patent No.: US 11,434,478 B2
(45) Date of Patent: *Sep. 6, 2022

(54) COMPOSITIONS AND METHODS FOR GENOME ENGINEERING WITH CAS12A PROTEINS

(71) Applicants: GFLAS Life Sciences, Inc., Seoul (KR); SEOUL NATIONAL UNIVERSITY R&DB FOUNDATION, Seoul (KR)

(72) Inventors: Sunghwa Choe, Seoul (KR); Jongjin Park, West Lafayette, IN (US); Ji Young Yoon, Seoul (KR); Han Seong Kim, Seoul (KR); Dong Wook Kim, Seoul (KR)

(73) Assignees: GFLAS LIFE SCIENCES, INC., Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/171,302

(22) Filed: Feb. 9, 2021

(65) Prior Publication Data

US 2021/0222140 A1 Jul. 22, 2021

Related U.S. Application Data

(63) Continuation of application No. PCT/IB2019/000946, filed on Aug. 9, 2019.

(60) Provisional application No. 62/752,950, filed on Oct. 30, 2018.

(30) Foreign Application Priority Data

Aug. 9, 2018 (KR) .................. 10-2018-0093336

(51) Int. Cl.
*C12N 9/22* (2006.01)
*C12N 15/11* (2006.01)
*C12N 15/90* (2006.01)

(52) U.S. Cl.
CPC ............... *C12N 9/22* (2013.01); *C12N 15/11* (2013.01); *C12N 15/907* (2013.01); *C12N 2310/20* (2017.05); *C12N 2800/80* (2013.01)

(58) Field of Classification Search
CPC ........ C12N 9/22; C12N 15/11; C12N 15/907; C12N 2310/20
See application file for complete search history.

(56) References Cited

U.S. PATENT DOCUMENTS

| | | |
|---|---|---|
| 9,896,696 B2 | 2/2018 | Begemann et al. |
| 9,982,279 B1 | 5/2018 | Gill et al. |
| 2016/0208243 A1 | 7/2016 | Zhang et al. |
| 2017/0233756 A1* | 8/2017 | Begemann ............... C12N 9/22 800/295 |

FOREIGN PATENT DOCUMENTS

| | | |
|---|---|---|
| KR | 20170068400 A | 6/2017 |
| KR | 20180018466 A | 2/2018 |
| WO | WO-2017017016 A1 | 2/2017 |
| WO | WO-2017083722 A1 | 5/2017 |
| WO | WO-2017127807 A1 | 7/2017 |
| WO | WO-2017141173 A2 | 8/2017 |
| WO | WO-2018013990 A1 | 1/2018 |
| WO | WO-2018094356 A2 | 5/2018 |
| WO | WO-2020030984 A2 | 2/2020 |
| WO | WO-2020032711 A1 | 2/2020 |

OTHER PUBLICATIONS

Baker et al., RAC-tagging: Recombineering And Cas9-assisted targeting for protein tagging and conditional analyses. Scientific Reports (6):25529 (2016).
Chen et al., CRISPR/Cas9-based Genome Editing in *Pseudomonas aeruginosa* and Cytidine Deaminase-Mediated Base Editing in *Pseudomonas* Species. Cell Press6(31): 222-231 (2018).
Clements et al., RICE CRISPR: Rapidly Increased Cut Ends by an Exonuclease Cas9 Fusion in Zebrafish. Genesis. 55(8): 11 pages (2017).
Higgins, et al. CLUSTAL: A Package for Performing Multiple Sequence Alignment on a Microcomputer. Gene. 73 (1988): 237-244.
Higgins, et al. Fast and sensitive multiple sequence alignments on a microcomputer. Comput Appl Biosci. Apr. 1989;5(2):151-3.
Jiang et al., CRISPR-Cpf1 assisted genome editing of Corynebacterium glutamicum. Nature Communications 8:15179(2017).
Kimple et al. Overview of Affinity Tags for Protein Purification. Curr Protoc Protein Sci 73: Unit-9.9 (2013). Published online Sep. 24, 2013. 26 pages, doi: 10.1002/0471140864.ps0909s73.
Lin et al., Fusion of SpCas9 to *E. coli* Rec A protein enhances CRISPR-Cas9 mediated gene knockout in mammalian cells. J Biotechnol.247:42-49 (2017).
Lovett et al., Identification and purification of a single-stranded-DNA-specific exonuclease encoded by the recJ gene of *Escherichia coli*. PNAS86(8):2627-2631 (1989).
NCBI. GenBank Accession No. OLA16049.1/ Type V CRISPR-associated protein Cpf1 [*Eubacterium* sp. 41_20] (2016).
Needleman et al. A general method applicable to the search for similarities in the amino acid sequence of two proteins. Journal of molecular biology 48(3):443-453 (1970).
PCT/IB2019/000946 International Search Report and Written Opinion dated Jun. 15, 2020.
PCT/KR2019/010110 International Search Report and Written Opinion dated Nov. 25, 2019.

(Continued)

*Primary Examiner* — Antonio Galisteo Gonzalez
(74) *Attorney, Agent, or Firm* — Wilson Sonsini Goodrich & Rosati

(57) ABSTRACT

The present disclosure provides novel Cas12a proteins, which cleave target nucleic acids and methods of use thereof.

18 Claims, 35 Drawing Sheets

Specification includes a Sequence Listing.

(56) References Cited

OTHER PUBLICATIONS

Pearson et al. Improved Tools for Biological Sequence Comparison. PNAS USA 85:2444-48 (1988).
Pearson et al., Searching protein sequence libraries: comparison of the sensitivity and selectivity of the Smith-Waterman and FASTA algorithms. Genomics 11(3):635-50 (1991).
Pearson, Using the FASTA program to search protein and DNA sequence databases. Methods Mol Biol 25:307-331 (1994).
Radovcic et al., CRISPR-Cas adaptation in *Escherichia coli* requires RecBCD helicase but not nuclease activity, is independent of homologous recombination, and is antagonized by 5' ssDNA exonucleases.Nucleic Acids Research 46(19):10173-10183 (2018).
Smith et al. Comparison of Biosequences. Advances in Applied Mathematics. 2:482-489 (1981).
Smith et al. Identification of common molecular subsequences. J Mol Biol 147:195-197 (1981).

* cited by examiner

```
                                    α11
               ℓℓℓℓ  ℓℓ.........        ℓℓℓℓℓℓℓℓℓℓ             TT         ℓℓℓℓℓℓℓ      η5
                                   220        230        240             ℓℓℓℓℓℓℓ  α
AsCas12a(WP_021)                                                          250
AsCas12a(WP_021)     LITAVPSL.....    .REHFENVKKAIGIFVSTSIEEVFSFPYNQLLT
LbCas12a(WP_035)     VDAIFD.......    .KHEVQEIKEKI.LNSDYDVEDFFEGEFFNFVLT
FnCas12a(WP_003)     LKDKAPEAINYEQIKKDLAEELTFDIDYKTSEVNQRV.....FSLDEVFEIANFNNYLN
emgCas12a-1(CDY)     IVKNLSND.....    DINKISEDIKDSL..KEMSLEEIYSYEKYGEFIT
emgCas12a-2(CDZ)     ICK.IAGL.....    DLHGLDNEITAYV..DGKTLKEVCSDEGFAKAIT α13           α14
                     ℓℓℓℓℓℓℓℓℓℓ      TT        ℓℓℓℓℓℓℓℓℓℓ              ℓℓℓℓℓℓℓ  TT
                         260          270        280       290          300          310
AsCas12a(WP_021)     TQIDLYNQLIGIGREAGTEKIKGLNEVINLYKNDETAHIIASLPHRFIPLFKQILSD
AsCas12a(WP_021)     EGIDVYNAIIG.FVTESGEKIKGLNEYINLYNQKTKQKLP......KFKFLYKQVSD
LbCas12a(WP_035)     SGTKENTIIG.GKFVNGENTKRGINEYINLHYSQINDKTL......KKYKMSVFKQIHD
FnCas12a(WP_003)     EGISFYNDICK.......YQSVNGFLDNISS........VNSFMNIYCKNKENK...NLYKLRKTICI
emgCas12a-1(CDY)     EGIDRYNFAICA.....    .VNQYMNILCKNKALKP....GQFKMKRIHKQICK
emgCas12a-2(CDZ)

α15                  α16
              ℓℓℓℓℓℓℓℓℓℓ           ℓℓℓℓℓℓℓℓℓℓ .ℓ  ℓℓℓℓℓℓℓℓℓℓ                  η6
                  320        330         340         350        360          ℓℓℓℓ
AsCas12a(WP_021)
AsCas12a(WP_021)     RNTLSFIIEEFKSDEVIQSFCKYKTLLRN.....ENVLETAEALFNELNS..IDLTH
LbCas12a(WP_035)     RESLSFYGEGYTSDEELEVFRNTLNKNSEI.....FSSIKKLEKLFKNFDE..YSSAGH
FnCas12a(WP_003)     TESKSFVIDKLESDEVVTTMQSFYEQIAAFKTVEEKSIKETLSLLFDDLKAQKLDLSK
emgCas12a-1(CDY)     ADTSYEVPYKFESDEEVYKFESDEEVYQSVNGFLDNISS..........KHIVERLRKIGDNYNG..YNLDK
emgCas12a-2(CDZ)     GTTSFDIFRKFENDKQVDAVNSFTEIVTK.........NNDLKRLLNITQNAND..YDMNK α17                 α18                       α19
              β2 ℓℓ ℓℓℓℓℓℓℓℓℓℓ        ℓℓℓℓℓℓℓℓℓℓ                  ℓℓℓℓℓℓℓℓℓℓ
              ↑      370        380         390                        400          410
AsCas12a(WP_021)
AsCas12a(WP_021)     FISH.KKLETISSALCDHWDTLRNALYERRIS..ELTG......KITKSAKEKVQR
LbCas12a(WP_035)     FVKNGPAISTISKDIFGEWNVIRDKWNAEYDD.I..HP......KKKAVVTEKYEDDRRK
FnCas12a(WP_003)     YFKNDKSLTDISQQVFDDYSVIGTAVLEYITQQIAPKNEDNPSKKEQLLIAKKTEKAKYL
emgCas12a-1(CDY)     YIVS.KFYESVSQKTYRDWETINTALEIHYNN.....IFPGNGKSKADRVKKAVKNDLQK
emgCas12a-2(CDZ)     YVVA.DAVSMISQFISKKWNLIEECLLDYYSD....NPGKGNAKENKVKKAVKEETYR
```

FIG. 4 emgCas12a-1: K925Q substitution
emgCas12a-1: K925Q substitution

```
AsCas12a(WP_021)              η13                              α45
                         TT  ΩΩ........Ω   TT    ΩΩΩΩΩΩΩΩΩΩΩΩΩΩΩΩΩΩΩΩΩ
                             1250              1260          1270      1280         1290
AsCas12a(WP_021)         DLNGVCFDSR........FQNPEWPMIADANGAYHIALKGQLLNHLKES..KDLKLQN..
LbCas12a(WP_035)         NSDGIFYDSRNYEA...QENAILPKNADANGAYNIARKVLWAIGQFKKA..EDEKLDKVK
FnCas12a(WP_003)         DVNGNFFDSR........QAPKNMPQDADANGAYHIGLKGLMILGRIKNN..QEGK..KLN
emgCas12a-1(CDY)         NENNIFYDSA........KAGDALPKDADANGAYCHALKGLYEIKQITENWKEDGKFSRDK
emgCas12a-2(CDZ)         NKNGEFFDSDEYNSYIDAQKAPLPILADANGAFCIALKGMYRANQIKENWVEGEKLPADC AsCas12a(WP_021)         α46
                         ΩΩΩΩΩΩΩΩΩΩΩΩΩ
                         1300
AsCas12a(WP_021)         .GISNQDWLAYIQELRN.
LbCas12a(WP_035)         IAHSNKEWLEYAQTSVKH
FnCas12a(WP_003)         LVIKNEEYFEFVQNRNN.
emgCas12a-1(CDY)         LKHSNKDWFDFIQNKRYL
emgCas12a-2(CDZ)         LKHEHASWLAFMQGERG.
```

FIG. 8
Continued

|  | Old | | | New | |
|---|---|---|---|---|---|
|  | AsCas12a (standard) | LbCas12a | FnCas12a | mgCas12a-1 | mgCas12a-2 |
| Reference | 2015, F. Zhang lab | 2015, F. Zhang lab | 2015, F. Zhang lab | 2018, S.H.Choe lab | 2018, S.H.Choe lab |
| Species | *Acidaminococcus sp.* | *Lachnospiraceae sp.* | *Francisella tularensis subsp. novicida* | metagenome CDYX01038443.1 | metagenome CDZH01035208.1 |
| Nucleotide length | 3,921 | 3,684 | 3,900 | 3,789 | 3,825 |
| Amino acid length | 1,307 | 1,228 | 1,300 | 1,263 | 1,275 |
| PAM sequence | 5'-TTTN-3' | 5'-TTTN-3' | 5'-TTTN-3' | 5'-TTTN-3' (speculative) | 5'-TTTN-3' (speculative) |
| Sequence identity | 100% | 33.41% | 34.45% | 32.65% | 31.29% |
| Critical residue identity (Yamano et al. Cell (2016)) | 100% (33) | 79% (26) | 79% (26) | 88% (29) | 88% (29) |

FIG. 9A

| Cas12a | As | Lb | Fn | mg-1 | mg-2 |
|---|---|---|---|---|---|
| As |  |  |  |  |  |
| Lb | 33.4 |  |  |  |  |
| Fn | 34.2 | 40.4 |  |  |  |
| mg-1 | 32.4 | 35.3 | 36.6 |  |  |
| mg-2 | 30.7 | 34.9 | 35.9 | 52.2 |  |

COMPOSITIONS AND METHODS FOR GENOME ENGINEERING WITH CAS12A PROTEINS

CROSS-REFERENCE

The present application is a continuation of International Application No. PCT/IB2019/000946, filed Aug. 9, 2019, which claims priority to and benefit from Korean Patent Application 10-2018-0093336 filed Aug. 9, 2018 and U.S. Provisional Application No. 62/752,950 filed Oct. 30, 2018, the entire contents of each of which are herein incorporated by reference.

SEQUENCE LISTING

The instant application contains a Sequence Listing which has been submitted electronically in ASCII format and is hereby incorporated by reference in its entirety. Said ASCII copy, created on Feb. 22, 2021, is named 53470-708_301_SL.txt and is 122,526 bytes in size.

BACKGROUND

Genome editing is a genetic engineering technique that targets the genetic insert into a specific location of the genome, thereby modifying defective genes and/or introduction of functional genes. Recent advancement in Clustered Regularly Interspaced Short Palindromic Repeat (CRISPR)-CRISPR-associated (Cas) technology using RNA guided endonuclease to cleave a nucleic acid sequence of interest further increases the efficiency and shortens the genome editing process. However, current CRISPR technology using the traditional endonuclease suffers from relatively low precision. Thus, there is still a significant need for novel, highly efficient endonucleases.

SUMMARY

The present disclosure provides a composition comprising at least one of i)-iv), and a guide RNA coupled the at least one of i)-iv): i) a polypeptide having at least 80% sequence identity with residue 829 through residue 991 of SEQ ID NO: 1, wherein the polypeptide comprises an amino acid sequence comprising a Lysine aligned to a Lysine at position 925 of SEQ ID NO: 1; ii) a polypeptide having at least 80% sequence identity with residue 825 through residue 996 of SEQ ID NO: 3, wherein the polypeptide comprises an amino acid sequence comprising a Lysine aligned to a Lysine at position 930 of SEQ ID NO: 3; iii) a polypeptide having at least 80% sequence identity with SEQ ID NO: 1, wherein the polypeptide comprises an amino acid sequence comprising a Lysine aligned to a Lysine at position 925 of SEQ ID NO: 1; or iv) a polypeptide having at least 80% sequence identity with SEQ ID NO: 3, wherein the polypeptide comprises an amino acid sequence comprising a Lysine aligned to a Lysine at position 930 of SEQ ID NO: 3. The guide RNA comprises a sequence that is reverse complementary to a eukaryotic nucleic acid sequence comprising from 6 to 60 bases.

In some embodiments, the a Lysine aligned to a Lysine at position 925 of SEQ ID NO: 1 or a Lysine aligned to a Lysine at position 930 of SEQ ID NO: 3 may not at positions 925 or 930, respectively, relative to SEQ ID NO: 1 or SEQ ID NO: 1 when optimally aligned.

In some embodiments, the eukaryotic nucleic acid sequence is a human nucleic acid sequence, which may comprise a region in KRAS, HER2/neu, PD-1, TCR, p53, CCR5, DNMT1, EMX1, and LKB1. Alternatively and/or additionally, the eukaryotic nucleic acid sequence is a plant nucleic acid sequence.

Preferably, the polypeptide is a type V CRISPR-associated protein. In such embodiment, it is preferred that the type V CRISPR-associated protein is a Cas12a protein.

In some embodiments, the polypeptide comprises a purification tag. The purification tag comprises at least one tag selected from the group consisting of a His tag, a FLAG tag, an AU1 epitope tag, an AU5 epitope tag, a bacteriophage T7 tag, a bacteriophage V5 epitope tag, a Bluetongue virus tag (B-tag), a Glu-Glu tag (EE-tag), an HSV epitope tag, a KT3 epitope tag, a Myc epitope tag, a PDZ ligand tag, a polyarginine tag, a polyaspartate tag, a polycysteine tag, a polyphenylalanine tag, a protein C tag, an S1-tag, an S-tag, a Step-tag, and a VSV-Gtag.

In some embodiments, the guide RNA comprises an A-rich protospacer adjacent motif (PAM) sequence, a G-rich PAM sequence, a T-rich PAM sequence, or a C-rich PAM sequence. Optionally, the PAM sequence comprises 3 T nucleobases, 2 T nucleobases, 1 T nucleobase, or TTTN. Alternatively and/or additionally, guide RNA comprises a crRNA and a tracrRNA.

It is preferred that the composition exhibits at least 2-fold increased genome editing efficiency than AsCas12a, FnCas12a, or LbCas12a. In some embodiments, the composition further comprises an excipient. In some embodiments, the excipient has a pH of from 7 to 8. In some embodiments, the excipient is a buffer, which may comprise at least one of Bis-Tris Propane-HCl, $MgCl_2$, or bovine serum albumin.

The present disclosure also disclose a method of gene editing, comprising: providing a composition comprising at least one of i)-iv), and a guide RNA coupled the at least one of i)-iv): i) a polypeptide having at least 80% sequence identity with residue 829 through residue 991 of SEQ ID NO: 1, wherein the polypeptide comprises an amino acid sequence comprising a Lysine aligned to a Lysine at position 925 of SEQ ID NO: 1; ii) a polypeptide having at least 80% sequence identity with residue 825 through residue 996 of SEQ ID NO: 3, wherein the polypeptide comprises an amino acid sequence comprising a Lysine aligned to a Lysine at position 930 of SEQ ID NO: 3; iii) a polypeptide having at least 80% sequence identity with SEQ ID NO: 1, wherein the polypeptide comprises an amino acid sequence comprising a Lysine aligned to a Lysine at position 925 of SEQ ID NO: 1; or iv) a polypeptide having at least 80% sequence identity with SEQ ID NO: 3, wherein the polypeptide comprises an amino acid sequence comprising a Lysine aligned to a Lysine at position 930 of SEQ ID NO: 3. The guide RNA comprises a sequence that is reverse complementary to a eukaryotic nucleic acid sequence comprising from 6 to 60 bases.

In some embodiments, the eukaryotic nucleic acid sequence is a human nucleic acid sequence, which may comprise a region in KRAS, HER2/neu, PD-1, TCR, p53, CCR5, DNMT1, EMX1, and LKB1. Alternatively and/or additionally, the eukaryotic nucleic acid sequence is a plant nucleic acid sequence.

Preferably, the polypeptide is a type V CRISPR-associated protein. In such embodiment, it is preferred that the type V CRISPR-associated protein is a Cas12a protein.

In some embodiments, the polypeptide comprises a purification tag. The purification tag comprises at least one tag selected from the group consisting of a His tag, a FLAG tag, an AU1 epitope tag, an AU5 epitope tag, a bacteriophage T7 tag, a bacteriophage V5 epitope tag, a Bluetongue virus tag (B-tag), a Glu-Glu tag (EE-tag), an HSV epitope tag, a KT3 epitope tag, a Myc epitope tag, a PDZ ligand tag, a polyarginine tag, a polyaspartate tag, a polycysteine tag, a polyphenylalanine tag, a protein C tag, an S1-tag, an S-tag, a Step-tag, and a VSV-Gtag.

In some embodiments, the guide RNA comprises an A-rich protospacer adjacent motif (PAM) sequence, a G-rich PAM sequence, a T-rich PAM sequence, or a C-rich PAM sequence. Optionally, the PAM sequence comprises 3 T nucleobases, 2 T nucleobases, 1 T nucleobase, or TTTN. Alternatively and/or additionally, guide RNA comprises a crRNA and a tracrRNA.

In some embodiments, the composition further comprises an excipient. In some embodiments, the excipient has a pH of from 7 to 8. In some embodiments, the excipient is a buffer, which may comprise at least one of Bis-Tris Propane-HCl, $MgCl_2$, or bovine serum albumin. It is preferred that an efficiency of the step of cleaving is at least 2-fold hither than genome editing efficiency of AsCas12a, FnCas12a, or LbCas12a.

The present disclosure also discloses a method of improving cleaving efficiency of a type V CRISPR-associated protein, comprising: providing the type V CRISPR-associated protein; identifying a residue of the type V CRISPR-associated protein that is aligned with at Lysine at position 925 of SEQ ID NO: 1 or at Lysine at position 930 of SEQ ID NO: 3; and mutating the residue to Lysine.

The present disclosure provides a composition comprising: a protein (or a polypeptide) having at least 80% sequence identity with residue 829 through residue 991 of SEQ ID NO: 1, wherein the protein comprises a Lysine at position 925; and a guide RNA comprising a sequence that is reverse complementary to a eukaryotic nucleic acid sequence comprising from 6 to 60 bases.

The present disclosure provides a composition comprising: a protein (or a polypeptide) having at least 80% sequence identity with residue 825 through residue 996 of SEQ ID NO: 3, wherein the protein comprises a Lysine at position 930; and a guide RNA comprising a sequence that is reverse complementary to a eukaryotic nucleic acid sequence comprising from 6 to 60 bases.

The present disclosure provides a composition comprising: a protein (or a polypeptide) having at least 80% sequence identity with SEQ ID NO: 1, wherein the protein comprises a Lysine at position 925; and a guide RNA comprising a sequence that is reverse complementary to a eukaryotic nucleic acid sequence comprising from 6 to 60 bases.

The present disclosure provides a composition comprising: a protein (or a polypeptide) having at least 80% sequence identity with SEQ ID NO: 3, wherein the protein comprises a Lysine at position 930; and a guide RNA comprising a sequence that is reverse complementary to a eukaryotic nucleic acid sequence comprising from 6 to 60 bases.

In these compositions, the eukaryotic nucleic acid sequence can be human nucleic acid sequence. Optionally, the human nucleic acid sequence is implicated in cancer. Alternatively, the eukaryotic nucleic acid sequence can be a plant nucleic acid sequence. In some embodiments, the nucleotide sequence encoding for SEQ ID NO: 1 comprises at least 80% sequence identity to SEQ ID NO: 2. Alternatively, and/or additionally, the nucleotide sequence encoding for SEQ ID NO: 3 comprises at least 80% sequence identity to SEQ ID NO: 4. It is contemplated that the protein is from, obtained from, or derived from the Eubacteriaceae family. In particular, disclosures provided herein, the protein comprises a nuclease.

Preferably, the protein comprises a nuclease. In such embodiments, the nuclease may comprise a type V CRISPR-associated protein. Further preferably, the type V CRISPR-associated protein may comprise a Cas12a protein. In some embodiments, such Cas12a protein is metagenomically mined.

In some embodiments, the composition comprises, or has pH ranged from 7 to 7.9, such as a pH of about or exactly 7. Alternatively, and/or additionally, the composition is formulated in a buffer, which may comprise Bis-Tris Propane-HCl, $MgCl_2$, and/or bovine serum albumin. For example, the buffer comprises from 0.1 to 50 mM Bis-Tris Propane-HCl. Additionally, the buffer comprises from 0.1 to 50 mM $MgCl_2$. The buffer may also comprise from 1 to 500 μg/ml bovine serum albumin. The buffer may, in particular, comprise about or exactly 10 mM Bis-Tris Propane-HCl. Further, the buffer may comprises about or exactly 10 mM $MgCl_2$. Additionally, the buffer comprises about or exactly 100 μg/ml of bovine serum albumin.

In some embodiments, the protein (or a polypeptide; protein and polypeptide can be used interchangeably herein) comprises a purification tag. For example, the purification tag comprises, or may include, at least one tag selected from the group consisting of a His tag, a FLAG tag, an AU1 epitope tag, an AU5 epitope tag, a bacteriophage T7 tag, a bacteriophage V5 epitope tag, a Bluetongue virus tag (B-tag), a Glu-Glu tag (EE-tag), an HSV epitope tag, a KT3 epitope tag, a Myc epitope tag, a PDZ ligand tag, a polyarginine tag, a polyaspartate tag, a polycysteine tag, a polyphenylalanine tag, a protein C tag, an S1-tag, an S-tag, a Step-tag, and a VSV-G tag. It is consistent with the present disclosure for the guide RNA to comprise an A-rich protospacer adjacent motif (PAM) sequence, a G-rich PAM sequence, a T-rich PAM sequence, or a C-rich PAM sequence.

The guide RNA in the composition may comprise a T-rich PAM sequence. For example, the PAM sequence comprises 3 T nucleobases, 2 T nucleobases, or 1 T nucleobase. A PAM sequence compatible with the present disclosure comprises TTTN. In some embodiments, the guide RNA sequence comprises from 1 to 100 nucleotides.

Alternatively, and/or additionally, the target human nucleic acid sequence comprises a region in KRAS, HER2/neu, PD-1, TCR, p53, CCR5, DNMT1, EMX1, and LKB1.

Several cancers are contemplated and compatible with the present disclosure, for example, the cancer comprises a bladder cancer, a bone cancer, a blood cancer, a breast cancer, a black colored tumor, a thyroid cancer, a parathyroid cancer, a bone marrow cancer, a laryngopharyngeal cancer, a laryngeal cancer, a lung cancer, an esophagus cancer, a pancreatic cancer, a colorectal cancer, a gastric cancer, a tongue cancer, a skin cancer, a brain tumor, a uterine cancer, a head or neck cancer, a gallbladder cancer, an oral cancer, a central nervous system tumor, or a liver cancer.

The present compositions are capable of exhibiting improved genome editing efficiency to other Cas12a orthologs. For example, in some aspects, the composition exhibits at least 2-fold increased genome editing efficiency than AsCas12a, FnCas12a, or LbCas12a. The presently disclosed proteins are capable of being complexed with a crRNA having a 5' handle compatible with other Cas12a orthologs. For example, in any of the above compositions, the guide RNA comprises a crRNA and a tracrRNA. Further, the crRNA comprises a 5' repeat recognition sequence of AAUU. In some aspects, the protein exhibits cleavage activity in the presence of $CaCl_2$, $CoCl_2$, $FeCl_2$, $MnSO_4$, or any combination thereof.

The present disclosure also provides a method of gene editing, wherein the method comprises contacting a cell with any one of the above compositions; binding the guide RNA to the target human nucleic acid sequence; and cleaving the human nucleic acid sequence.

The present disclosure additionally provides a method of gene editing, wherein the method comprises providing a composition comprising a protein (or a polypeptide) having at least 80% sequence identity with residue 829 through residue 991 of SEQ ID NO: 1, wherein the protein comprises a Lysine at position 925; and a guide RNA comprising a sequence that is reverse complementary to a nucleic acid sequence comprising from 6 to 60 nucleotides; contacting a cell with the composition; binding the guide RNA to a eukaryotic nucleic acid sequence; and cleaving the nucleic acid sequence.

The present disclosure provides a method of gene editing, wherein the method comprises providing a composition comprising a protein (or a polypeptide) having at least 80% sequence identity with residue 825 through residue 996 of SEQ ID NO: 3, wherein the protein comprises a Lysine at position 930; and a guide RNA comprising a sequence that is reverse complementary to a nucleic acid sequence comprising from 6 to 60 nucleotides; contacting a cell with the composition; binding the guide RNA to a eukaryotic nucleic acid sequence; and cleaving the nucleic acid sequence.

The present disclosure additionally provides a method of gene editing, wherein the method comprises providing a composition comprising a protein (or a polypeptide) having at least 80% sequence identity with SEQ ID NO: 1, wherein the protein comprises a Lysine at position 925; and a guide RNA comprising a sequence that is reverse complementary to a nucleic acid sequence comprising from 6 to 60 nucleotides; contacting a cell with the composition; binding the guide RNA to a eukaryotic nucleic acid sequence; and cleaving the nucleic acid sequence.

The present disclosure also provides a method of gene editing, wherein the method comprises providing a composition comprising a protein (or a polypeptide) having at least 80% sequence identity with SEQ ID NO: 3, wherein the protein comprises a Lysine at position 930; and a guide RNA comprising a sequence that is reverse complementary to a nucleic acid sequence comprising from 6 to 60 nucleotides; contacting a cell with the composition; binding the guide RNA to a eukaryotic nucleic acid sequence; and cleaving the nucleic acid sequence.

In these compositions, the eukaryotic nucleic acid sequence can be human nucleic acid sequence. Optionally, the human nucleic acid sequence is implicated in cancer. Alternatively, the eukaryotic nucleic acid sequence can be a plant nucleic acid sequence. In some embodiments, the nucleotide sequence encoding for SEQ ID NO: 1 comprises at least 80% sequence identity to SEQ ID NO: 2. Alternatively, and/or additionally, the nucleotide sequence encoding for SEQ ID NO: 3 comprises at least 80% sequence identity to SEQ ID NO: 4. Oftentimes, it may be the case that the nucleic acid sequence comprises a human nucleic acid sequence or a plant nucleic acid sequence. The present disclosure provides that the contacting the cell with the composition comprises administering the composition to a subject in need thereof. For example, the administering comprises intravenous, subcutaneous, intramuscular, oral, or mucosal administration. In some aspects, the contacting the cell with the composition comprises administering the composition to the cell ex vivo.

It is contemplated that the protein (or a polypeptide) is from, obtained from, or derived from the Eubacteriaceae family. In particular disclosures provided herein, the protein comprises a nuclease. Preferably, the protein comprises a nuclease. In such embodiments, the nuclease may comprise a type V CRISPR-associated protein. Further, preferably, the type V CRISPR-associated protein may comprise a Cas12a protein. In some embodiments, such Cas12a protein is metagenomically mined.

In some embodiments, the composition comprises, or has pH ranged from 7 to 7.9, such as a pH of about or exactly 7. Alternatively, and/or additionally, the composition is formulated in a buffer, which may comprise Bis-Tris Propane-HCl, $MgCl_2$, and/or bovine serum albumin. For example, the buffer comprises from 0.1 to 50 mM Bis-Tris Propane-HCl. The buffer also comprises from 0.1 to 50 mM $MgCl_2$. The buffer additionally comprises from 1 to 500 µg/ml bovine serum albumin. The buffer also comprises about or exactly 10 mM Bis-Tris Propane-HCl. Further, the buffer comprises about or exactly 10 mM $MgCl_2$. Additionally, the buffer comprises about or exactly 100 µg/ml of bovine serum albumin.

In some embodiments, the protein (or a polypeptide) comprises a purification tag. For example, the purification tag comprises, or may include, at least one tag selected from the group consisting of a His tag, a FLAG tag, an AU1 epitope tag, an AU5 epitope tag, a bacteriophage T7 tag, a bacteriophage V5 epitope tag, a Bluetongue virus tag (B-tag), a Glu-Glu tag (EE-tag), an HSV epitope tag, a KT3 epitope tag, a Myc epitope tag, a PDZ ligand tag, a polyarginine tag, a polyaspartate tag, a polycysteine tag, a polyphenylalanine tag, a protein C tag, an S1-tag, an S-tag, a Step-tag, and a VSV-G tag.

The guide RNA in the composition may comprise an A-rich protospacer adjacent motif (PAM) sequence, a G-rich PAM sequence, a T-rich PAM sequence, or a C-rich PAM sequence. The guide RNA in the composition may comprise a T-rich PAM sequence. For example, the PAM sequence comprises 3 T nucleobases, 2 T nucleobases, or 1 T nucleobase. A PAM sequence compatible with the present disclosure comprises TTTN. In some embodiments, the guide RNA sequence comprises from 1 to 100 bases. Alternatively, and/or additionally, the target human nucleic acid sequence comprises a region in KRAS, HER2/neu, PD-1, TCR, p53, CCR5, DNMT1, EMX1, and LKB1.

In some embodiments, the cell comprises cancer cells, preferably human cancer cells, including, but not limited to a bladder cancer cell, a bone cancer cell, a blood cancer cell, a breast cancer cell, a black colored tumor cell, a thyroid cancer cell, a parathyroid cancer cell, a bone marrow cancer cell, a laryngopharyngeal cancer cell, a laryngeal cancer cell, a lung cancer cell, an esophagus cancer cell, a pancreatic cancer cell, a colorectal cancer cell, a gastric cancer cell, a tongue cancer cell, a skin cancer cell, a brain tumor cell, a uterine cancer cell, a head or neck cancer cell, a gallbladder cancer cell, an oral cancer cell, a central nervous system tumor cell, or a liver cancer cell.

In some aspects, any of the above described methods results in an at least 2-fold increased genome editing efficiency than AsCas12a, FnCas12a, or LbCas12a. The presently disclosed methods further include a composition, wherein the guide RNA comprises a crRNA and a tracrRNA. Further, the crRNA comprises a 5' repeat recognition sequence of AAUU. Still further, in the presently disclosed methods the composition exhibit cleaving activity in the presence of CaCl2, CoCl2, FeCl$_2$, MnSO$_4$, or any combination thereof.

The present disclosure additionally provides a method of improving cleaving efficiency of a type V CRISPR-associated protein, the method comprising providing the type V CRISPR-associated protein; identifying a residue at position 925 or 930; and mutating the residue at position 925 or 930 to a Lysine, thereby improving cleaving efficiency of the type V CRISPR-associated protein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 shows a dendrogram of Cas12a.

FIG. 4 shows a continuation of the alignment of Cas12a proteins of the present disclosure, including SEQ ID NO: 1 (mgCas12a-1), SEQ ID NO: 3 (mgCas12a-2), SEQ ID NO: 9 (AsCas12a), SEQ ID NO: 67 (LbCas12a), and SEQ ID NO: 11 (FnCas12a) from FIG. 3.

FIG. 9A shows a chart of characteristics of Cas12a proteins of the present disclosure, including Cas12a proteins discovered by metagenomics mining (e.g., SEQ ID NO: 1 (mgCas12a-1) and SEQ ID NO: 3 (mgCas12a-2), AsCas12a, LbCas12a, and FnCas12a.

FIG. 9B shows a chart of amino acid sequence identities (%) between Cas12a orthologs. AsCas12 has less than 40% sequence identity to all other orthologs in the table. LbCas12a and FnCas12a have less than 40% sequence identity to mgCas12a-1 and mgCas12a-2. LbCas12a has between 40% and 50% sequence identity to FnCas12a. mgCas12a-1 has greater than 50% sequence identity to mgCas12a-2.

FIG. 15A illustrates that FnCas12a exhibited genome editing efficiencies in rice of 0.5%, 0.3%, and 0.9% in crRNA1-1, crRNA1-2, crRNA2, respectively and He-MgCas12a-1 exhibited genome editing efficiencies in rice of 1.9%, 0.7%, and 10.2% in crRNA1-1, crRNA1-2, crRNA2.

FIG. 15B illustrates that FnCas12a exhibited genome editing efficiencies in *N. benthamiana* of 0.8%, 1.4%, and 4.8% in crRNA1, crRNA2, and crRNA3, respectively and He-MgCas12a-1 exhibited genome editing efficiencies in *N. benthamiana* of 0.7%, 3.7%, and 3.4% in crRNA1, crRNA2, and crRNA3, respectively.

FIG. 16 shows an in vitro cleavage assay of Cas12a nucleases including mgCas12a-1 (wild-type), he_mgCas12a-1 (humanized and engineered mgCas12a-1), de_mgCas12a-1 (dead and engineered mgCas12a), mg Cas12a-2, he_mgCas12a-2, de_mgCas12a-2, AsCas12a, FnCas12a, and LbCas12a.

FIG. 18 shows an in vitro cleavage assay of target plasmid DNA with Cas12a nucleases including mgCas12a-1 (wild-type), he_mgCas12a-1 (humanized and engineered mgCas12a-1), de_mgCas12a-1 (dead and engineered mgCas12a), mg Cas12a-2, he_mgCas12a-2, de_mgCas12a-2, AsCas12a, FnCas12a, and LbCas12a.

FIG. 20A shows a condensed schematic relative to FIG. 1, showing the pipeline for mining Cas12a proteins from metagenome data.

FIG. 20B shows a phylogenetic tree of metagenome-derived Cas12a proteins of the disclosure and other Cas12a orthologs.

FIG. 20C shows schematics of functionally-characterized novel Cas12a's and AsCas12a (Yamano et al. 2016).

FIG. 22A shows sequence-specific cleavage of linear dsDNA by crRNA guided-Cas12a proteins including FnCas12a, WT mgCas12a-1 and WT mgCas12a-2.

FIG. 22B shows sequence-specific cleavage of circular dsDNA by crRNA guided-Cas12a proteins including FnCas12a, WT mgCas12a-1 and WT mgCas12a-2.

FIG. 23A shows cleavage of target linear dsDNA by WT mgCas12a-1 complexed with a crRNA having a 5' handle from AsCas12a, FnCas12a, and LbCas12a.

FIG. 23B shows cleavage of target linear dsDNA by WT mgCas12a-2 complexed with a crRNA having a 5' handle from AsCas12a (SEQ ID NO: 64), FnCas12a (SEQ ID NO: 65), and LbCas12a (SEQ ID NO: 66).

FIG. 25A shows each Cas12a incubated with dsDNA for different time periods.

FIG. 25B shows a graph of time versus dsDNase activity of each Cas12a.

FIG. 26A shows the results from Cas12a-RNP cleavage of target, linear dsDNA in the presence of seven different divalent cations were given to each Cas12a-RNP.

FIG. 26B shows sequence-specific dsDNA cleavage of FnCas12a-RNP under presence of different divalent cations.

FIG. 26C shows sequence-specific dsDNA cleavage of each WT mgCas12a-1RNP under presence of different divalent cations.

FIG. 26D shows sequence-specific dsDNA cleavage of each WT mgCas12a-2-RNP under presence of different divalent cations.

DETAILED DESCRIPTION

Definitions

Figure 1:
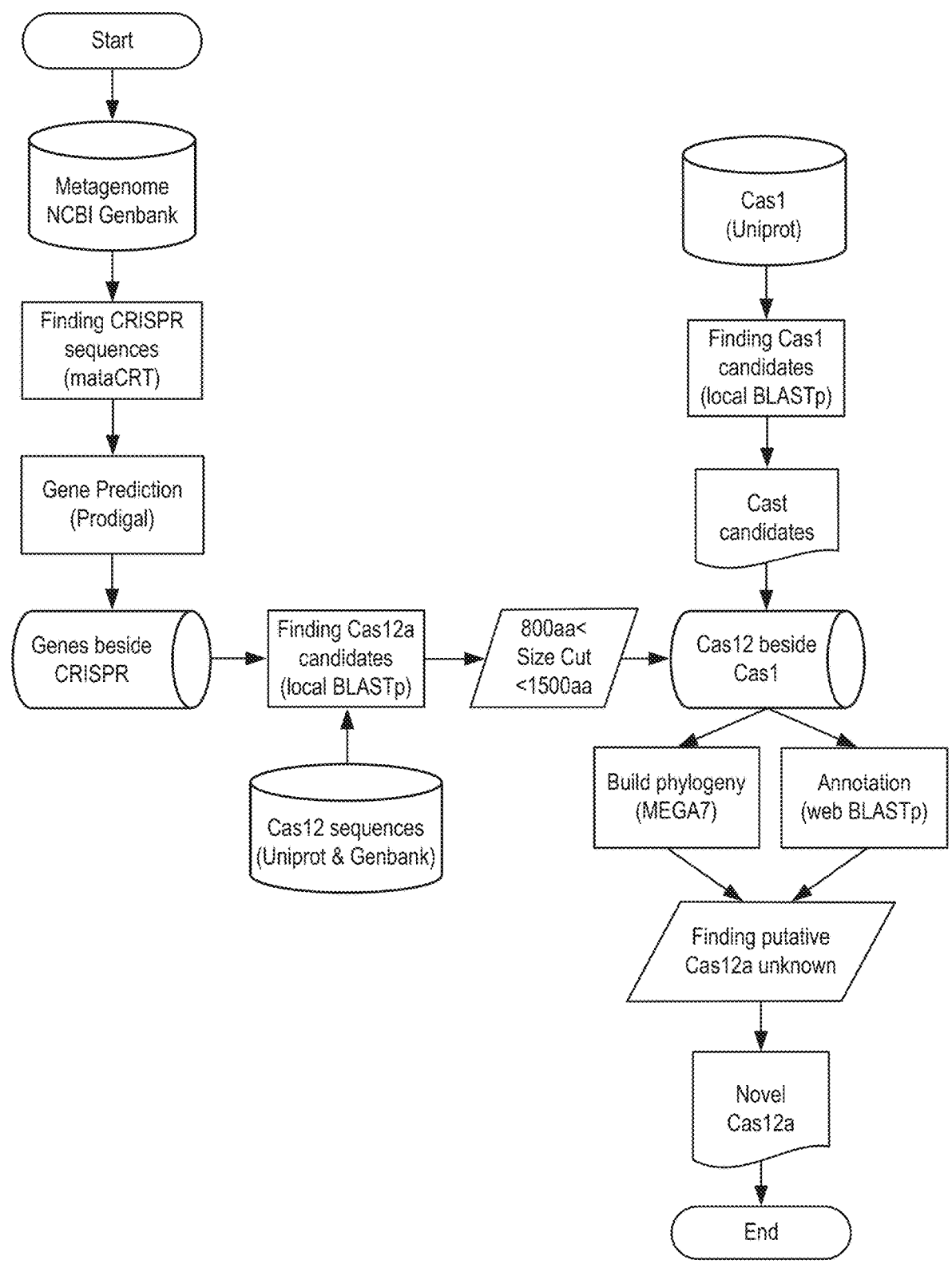
FIG. 1 shows a process by which a CRISPR associated protein (CAS protein) of the present disclosure was identified by metagenomic mining.

As used in the specification and appended claims, unless specified to the contrary, the following terms have the meaning indicated below.

As used herein, the term "comprise" or variations thereof such as "comprises" or "comprising" are to be read to indicate the inclusion of any recited feature but not the exclusion of any other features. Thus, as used herein, the term "comprising" is inclusive and does not exclude additional, unrecited features. In some embodiments of any of the compositions and methods provided herein, "comprising" may be replaced with "consisting essentially of" or "consisting of" The phrase "consisting essentially of" is used herein to require the specified feature(s) as well as those which do not materially affect the character or function of the claimed disclosure. As used herein, the term "consisting" is used to indicate the presence of the recited feature alone.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well of any individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well of any individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers+/−10% thereof, or 10% below the lower listed limit and 10% above the higher listed limit for the values listed for a range.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

As used herein, "treatment of" or "treating," "applying", or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease or condition, or to a patient reporting one or more of the physiological symptoms of a disease, even though a diagnosis of this disease has not been made.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

The section headings used herein are for organizational purposes only and are not to be construed as limiting the subject matter described.

The present disclosure provides novel endonuclease identified by metagenomics analysis. The identified novel endonuclease is preferentially DNA endonucleases, which may additionally cleave RNA. It is contemplated that the identified endonucleases can cleave double stranded DNA, single stranded DNA, or both double stranded DNA (dsDNA) and single stranded DNA (ssDNA). Preferably, the identified endonuclease may include Class II, Type V CRIRSPR/Cas proteins, such as Cas12a endonucleases. Further, preferably, Cas12a proteins may comprise a RuvC-like domain and may lack the HNH domain found in Cas9.

The present disclosure also provides synthetic tools for genome editing comprising a clustered regularly interspaced short palindromic repeats (CRISPR)/CRISPR-associated (Cas) system, which includes guide RNA (crRNA and/or tracrRNA) that directs a DNA endonuclease (Cas protein) to a region of double stranded DNA (dsDNA) to be cleaved. Guide RNAs (gRNA) are synthetically engineered and include the crRNA and tracrRNA, which are linked together with a linker to form gRNA. It is contemplated that the linkers can be of any length and with any combination of nucleobases, which may include G-rich linkers, A-rich linker, T-rich linkers, and C-rich linkers. Linkers of the present disclosure comprise 1 to 50 nucleobases, 5 to 50 nucleobases, 10 to 50 nucleobases, 15 to 50 nucleobases, 20 to 50 nucleobases, 25 to 50 nucleobases, 30 to 50 nucleobases, 35 to 50 nucleobases, 40 to 50 nucleobases, or 45 to 50 nucleobases. The present disclosure alternatively provides a linker having a sequence of GAAA to form gRNA. The present disclosure provides any guide RNA-directed endonuclease. Cas proteins of the present disclosure include any nuclease selected from Cas1, Cas1B, Cas2, Cas3, Cas4, Cas5, Cas6, Cas7, Cas8, Cas9, Cas10, Cas12a, Cas12b, Cas12c, Cas12d, Cas12e, Cas13a, Cas13b, Cas13c, Cas13d, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3 and Csf4. The present disclosure also provides one or more Cas proteins that are, in particular, Cas12a proteins, which is also referred to as Cpf1. Cas12a proteins do not require a tracrRNA and, thus, are complexed with a crRNA sequence to guide the endonuclease to a region of dsDNA of interest.

The present disclosure also provides Cas12a proteins that are complexed with a guide RNA that is smaller than would be used for Cas9 proteins, which comprises up to about 100 nucleotides. As such, CRISPR-Cas12a endonuclease of the present disclosure are much smaller than CRISPR/Cas9 systems and, thus, easier to package in viral vectors for delivery. Cas12a proteins of the present disclosure are able to recognize a protospacer adjacent motif (PAM) sequence, which is a recognition sequence adjacent to the target nucleic acid sequence to be bound. Some Cas12a proteins of the present disclosure recognize nucleic acid sequence stretches. Unlike Cas9 proteins that recognize G-rich PAM sequences, Cas12a proteins of the present disclosure are capable of recognizing T-rich PAM sequences increasing the number of regions of double stranded DNA that may be targeted and cleaved. Alternatively, Cas12a proteins of the present disclosure are also capable of recognizing A-rich PAM sequences, G-rich PAM sequences, and C-rich PAM sequences. The PAM comprises a three nucleobase PAM such as a T-rich PAM. For example, some guide RNA-directed endonucleases, such as Cas12a proteins described herein, recognize a PAM sequence of 5'-TTTN-3'. Alternatively a PAM sequence having two T nucleobases or 1 T nucleobase is also consistent with the present disclosure. Also consistent with the present disclosure is a PAM sequence that is pyrimidine rich or purine rich.

Unlike Cas9 proteins that cleave close to the recognition site, Cas12a proteins of the present disclosure cleave farther away from the recognition site. This is particularly advantageous because resulting non-homologous end joining (NHEJ) results in preservation of the PAM sequence, allowing for further editing and improves homology directed repair (HDR). Finally, unlike Cas9 proteins which generate blunt ends in dsDNA upon cleavage, Cas12a endonucleases of the present disclosure generate staggered or sticky ends in dsDNA upon cleavage. Accordingly, some guide RNA-directed endonucleases, such as the Cas12a proteins of the present disclosure, facilitate genome editing by generating staggered or sticky ends that are more likely to be repaired through HDR rather than random NHEJ.

Cas12a Proteins

The present disclosure provides Cas12a proteins (e.g., SEQ ID NO: 1 or SEQ ID NO: 3 or any sequence related thereto as disclosed herein) identified by metagenomics mining. The present disclosure interchangeably refers to polypeptides and proteins. Thus, a polypeptide of the present disclosure is a Cas12a protein, which may also be referred to as a Cas12a polypeptide. For example, metagenome base sequences are downloaded from the NCBI Genbank BLAST database and saved as a local BLASTp database. A number of different Cas12a and Cas1 amino acid sequences are downloaded from the Uniprot database. MetaCRT is used to identify key CRISPR repeat and spacer sequences from the metagenome and all metagenome sequences having CRISPR sequences are extracted using the Prodigal program. Taxonomic hierarchies are built based on CRISPR sequences and novel Cas12a proteins are identified by search for homology to other Cas12a sequences. These Cas12a sequences are interchangeably referred to as Cas12a proteins or metagenome Cas12a endonucleases (mgCas12a).

In some embodiments, the Cas12a proteins are obtained or derived (or modified) from the Eubacteriaceae bacteria family. For example, the Cas12a proteins described herein are obtained or derived (or modified) from *Eubacterium rectale* or *Eubacterium eligens*.

In some embodiments, Cas12a proteins discovered via metagenomics mining can be wild-type proteins. However, the Cas12a proteins described herein can be humanized and/or engineered to be compatible for administration to a subject in need thereof. In some cases, a humanized Cas12a protein may include mutations in a wild-type Cas12a protein sequence, which may make the humanized Cas12a protein less likely to elicit immunogenicity relative to a wild-type Cas12a protein without impacting protein function. If administered using a plasmid, a humanized Cas12a sequence are codon optimized to facilitate expression in a mammalian or human system. An engineered Cas12a protein includes mutations in the sequence, which improve nuclease activity and function. In some cases, humanization and engineering of a Cas12a disclosed herein increases cleavage efficiency. Alternatively, or in combination, humanization or engineering can increase cleavage specificity. In some cases, a dead and engineered ("de") Cas12a protein is used as a control to compare relative activity to a wild-type or humanized and/or engineered Cas12a protein. A dead Cas12a protein includes mutations in a wild-type Cas12a protein sequence which make the protein non-functional and inactive.

The Cas12a proteins of the present disclosure (e.g., SEQ ID NO: 1 or SEQ ID NO: 3 or any sequence related thereto as disclosed herein) cleave a nucleic acid sequence at a particular pH. For example, a Cas12a endonuclease cleaves a nucleic acid sequence from about pH 7 to about pH 7.9, or from about pH 7 to about pH 8.0. In some cases, a Cas12a endonuclease cleaves at about pH 7, about pH 7.1, about pH 7.2, about pH 7.3, about pH 7.4, about pH 7.5, about pH 7.6, about pH 7.7, about pH 7.8, or about pH 7.9. A Cas12a endonuclease described herein is capable of cleaving a nucleic acid sequence from about pH 7 to about pH 7.3, about pH 7.3 to about pH 7.6, or about pH 7.6 to about pH 7.9. Cas12a endonucleases disclosed herein does not exhibit cleaving activity and is, thus, inactive at a pH greater than 7.9. For example, Cas12a endonuclease described herein (e.g., SEQ ID NO: 1 or SEQ ID NO: 3 or any sequence related thereto as disclosed herein) is activated and capable of cleaving cellular environments comprising a pH of from about 7.0 to about 7.9. Accordingly, Cas12a endonucleases described herein (e.g., SEQ ID NO: 1 or SEQ ID NO: 3 or any sequence related thereto as disclosed herein) is inactivated and becomes inert if the environmental pH is outside of from about 7.0 to about 7.9. Alternatively, Cas12a proteins of the present disclosure is capable of cleaving a nucleic acid sequence at any pH, for example, a Cas12a endonuclease described herein is capable of cleaving a nucleic acid sequence at about pH 2, about pH 2.5, about pH 3, about pH 3.5, about pH 4, about pH 4.5, about pH 5, about pH 5.5, about pH 6, about pH 6.5, about pH 7, about pH 7.5, about pH 8, about pH 8.5, about pH 9, about pH 9.5, about pH 10, about pH 10.5, about pH 11, about pH 11.5, about pH 12, about pH 2 to about pH 12, about pH 2 to about pH 2.5, about pH 3 to about pH 3.5, about pH 4 to about pH 4.5, about pH 5 to about pH 5.5, about pH 6 to about pH 6.5, about pH 7 to about pH 7.5, about pH 8 to about pH 8.5, about pH 9 to about pH 9.5, about pH 10 to about pH 10.5, about pH 11 to about pH 11.5, or about pH 12 to about pH 12.5. Cas12a proteins of the present disclosure may also be inactivated and inert at any environmental pH, for example, a Cas12a endonuclease described herein may be inert at about pH 2, about pH 2.5, about pH 3, about pH 3.5, about pH 4, about pH 4.5, about pH 5, about pH 5.5, about pH 6, about pH 6.5, about pH 7, about pH 7.5, about pH 8, about pH 8.5, about pH 9, about pH 9.5, about pH 10, about pH 10.5, about pH 11, about pH 11.5, about pH 12, about pH 2 to about pH 12, about pH 2 to about pH 2.5, about pH 3 to about pH 3.5, about pH 4 to about pH 4.5, about pH 5 to about pH 5.5, about pH 6 to about pH 6.5, about pH 7 to about pH 7.5, about pH 8 to about pH 8.5, about pH 9 to about pH 9.5, about pH 10 to about pH 10.5, about pH 11 to about pH 11.5, or about pH 12 to about pH 12.5.

Thus, it is preferred that the composition comprising the Cas12a proteins may have pH in a range of from about pH 7 to about pH 7.9, from about pH 7 to about pH 7.3, about pH 7.3 to about pH 7.6, or about pH 7.6 to about pH 7.9, or about pH 7, about pH 7.1, about pH 7.2, about pH 7.3, about pH 7.4, about pH 7.5, about pH 7.6, about pH 7.7, about pH 7.8, or about pH 7.9. Yet, where the Cas12a proteins can maintain its activity (e.g., can cleave a nucleic acid sequence) at any other pH range, it is also contemplated that the composition comprising the Cas12a proteins may have other pH range (e.g., at about pH 2, about pH 2.5, about pH 3, about pH 3.5, about pH 4, about pH 4.5, about pH 5, about pH 5.5, about pH 6, about pH 6.5, about pH 7, about pH 7.5, about pH 8, about pH 8.5, about pH 9, about pH 9.5, about pH 10, about pH 10.5, about pH 11, about pH 11.5, about pH 12, about pH 2 to about pH 12, about pH 2 to about pH 2.5, about pH 3 to about pH 3.5, about pH 4 to about pH 4.5, about pH 5 to about pH 5.5, about pH 6 to about pH 6.5, about pH 7 to about pH 7.5, about pH 8 to about pH 8.5, about pH 9 to about pH 9.5, about pH 10 to about pH 10.5, about pH 11 to about pH 11.5, or about pH 12 to about pH 12.5).

The Cas12a proteins of the present disclosure (e.g., SEQ ID NO: 1 or SEQ ID NO: 3 or any sequence related thereto as disclosed herein) cleave a nucleic acid sequence at a particular temperature. For example, a Cas12a endonuclease cleaves a nucleic acid sequence from about 0° to about 100° C., from about 10° C. to about 20° C., from about 20° C. to about 30° C., from about 30° C. to about 40° C., from about 40° C. to about 50° C., from about 50° C. to about 60° C., from about 60° C. to about 70° C., from about 70° C. to about 80° C., from about 80° C. to about 90° C., from about 90° C. to about 100° C., from about 100° C. to about 110° C., from about 110° C. to about 120° C., or from about 120° C. to about 130° C.

A Cas12a endonuclease described in the present disclosure (e.g., SEQ ID NO: 1 or SEQ ID NO: 3 or any sequence related thereto as disclosed herein) is formulated in an excipient, preferably pharmaceutically acceptable excipient (e.g., diluent, carrier, buffer). In other words, the composition comprising the Cas12a endonuclease may further comprise an excipient, preferably pharmaceutically acceptable excipient (e.g., diluent, carrier, buffer). In some embodiments, the buffer comprises Bis-Tris propane-HCl. The buffer alternatively, additionally, or optionally, comprises $MgCl_2$. The buffer, additionally or optionally, is supplemented with protein, for example, a buffer used with the Cas12 endonucleases described herein may further comprise bovine serum albumin (BSA). Cas12a endonucleases described herein (e.g., SEQ ID NO: 1 or SEQ ID NO: 3 or any sequence related thereto as disclosed herein) is formulated, for example, in a buffer comprising from 0.1 to 50 mM Bis-Tris Propane-HCl, from 0.1 to 5 mM Bis-Tris Propane-HCl, from 5 to 15 mM Bis-Tris Propane-HCl, from 15 to 25 mM Bis-Tris Propane-HCl, from 25 to 35 mM Bis-Tris Propane-HCl, from 35 to 45 mM Bis-Tris Propane-HCl, from 45 to 50 mM Bis-Tris Propane-HCl, less than 0.1 mM Bis-Tris Propane-HCl, less than 0.5 mM Bis-Tris Propane-HCl, less than 1 mM Bis-Tris Propane-HCl, less than 5 mM Bis-Tris Propane-HCl, less than 10 mM Bis-Tris Propane-HCl, less than 15 mM Bis-Tris Propane-HCl, less than 20 mM Bis-Tris Propane-HCl, less than 25 mM Bis-Tris Propane-HCl, less than 30 mM Bis-Tris Propane-HCl, less than 35 mM Bis-Tris Propane-HCl, less than 40 mM Bis-Tris Propane-HCl, less than 45 mM Bis-Tris Propane-HCl, or less than 50 mM Bis-Tris Propane-HCl. The buffer additionally comprises 0.1 to 50 mM $MgCl_2$, from 0.1 to 5 mM $MgCl_2$, from 5 to 15 mM $MgCl_2$, from 15 to 25 mM $MgCl_2$, from 25 to 35 mM $MgCl_2$, from 35 to 45 mM $MgCl_2$, from 45 to 50 mM $MgCl_2$, less than 0.1 mM $MgCl_2$, less than 0.5 mM $MgCl_2$, less than 1 mM $MgCl_2$, less than 5 mM $MgCl_2$, less than 10 mM $MgCl_2$, less than 15 mM $MgCl_2$, less than 20 mM $MgCl_2$, less than 25 mM $MgCl_2$, less than 30 mM $MgCl_2$, less than 35 mM $MgCl_2$, less than 40 mM $MgCl_2$, less than 45 mM $MgCl_2$, or less than 50 mM $MgCl_2$. Additionally, the buffer comprise 1 to 500 µg/ml BSA, from 1 to 50 µg/ml BSA, from 50 to 100 µg/ml BSA, from 100 to 150 µg/ml BSA, from 150 to 200 µg/ml BSA, from 200 to 250 g/ml BSA, from 250 to 300 µg/ml BSA, from 300 to 350 µg/ml BSA, from 350 to 400 µg/ml BSA, from 400 to 450 µg/ml BSA, from 450 to 500 µg/ml BSA, less than 1 µg/ml BSA, less than 10 µg/ml BSA, less than 20 µg/ml BSA, less than 30 µg/ml BSA, less than 40 µg/ml BSA, less than 50 µg/ml BSA, less than 100 µg/ml BSA, less than 150 µg/ml BSA, less than 200 µg/ml BSA, less than 250 g/ml BSA, less than 300 µg/ml BSA, less than 350 µg/ml BSA, less than 400 µg/ml BSA, less than 450 µg/ml BSA, or less than 500 µg/ml BSA. The present disclosure additionally describes Cas12a endonucleases formulated in a buffer comprising 10 mM Bis-Tris Propane-HCl, 10 mM $MgCl_2$, and 100 µg/ml of BSA. Alternatives outside of the ranges provided above for Bis-Tris Propane, $MgCl_2$, and BSA are also consistent with the invention.

A Cas12a protein of the present disclosure cleaves 1% to 100%, 10% to 90%, 50% to 100%, 1% to 10%, 10% to 20%, 20% to 30%, 30% to 40%, 40% to 50%, 50% to 60%, 60% to 70%, 70% to 80%, 80% to 90%, 90% to 100%, or 80% to 100% of the target DNA. Target DNA compatible with the present invention includes linear DNA or plasmid DNA. Cas12a proteins of the present disclosure cleave 1% to 100%, 10% to 90%, 50% to 100%, 1% to 10%, 10% to 20%, 20% to 30%, 30% to 40%, 40% to 50%, 50% to 60%, 60% to 70%, 70% to 80%, 80% to 90%, 90% to 100%, or 80% to 100% of the target DNA in 0 to 1 hour, 1 hour to 5 hours, 5 hours to 10 hours, 10 hours to 20 hours, 20 hours to 30 hours, 30 hours to 40 hours, 40 hours to 50 hours, 50 hours to 60 hours, 60 hours to 70 hours, 70 hours to 80 hours, 80 hours to 90 hours, or 90 hours to 100 hours. The Cas12a proteins of the present disclosure cleave 90 to 100% of the target DNA within 1 hour. In addition, Cas12a proteins of the present disclosure cleave 90 to 100% of the target DNA within 12 hours. Cas12a proteins of the present disclosure cleave 90 to 100% of the target DNA within 24 hours. The above described cleavage efficiencies are achieved by reacting 0.1 pmol to 100 pmol, 0.1 to 10 pmol, 10 pmol to 20 pmol, 20 pmol to 30 pmol of a Cas12a protein of the present disclosure, 30 pmol to 40 pmol, 40 pmol to 50 pmol, 50 pmol to 60 pmol, 60 pmol to 70 pmol, 70 pmol to 80 pmol, 80 pmol to 90 pmol, or 90 to 100 pmol of a Cas12a protein of the present disclosure with 1 ng to 1000 ng of target DNA, 1 ng to 100 ng of target DNA, 100 ng to 200 ng of target DNA, 200 ng to 300 ng of target DNA, 300 ng to 400 ng of target DNA, 400 ng to 500 ng target DNA, 500 ng to 600 ng of target DNA, 600 ng to 700 ng of target DNA, 700 ng to 800 ng of target DNA, 800 ng to 900 ng of target DNA, or 900 ng to 1000 ng of target DNA. The above described cleavage efficiencies are achieved by reacting 6 pmol of a Cas12a protein of the present disclosure with 300 ng of target DNA The above described cleavage efficiencies are achieved at 37° C.

In some cases, a Cas12a protein of the present disclosure cleaves the target DNA into cleaved products without fully degrading the DNA, or in other words, without exhibiting interminable DNase activity. Target DNAs that are cleaved by a Cas12a protein of the present disclosure include any double stranded DNA (dsDNA), any linearized dsDNA, and any plasmid dsDNA.

Preferably, a functional domain of the CAS12A protein includes residues 829 through 991 of SEQ ID NO: 1 or residues 825 through 996 of SEQ ID NO: 3. Alternatively, a Cas12a protein has at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the residues 829 through 991 of SEQ ID NO: 1 or residues 825 through 996 of SEQ ID NO: 3.

Alternatively and/or additionally a Cas12a protein of the present disclosure has at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a functional domain in SEQ ID NO: 1.

Alternatively, a Cas12a protein of the present disclosure has at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a functional domain in SEQ ID NO: 3.

As another example, some proteins disclosure herein share at least 20 consecutive residues, at least 25 consecutive residues, at least 40 consecutive residues, at least 55 consecutive residues, at least 70 consecutive residues, at least 85 consecutive residues, at least 100 consecutive residues, at least 115 consecutive residues, at least 130 consecutive residues, at least 145 consecutive residues, at least 160 consecutive residues, at least 175 consecutive residues, at least 190 consecutive residues, at least 205 consecutive residues, at least 220 consecutive residues, at least 235 consecutive residues, at least 250 consecutive residues, at least 265 consecutive residues, at least 280 consecutive residues, at least 295 consecutive residues, at least 310 consecutive residues, at least 325 consecutive residues, at least 340 consecutive residues, at least 355 consecutive residues, at least 370 consecutive residues, at least 385 consecutive residues, at least 400 consecutive residues, at least 415 consecutive residues, at least 430 consecutive residues, at least 445 consecutive residues, at least 460 consecutive residues, at least 475 consecutive residues, at least 490 consecutive residues, at least 505 consecutive residues, at least 520 consecutive residues, at least 535 consecutive residues, at least 550 consecutive residues, at least 565 consecutive residues, at least 580 consecutive residues, at least 595 consecutive residues, at least 610 consecutive residues, at least 625 consecutive residues, at least 640 consecutive residues, at least 655 consecutive residues, at least 670 consecutive residues, at least 685 consecutive residues, at least 700 consecutive residues, at least 715 consecutive residues, at least 730 consecutive residues, at least 745 consecutive residues, at least 760 consecutive residues, at least 775 consecutive residues, at least 790 consecutive residues, at least 805 consecutive residues, at least 820 consecutive residues, at least 835 consecutive residues, at least 850 consecutive residues, at least 865 consecutive residues, at least 880 consecutive residues, at least 895 consecutive residues, at least 910 consecutive residues, at least 925 consecutive residues, at least 940 consecutive residues, at least 955 consecutive residues, at least 970 consecutive residues, at least 985 consecutive residues, at least 1000 consecutive residues, at least 1015 consecutive residues, at least 1030 consecutive residues, at least 1045 consecutive residues, at least 1060 consecutive residues, at least 1075 consecutive residues, at least 1090 consecutive residues, at least 1105 consecutive residues, at least 1120 consecutive residues, at least 1135 consecutive residues, at least 1150 consecutive residues, at least 1165 consecutive residues, at least 1180 consecutive residues, at least 1195 consecutive residues, at least 1210 consecutive residues, at least 1225 consecutive residues, at least 1240 consecutive residues, or at least 1250 consecutive residues, with a Cas12a protein of the present disclosure.

A Cas12a protein of the present disclosure has at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to at least 50 consecutive residues, at least 100 consecutive residues, at least 150 consecutive residues, at least 200 consecutive residues, at least 250 consecutive residues at least 300 consecutive residues, at least 350 consecutive residues, at least 400 consecutive residues, at least 450 consecutive residues, at least 500 consecutive residues, at least 550 consecutive residues, at least 600 consecutive residues, at least 650 consecutive residues, at least 700 consecutive residues, at least 750 consecutive residues, at least 800 consecutive residues, at least 850 consecutive residues, at least 900 consecutive residues, at least 950 consecutive residues, at least 1000 consecutive residues, at least 1050 consecutive residues, at least 1100 consecutive residues, at least 1150 consecutive residues, at least 1200 consecutive residues, at least 1250 consecutive residues, or at least 1263 consecutive residues of SEQ ID NO: 1.

A Cas12a protein of the present disclosure has at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to at least 50 consecutive residues, at least 100 consecutive residues, at least 150 consecutive residues, at least 200 consecutive residues, at least 250 consecutive residues at least 300 consecutive residues, at least 350 consecutive residues, at least 400 consecutive residues, at least 450 consecutive residues, at least 500 consecutive residues, at least 550 consecutive residues, at least 600 consecutive residues, at least 650 consecutive residues, at least 700 consecutive residues, at least 750 consecutive residues, at least 800 consecutive residues, at least 850 consecutive residues, at least 900 consecutive residues, at least 950 consecutive residues, at least 1000 consecutive residues, at least 1050 consecutive residues, at least 1100 consecutive residues, at least 1150 consecutive residues, at least 1200 consecutive residues, at least 1250 consecutive residues, or at least 1275 consecutive residues of SEQ ID NO: 3.

A Cas12a protein of the present disclosure has at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the full length sequence of SEQ ID NO: 1. Alternatively, a Cas12a protein of the present disclosure has at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the full length sequence of SEQ ID NO: 3.

A Cas12a protein of the present disclosure has at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to residues 1 through 100, residues 100 through 200, residues 200 through 300, residues 300 through 400, residues 400 through 500, residues 500 through 600, residues 600 through 700, residues 700 through 800, residues 800 through 900, residues 900 through 1000, residues 1000 through 1100, residues 1100 through 1200 or residues 1200 through 1263 of SEQ ID NO: 1.

A Cas12a protein of the present disclosure has at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to residues 1 through 100, residues 100 through 200, residues 200 through 300, residues 300 through 400, residues 400 through 500, residues 500 through 600, residues 600 through 700, residues 700 through 800, residues 800 through 900, residues 900 through 1000, residues 1000 through 1100, residues 1100 through 1200 or residues 1200 through 1275 of SEQ ID NO: 3.

The present disclosure provides a Cas12a protein having an amino acid sequence comprising SEQ ID NO: 1 and is also referred to herein as mgCas12a-1. Additionally, a Cas12a protein of the present disclosure is encoded for by a nucleotide sequence comprising SEQ ID NO: 2. A nucleotide sequence of SEQ ID NO: 2 encodes for an mgCas12a protein of SEQ ID NO: 1.

The present disclosure additionally provides a Cas12a protein having an amino acid sequence comprising SEQ ID NO: 3 and is also referred to herein as mgCas12a-2. Additionally a Cas12a protein of the present disclosure is encoded for by a nucleotide sequence comprising SEQ ID NO: 4. A nucleotide sequence of SEQ ID NO: 4 encodes for an mgCas12a protein of SEQ ID NO: 3.

The present disclosure provides a Cas12a protein of the present disclosure has a Lysine (K) at position (residue) 925, as in SEQ ID NO: 1. Additionally, a Cas12a protein of the present disclosure has a Lysine (K) at position (residue) 930, as in SEQ ID NO: 3. Thus, in some embodiments, the Cas12a protein or a variant thereof may have Lysine (K) at position (residue) 925 or 930, or in a position other than position (residue) 925 or 930, when it is optimally aligned with SEQ ID NO: 1 or with SEQ ID NO: 3, respectively. In other words, a Cas12a protein of the present disclosure having a Lysine (K) at position (residue) 925 includes a Cas12a protein or Cas12a protein variants (a portion of Cas12a protein, a polypeptide that includes some domains of Cas12a protein, etc.) that has a Lysine (K) in a position corresponding to residue 925 of SEQ ID NO: 1, a Lysine (K) in a position aligned to residue 925 of SEQ ID NO: 1, or residue 925 relative to SEQ ID NO: 1. For example, if amino acid residues 915-930 of the Cas12a protein or its variant are aligned with amino acid residues 918-933 of the SEQ ID NO: 1, a Lysine (K) is preferably located in amino acid residue 922 that is relative to, equivalent to, or aligned to residue 925 of SEQ ID NO: 1.

A Cas12a polypeptide of the present disclosure can also have an amino acid sequence comprising a Lysine aligned to a Lysine at position 925 of SEQ ID NO: 1, a Lysine aligned to a Lysine at position 930 of SEQ ID NO: 3, a Lysine aligned to a Lysine at position 925 of SEQ ID NO: 1, a Lysine aligned to a Lysine at position 930 of SEQ ID NO: 3, or any combination thereof. For example, the present disclosure provides a composition comprising a polypeptide having at least 80% sequence identity with residue 829 through residue 991 of SEQ ID NO: 1, wherein the polypeptide comprises an amino acid sequence comprising a Lysine aligned to a Lysine at position 925 of SEQ ID NO: 1; a polypeptide having at least 80% sequence identity with residue 825 through residue 996 of SEQ ID NO: 3, wherein the polypeptide comprises an amino acid sequence comprising a Lysine aligned to a Lysine at position 930 of SEQ ID NO: 3; a polypeptide having at least 80% sequence identity with SEQ ID NO: 1, wherein the polypeptide comprises an amino acid sequence comprising a Lysine aligned to a Lysine at position 925 of SEQ ID NO: 1; or a polypeptide having at least 80% sequence identity with SEQ ID NO: 3, wherein the polypeptide comprises an amino acid sequence comprising a Lysine aligned to a Lysine at position 930 of SEQ ID NO: 3. In the Cas12a polypeptides disclosed herein, a first residue aligned to a second residue at a position can indicate that the first residue is in a candidate polypeptide sequence and the alignment is in reference to a second residue and a position in a reference polypeptide sequence. For example, a polypeptide having at least 80% sequence identity with residue 829 through residue 991 of SEQ ID NO: 1, wherein the polypeptide comprises an amino acid sequence comprising a Lysine aligned to a Lysine at position 925 of SEQ ID NO: 1 can refer to the candidate polypeptide having an Lysine that can be aligned to Lys925 of SEQ ID NO: 1. Alignment can be done using any of the methods disclosed herein and aligned residues will be readily apparent to one of skill.

Additionally, a Cas12a protein of the present disclosure has an amino acid sequence comprising SEQ ID NO: 5, which comprises the SEQ ID NO: 1 having a Lysine to glutamine mutation at position 925 (K925Q). The present disclosure additionally provides a Cas12a protein having an amino acid sequence comprising SEQ ID NO: 6, which comprises the SEQ ID NO: 3 having a Lysine to glutamine mutation at position 930 (K930Q).

It is consistent with the present disclosure for the Lysine at position 925 of SEQ ID NO: 1 to be substituted with any other amino acid residue. The Lysine at position 925 of SEQ ID NO: 1 may also be substituted with arginine (Arg), histidine (His), aspartic acid (Asp), glutamic acid (Glu), serine (Ser), threonine (Thr), asparagine (Asn), glutamine (Gln), tyrosine (Tyr), alanine (Ala), isoleucine (Ile), leucine (Leu), valine (Val), phenylalanine (Phe), methionine (Met), tryptophan(e) (Trp), glycine (Gly), proline (Pro), or cysteine (Cys). Additionally, the present disclosure also describes that the Lysine at position 930 of SEQ ID NO: 3 is substituted with any other amino acid residue. The Lysine at position 925 of SEQ ID NO: 1 may be substituted with arginine (Arg), histidine (His), aspartic acid (AsP), glutamic acid (Glu), serine (Ser), threonine (Thr), asparagine (Asp), glutamine (Gln), tyrosine (Tyr), alanine (Ala), isoleucine (le), leucine (Leu), valine (Val), phenylalanine (Phe), methionine (Met), tryptophan(e) (Trp), glycine (Gly), proline (Pro), or cysteine (Cys).

A base sequence of a Cas12a of the present disclosure (e.g., mgCas12a-1) is human codon optimized, which in some cases can improve protein expression, and has a sequence comprising SEQ TD NO: 7. A base sequence of a Cas12a of the present disclosure (e.g., mgCas12a-2) is human codon optimized, which in some cases can improve protein expression, and has a sequence comprising SEQ TD NO: 8.

Cas12a proteins disclosed herein (e.g., SEQ TD NO: 1 or SEQ ID NO: 3 or any sequence related thereto as disclosed herein) cleave DNA or RNA.

TABLE 1 shows exemplary Cas12a sequences of the present disclosure, including SEQ TD NO: 1-SEQ ID NO: 8.

TABLE 1

Exemplary Cas12a Sequences

| SEQ ID NO | Sequence |
| --- | --- |
| SEQ ID NO: 1 | MNNGTNNFQNFIGISSLQKTLRNALIPTETTQQFIVKNGIIKEDELRGENRQIL<br>KDIMDDYYRGFISETLSSIDDIDWTSLFEKMEIQLKNGDNKDTLIKEQAEKRKA<br>IYKKFADDDRFKNMFSAKLISDILPEFVIHNNNYSASEKEEKTQVIKLFSRFAT<br>SFKDYFKNRANCFSADDISSSSCHRIVNDNAEIFFSNALVYRRIVKNLSNDDIN<br>KISGDIKDSLKEMSLEEIYSYEKYGEFITQEGISFYNDICGKVNSFMNLYCQKN<br>KENKNLYKLRKLHKQILCIADTSYEVPYKFESDEEVYQSVNGFLDNISSKHIVE<br>RLRKIGDNYNGYNLDKIYIVSKFYESVSQKTYRDWETINTALEIHYNNILPGNG<br>KSKADKVKKAVKNDLQKSITEINELVSNYKLCPDDNIKAETYIHEISHILNNFE<br>AQELKYNPEIHLVESELKASELKNVLDVIMNAFHWCSVFMTEELVDKDNNFYAE<br>LEEIYDEIYTVISLYNLVRNYVTQKPYSTKKIKLNFGIPTLADGWSKSKEYSNN<br>AIILMRDNLYYLGIFNAKNKPDKKIIEGNTSENKGDYKKMIYNLLPGPNKMIPK<br>VFLSSKTGVETYKPSAYILEGYKQNKHLKSSKDFDITFCHDLIDYFKNCIAIHP<br>EWKNFGFDFSDTSTYEDISGFYREVELQGYKIDWTYISEKDIDLLQEKGQLYLF<br>QIYNKDFSKKSTGNDNLHTMYLKNLFSEENLKDIVLKLNGEAEIFFRKSSIKNP<br>IIHKKGSILVNRTYEAEEKDQFGNIQIVRKTIPENIYQELYKYFNDKSDKELSD<br>EAAKLKNVVGHHEAATNIVKDYRYTYDKYFLHMPITINFKANKTSFINDRILQY<br>IAKEKNLHVIGIDRGERNLIYVSVIDTCGNIVEQKSFNIVNGYDYQIKLKQQEG<br>ARQIARKEWKEIGKIKEIKEGYLSLVIHEISKMVIKYNAIIAMEDLSYGFKKGR<br>FKVERQVYQKFETMLINKLNYLVFKDISITENGGLLKGYQLTYIPDKLKNVGHQ<br>CGCIFYVPAAYTSKIDPTTGFVNIFKFKDLTVDAKREFIKKFDSIRYDSEKKLF<br>CFTFDYNNFITQNTVMSKSSWSVYTYGVRIKRRFVNGRFSNESDTIDITKDMEK |

TABLE 1-continued

Exemplary Cas12a Sequences

| SEQ ID NO | Sequence |
|---|---|
| | TLEMTDINWRDGHDLRQDIIDYEIVQHIFEIFRLTVQMRNSLSELEDRDYDRLI<br>SPVLNENNIFYDSAKAGDALPKDADANGAYCIALKGLYEIKQITENWKEDGKFS<br>RDKLKISNKDWFDFIQNKRYL |
| SEQ ID NO: 2 | ATGAATAACGGAACAAATAACTTTCAGAACTTTATCGGAATTTCTTCTTTGCAG<br>AAGACTCTTAGGAATGCTCTCATTCCAACAGAAACAACACAGCAATTTATTGTT<br>AAAAATGGAATAATTAAAGAAGATGAACTCAGAGGAGAAAATCGTCAGATACTT<br>AAAGATATCATGGATGATTATTACAGAGGTTTCATTTCAGAAACTTTATCGTCA<br>ATTGATGATATTGACTGGACCTCTTTATTTGAGAAAATGGAAATTCAGTTAAAA<br>AATGGAGATAATAAAGACACTCTTATAAAAGAACAGGCTGAAAAACGTAAGGCA<br>ATCTATAAAAAATTTGCAGATGATGATAGATTTAAAAATATGTTCAGTGCAAAA<br>TTAATCTCAGATATTCTTCCTGAATTTGTCATTCATAACAATAATTATTCTGCA<br>TCAGAAAAGGAAGAAAAAACACAGGTAATTAAATTATTTTCCAGATTTGCAACA<br>TCATTCAAGGACTATTTTAAAAACAGGGCTAATTGTTTTTCTGCTGATGATATA<br>TCTTCTTCTTCTTGTCATAGAATAGTTAATGATAATGCAGAAATATTTTTTAGT<br>AATGCATTGGTGTATAGGAGAATTGTAAAAAATCTTTCAAATGATGATATAAAT<br>AAAATATCCGGAGATATTAAGGATTCATTAAAGGAAATGTCTCTGGAGGAAATT<br>TATTCTTATGAAAAATATGGGGAATTTATTACACAGGAAGGTATATCTTTTTAT<br>AATGATATATGCGGTAAAGTAAATTCATTTATGAATTTATATTGCCAGAAAAAT<br>AAAGAAAACAAAAATCTCTATAAGCTGCGAAAGCTTCATAAACAGATACTGTGC<br>ATAGCAGATACTTCTTATGAGGTGCCGTATAAATTTGAATCAGATGAAGAGGTT<br>TATCAATCAGTGAATGGATTTTTGGACAATATTAGTTCAAAACATATCGTTGAA<br>AGATTGCGTAAGATTGGAGACAACTATAACGGCTACAATCTTGATAAGATTTAT<br>ATTGTTAGTAAATTCTATGAATCAGTTTCACAAAAGACATATAGAGATTGGGAA<br>ACAATAAATACTGCATTAGAAATTCATTACAACAATATATTACCCGGAAATGGT<br>AAATCTAAAGCTGACAAGGTAAAAAAAGCGGTAAAGAATGATCTGCAAAAAAGC<br>ATTACTGAAATCAATGAGCTTGTTAGCAATTATAAATTATGTCCGGATGATAAT<br>ATTAAAGCAGAGACATATATACATGAAATATCACATATTTTGAATAATTTTGAA<br>GCACAGGAGCTTAAGTATAATCCTGAAATTCATCTGGTGGAAAGTGAATTGAAA<br>GCATCTGAATTAAAAAATGTTCTCGATGTAATAATGAATGCTTTTCATTGGTGT<br>TCGGTTTTCATGACAGAGGAGCTGGTAGATAAAGATAATAATTTTTATGCGGAG<br>TTAGAAGAGATATATGACGAAATATATACGGTAATTTCATTGTATAATCTTGTG<br>CGTAATTATGTAACGCAGAAGCCATATAGTACAAAAAAAATTAAATTGAATTTT<br>GGTATTCCTACACTAGCGGATGGATGGAGTAAAAGTAAAGAATATAGTAATAAT<br>GCAATTATTCTCATGCGTGATAATTTGTACTATTTAGGAATATTTAATGCAAAA<br>AATAAGCCTGACAAAAAGATAATTGAAGGTAATACATCAGAAAATAAAGGGGAT<br>TATAAGAAGATGATTTATAATCTTCTGCCAGGACCAAATAAAATGATCCCCAAG<br>GTATTCCTCTCTTCAAAAACCGGAGTGGAAACATATAAGCCGTCTGCCTATATA<br>TTGGAGGGCTATAAACAAAACAAGCATCTTAAATCCTCTAAGGATTTTGATATA<br>ACGTTTTGTCACGATTTGATTGATTATTTTAAGAACTGTATAGCAATACATCCT<br>GAATGGAAGAATTTTGGCTTTGATTTTTCTGACACCTCCACATATGAAGATATC<br>AGCGGATTTTACAGAGAAGTCGAATTGCAAGGTTATAAAATTGACTGGACATAT<br>ATCAGCGAAAAGGATATTGATTTGTTGCAGGAAAAAGGACAGTTATATTTATTT<br>CAAATATATAACAAAGATTTTTCCAAGAAAAGTACCGGAAATGATAATCTTCAT<br>ACTATGTATTTGAAGAATTTGTTTAGCGAAGAGAATTTAAAGGATATTGTACTG<br>AAATTAAACGGTGAGGCGGAAATCTTCTTTAGAAAATCAAGCATAAAGAATCCA<br>ATAATTCATAAAAAAGGCTCTATTCTTGTTAATAGAACATATGAAGCAGAGGAA<br>AAAGATCAATTTGGAAATATCCAGATAGTCAGAAAAACCATACCGGAAATATA<br>TATCAGGAGCTTTATAAATATTTCAATGATAAAGTGATAAAGAACTTTCGGAT<br>GAAGCAGCTAAGCTTAAGAATGTAGTAGGTCATCATGAGGCTGCTACAAACATA<br>GTAAAAGATTATAGATATACATATGATAAATATTTTCTTCATATGCCTATTACA<br>ATCAATTTTAAAGCCAATAAGACAAGCTTTATTAATGACAGAATATTACAATAT<br>ATTGCTAAAGAAAAGAATTTGCATGTAATAGGCATTGATCGTGGTGAAAGAAAC<br>CTGATATATGTTTCAGTAATTGATACTTGTGGAAATATTGTTGAACAAAAATCG<br>TTTAACATTGTTAATGGATATGATTATCAGATTAAGCTCAAGCAGCAGGAGGGG<br>GCGCGACAAATCGCACGAAAAGAATGGAAAGAAATCGGCAAATAAAAGAAATT<br>AAAGAAGGCTATTTATCTCTTGTAATTCATGAAATTTCAAAGATGGTTATTAAA<br>TATAATGCCATAATTGCAATGGAGGATTTAAGCTACGGATTTAAAAAAGGTCGT<br>TTCAAGGTTGAGCGACAGGTTTACCAGAAGTTTGAGACAATGCTTATCAACAA<br>CTCAACTATCTGGTATTTAAAGATATATCCATAACTGAAAACGGTGGTCTTCTA<br>AAGGGATATCAGCTTACATATATTCCAGATAAACTGAAAAATGTGGGTCATCAA<br>TGTGGTTGTATATTTTACGTACCTGCTGCCTATACATCAAAAATAGATCCTACA<br>ACCGGATTTGTAAATATATTCAAATTTAAAGATTTAACAGTTGATGCAAAGAGA<br>GAATTTATAAAAAAATTTGACAGTATCAGATATGATTCAGAAAAAAAACTGTTT<br>TGTTTTACATTTGATTATAATAACTTTATTACGCAAAATACTGTTATGTCAAAG<br>TCAAGCTGGAGTGTATATACGTACGGAGTTAGGATAAAAGAAGATTTGTCAAT<br>GGCAGGTTCTCAAATGAATCGGATACAATTGATATAACAAAAGATATGAAAAA<br>ACCCTCGAAATGACAGATATAAATTGGAGAGATGGTCATGATCTGAGGCAGGAT<br>ATTATTGATTATGAAATCGTACAACACATATTTGAGATTTTTAGATTGACTGTA<br>CAAATGAGAAACAGTTTAAGTGAATTAGAAGACAGGGATTATGACCGTTTGATT<br>TCTCCGGTGCTCAATGAAAATAATATATTTTATGATTCAGCTAAAGCAGGAGAT<br>GCGTTACCTAAAGACGCAGATGCTAATGGTGCATATTGTATAGCTCTAAAAGGC<br>TTGTATGAAATCAAACAAATTACAGAGAATTGGAAAGAAGACGGTAAGTTTTCA<br>AGAGATAAACTTAAAATTTCCAATAAGGACTGGTTTGACTTTATTCAAAATAAA<br>AGGTATTTATAA |

TABLE 1-continued

Exemplary Cas12a Sequences

| SEQ ID NO | Sequence |
|---|---|
| SEQ ID NO: 3 | MGKNQNFQEFIGVSPLQKTLRNELIPTETTKKNITQLDLLTEDEIRAQNREKLK<br>EMMDDYYRNVIDSTLHVGIAVDWSYLFSCMRNHLRENSKESKRELERTQDSIRS<br>QIHNKFAERADFKDMFGASIITKLLPTYIKQNSEYSERYDESMEILKLYGKFTT<br>SLTDYFETRKNIFSKEKISSAVGYRIVEENAEIFLQNQNAYDRICKIAGLDLHG<br>LDNEITAYVDGKTLKEVCSDEGFAKAITQEGIDRYNEAIGAVNQYMNLLCQKNK<br>ALKPGQFKMKRLHKQILCKGTISFDIPKKFENDKQVYDAVNSFTEIVTKNNDLK<br>RLLNITQNANDYDMNKIYVVADAYSMISQFISKKWNLIEECLLDYYSDNLPGKG<br>NAKENKVKKAVKEETYRSVSQLNEVIEKYYVEKTGQSVWKVESYISSLAEMIKL<br>ELCHEIDNDEKHNLIEDDEKISEIKELLDMYMDVFHIIKVFRVNEVLNFDETFY<br>SEMDEIYQDMQEIVPLYNHVRNYVTQKPYKQEKYRLYFHTPTLANGWSKSKEYD<br>NNAIILVREDKYYLGILNAKKKPSKEIMAGKEDCSEHAYAKMNYYLLPGANKML<br>PKVFLSKKGIQDYHPSSYIVEGYNEKKHIKGSKNFDIRFCRDLIDYFKECIKKH<br>PDWNKFNFEFSATETYEDISVFYREVEKQGYRVEWTYINSEDIQKLEEDGQLFL<br>FQIYNKDFAVGSTGKPNLHTLYLKNLFSEENLRDIVLKLNGEAEIFFRKSSVQK<br>PVIHKCGSILVNRTYEITESGTTRVQSIPESEYMELYRYFNSEKQIELSDEAKK<br>YLDKVQCNKAKTDIVKDYRTMDKFFIHLPITINFKVDKGNNVNAIAQQYIAGR<br>KDLHVIGIDRGERNLIYVSVIDMYGRILEQKSFNLVEQVSSQGTKRYYDYKEKL<br>QNREEERDKARKSWKTIGKIKELKEGYLSSVIHEIAQMVVKYNAIIAMEDLNYG<br>FKRGRFKVERQVYQKFETMLISKLNYLADKSQAVDEPGGILRGYQMTYVPDNIK<br>NVGRQCGIIFYVPAAYTSKIDPTTGFINAFKRDVVSTNDAKENFLMKFDSIQYD<br>IEKGLFKFSFDYKNFATHKLTLAKTKWDVYTNGTRIQNMKVEGHWLSMEVELTT<br>KMKELLDDSHIPYEEGQNILDDLREMKDITTIVNGILEIFWLTVQLRNSRIDNP<br>DYDRIISPVLNKNGEFFDSDEYNSYIDAQKAPLPIDADANGAFCIALKGMYTAN<br>QIKENWVEGEKLPADCLKIEHASWLAFMQGERG |
| SEQ ID NO: 4 | ATGGGTAAAAATCAAAATTTTCAGGAATTTATTGGGGTATCACCACTTCAAAAG<br>ACTTTAAGAAACGAATTAATCCCAACAGAAACAACAAAAAGAATATTACTCAG<br>CTTGATCTTTTGACTGAGGATGAAATCCGCGCGCAAAATCGAGAGAAGCTGAAA<br>GAGATGATGGATGACTACTACCGGAATGTGATTGATAGCACTTTGCATGTGGGT<br>ATAGCTGTTGATTGGAGCTATTTATTTTCGTGTATGCGAAATCATCTAAGGGAG<br>AATTCCAAAGAGTCAAAGCGGGAATTGGAACGAACACAGGATTCTATTCGTTCA<br>CAAATCCATAATAAGTTTGCTGAACGAGCGGATTTTAAGGATATGTTTGGAGCA<br>TCGATAATAACAAAATTACTTCCGACATATATAAAACAGAATTCAGAATATTCC<br>GAGCGGTATGACGAGAGCATGGAAATTTTGAAACTGTATGGAAAATTCACAACA<br>TCGTTGACCGATTACTTTGAGACAAGAAAGAATATCTTTTCTAAAGAGAAAATA<br>TCTTCTGCCGTTGGATATCGAATCGTAGAGGAAATGCTGAGATCTTCTTGCAG<br>AATCAGAATGCTTACGACAGAATCTGTAAGATAGCGGGACTGGATTTACATGGA<br>TTGGATAATGAAATAACAGCATATGTTGATGGAAAAACATTAAAAGAAGTATGT<br>TCGGATGAAGGATTTGCAAAGGCTATTACAAGAAGGGATTGATCGCTACAAC<br>GAGGCAATCGGTGCAGTAAATCAATATATGAATCTGTTATGCCAGAAGAATAAG<br>GCATTAAAACCGGGACAATTTAAGATGAAGCGGCTACATAAACAGATTCTTTGC<br>AAAGGAACAACCTCTTTCGATATTCCAAAGAAGTTTGAAAATGATAAACAGGTG<br>TATGACGCAGTTAATTCTTTTACAGAGATAGTAACGAAGAATAATGATTTGAAG<br>CGACTGTTAAATATTACACAGAATGCAAATGATTATGACATGAATAAAATCTAT<br>GTAGTAGCCGATGCATATAGTATGATTTCACAGTTTATCAGTAAAAAATGGAAT<br>CTGATTGAAGAATGCTTGCTGGATTATTATAGCGATAATTTGCCGGGAAAAGGA<br>AATGCGAAAGAAAACAAAGTTAAAAAGGCGGTAAAGGAAGAAACGTATCGCAGT<br>GTTTCACAGTTGAATGAAGTTATTGAGAAATATTATGTGGAAAAGACCGGACAG<br>TCAGTATGGAAAGTGGAAAGTTATATTTCTAGTCTGGCAGAAATGATTAAGCTG<br>GAATTGTGCCACAGATAGATAACGATGAGAAGCATAATCTGATTGAAGATGAT<br>GAGAAGATATCCGAGATTAAGGAACTGTTGGATATGTACATGGATGTATTTCAT<br>ATTATAAAAGTGTTCCGGGTGAATGAAGTATTGAATTTCGATGAAACCTTTTAT<br>TCGGAGATGGATGAGATCTATCAGGATATGCAGGAAATCGTTCCATTATACAAT<br>CATGTTCGAAACTATGTTACACAGAAACCATATAAGCAGGAGAAATATCGTTTA<br>TATTTCCACACTCCAACATTGGCAAATGGCTGGTCCAAGAGTAAGGAATATGAC<br>AACAACGCAATTATATTGGTGCGAGAAGATAAATATTATTAGGTATTCTGAAT<br>GCGAAAAAGAAACCATCGAAAGAAATTATGGCGGGCAAAGAGGATTGTTCAGAA<br>CATGCATATGCAAAGATGAATTATTATTTGTTGCCGGGCGCGAACAAGATGCTT<br>CCAAAAGTATTTTTATCTAAGAAAGGAATACAGGACTATCACCCATCATCATAT<br>ATTGTTGAAGGATATAATGAAAAGAAACATATTAAAGGTTCCAAGAATTTTGAT<br>ATCCGGTTTTGTAGGGATTTGATTGACTACTTCAAGGAATGCATTAAAAAACAT<br>CCGGATTGGAATAAGTTTAACTTTGAATTTTCTGCGACAGAAACATATGAGGAT<br>ATCAGTGTCTTTTATCGCGAAGTTGAAAAGCAAGGATATCGCGTAGAGTGGACG<br>TATATCAATAGTGAAGATATTCAGAAACTGGAAGAAGATGGACAGTTGTTTTTA<br>TTTCAGATATATAACAAAGATTTTGCTGTGGGAAGTACAGGTAAACCAAATCTT<br>CATACATTGTATCTGAAAAATCTGTTCAGCGAAGAAAATTTGCGGGACATTGTA<br>TTAAAACTAAATGGGGAAGCAGAAATATTCTTCCGTAAATCAAGTGTTCAAAAA<br>CCGGTTGATTCATAAGTGCGGCAGTATTTTAGTCAATCGTACCTATGAGATTACC<br>GAGAGTGGAACAACACGGGTACAATCAATTCCGGAAAGTGAATACATGGAATTA<br>TATCGCTACTTTAATAGTGAAAGCAGATAGAATTATCAGATGAGGCAAAAAAA<br>TATTTGGACAAGGTGCAATGTAATAAGGCAAAGACAAGATATTGTGAAAGACTAC<br>CGATACACCATGGACAAGTTTTTTATTCATCTTCCGATTACGATTAATTTTAAG<br>GTTGATAAGGGTAACAATGTTAATGCCATTGCACAGCAATATATTGCAGGGCGG<br>AAAGATTTACATGTGATAGGAATTGATCGAGGAGAACGGAATCTGATTTACGTT<br>TCTGTAATTGACATGTATGGTAGAATTTTAGAGCAGAAATCCTTTAACCTTGTG<br>GAACAGGTATCGTCGCAGGGAACGAAGCGATATTACGATTACAAAGAAAAATTA |

TABLE 1-continued

Exemplary Cas12a Sequences

| SEQ ID NO | Sequence |
|---|---|
| | CAGAACCGGGAAGAGGAACGGGATAAAGCAAGAAAGAGTTGGAAGACAATCGGC<br>AAGATTAAGGAATTAAAAGAGGGGTATCTGTCGTCAGTAATTCATGAGATTGCA<br>CAGATGGTCGTAAAGTATAACGCAATCATTGCAATGGAAGATTTGAATTATGGA<br>TTTAAGCGGGGAAGATTCAAAGTAGAGCGCCAGGTATATCAGAAATTTGAAACG<br>ATGTTGATCAGTAAGTTGAATTATCTGGCAGATAAATCTCAGGCTGTGGATGAA<br>CCGGGAGGTATATTACGGGGATATCAGATGACTTATGTGCCGGATAATATTAAG<br>AATGTTGGAAGACAATGTGGAATAATCTTTTATGTGCCGGCAGCATATACCTCC<br>AAGATTGATCCGACAACCGGATTTATCAATGCATTTAAGCGGGATGTGGTATCA<br>ACAAATGATGCAAAAGAGAATTTCCTGATGAAGTTTGATTCTATTCAGTACGAT<br>ATAGAAAAAGGCTTATTTAAGTTTTCATTTGATTACAAAAATTTTGCCACACAT<br>AAACTTACACTTGCAAGACAAAATGGGACGTATATACAAATGGAACTCGAATA<br>CAAAACATGAAAGTTGAAGGACATTGGCTTTCAATGGAAGTTGAACTTACAACG<br>AAAATGAAAGAGTTGCTGGATGACTCGCATATTCCATATGAAGAAGGACAGAAT<br>ATATTGGATGATTTGCGGGAGATGAAAGATATAACAACCATTGTGAATGGTATA<br>TTGGAAATCTTCTGGTTGACAGTCCAGCTTCGGAATAGCAGGATAGATAATCCG<br>GATTACGATAGAATTATCTCACCGGTATTGAATAAAAATGGAGAATTTTTTGAT<br>TCTGATGAATATAATTCATATATTGATGCGCAAAAGGCACCGTTACCGATAGAT<br>GCCGATGCAAATGGCGCATTTTGCATTGCATTAAAAGGAATGTATACTGCCAAT<br>CAGATCAAGAAAACTGGGTTGAAGGGGAGAAACTTCCGGCGGATTGCTTGAAG<br>ATCGAACATGCGAGTTGGTTAGCATTTATGCAAGGAGAAAGGGGATAG |
| SEQ ID NO: 5 | MNNGTNNFQNFIGISSLQKTLRNALIPTETTQQFIVKNGIIKEDELRGENRQIL<br>KDIMDDYYRGFISETLSSIDDIDWTSLFEKMEIQLKNGDNKDTLIKEQAEKRKA<br>IYKKFADDDRFKNMFSAKLISDILPEFVIHNNNYSASEKEEKTQVIKLFSRFAT<br>SFKDYFKNRANCFSADDISSSSCHRIVNDNAEIFFSNALVYRRIVKNLSNDDIN<br>KISGDIKDSLKEMSLEEIYSYEKYGEFITQEGISFYNDICGKVNSFMNLYCQKN<br>KENKNLYKLRKLHKQILCIADTSYEVPYKFESDEEVYQSVNGFLDNISSKHIVE<br>RLRKIGDNYNGYNLDKIYIVSKFYESVSQKTYRDWETINTALEIHYNNILPGNG<br>KSKADKVKKAVKNDLQKSITEINELVSNYKLCPDDNIKAETYIHEISHILNNFE<br>AQELKYNPEIHLVESELKASELKNVLDVIMNAFHWCSVFMTEELVDKDNNFYAE<br>LEEIYDEIYTVISLYNLVRNYVTQKPYSTKKIKLNFGIPTLADGWSKSKEYSNN<br>AIILMRDNLYYLGIFNAKNKPDKKIIEGNTSENKGDYKKMIYNLLPGPNKMIPK<br>VFLSSSKTGVETYKPSAYILEGYKQNKHLKSSKDFDITFCHDLIDYFKNCIAIHP<br>EWKNFGFDFSDTSTYEDISGFYREVELQGYKIDWTYISEKDIDLLQEKGQLYLF<br>QIYNKDFSKKSTGNDNLHTMYLKNLFSEENLKDIVLKLNGEAEIFFRKSSIKNP<br>IIHKKGSILVNRTYEAEEKDQFGNIQIVRKTIPENIYQELYKYFNDKSDKELSD<br>EAAKLKNVVGHHEAATNIVKDYRYTDKYFLHMPITINFKANKTSFINDRILQY<br>IAKEKNLHVIGIDRGERNLIYVSVIDTCGNIVEQKSFNIVNGYDYQIKLKQQEG<br>ARQIARQEWKEIGKIKEIKEGYLSLVIHEISKMVIKYNAIIAMEDLSYGFKKGR<br>FKVERQVYQKFETMLINKLNYLVFKDISITENGGLLKGYQLTYIPDKLKNVGHQ<br>CGCIFYVPAAYTSKIDPTTGFVNIFKFKDLTVDAKREFIKKFDSIRYDSEKKLF<br>CFIFDYNNFITQNTVMSKSSWSVYTYGVRIKRRFVNGRFSNESDTIDITKDMEK<br>TLEMTDINWRDGHDLRQDIIDYEIVQHIFEIFRLTVQMRNSLSELEDRDYDRLI<br>SPVLNENNIFYDSAKAGDALPKDADANGAYCIALKGLYEIKQITENWKEDGKFS<br>RDKLKISNKDWFDFIQNKRYL |
| SEQ ID NO: 6 | MGKNQNFQEFIGVSPLQKTLRNELIPTETTKKNITQLDLLTEDEIRAQNREKLK<br>EMMDDYYRNVIDSTLHVGIAVDWSYLFSCMRNHLRENSKESKRELERTQDSIRS<br>QIHNKFAERADFKDMFGASIITKLLPTYIKQNSEYSERYDESMEILKLYGKFTT<br>SLTDYFETRKNIFSKEKISSAVGYRIVEENAEIFLQNQNAYDRICKIAGLDLHG<br>LDNEITAYVDGKTLKEVCSDEGFAKAITQEGIDRYNEAIGAVNQYMNLLCQKNK<br>ALKPGQFKMKRLHKQILCKGTISFDIPKKFENDKQVYDAVNSFTEIVTKNNDLK<br>RLLNITQNANDYDMNKIYVVADAYSMISQFISKKWNLIEECLLDYYSDNLPGKG<br>NAKENKVKKAVKEETYRSVSQLNEVIEKYYVEKTGQSVWKVESYISSLAEMIKL<br>ELCHEIDNDEKHNLIEDDEKISEIKELLDMYMDVFHIIKVFRVNEVLNFDETFY<br>SEMDEIYQDMQEIVPLYNHVRNYVTQKPYKQEKYRLYFHTPTLANGWSKSKEYD<br>NNAIILVREDKYYLGILNAKKKPSKEIMAGKEDCSEHAYAKMNYYLLPGANKML<br>PKVFLSKKGIQDYHPSSYIVEGYNEKKHIKGSKNFDIRFCRDLIDYFKECIKKH<br>PDWNKFNFEFSATETYEDISVFYREVEKQGYRVEWTYINSEDIQKLEEDGQLFL<br>FQIYNKDFAVGSTGKPNLHTLYLKNLFSEENLRDIVLKLNGEAEIFFRKSSVQK<br>PVIHKCGSILVNRTYEITESGTTRVQSIPESEYMELYRYFNSEKQIELSDEAKK<br>YLDKVQCNKAKTDIVKDYRYTMDKFFIHLPITINFKVDKGNNVNAIAQQYIAGR<br>KDLHVIGIDRGERNLIYVSVIDMYGRILEQKSFNLVEQVSSQGTKRYYDYKEKL<br>QNREEERDKARQSWKTIGKIKELKEGYLSSVIHEIAQMVVKYNAIIAMEDLNYG<br>FKRGRFKVERQVYQKFETMLISKLNYLADKSQAVDEPGGILRGYQMTYVPDNIK<br>NVGRQCGIIFYVPAAYTSKIDPTTGFINAFKRDVVSTNDAKENFLMKFDSIQYD<br>IEKGLFKFSFDYKNFATHKLTLAKTKWDVYTNGTRIQNMKVEGHWLSMEVELTT<br>KMKELLDDSHIPYEEGQNILDDLREMKDITTIVNGILEIFWLTVQLRNSRIDNP<br>DYDRIISPVLNKNGEFFDSDEYNSYIDAQKAPLPIDADANGAFCIALKGMYTAN<br>QIKENWVEGEKLPADCLKIEHASWLAFMQGERG |
| SEQ ID NO: 7 | ATGAACAATGGCACCAACAATTTCCAGAACTTTATCGGAATTAGCAGTCTGCAA<br>AAGACTCTCCGGAATGCCCTTATACCCACCGAGACAACCCAGCAGTTCATCGTG<br>AAAAACGGGATTATCAAGGAAGACGAGCTGCGCGGCGAAAATCGGCAAATTTTG<br>AAAGATATAATGGACGATTATTACCGCGGTTTTATCTCTGAGACTCTGAGCTCC<br>ATTGACGATATCGACTGGACCTCACTCTTCGAAAAGATGGAGATTCAGCTTAAA |

TABLE 1-continued

Exemplary Cas12a Sequences

| SEQ ID NO | Sequence |
|---|---|
| | AACGGCGATAATAAGGACACACTGATAAAAGAACAGGCTGAGAAGCGGAAAGCC<br>ATCTATAAGAAATTTGCAGATGACGATCGCTTCAAGAACATGTTTAGCGCCAAA<br>TTGATTAGTGACATCCTGCCGGAATTCGTTATTCACAATAACAATTACTCTGCT<br>AGCGAGAAGGAAGAGAAAACCCAAGTCATAAAGCTCTTTTCCCGGTTCGCCACT<br>TCATTTAAAGATTATTTCAAGAACCGCGCAAATTGCTTTAGCGCCGACGATATC<br>AGTTCTAGCTCCTGTCATCGGATTGTGAACGACAATGCTGAAATCTTCTTTTCA<br>AACGCCCTTGTATACCGCCGGATTGTGAAAAATCTGAGCAACGATGACATAAAT<br>AAGATCAGTGGAGATATTAAAGACTCTTTGAAGGAGATGAGCCTGGAAGAGATC<br>TATTCCTACGAAAAATATGGGGAGTTCATTACCCAGGAAGGCATATCATTTTAC<br>AACGATATCTGCGGTAAGGTTAATAGCTTCATGAACCTCTATTGTCAGAAAAAT<br>AAGGAGAACAAAATCTTTACAAGCTGCGCAAATTGCACAAGCAAATTCTGTGC<br>ATCGCAGACACAAGTTATGAAGTCCCTTACAAATTTGAGTCTGATGAAGAGGTG<br>TATCAGAGCGTAAACGGCTTCCTCGACAATATTTCCTCAAAGCATATAGTGGAA<br>CGGCTTCGCAAAATCGGAGATAACTACAATGGGTATAACCTGGACAAGATTTAC<br>ATCGTTAGCAAATTTTATGAGAGTGTCTCTCAGAAGACCTACCGGGATTGGGAA<br>ACTATTAATACCGCCTTGGAGATACACTATAACAATATCCTGCCCGGCAACGGT<br>AAAAGCAAGGCTGACAAAGTGAAGAAAGCCGTAAAGAATGATCTCCAAAAATCC<br>ATTACAGAAATCAACGAGCTTGTGTCAAATTACAAGCTGTGTCCGGACGATAAC<br>ATTAAAGCAGAAACCTATATACATGAGATCAGCCACATTTTGAATAACTTCGAA<br>GCCCAGGAGCTGAAGTACAATCCAGAAATCCATCTCGTTGAGAGTGAACTTAAA<br>GCTTCTGAGCTGAAGAACGTCTTGGACGTGATTATGAATGCCTTTCACTGGTGC<br>AGCGTATTCATGACTGAAGAGCTGGTGGATAAAGACAACAATTTTTATGCAGAA<br>CTCGAGGAAATATACGATGAGATCTATACCGTTATTTCCCTTTACAACCTGGTC<br>CGCAATTATGTGACACAGAAGCCCTACTCAACCAAAAAGATCAAATTGAACTTC<br>GGCATTCCGACTCTGGCCGACGGATGGAGCAAGAGTAAAGAATATTCTAATAAC<br>GCTATAATCCTCATGCGGGATAATCTTTACTATCTGGGGATTTTTAACGCCAAG<br>AATAAACCTGACAAGAAAATCATTGAGGGCAACACCAGCGAAAATAAGGGTGAT<br>TACAAAAAGATGATATATAACTTGCTGCCCGGCCCGAATAAAATGATCCCAAAG<br>GTATTCCTCTCCTCAAAAACAGGAGTGGAGACCTACAAGCCCAGCGCATATATT<br>CTTGAAGGGTACAAACAAAACAAGCATCTGAAAAGTTCTAAGGACTTTGATATC<br>ACTTTCTGTCACGACTTGATTGATTATTTTAAAAATTGCATAGCCATCCATCCG<br>GAGTGGAAGAACTTCGGCTTTGACTTCAGCGATACCTCCACATACGAAGACATT<br>TCAGGTTTTTATCGCGAGGTTGAACTGCAGGGCTACAAAATCGATTGGACCTAT<br>ATTAGCGAGAAGGACATAGATCTCCTTCAGGAAAAAGGACAACTGTACTTGTTC<br>CAGATCTATAATAAGGACTTTAGTAAAAAGTCTACTGGGAACGATAATCTGCAC<br>ACCATGTACCTCAAAAACCTTTTCAGCGAGGAAAATCTGAAGGACATTGTCTTG<br>AAACTGAACGGCGAGGCTGAAATCTTTTTCCGGAAGTCCTCAATTAAAAATCCT<br>ATAATCCATAAGAAAGGTAGCATTCTCGTGAACCGCACATATGAGGCCGAAGAG<br>AAGGATCAGTTTGGCAATATCCAAATTGTACGGAAAACCATACCCGAAAACATC<br>TACCAGGAGCTTTATAAGTACTTCAATGACAAAGTGATAAGGAACTGTCTGAC<br>GAGGCAGCCAAATTGAAGAACGTGGTTGGACACCATGAAGCTGCCACTAATATT<br>GTCAAAGATTATCGCTACACCTATGACAAGTACTTTCTGCACATGCCGATCACA<br>ATTAACTTCAAAGCAAATAAGACCAGCTTTATAAACGATCGGATTCTCCAGTAT<br>ATTGCCAAAGAGAAGAATCTTCATGTGATCGGGATTGACCGCGGCGAACGGAAC<br>CTGATATACGTATCCGTGATCGATACTTGTGGTAATATTGTTGAGCAAAAATCA<br>TTCAACATCGTCAATGGCTATGACTACCAGATTAAGTTGAAACAGCAAGAAGGA<br>GCTCGCCAGATAGCCCGGCAGGAGTGGAAGGAAATCGGGAAAATTAAGGAGATC<br>AAAGAAGGCTATCTGAGCCTCGTGATTCACGAGATAAGTAAGATGGTAATCAAA<br>TACAACGCAATTATCGCCATGGAAGATCTTTCTTATGGTTTTAAGAAAGGCCGC<br>TTCAAGGTGGAGCGGCAAGTTTACCAGAAATTTGAAACCATGCTGATTAATAAG<br>TTGAACTATCTGGTCTTCAAAGACATAAGCATCACAGAGAATGGAGGGCTCCTT<br>AAGGGCTACCAGCTGACCTATATTCCAGATAAATTGAAGAACGTGGGTCATCAA<br>TGCGGCTGTATCTTTTACGTACCCGCTGCCTATACTTCCAAAATTGACCCGACC<br>ACAGGATTCGTGAATATATTTAAGTTCAAAGATCTGACCGTTGACGCAAAGCGC<br>GAATTTATCAAAAAGTTCGATTCAATTCGGTACGACAGCGAGAAAAAGCTCTTT<br>TGCTTCACTTTTGATTATAACAATTTCATCACCCAGAACACAGTCATGAGTAAA<br>TCTAGCTGGTCCGTGTACACCTATGGGGTACGCATTAAGCGGCGCTTTGTGAAT<br>GGCCGGTTCTCAAACGAAAGCGACACTATAGATATCACCAAAGACATGGAGAAG<br>ACACTTGAAATGACCGATATTAATTGGCGCGACGGTCACGATCTGCGGCAGGAC<br>ATCATTGATTACGAGATAGTTCAACATATCTTTGAAATTTTCCGCTTGACTGTC<br>CAGATGCGGAACAGTCTGTCTGAGCTCGAAGACCGCGATTATGACCGGCTTATC<br>AGCCCTGTGCTGAATGAGAACAATATTTTTACGATTCCGCCAAAGCTGGCGAC<br>GCCTTGCCCAAGGATGCAGACGCCAACGGAGCTTATTGTATAGCCCTGAAAGGG<br>CTCTACGAAATCAAGCAGATTACCGAGAATTGGAAAGAAGATGGCAAGTTCTCA<br>CGCGACAAACTTAAGATCAGCAACAAAGATTGGTTTGACTTCATTCAAAATAAG<br>CGGTATCTG |
| SEQ ID NO: 8 | ATGGGCAAAAACCAAAATTTCCAAGAATTTATCGGAGTGAGCCCCCTGCAGAAG<br>ACCCTCCGGAACGAGCTTATTCCGACTGAGACCACAAAGAAAAATATAACCCAG<br>CTGGACTTGCTGACTGAAGATGAGATCCGCGCCCAGAACCGGGAAAAGCTCAAA<br>GAGATGATGGACGATTATTACCGCAATGTTATTGACAGTACCCTTCACGTCGGG<br>ATCGCTGTGGATTGGTCTTATCTGTTCAGCTGCATGCGGAACCATTTGCGCGAA<br>AATTCCAAGGAGTCAAAACGGGAACTGGAGCGCACACAGGACAGCATTCGGAGT<br>CAGATACACAACAAGTTTGCCGAACGCGCAGATTTCAAAGACATGTTTGGCGCC<br>TCTATCATTACCAAGCTCCTTCCTACTTACATCAAACAAAATAGCGAGTATTCC<br>GAACGGTACGATGAGTCAATGGAAATTCTGAAGTTGTATGGTAAATTCACCACA |

TABLE 1-continued

Exemplary Cas12a Sequences

| SEQ ID NO | Sequence |
|---|---|
| | AGCCTGACCGACTACTTTGAGACTCGCAAGAACATATTCAGTAAAGAAAAGATC<br>TCTAGCGCTGTAGGCTATCGGATTGTGGAGGAAAATGCCGAGATCTTTCTCCAG<br>AACCAGAATGCATACGATCGCATTTGTAAAATAGCCGGACTTGACCTGCATGGG<br>TTGGATAACGAAATCACCGCTTATGTTGACGGCAAGACACTGAAAGAGGTCTGC<br>TCCGATGAAGGTTTCGCCAAGGCAATTACCCAAGAGGGCATCGACCGGTACAAT<br>GAAGCCATTGGAGCTGTGAACCAGTATATGAATCTCCTTTGTCAGAAAAACAAG<br>GCCCTGAAACCCGGGCAATTTAAGATGAAACGCTTGCACAAGCAGATACTGTGC<br>AAAGGCACTACCTCATTCGATATCCCGAAGAAATTTGAGAATGACAAGCAGGTA<br>TACGATGCAGTGAACAGCTTCACAGAAATTGTTACCAAAAATAACGACCTCAAG<br>CGGCTTCTGAATATCACTCAAAACGCCAATGATTATGACATGAACAAAATTTAC<br>GTCGTGGCTGATGCCTATAGTATGATATCTCAGTTTATCAGCAAGAAATGGAAT<br>TTGATTGAGGAATGTCTGCTCGACTACTATTCCGATAACCTTCCAGGTAAGGGC<br>AATGCAAAAGAGAACAAGGTAAAAAAGGCCGTGAAAGAAGAGACCTACCGCTCA<br>GTTAGCCAGCTGAATGAAGTCATCGAGAAGTATTACGTGGAAAAAACAGGACAA<br>AGTGTATGGAAGGTGGAGTCTTATATTAGCTCCTTGGCTGAAATGATAAAACTG<br>GAGCTCTGCCATGAAATCGACAACGATGAGAAGCACAATCTTATTGAAGACGAT<br>GAGAAAATCTCAGAAATTAAGGAGCTGTTGGACATGTACATGGATGTTTTCCAT<br>ATAATCAAAGTCTTTCGGGTGAACGAAGTACTGAATTTCGACGAGACCTTTTAT<br>AGCGAAATGGATGAGATTTACCAGGACATGCAGGAAATCGTGCCCCTCTATAAC<br>CACGTTCGCAATTACGTCACTCAAAAGCCGTATAAACAGGAGAAGTACCGGCTT<br>TATTTCCATACCCCTACACTGGCCAACGGGTGGAGTAAATCTAAGGAATACGAT<br>AATAACGCAATTATATTGGTGCGCGAGGACAAATATTACCTGGGCATCCTCAAT<br>GCCAAGAAAAAGCCCAGCAAAGAAATTATGGCTGGTAAGGAGGATTGTTCCGAA<br>CACGCCTATGCAAAAATGAACTACTATCTTCTGCCGGGCGCCAATAAGATGTTG<br>CCAAAAGTATTTCTGTCAAAGAAAGGAATCCAGGACTACCATCCCAGCAGTTAT<br>ATTGTGGAGGGGTACAACGAAAAGAAACACATAAAGGGCTCTAAAAATTTCGAT<br>ATCCGGTTTTGCCGCGACCTCATTGATTATTTCAAGGAGTGTATCAAAAAGCAT<br>CCGGACTGGAACAAATTTAATTTCGAATTTAGCGCTACCGAGACTTACGAAGAT<br>ATTTCCGTTTTCTATCGGGAGGTCGAAAAGCAAGGTTACCGCGTGGAGTGGACC<br>TATATAAACTCAGAAGACATCCAGAAACTTGAGGAAGATGGCCAGCTGTTTTTG<br>TTCCAAATTTACAATAAGGACTTTGCCGTAGGAAGCACAGGGAAACCTAACCTG<br>CACACCCTCTATCTTAAGAATCTGTTCAGTGAGGAAAACTTGCGGGATATCGTG<br>CTGAAACTCAATGGCGAGGCAGAAATTTTTTTCCGCAAGTCTAGCGTTCAGAAA<br>CCCGTCATACATAAGTGCGGTTCCATCCTTGTGAACCGGACTTACGAGATTACC<br>GAATCAGGCACAACCCGCGTACAGAGCATCCCGGAGAGTGAATATATGGAGCTG<br>TACCGGTATTTTAATTCTGAAAAACAAATTGAGTTGAGCGACGAAGCCAAGAAA<br>TACCTGGATAAGGTGCAGTGTAACAAAGCTAAGACTGACATAGTTAAAGATTAT<br>CGCTACACCATGGACAAGTTCTTTATCCACCTCCCAATTACAATCAATTTCAAA<br>GTCGATAAGGGAAACAATGTGAACGCCATTGCACAGCAATATATAGCCGGGCGG<br>AAAGACCTTCATGTAATCGGCATTGATCGCGGTGAGCGGAATCTGATCTACGTG<br>TCCGTTATTGACATGTATGGCCGCATATTGGAACAGAAGTCATTTAACCTGGTC<br>GAGCAGGTGAGCAGTCAAGGAACCAAACGGTACTATGATTACAAGGAAAAACTC<br>CAGAATCGCGAGGAAGAGCGGGACAAGGCTCGCCAGTCTTGGAAAACTATCGGG<br>AAGATTAAAGAACTTAAGGAGGGCTATCTGAGCTCCGTAATCCACGAAATTGCC<br>CAAATGGTGGTTAAATACAACGCAATAATCGCCATGGAGGATTTGAATTATGGT<br>TTCAAGCGGGGCCGCTTTAAAGTCGAACGGCAGGTGTACCAGAAGTTCGAGACC<br>ATGCTGATTTCAAAACTCAACTATCTTGCTGACAAGAGCCAAGCCGTAGATGAA<br>CCCGGAGGGATTCTGCGCGGCTACCAGATGACATATGTGCCGGACAATATTAAA<br>AACGTTGGTCGGCAGTGCGGCATAATCTTTTACGTCCCTGCAGCCTATACCAGT<br>AAGATTGATCCCACTACCGGATTCATCAATGCTTTTAAACGCGACGTGGTATCT<br>ACAAACGATGCCAAGGAGAATTTCTTGATGAAATTTGACAGCATTCAATACGAT<br>ATAGAAAAGGGGCTGTTCAAATTTTCCTTCGACTATAAGAACTTTGCAACCCAT<br>AAACTCACTCTTGCCAAGACCAAATGGGATGTGTACACAAATGGCACCCGGATT<br>CAGAACATGAAGGTTGAGGGTCACTGGCTGTCAATGGAAGTCGAGTTGACTACC<br>AAAATGAAGGAACTGCTCGACGATAGCCATATTCCGTATGAGGAAGGCCAGAAT<br>ATCCTTGACGATCTGCGCGAGATGAAAGACATTACAACCATAGTGAACGGAATC<br>TTGGAAATTTTCTGGCTGACTGTACAACTCCGGAATAGTCGCATCGATAACCCA<br>GACTACGATCGGATTATATCTCCCGTGCTTAATAAGAACGGGGAGTTTTTCGAC<br>AGCGATGAATATAATTCCTACATCGACGCTCAGAAAGCCCCGCTGCCTATTGAT<br>GCAGACGCCAACGGCGCTTTTTGTATCGCCTTGAAGGGTATGTATACCGCAAAT<br>CAGATTAAGAGAACTGGGTTGAAGGCGAGAAGCTGCCCGCCGATTGCCTCAAA<br>ATAGAACACGCTTCATGGCTTGCCTTCATGCAAGGAGAGCGCGGG |

A Cas12a (e.g., SEQ ID NO: 1 or SEQ ID NO: 3 or any sequence related thereto as disclosed herein) protein of the present disclosure comprises one or more of the following stretches of amino acid residues: LTPTETT (SEQ TD NO: 12), MIJDYYR (SEQ TD NO: 13), NAEIF (SEQ TD NO: 14), CQKNK((SEQ TD NO: 15), LHIKQTLC (SEQ TD NO: 16), KVKKAVK (SEQ TD NO: 17), VRNYVTQKPY (SEQ ID NO: 18), GWSKSKEY (SEQ TD NO: 19), DLIDYFK (SEQ TD NO: 20), DIVLKLNGEAEIFFRKSS (SEQ TD NO: 21), GSILVNRTYE (SEQ TD NO: 22), ELSDEA (SEQ TD NO: 23), IVKDYRYT (SEQ TD NO: 24), LHVIGIDRGERNLIYVSVID (SEQ TD NO: 25), KYNAIIAMEDL (SEQ ID NO: 26), GRFKVERQVYQKFETMLI (SEQ ID NO: 27), IFYVPAAYTSKIDPTTGF (SEQ TD NO: 28), or ISPVLN (SEQ ID NO: 29).

The present disclosure also provides a method of improving the cleaving efficiency of a type V CRISPR-associated protein, wherein the method comprises providing a type V CRISPR-associated protein, identifying a residue at a critical position, such as position 925 of SEQ TD NO: 1 or position 930 of SEQ TD NO: 3, and mutating the residue at the critical position to a Lysine, thereby improving cleaving efficiency of the endonuclease.

The metagenomically mined Cas12a proteins of the present disclosure (e.g., mgCas12a-1 or mgCas12a-2) exhibit superior editing efficiency as compared to other Cas12a orthologs (e.g., AsCas12a, FnCas12a, or LbCas12a). For example, in some cases, the metagenomically mined Cas12a proteins of the present disclosure exhibit at least 1.5 fold, at least 2 fold, at least 5 fold, at least 10 fold, at least 15 fold, at least 20 fold, at least 25 fold, at least 30 fold, at least 35 fold, at least 40 fold, at least 45 fold, at least 50 fold, at least 60 fold, at least 70 fold, at least 80 fold, at least 90 fold, at least 100 fold, at least 150 fold, at least 200 fold, at least 250 fold, at least 300 fold, at least 350 fold, at least 400 fold, at least 450 fold, at least 500 fold, at least 600 fold, at least 700 fold, at least 800 fold, at least 900 fold, at least 1000 fold, at least 2000 fold, from 1.5 to 5 fold, from 5 to 10 fold, from 10 to 15 fold, from 15 to 20 fold, from 20 to 25 fold, from 25 to 30 fold, from 30 to 35 fold, from 35 to 40 fold, from 40 to 45 fold, from 45 to 50 fold, from 50 to 60 fold, from 60 to 70 fold, from 70 to 80 fold, from 80 to 90 fold, from 90 to 100 fold, from 100 to 150 fold, from 150 to 200 fold, from 200 to 250 fold, from 250 to 300 fold, from 300 to 350 fold, from 350 to 400 fold, from 400 to 450 fold, from 450 to 500 fold, from 500 to 600 fold, from 600 to 700 fold, from 700 to 800 fold, from 800 to 900 fold, from 900 to 1000 fold, from 1000 to 2000 fold, from 1.5 to 2000 fold, from 1.5 to 20 fold, from 5 to 10 fold, from 10 to 40 fold, from 20 to 40 fold, from 5 to 15 fold, from 5 to 100 fold, from 50 to 80 fold, from 2 to 4 fold, from 4 to 8 fold, from 8 to 10 fold, or from 10 to 14 fold more efficient genome editing than other Cas12a orthologs, such as FnCas12a, AsCas12, and/or LbCas12a. Editing efficiency can be measured by any known methods of quantification, such as measuring percent indels or amplicon targeted deep sequencing.

Figure 24:
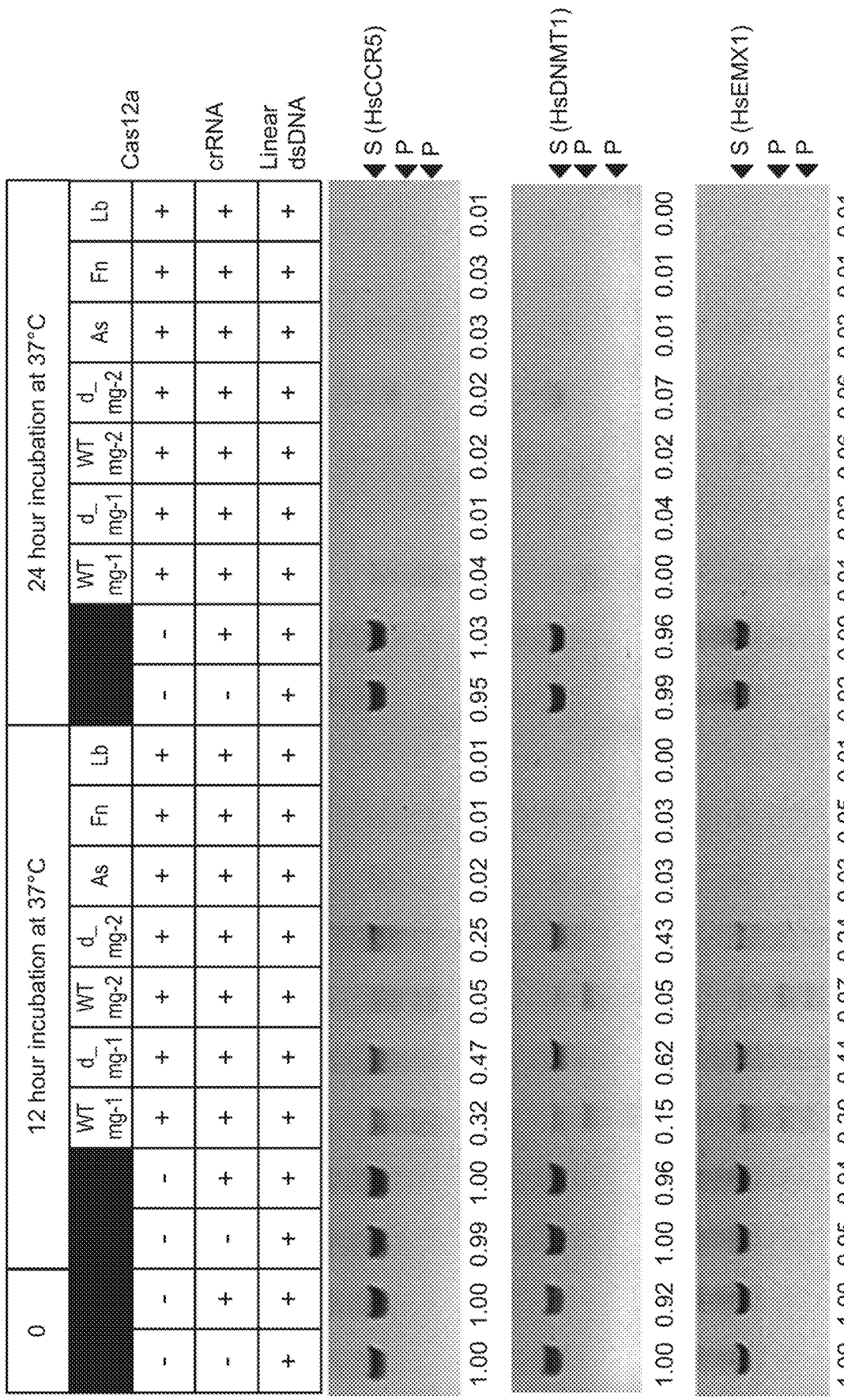
FIG. 24 shows that some Cas12a-RNPs exhibits uncontrolled dsDNase activity. Seven different Cas12a-RNPs were incubated with target dsDNA for 12 or 24 hours.
Figure 25A:
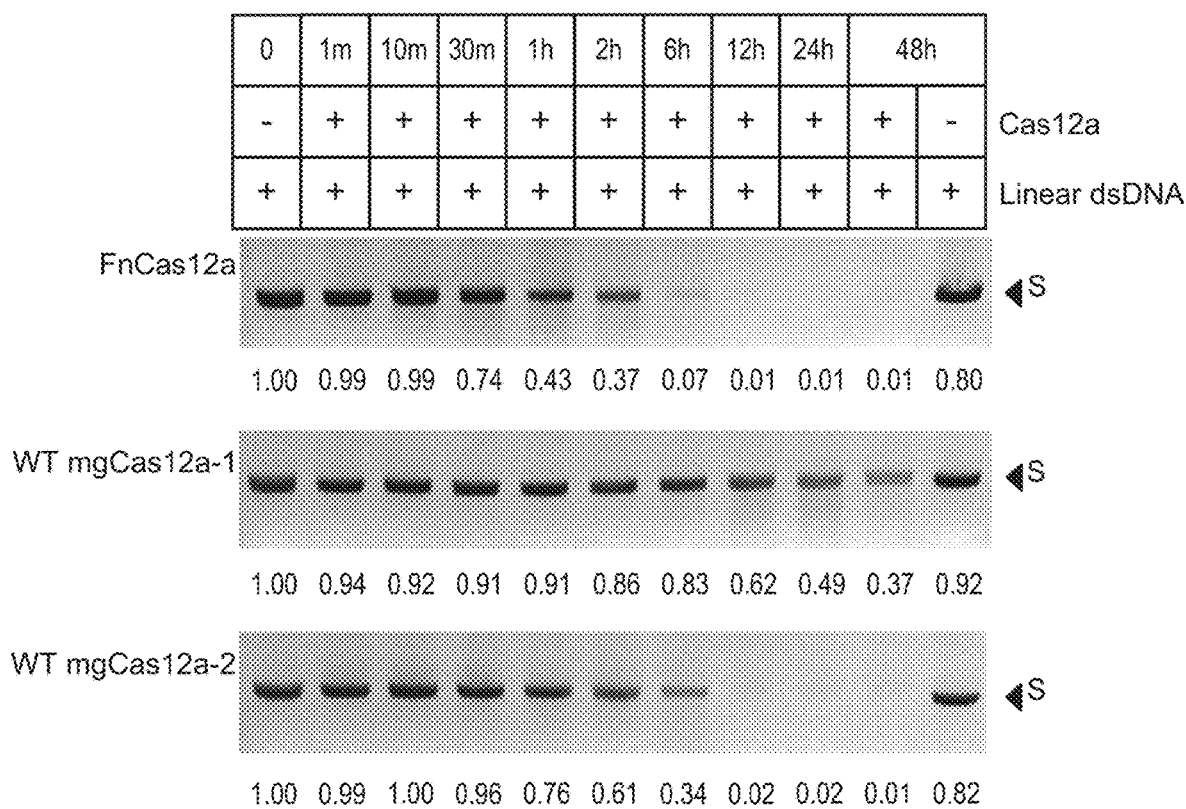
FIGS. 25A-25B show that Cas12a exhibits random dsDNase activity.
Figure 25B:
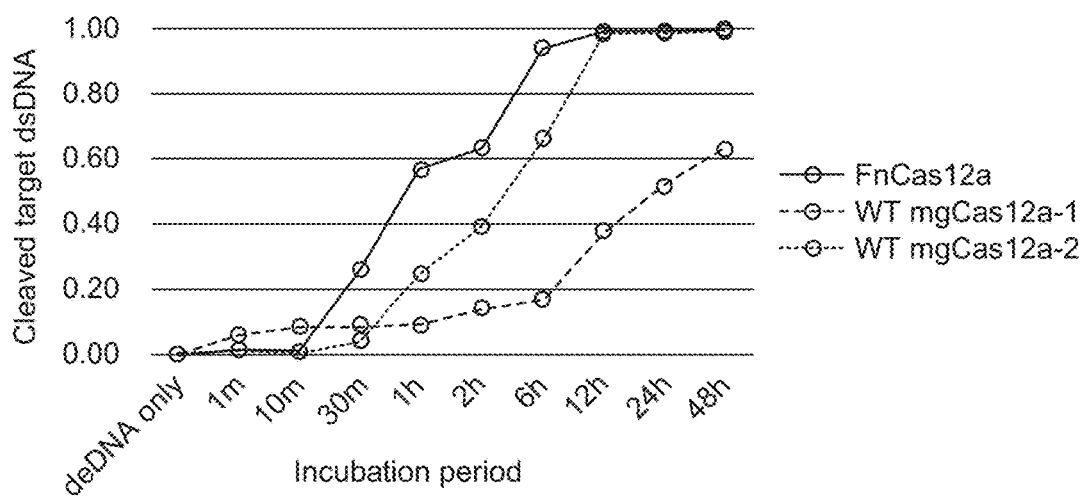

It is contemplated that metagenomically mined Cas12a proteins of the present disclosure can exhibit low random DNase activity, at least similar random DNase activity to other Cas12a orthologs, or even lower random DNase activity than other Cas12a orthologs, depending on the reaction conditions, while also achieving higher editing efficiency than other Cas12a orthologs or while maintaining comparable editing efficiency to other Cas12a orthologs. For example, as shown in FIG. 24, and FIG. 25A, dsDNA substrate and cleaved product were almost entirely degraded, potentially due to random DNase activity of certain Cas12a orthologs (e.g., FnCas12a, LbCas12a) after incubation of the reaction for 12 hours and 24 hours, while both substrate and cleaved products were detected in the 12 hour reaction with metagenomically mined Cas12a proteins of the present disclosure (WT mg-1 and WT mg-2). FIG. 25B shows a graph of time versus dsDNase activity of each Cas12a, demonstrating that the target substrate dsDNA remains at later time points for mgCas12a-1, indicating lower random DNase activity of the mgCas12a-1.

In some embodiments, metagenomically mined Cas12a proteins (e.g., mgCas12a-1 or mgCas12a-2) of the present disclosure display cleavage activity in the presence of a wide range of divalent cations. For example, metagenomically mined Cas12a proteins (e.g., mgCas12a-1 or mgCas12a-2) of the present disclosure display can display cleavage activity in the presence of $CaCl_2$, $CoCl_2$, $FeCl_2$, $MnSO_4$, or any combination thereof.

TABLE 2 below shows sequences of other Cas12a proteins including Acidaminococcus sp. Cas12a (AsCas12a) as set forth in SEQ TD NO: 9, Lachnospiraceae sp. (LbCas12a) as set forth in SEQ ID NO: 10, and *Francisella tularensis* subsp. *novicidia* (FnCas12a) as set forth in SEQ TD NO: 11.

TABLE 2

Additional Cas12a Proteins

| SEQ ID NO | Sequence |
| --- | --- |
| SEQ ID NO: 9 | MTQFEGFTNLYQVSKTLRFELIPQGKTLKHIQEQGFIEEDKARNDHYKELKPI<br>IDRIYKTYADQCLQLVQLDWENLSAAIDSYRKEKTEETRNALIEEQATYRNAI<br>HDYFIGRTDNLTDAINKRHAEIYKGLFKAELFNGKVLKQLGTVTTTEHENALL<br>RSFDKFTTYFSGFYENRKNVFSAEDISTAIPHRIVQDNFPKFKENCHIFTRLI<br>TAVPSLREHFENVKKAIGIFVSTSIEEVFSFPFYNQLLTQTQIDLYNQLLGGI<br>SREAGTEKIKGLNEVLNLAIQKNDETAHIIASLPHRFIPLFKQILSDRNTLSF<br>ILEEFKSDEEVIQSFCKYKTLLRNENVLETAEALFNELNSIDLTHIFISHKKL<br>ETISSALCDHWDTLRNALYERRISELTGKITKSAKEKVQRSLKHEDINLQEII<br>SAAGKELSEAFKQKTSEILSHAHAALDQPLPTTLKKQEEKEILKSQLDSLLGL<br>YHLLDWFAVDESNEVDPEFSARLTGIKLEMEPSLSFYNKARNYATKKPYSVEK<br>FKLNFQMPTLASGWDVNKEKNNGAILFVKNGLYYLGIMPKQKGRYKALSFEPT<br>EKTSEGFDKMYYDYFPDAAKMIPKCSTQLKAVTAHFQTHTTPILLSNNFIEPL<br>EITKEIYDLNNPEKEPKKFQTAYAKKTGDQKGYREALCKWIDFTRDFLSKYTK<br>TTSIDLSSLRPSSQYKDLGEYYAELNPLLYHISFQRIAEKEIMDAVETGKLYL<br>FQIYNKDFAKGHHGKPNLHTLYWTGLFSPENLAKTSIKLNGQAELFYRPKSRM<br>KRMAHRLGEKMLNKKLKDQKTPIPDTLYQELYDYVNHRLSHDLSDEARALLPN<br>VITKEVSHEIIKDRRFTSDKFFFHVPITLNYQAANSPSKFNQRVNAYLKEHPE<br>TPIIGIDRGERNLIYITVIDSTGKILEQRSLNTIQQFDYQKKLDNREKERVAA<br>RQAWSVVGTIKDLKQGYLSQVIHEIVDLMIHYQAVVVLENLNFGFKSKRTGIA<br>EKAVYQQFEKMLIDKLNCLVLKDYPAEKVGGVLNPYQLTDQFTSFAKMGTQSG<br>FLFYVPAPYTSKIDPLTGFVDPFVWKTIKNHESRKHFLEGFDFLHYDVKTGDF<br>ILHFKMNRNLSFQRGLPGFMPAWDIVFEKNETQFDAKGTPFIAGKRIVPVIEN<br>HRFTGRYRDLYPANELIALLEEKGIVFRDGSNILPKLLENDDSHAIDTMVALI<br>RSVLQMRNSNAATGEDYINSPVRDLNGVCFDSRFQNPEWPMDADANGAYHIAL<br>KGQLLLNHLKESKDLKLQNGISNQDWLAYIQELRN |
| SEQ ID NO: 10 | AASKLEKFTNCYSLSKTLRFKAIPVGKTQENIDNKRLLVEDEKRAEDYKGVKK<br>LLDRYYLSFINDVLHSIKLKNLNNYISLFRKKTRTEKENKELENLEINLRKEI<br>AKAFKGAAGYKSLFKKDIIETILPEAADDKDEIALVNSFNGFTTAFTGFFDNR<br>ENXFSEEAKSTSIAFRCINENLTRYISNXDIFEKVDAIFDKHEVQEIKEKILN<br>SDYDVEDFFEGEFFNFVLTQEGIDVYNAIIGGFVTESGEKIKGLNEYINLYNA |

TABLE 2-continued

Additional Cas12a Proteins

| SEQ ID NO | Sequence |
|---|---|
| | KTKQALPKFKPLYKQVLSDRESLSFYGEGYTSDEEVLEVFRNTLNKNSEIFSS<br>IKKLEKLFKNFDEYSSAGIFVKNGPAISTISKDIFGEWNLIRDKWNAEYDDIH<br>LKKKAVVTEKYEDDRRKSFKKIGSFSLEQLQEYADADLSVVEKLKEIIIQKVD<br>EIYKVYGSSEKLFDADFVLEKSLKKNDAVVAIXKDLLDSVKSFENYIKAFFGE<br>GKETNRDESFYGDFVLAYDILLKVDHIYDAIRNYVTQKPYSKDKFKLYFQNPQ<br>FXGGWDKDKETDYRATILRYGSKYYLAIXDKKYAKCLQKIDKDDVNGNYEKIN<br>YKLLPGPNKXLPKVFFSKKWXAYYNPSEDIQKIYKNGTFKKGDXFNLNDCHKL<br>IDFFKDSISRYPKWSNAYDFNFSETEKYKDIAGFYREVEEQGYKVSFESASKK<br>EVDKLVEEGKLYXFQIYNKDFSDKSHGTPNLHTXYFKLLFDENNHGQIRLSGG<br>AELFXRRASLKKEELVVHPANSPIANKNPDNPKKTTTLSYDVYKDKRFSEDQY<br>ELHIPIAINKCPKNIFKINTEVRVLLKHDDNPYVIGIDRGERNLLYIVVVDGK<br>GNIVEQYSLNEIINNFNGIRIKTDYHSLLDKKEKERFEARQNWTSIENIKELK<br>AGYISQVVHKICELVEKYDAVIALEDLNSGFKNSRVKVEKQVYQKFEKXLIDK<br>LNYXVDKKSNPCATGGALKGYQITNKFESFKSXSTQNGFIFYIPAWLTSKIDP<br>STGFVNLLKTKYTSIADSKKFISSFDRIXYVPEEDLFEFALDYKNFSRTDADY<br>IKKWKLYSYGNRIRIFAAAKKNNVFAWEEVCLTSAYKELFNKYGINYQQGDIR<br>ALLCEQSDKAFYSSFXALXSLXLQXRNSITGRTDVDFLISPVKNSDGIFYDSR<br>NYEAQENAILPKNADANGAYNIARKVLWAIGQFKKAEDEKLDKVKIAISNKEW<br>LEYAQTSVK |
| SEQ ID NO: 11 | MSIYQEFVNKYSLSKTLRFELIPQGKTLENIKARGLILDDEKRAKDYKKAKQI<br>IDKYHQPFIEEILSSVCISEDLLQNYSDVYFKLKKSDDDNLQKDFKSAKDTIK<br>KQISEYIKDSEKFKNLFNQNLIDAKKGQESDLILWLKQSKDNGIELFKANSDI<br>TDIDEALEIIKSFKGWTTYFKGFHENRKNVYSSNDIPTSIIYRIVDDNLPKFL<br>ENKAKYESLKDKAPEAINYEQIKKDLAEELTFDIDYKTSEVNQRVFSLDEVFE<br>IANFNNYLNQSGITKFNTIIGGKFVNGENTKRKGINEYINLYSQQINDKTLKK<br>YKMSVLFKQILSDTESKSFVIDKLEDDSDVVTTMQSFYEQIAAFKTVEEKSIK<br>ETLSLLFDDLKAQKLDLSKIYFKNDKSLTDLSQQVFDDYSVIGTAVLEYITQQ<br>IAPKNLDNPSKKEQELIAKKTEKAKYLSLETIKLALEEFNKHRDIDKQCRFEE<br>ILANFAAIPMIFDEIAQNKDNLAQISIKYQNQGKKDLLQASAEDDVKAIKDLL<br>DQTNNLLHKLKIFHISQSEDKANILDKDEHFYLVFEECYFELANIVPLYNKIR<br>NYITQKPYSDEKFKLNFENSTLANGWDKNKEPDNTAILFIKDDKYYLGVMNKK<br>NNKIFDDKAIKENKGEGYKKIVYKLLPGANKMLPKVFFSAKSIKFYNPSEDIL<br>RIRNHSTHTKNGSPQKGYEKFEFNIEDCRKFIDFYKQSISKHPEWKDFGFRFS<br>DTQRYNSIDEFYREVENQGYKLTFENISESYIDSVVNQGKLYLFQIYNKDFSA<br>YSKGRPNLHTLYWKALFDERNLQDVVYKLNGEAELFYRKQSIPKKITHPAKEA<br>IANKNKDNPKKESVFEYDLIKDKRFTEDKFFFHCPITINFKSSGANKFNDEIN<br>LLLKEKANDVHILSIDRGERHLAYYTLVDGKGNIIKQDTFNIIGNDRMKTNYH<br>DKLAAIEKDRDSARKDWKKINNIKEMKEGYLSQVVHEIAKLVIEYNAIVVFED<br>LNFGFKRGRFKVEKQVYQKLEKMLIEKLNYLVFKDNEFDKTGGVLRAYQLTAP<br>FETFKKMGKQTGIIYYVPAGFTSKICPVTGFVNQLYPKYESVSKSQEFFSKFD<br>KICYNLDKGYFEFSFDYKNFGDKAAKGKWTIASFGSRLINFRNSDKNHNWDTR<br>EVYPTKELEKLLKDYSIEYGHGECIKAAICGESDKKFFAKLTSVLNTILQMRN<br>SKTGTELDYLISPVADVNGNFFDSRQAPKNMPQDADANGAYHIGLKGLMLLGR<br>IKNNQEGKKLNLVIKNEEYFEFVQNRNN |

Purification Tags

In some embodiments, the it is contemplated that the Cas12a proteins of the present disclosure forms a heterologous proteins, fused N-terminally or C-terminally to a purification tag. A Cas12a protein of the present disclosure (e.g., SEQ ID NO: 1 or SEQ ID NO: 3 or any sequence related thereto as disclosed herein) includes a purification tag incorporated at its N-terminus or C-terminus. A purification tag is incorporated at the N-terminus or C-terminus of a Cas12a protein of the present disclosure to provide a recombinant polypeptide that are easily purified. Said purification tags, thus, facilitate purification of the Cas12a proteins.

For example, a Cas12 protein of the present disclosure (e.g., SEQ ID NO: 1 or SEQ ID NO: 3 or any sequence related thereto as disclosed herein) has a His-tag, such as a 6×His (SEQ ID NO: 63) or a poly-His-tag. Said His-tags are capable of binding to several metal ions such as nickel, cobalt, and copper. Thus, a His-tagged Cas12a protein of the present disclosure (e.g., SEQ ID NO: 1 or SEQ ID NO: 3 or any sequence related thereto as disclosed herein) is rapidly purified using metal affinity chromatography. Alternatively, the present disclosure provides a Cas12a protein (e.g., SEQ ID NO: 1 or SEQ ID NO: 3 or any sequence related thereto as disclosed herein) having a FLAG®-tag, which comprises the FLAG® peptide having a sequence of DYKDDDDK (SEQ ID NO: 30). Said FLAG®-tags is recognized by an anti-FLAG® antibody. Thus, a FLAG®-tagged Cas12a protein of the present disclosure (e.g., SEQ ID NO: 1 or SEQ ID NO: 3 or any sequence related thereto as disclosed herein) is rapidly purified using affinity chromatography.

A Cas12a protein of the present disclosure (e.g., SEQ ID NO: 1 or SEQ ID NO: 3 or any sequence related thereto as disclosed herein) has a purification tag selected from the group consisting of a His tag, a FLAG tag, an AU1 epitope tag, an AU5 epitope tag, a bacteriophage T7 tag, a bacteriophage V5 epitope tag, a Bluetongue virus tag (B-tag), a Glu-Glu tag (EE-tag), an HSV epitope tag, a KT3 epitope tag, a Myc epitope tag, a PDZ ligand tag, a polyarginine tag, a polyaspartate tag, a polycysteine tag, a polyphenylalanine tag, a protein C tag, an S1-tag, an S-tag, a Step-tag, and a VSV-G tag.

Guide RNA for Cas12a Endonucleases

Cas12a endonucleases of the present disclosure (e.g., SEQ ID NO: 1 or SEQ ID NO: 3 or any sequence related thereto as disclosed herein) is coupled to a crRNA sequence, which guides the Cas12a endonuclease to a nucleic acid sequence of interest. Thus, the crRNA is also referred to as guide RNA, or gRNA for short. The crRNA sequence is reverse complementary to a nucleic acid sequence of interest, for example, a eukaryotic nucleic acid sequence. Eukaryotic nucleic acid sequence can be a human nucleic acid sequence or a plant nucleic acid sequence. In other words, the crRNA targets Cas12a endonucleases described herein to a region of interest in the genome. Specifically, crRNAs are designed to be reverse complementary to a nucleic acid sequence that exists solely in cancer cells, and not in normal cells. In some cases, the nucleic acid sequence existing solely in cancer cells, may only have a one base difference from a nucleic acid sequence existing in normal cells. In some cases, the nucleic acid sequence existing solely in cancer cells may comprise a portion of a gene or may comprise a gene, which has been partially substituted or loss. For example, a nucleic acid sequence that exists solely in cancer cells may be a nucleic acid sequence in cancer cells comprising a single nucleotide polymorphism (SNP). A guide RNA having a reverse complementary sequence to a nucleic acid sequence existing solely in cancer cells bind said nucleic acid sequence and will not bind to off-target nucleic acid sequences or nucleic acid sequences not in cancer cells.

The guide RNA, also referred to as the crRNA sequence, used to guide a Cas12a endonuclease of the present disclosure is from 10 to 60 nucleotides long, from 10 to 15 nucleotides long, from 15 to 20 nucleotides long, from 20 to 25 nucleotides long, from 25 to 30 nucleotides long, from 30 to 35 nucleotides long, from 35 to 40 nucleotides long, from 40 to 45 nucleotides long, from 45 to 50 nucleotides long, from 50 to 55 nucleotides long, from 55 to 60 nucleotides long, from 1 to 100 nucleotide long, from 1 to 200 nucleotides long, from 1 to 200 nucleotides long, from 1 to 300 nucleotides long, from 1 to 50 nucleotides long, from 50 to 100 nucleotides long, from 100 to 150 nucleotides long, from 150 to 200 nucleotides long, from 200 to 250 nucleotides long, from 250 to 300 nucleotides long, from 300 to 350 nucleotides long, from 350 to 400 nucleotides long, from 400 to 450 nucleotides long, or from 450 to 500 nucleotides long. The crRNA sequence used to guide a Cas12a endonuclease of the present disclosure is about 10 nucleotides in length, about 15 nucleotides in length, about 20 nucleotides in length, about 25 nucleotides in length, about 30 nucleotides in length, about 35 nucleotides in length, about 40 nucleotides in length, about 45 nucleotides in length, about 50 nucleotides in length, about 55 nucleotides in length, about 60 nucleotides in length, about 65 nucleotides long, about 70 nucleotides long, about 75 nucleotides long, about 80 nucleotides long, about 85 nucleotides long, about 90 nucleotides long, about 95 nucleotides long, about 100 nucleotides long, about 150 nucleotides long, about 200 nucleotides long, about 250 nucleotides long, about 300 nucleotides long, about 350 nucleotides long, about 400 nucleotides long, about 450 nucleotides long, or about 500 nucleotides long. The crRNA sequence used to guide a Cas12a endonuclease of the present disclosure is about 42 nucleotides in length.

The metagenomically mined Cas12a proteins of the present disclosure possess flexible and superior properties due to their ability to maintain cleavage activity when complexed with crRNAs having 5' repeat recognition sequences (the nucleotides upstream of the step-loop region of the crRNA) of AsCas12a, FnCas12a, and/or LbCas12a. For example, a Cas12a protein of the present disclosure (e.g., mgCas12a-1 or mgCas12a-2) can be complexed with a crRNA having a 5'handle of crRNA complexed to AsCas12a, FnCas12a, and/or LbCas12a, and still retain cleavage activity of target nucleic acids.

Delivery of CRISPR/Cas Systems

It is further contemplated that Cas12a and the guide RNA can form a CRISPR/Cas complex, and such formed complex can be delivered to the target cell via various methods. One exemplary method includes plasmids or viral vectors comprising a nucleic acid encoding the endonuclease and guide RNA. Exemplary viral vector-based delivery methods include lentiviral-based delivery or adeno-associated virus (AAV)-based delivery. Alternatively, CRISPR/Cas complex disclosed herein can be delivered using ribonucleoproteins (RNPs) for delivery of the intact protein assembled to the gRNA. Intact proteins assembled to the gRNA are then delivered directly to cells.

Applications

A CRISPR/Cas complex, or CRISPR/Cas12a endonuclease complex (or CRISPR/Cas12a complex), described herein is used to edit the genome of a nucleic acid sequence. The nucleic acid sequence is a mammalian nucleic acid sequence. For example, the nucleic acid sequence is a human nucleic acid sequence. The nucleic acid sequence is also a non-human nucleic acid sequence. The nucleic acid sequence is from any animal. For genome editing, the crRNA, also referred to as the guide RNA (gRNA), is reverse complementary to a nucleic acid sequence of interest. For example, the crRNA is reverse complementary to a human nucleic acid sequence.

For example, a CRISPR/Cas12a complex can be used for genome editing of a nucleic acid sequence in a cancer cell, which comprises cancer-specific sequences (e.g., single nucleotide polymorphisms (SNPs) or cancer specific mutations) identified by sequence analysis of genomes of various cell tissues. crRNA sequences are synthesized that are reverse complementary to these nucleic acid sequences, which exist uniquely in cancer cells. CRISPR/Cas12a complexes can be generated using the crRNA reverse-complementary to the cancer-specific sequence, and administered to a subject having a cancer in a dose and schedule effective to treat the tumor cells as a customized therapy.

The cancer that can be treated with the CRISPR/Cas complexes of the present disclosure can include bladder cancer, bone cancer, blood cancer, breast cancer, black colored tumor, thyroid cancer, parathyroid cancer, bone marrow cancer, rectal cancer, laryngopharyngeal cancer, laryngeal cancer, lung cancer, esophagus cancer, pancreatic cancer, colorectal cancer, gastric cancer, tongue cancer, skin cancer, brain tumor, uterine cancer, head or neck cancer, gallbladder cancer, oral cancer, colon cancer, cancer around the anus area, central nervous system tumor, liver cancer, or colorectal cancer. In particular instances, the cancer comprises gastric cancer, colorectal cancer, liver cancer, lung cancer, or breast cancer. As such, the cancer cell includes a bladder cancer cell, a bone cancer cell, a blood cancer cell, a breast cancer cell, a black colored tumor cell, a thyroid cancer cell, a parathyroid cancer cell, a bone marrow cancer cell, a laryngopharyngeal cancer cell, a laryngeal cancer cell, a lung cancer cell, an esophagus cancer cell, a pancreatic cancer cell, a colorectal cancer cell, a gastric cancer cell, a tongue cancer cell, a skin cancer cell, a brain tumor cell, a uterine cancer cell, a head or neck cancer cell, a gallbladder cancer cell, an oral cancer cell, a central nervous system tumor cell, or a liver cancer cell.

Alternatively, and/or additionally, a nucleic acid sequence targeted by the RNA-guided nucleases of the present disclosure include regions in genes of KRAS, BRCA1, HER2/neu, PD-1, TCR, p53, CCR5, DNMT1, EMX1, and LKB1.

For example, CRISPR/Cas12a complexes of the present disclosure include crRNAs designed to be reverse complementary to exon 10 or exon 11 of BRCA1, which is implicated in ovarian cancer and breast cancer. Two or more gRNAs that target exon 11 of BRCA1 are used in a CRISPR/Cas12a complex of the present disclosure. Thus, combinations of gRNA are selected based on the purpose of the cancer treatment or the type of cancer.

Disclosed herein are also methods of using the RNA-guided Cas12a endonuclease of the present disclosure for treating, curing, or ameliorating a symptom of cancer or the cancer itself. For example, said method includes identifying a subject in need thereof having a symptom of cancer and administering a CRISPR/Cas12a complex disclosed herein. Several cancer indications are consistent with the compositions disclosed herein. The present disclosure provides a Cas12a protein that is used in a CRISPR/Cas12a complex for genome editing of a nucleic acid sequence in a cancer cell. For example, a Cas12a protein of the present disclosure (e.g., SEQ ID NO: 1 or SEQ ID NO: 3 or any sequence related thereto as disclosed herein) is used in a CRISPR/Cas12a complex for genome editing of a target nucleic acid sequence in cancer cell from a cancer such as acute lymphoblastic leukemia (ALL), acute myeloid leukemia (AML), adolescents, cancer in, adrenocortical carcinoma, childhood adrenocortical carcinoma, aids-related cancers, kaposi sarcoma (soft tissue sarcoma), aids-related lymphoma (lymphoma), primary cns lymphoma (lymphoma), anal cancer, appendix cancer, astrocytomas, childhood (brain cancer), atypical teratoid/rhabdoid tumor, childhood, central nervous system (brain cancer), basal cell carcinoma of the skin, bile duct cancer, bladder cancer, childhood bladder cancer, bone cancer (includes ewing sarcoma and osteosarcoma and malignant fibrous histiocytoma), brain tumors, breast cancer, childhood breast cancer, bronchial tumors, childhood, burkitt lymphoma, carcinoid tumor (gastrointestinal), childhood carcinoid tumors, carcinoma of unknown primary, childhood carcinoma of unknown primary, cardiac (heart) tumors, childhood, central nervous system, atypical teratoid/rhabdoid tumor, childhood (brain cancer), embryonal tumors, childhood (brain cancer), germ cell tumor, childhood (brain cancer), primary cns lymphoma, cervical cancer, childhood cervical cancer, childhood cancers, cancers of childhood, unusual, cholangiocarcinoma, chordoma, childhood, chronic lymphocytic leukemia (CLL), chronic myelogenous leukemia (CML), chronic myeloproliferative neoplasms, colorectal cancer, childhood colorectal cancer, craniopharyngioma, childhood (brain cancer), cutaneous t-cell lymphoma, ductal carcinoma in situ (DCIS), embryonal tumors, central nervous system, childhood (brain cancer), endometrial cancer (uterine cancer), ependymoma, childhood (brain cancer), esophageal cancer, childhood esophageal cancer, esthesioneuroblastoma (head and neck cancer), ewing sarcoma (bone cancer), extracranial germ cell tumor, childhood, extragonadal germ cell tumor, eye cancer, childhood intraocular melanoma, intraocular melanoma, retinoblastoma, fallopian tube cancer, fibrous histiocytoma of bone, malignant, and osteosarcoma, gallbladder cancer, gastric (stomach) cancer, childhood gastric (stomach) cancer, gastrointestinal carcinoid tumor, gastrointestinal stromal tumors (GIST) (soft tissue sarcoma), childhood gastrointestinal stromal tumors, germ cell tumors, childhood central nervous system germ cell tumors (brain cancer), childhood extracranial germ cell tumors, extragonadal germ cell tumors, ovarian germ cell tumors, testicular cancer, gestational trophoblastic disease, hairy cell leukemia, head and neck cancer, heart tumors, childhood, hepatocellular (liver) cancer, histiocytosis, langerhans cell, hodgkin lymphoma, hypopharyngeal cancer (head and neck cancer), intraocular melanoma, childhood intraocular melanoma, islet cell tumors, pancreatic neuroendocrine tumors, kaposi sarcoma (soft tissue sarcoma), kidney (renal cell) cancer, langerhans cell histiocytosis, laryngeal cancer (head and neck cancer), leukemia, lip and oral cavity cancer (head and neck cancer), liver cancer, lung cancer (non-small cell and small cell), childhood lung cancer, lymphoma, male breast cancer, malignant fibrous histiocytoma of bone and osteosarcoma, melanoma, childhood melanoma, melanoma, intraocular (eye), childhood intraocular melanoma, merkel cell carcinoma (skin cancer), mesothelioma, malignant, childhood mesothelioma, metastatic cancer, metastatic squamous neck cancer with occult primary (head and neck cancer), midline tract carcinoma with nut gene changes, mouth cancer (head and neck cancer), multiple endocrine neoplasia syndromes, multiple myeloma/plasma cell neoplasms, mycosis fungoides (lymphoma), myelodysplastic syndromes, myelodysplastic/myeloproliferative neoplasms, myelogenous leukemia, chronic (CML), myeloid leukemia, acute (AML), myeloproliferative neoplasms, chronic, nasal cavity and paranasal sinus cancer (head and neck cancer), nasopharyngeal cancer (head and neck cancer), neuroblastoma, non-hodgkin lymphoma, non-small cell lung cancer, oral cancer, lip and oral cavity cancer and oropharyngeal cancer (head and neck cancer), osteosarcoma and malignant fibrous histiocytoma of bone, ovarian cancer, childhood ovarian cancer, pancreatic cancer, childhood pancreatic cancer, pancreatic neuroendocrine tumors (islet cell tumors), papillomatosis (childhood laryngeal), paraganglioma, childhood paraganglioma, paranasal sinus and nasal cavity cancer (head and neck cancer), parathyroid cancer, penile cancer, pharyngeal cancer (head and neck cancer), pheochromocytoma, childhood pheochromocytoma, pituitary tumor, plasma cell neoplasm/multiple myeloma, pleuropulmonary blastoma, pregnancy and breast cancer, primary central nervous system (CNS) lymphoma, primary peritoneal cancer, prostate cancer, rectal cancer, recurrent cancer, renal cell (kidney) cancer, retinoblastoma, rhabdomyosarcoma, childhood (soft tissue sarcoma), salivary gland cancer (head and neck cancer), sarcoma, childhood rhabdomyosarcoma (soft tissue sarcoma), childhood vascular tumors (soft tissue sarcoma), ewing sarcoma (bone cancer), kaposi sarcoma (soft tissue sarcoma), osteosarcoma (bone cancer), soft tissue sarcoma, uterine sarcoma, sezary syndrome (lymphoma), skin cancer, childhood skin cancer, small cell lung cancer, small intestine cancer, soft tissue sarcoma, squamous cell carcinoma of the skin—, squamous neck cancer with occult primary, metastatic (head and neck cancer), stomach (gastric) cancer, childhood stomach (gastric) cancer, t-cell lymphoma, cutaneous, testicular cancer, childhood testicular cancer, throat cancer (head and neck cancer), nasopharyngeal cancer, oropharyngeal cancer, hypopharyngeal cancer, thymoma and thymic carcinoma, thyroid cancer, transitional cell cancer of the renal pelvis and ureter (kidney (renal cell) cancer), childhood cancer of unknown primary, unusual cancers of childhood, ureter and renal pelvis, transitional cell cancer (kidney (renal cell) cancer, urethral cancer, uterine cancer, endometrial, uterine sarcoma, vaginal cancer, childhood vaginal cancer, vascular tumors (soft tissue sarcoma), vulvar cancer, wilms tumor, other childhood kidney tumors, or any combination thereof.

The present disclosure additionally provides a method of genome editing comprising the steps of contacting a cell with a CRISPR/Cas12a described herein, allowing the guide RNA to bind to the human nucleic acid sequence of interest, and cleaving the human nucleic acid sequence. CRISPR/Cas12a endonucleases described herein are administered to a plurality of cells ex vivo, thereby allows for the generation of engineered cells. Said engineered cells are administered as a cell therapy to a subject in need thereof, wherein the subject is a human and has any of the above described cancers. CRISPR/Cas12a endonucleases described herein are directly administered to a subject in need thereof. Direct administration comprises intravenous administration, subcutaneous administration, intramuscular administration, oral administration, or mucosal administration.

In other cases, the crRNA is reverse complementary to a plant nucleic acid sequence. For example, a Cas12a protein of the present disclosure is used in a CRIPSR/Cas12a complex for genome editing of a nucleic acid sequence in a plant cell. Non-limiting examples of plant cells of interest include rice and N. benthamiana.

The present disclosure additionally provides a method of improving the cleaving efficiency of a type V CRISPR-associated protein. For example, the methods provided herein include identifying a residue at a position corresponding to residue 925 or residue 930 of a type V CRISPR-associated protein and mutating these residues to Lysine, Either the mutation to Lysine at residue 925, the mutation to Lysine at residue 930, or both, can improve the cleaving efficiency of the type V CRISPR-associated protein. Lysines at residues corresponding to 925 or 930 of a type V CRISPR-associated protein (e.g., SEQ ID NO: 1 or SEQ ID NO: 3) disclosed herein are critical for maintaining function. Thus, Lysines (Lys) may be introduced into a type V CRISPR-associated protein at residues corresponding these positions to improve the function of a type V CRISPR-associated protein that doesn't have a Lysine at positions corresponding to residues 925 or 930.

Turning to the figures, one sees the following. FIG. 1 shows the process by which a CRISPR associated protein (CAS protein) of the present disclosure was identified by metagenomic mining. CRISPRI sequences are found using metaCRT and gene prediction is carried out using Prodigal. Cas12a candidate proteins are identified using local BLASTp of Cas12a sequences from Uniprot and Genbank. Next, sequences of 800 amino acids to 1500 amino acids are identified. Cas 12a candidates beside Cas1 are identified, where Cas1 candidates are identified from local BLASTp analysis of Cas1 sequences from Uniprot. Phylogenies were built using MEGA7 and sequences were annotated with web BLASTp. Putative Cas12a proteins were identified.

Figure 2:
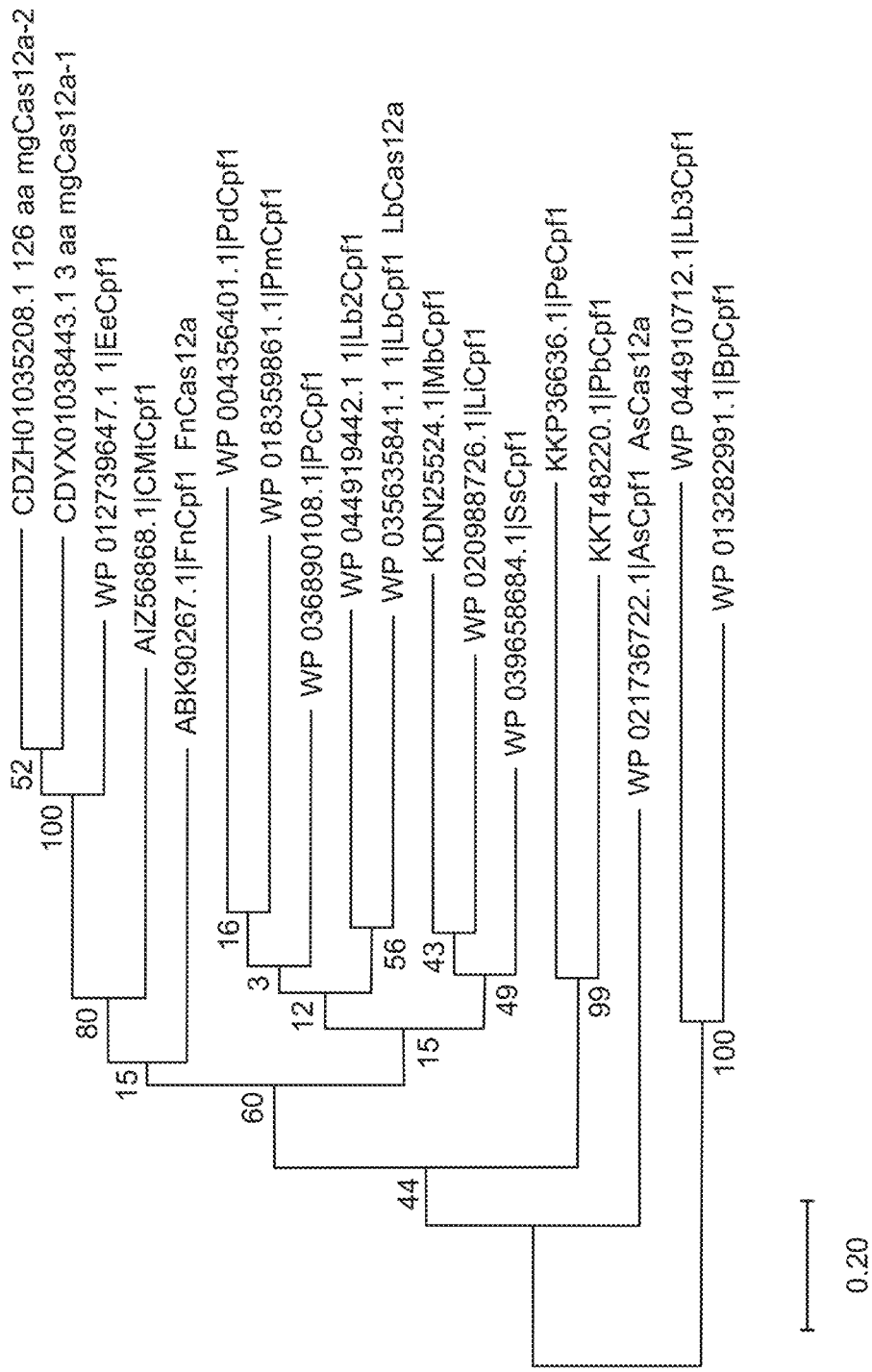
Figure 3:
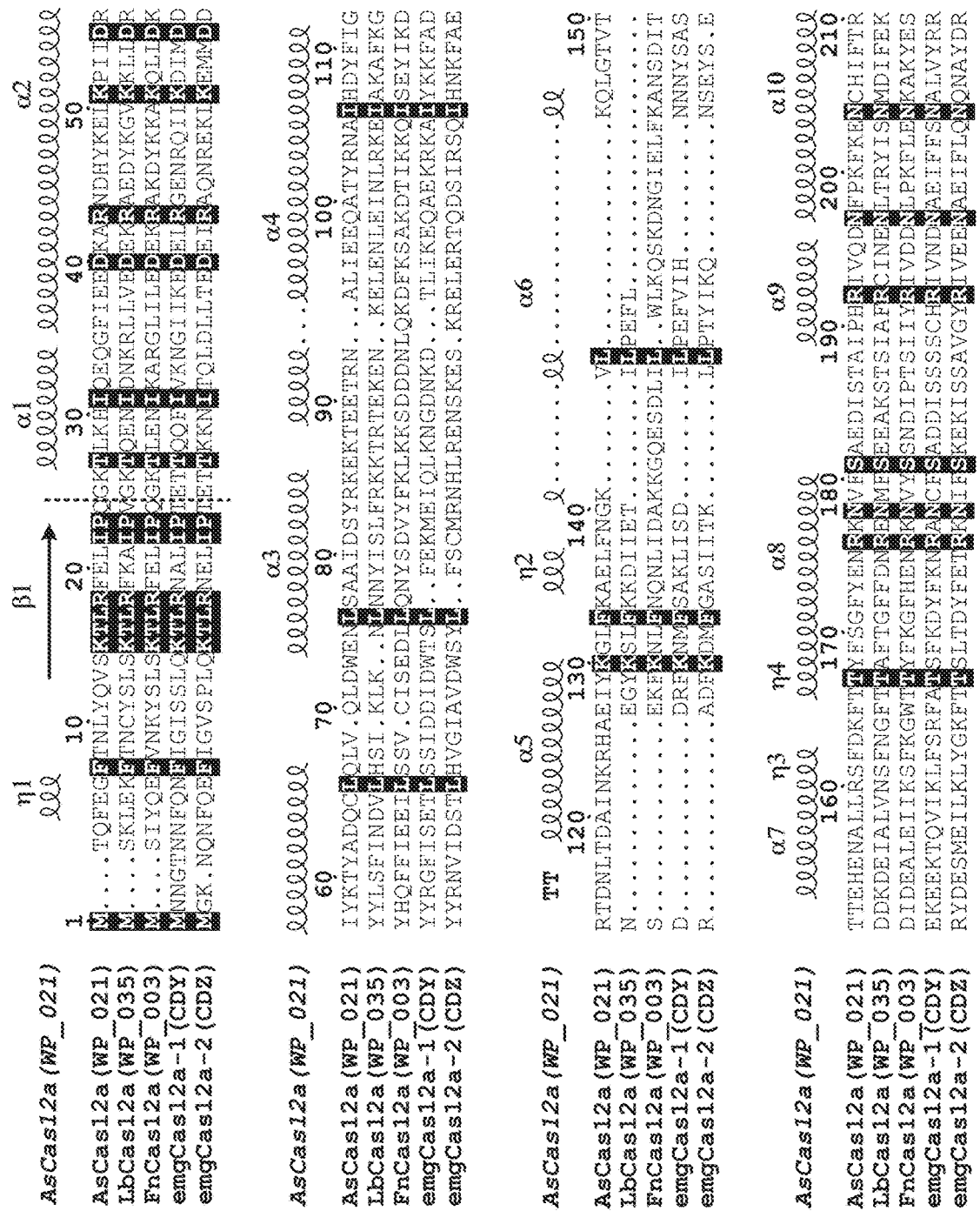
FIG. 3 shows an alignment of Cas12a proteins of the present disclosure, including SEQ ID NO: 1 (mgCas12a-1), SEQ ID NO: 3 (mgCas12a-2), SEQ ID NO: 9 (AsCas12a), SEQ ID NO: 67 (LbCas12a), and SEQ ID NO: 11 (FnCas12a).
Figure 5:
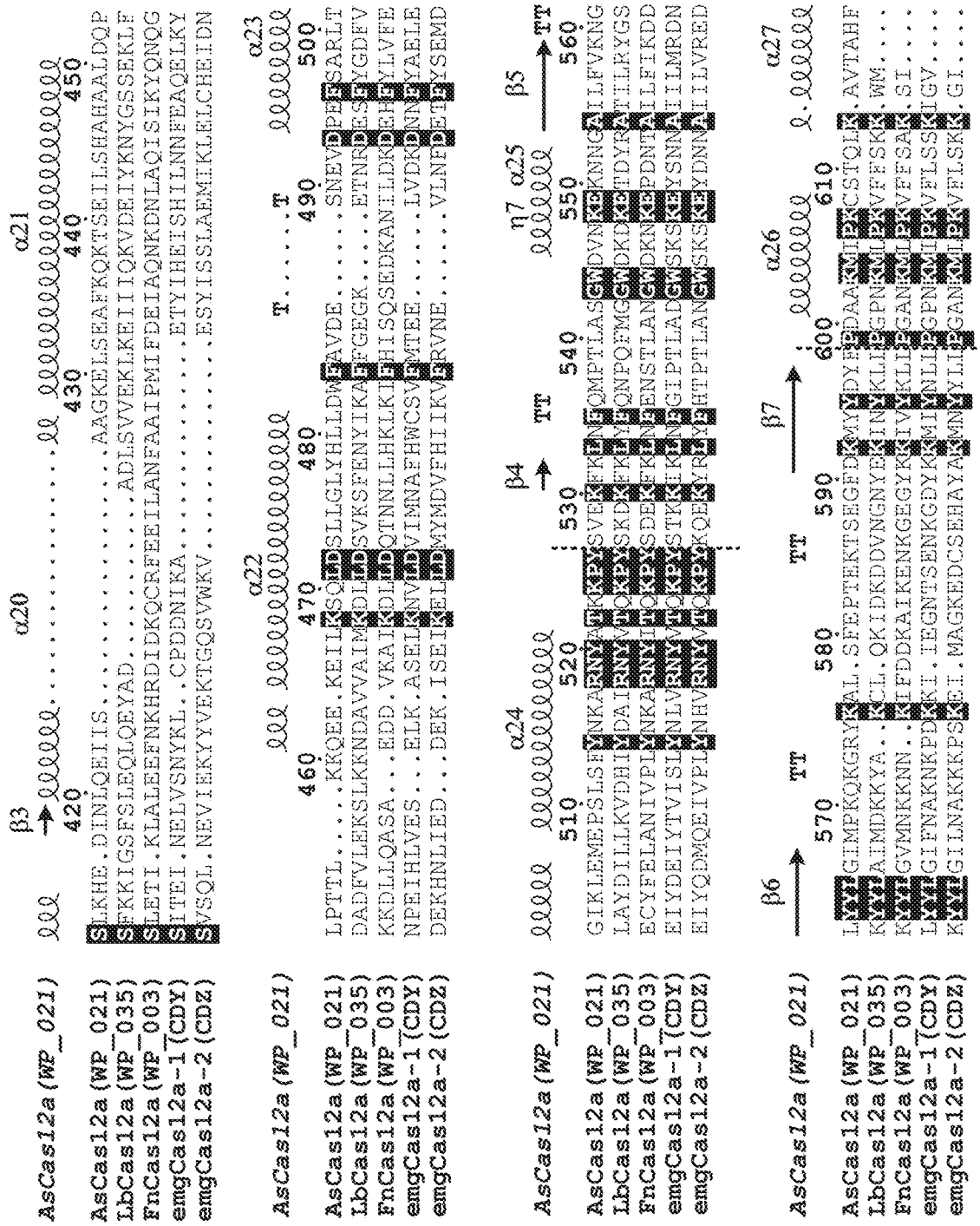
FIG. 5 shows a continuation of the alignment of Cas12a proteins of the present disclosure, including SEQ ID NO: 1 (mgCas12a-1), SEQ ID NO: 3 (mgCas12a-2), SEQ ID NO: 9 (AsCas12a), SEQ ID NO: 67 (LbCas12a), and SEQ ID NO: 11 (FnCas12a) from FIG. 4.
Figure 6:
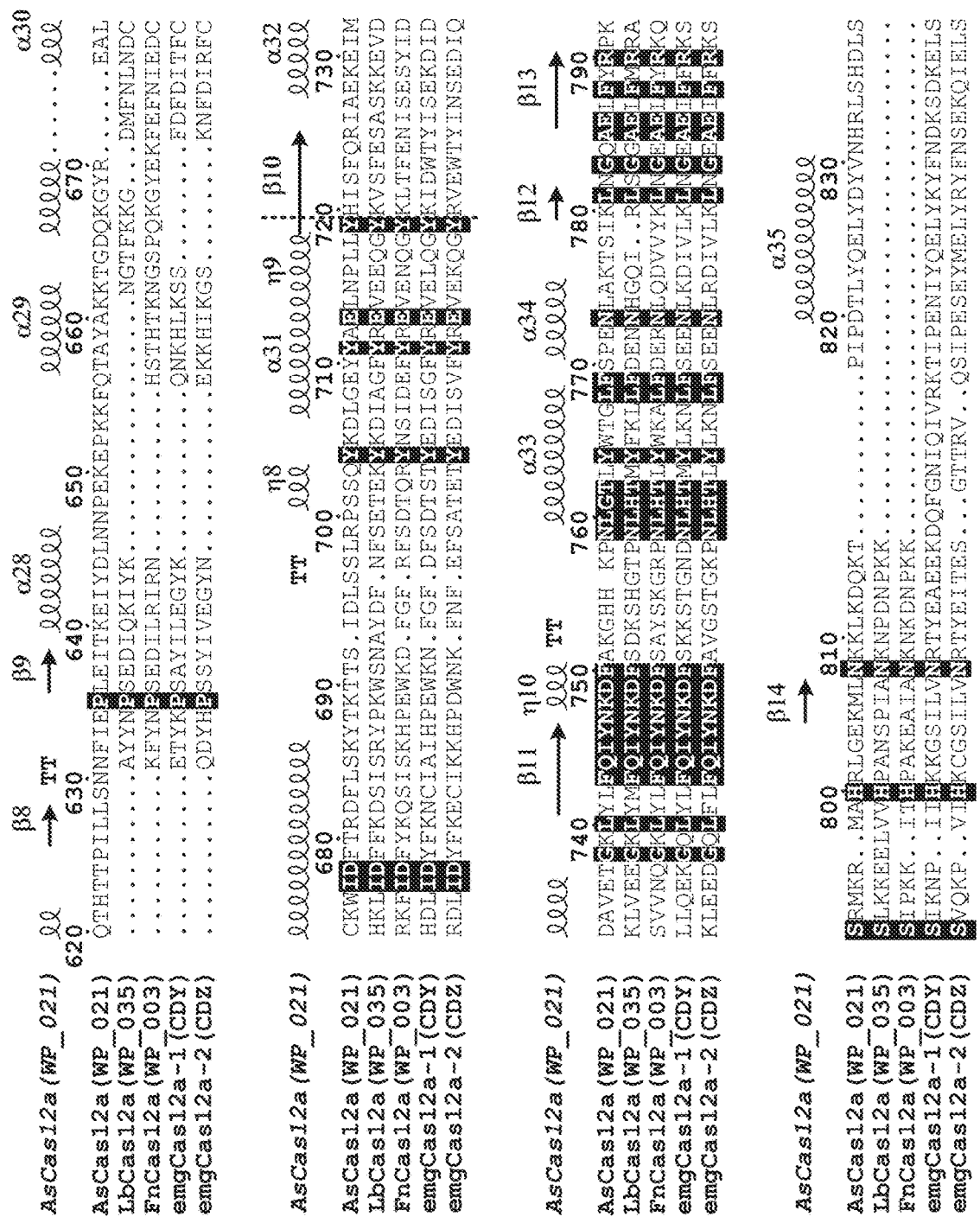
FIG. 6 shows a continuation of the alignment of Cas12a proteins of the present disclosure, including SEQ ID NO: 1 (mgCas12a-1), SEQ ID NO: 3 (mgCas12a-2), SEQ ID NO: 9 (AsCas12a), SEQ ID NO: 67 (LbCas12a), and SEQ ID NO: 11 (FnCas12a) from FIG. 5.

FIG. 2 is a cladogram in which SEQ ID NO: 3 (mg Cas12a-2) and SEQ ID NO: 1 (mgCas12a-1) resolve at the top from FnCas12a, which is related to LbCas12a, both of which are related to AsCas12a. FIG. 2 additionally shows the relationship between many Cas12a proteins. The methods of metagenomics mining disclosed herein are, thus, capable of identifying the relationship between Cas12a proteins and excavating new Cas12a proteins. FIG. 2 additionally shows bootstrap values. mGCas12a-2 and mgCas12a-1 showed a bootstrap value of 52.

Figure 7:
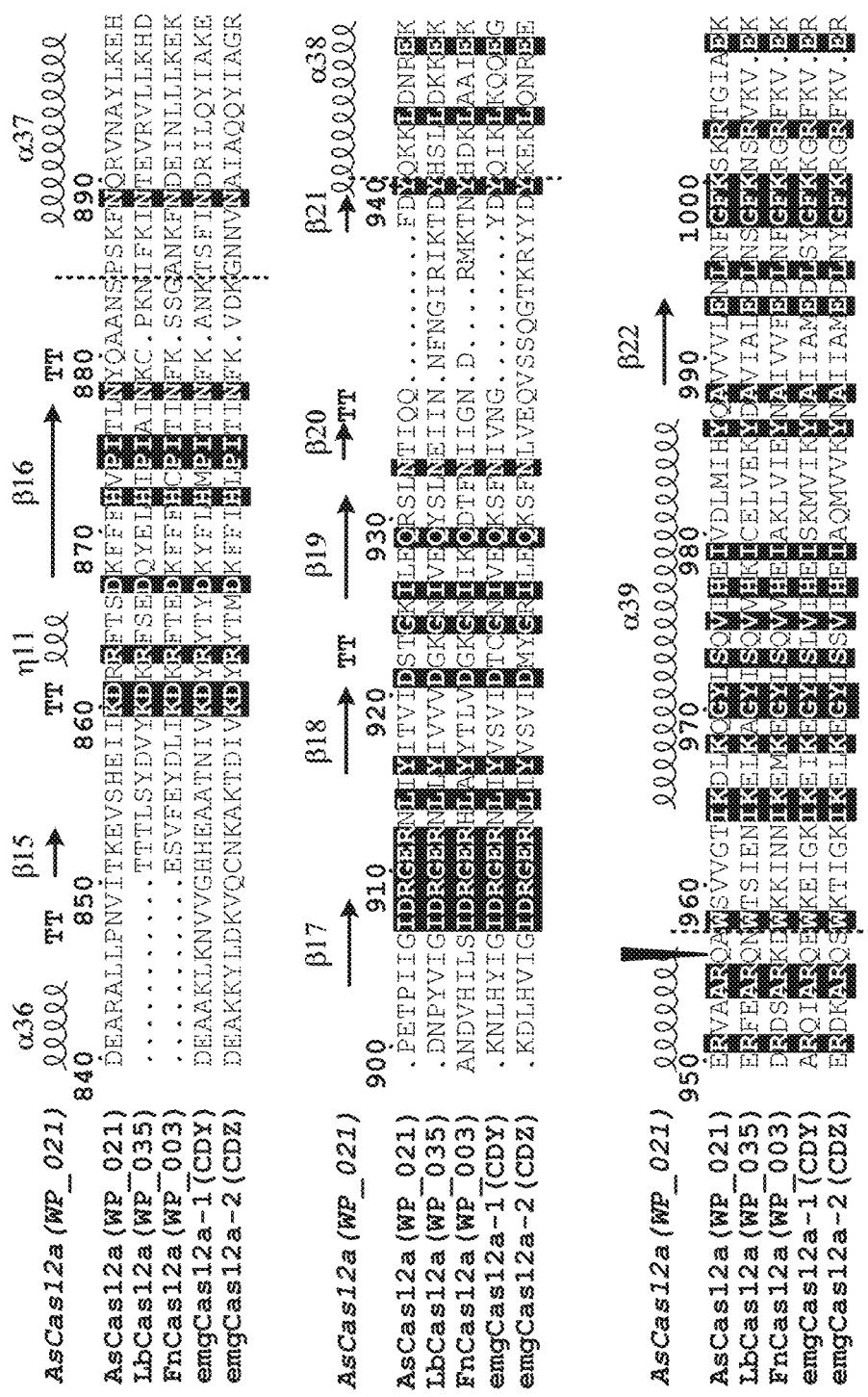
FIG. 7 shows a continuation of the alignment of Cas12a proteins of the present disclosure, including SEQ ID NO: 1 (mgCas12a-1), SEQ ID NO: 3 (mgCas12a-2), SEQ ID NO: 9 (AsCas12a), SEQ ID NO: 67 (LbCas12a), and SEQ ID NO: 11 (FnCas12a) from FIG. 6.
Figure 8:
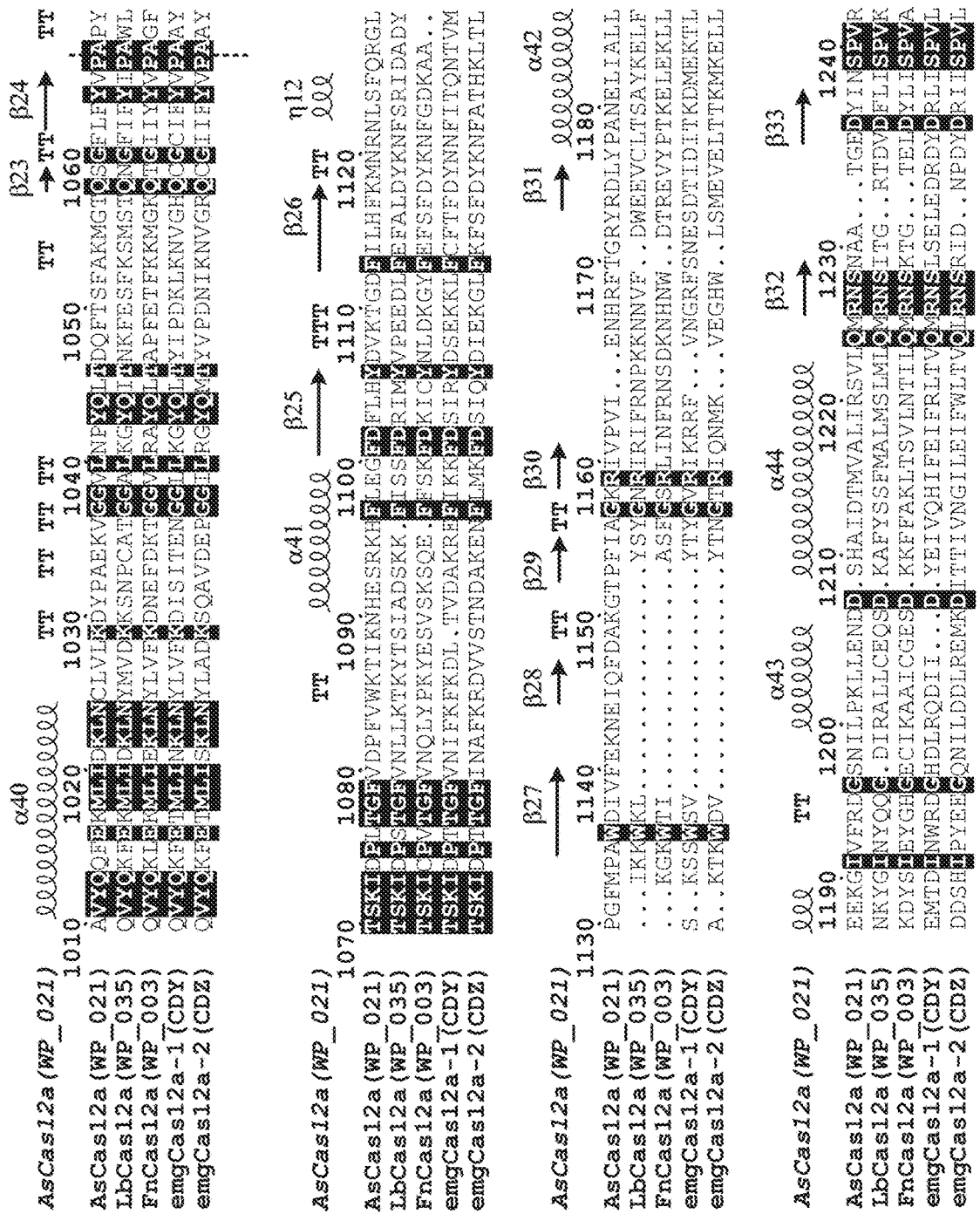
FIG. 8 shows a continuation of the alignment of Cas12a proteins of the present disclosure, including SEQ ID NO: 1 (mgCas12a-1), SEQ ID NO: 3 (mgCas12a-2), SEQ ID NO: 9 (AsCas12a), SEQ ID NO: 67 (LbCas12a), and SEQ ID NO: 11 (FnCas12a) from FIG. 7.

FIG. 3 through FIG. 8 show an alignment of proteins selected from the phylogenetic tree of FIG. 2 including SEQ ID NO: 1 (mgCas12a-1, CDY), SEQ ID NO: 3 (mgCas12a-2, CDZ), SEQ ID NO: 9 (AsCas12a, WP_021), SEQ ID NO: 67 (LbCas12a, WP_035), and SEQ ID NO: 11 (FnCas12a, WP_003). Residues that are absolutely conserved are back shaded. Predictive structures including alpha helices and beta sheets are shown at the top of the alignment. Unidentified positions are shown with dots. FIG. 7 shows a wedge indicating a critical residue in mgCas12a-1 (position 925) and mgCas12a-2 (position 930), which has been substituted from a K residue to a Q residue.

FIG. 9A shows a chart of characteristics of Cas12a proteins including AsCas12a, which is from the species Acidaminococcus sp. and has a nucleotide length of 3,921, an amino acid length of 1,307, a PAM sequence of 5'-TTTN-3', a sequence identity (in comparison to AsCas12a) of 100%, and a critical residue identity of 100% (33). The chart also shows the LbCas12a protein, which is from the species Lachnospiraceae sp. and has a nucleotide length of 3,684, an amino acid length of 1,228, has a PAM sequence of 5'-TTTN-3', a sequence identity (in comparison to AsCas12a) of 33.41%, and a critical residue identity of 79% (26). The chart also shows the FnCas12a protein, which is from the species *Francisella tularensis* subsp. *novicida* and has a nucleotide length of 3,900, an amino acid length of 1,300, a PAM sequence of 5'-TTTN-3', a sequence identity (in comparison to AsCas12a) of 34.45%, and a critical residue identity of 79% (26). The chart also shows the mgCas12a-1 (SEQ ID NO: 1) protein, which is from metagenome CDYX01038443.1 and has a nucleotide length of 3,789, an amino acid length of 1,263, a speculative PAM sequence of 5'-TTTN-3', a sequence identity (in comparison to AsCas12a) of 32.65%, and a critical residue identity of 88% (29). The chart also shows the mgCas12a-2 (SEQ ID NO: 3) protein, which is from metagenome CDZH01035208.1 and has a nucleotide length of 3,825, an amino acid length of 1,275, a speculative PAM sequence of 5'-TTTN-3', a sequence identity (in comparison to AsCas12a) of 32.65%, and a critical residue identity of 88% (29). FIG. 9B shows a chart of various Cas12 orthologs and the percent sequence identity between different Cas12a orthologs. The top row, from left to right, includes Cas12a, As, Lb, Fn, mg-1, and mg-2. The second row, from left to right, includes As followed by 5 blank cells. The third row, from left to right, includes Lb, 33.4, followed by 4 blank cells. The fourth row, from left to right, includes Fn, 34.2, 40.4, followed by 3 blank cells. The fifth row, from left to right, includes mg-1, 32.4, 35.3, 36.6, followed by 2 blank cells. The last row, from left to right, includes mg-2, 30.7, 34.9, 35.9, 52.5, followed by 1 blank cell.

Figure 10:
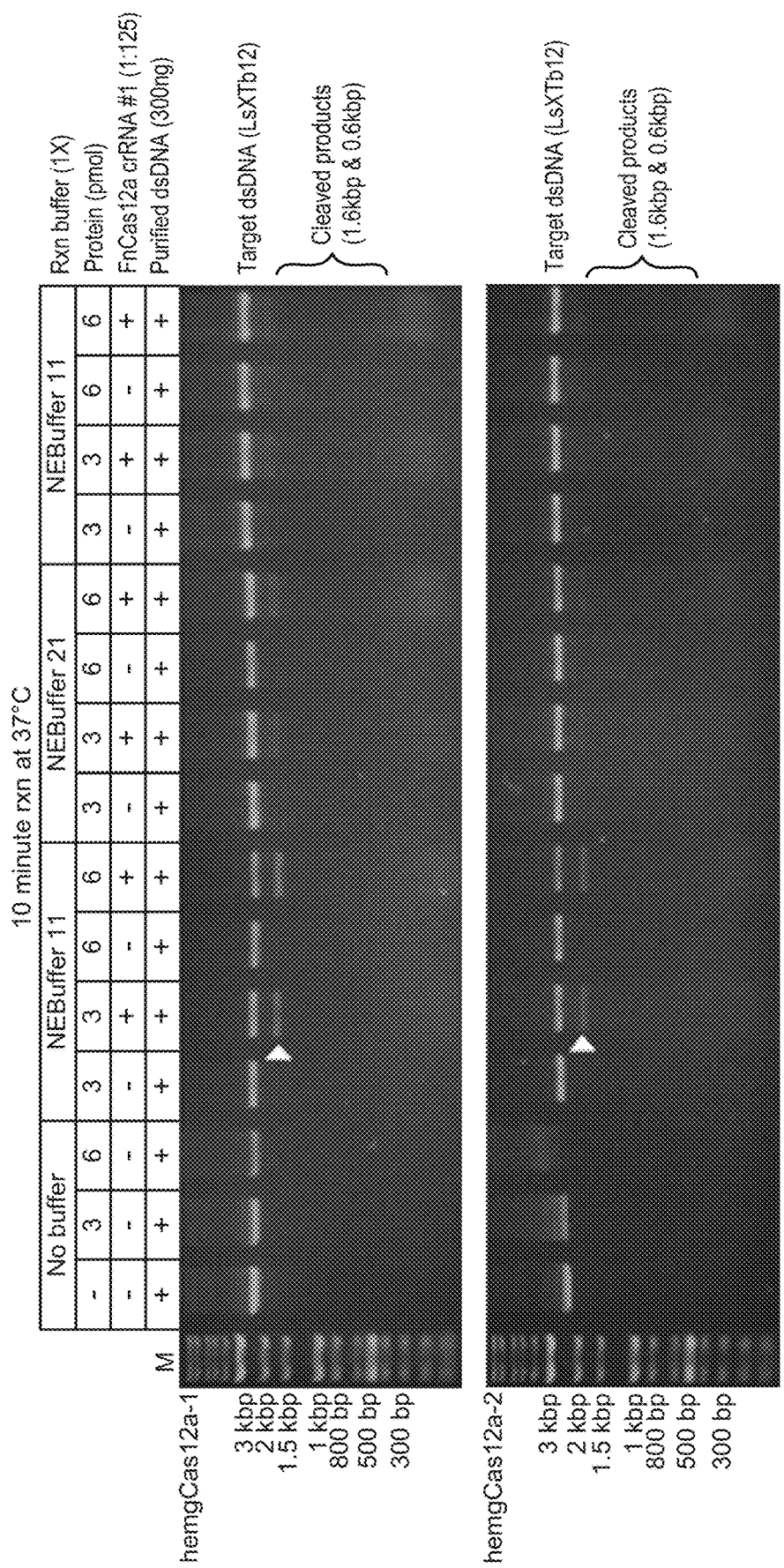
FIG. 10 shows gel electrophoresis of target dsDNA #1 after exposure to mgCas12a-1 (SEQ ID NO: 1) or mgCas12a-2 (SEQ ID NO: 3) complexed with crRNA #1 in no buffer, NEBuffer 1.1, NEBuffer 2.1, or NEBuffer 3.1.

FIG. 10 shows gel electrophoresis of target dsDNA after exposure to mgCas12a-1 (SEQ ID NO: 1) or mgCas12a-2 (SEQ ID NO: 3) complexed with crRNA in no buffer, NEBuffer 1.1, NEBuffer 2.1, and NEBuffer 3.1 for a 10 minute reaction run at 37° C. Cleaved products are indicated by an arrow. The target dsDNA (LsXTb12) resolves ~2.2 kbp. Cleavage was found to occur in the presence of 3 pmol mgCas12a-1 protein, FnCas12a crRNA #1 at a ratio of 1:1.25, and 300 ng of purified dsDNA in NEBuffer 1.1. Cleavage also occurred in the presence of 6 pmol mgCas12a-1 protein, FnCas12a crRNA #1 at a ratio of 1:1.25, and 300 ng of purified dsDNA in NEBuffer 1.1. Cleavage was also observed in the above conditions in NEBuffer 2.1 and NEBuffer 3.1, however, cleavage was strongest in the NEBuffer 1.1. For mgCas12a-2, cleavage was primarily seen in the presence of 3 pmol mgCas12a-2, FnCas12a crRNA #1 at a ratio of 1:1.25, and 300 ng of purified dsDNA in NEBuffer 1.1 and 6 pmol mgCas12a-1 protein, FnCas12a crRNA #1 at a ratio of 1:1.25, and 300 ng of purified dsDNA in NEBuffer 1.1. In both cases, cleaved products were detected at 1.6 kbp and 0.6 kpb.

Figure 11:
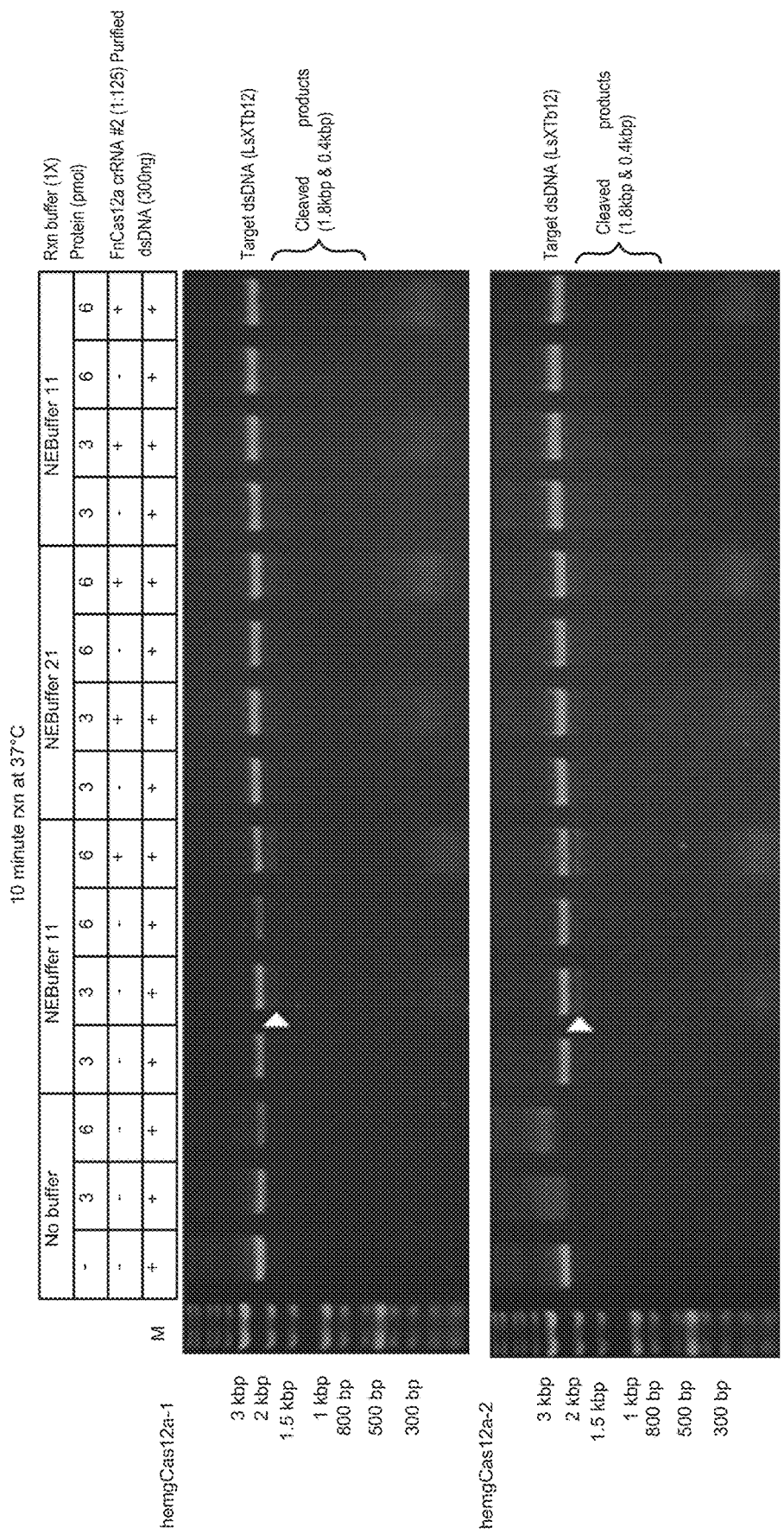
FIG. 11 shows another gel electrophoresis of target dsDNA #2 after exposure to mgCas12a-1 (SEQ ID NO: 1) or mgCas12a-2 (SEQ ID NO: 3) complexed with crRNA #2 in no buffer, NEBuffer 1.1, NEBuffer 2.1, or NEBuffer 3.1.

FIG. 11 shows gel electrophoresis of target dsDNA after exposure to mgCas12a-1 (SEQ ID NO: 1) or mgCas12a-2 (SEQ ID NO: 3) complexed with crRNA in no buffer, NEBuffer 1.1, NEBuffer 2.1, and NEBuffer 3.1 for a 10 minute reaction run at 37° C. Cleaved products are indicated by an arrow. The target dsDNA (LsXTb12) resolves ~2.2 kbp. Cleavage was found to occur in the presence of 3 pmol mgCas12a-1 protein, FnCas12a crRNA #1 at a ratio of 1:1.25, and 300 ng of purified dsDNA in NEBuffer 1.1. For mgCas12a-2, cleavage was primarily seen in the presence of 3 pmol mgCas12a-2, FnCas12a crRNA #1 at a ratio of 1:1.25, and 300 ng of purified dsDNA in NEBuffer 1.1 and 6 pmol mgCas12a-1 protein, FnCas12a crRNA #1 at a ratio of 1:1.25, and 300 ng of purified dsDNA in NEBuffer 1.1. In both cases, cleaved products were detected at 1.8 kbp and 0.4 kpb. While FIG. 11 and FIG. 10 have similar reaction conditions, FIG. 10 and FIG. 11 use two different crRNAs (crRNA #1 for FIG. 10 and crRNA #2 for FIG. 11). Thus, the resulting cleaved products are of different sizes in FIG. 11 as compared to FIG. 10.

Figure 12:
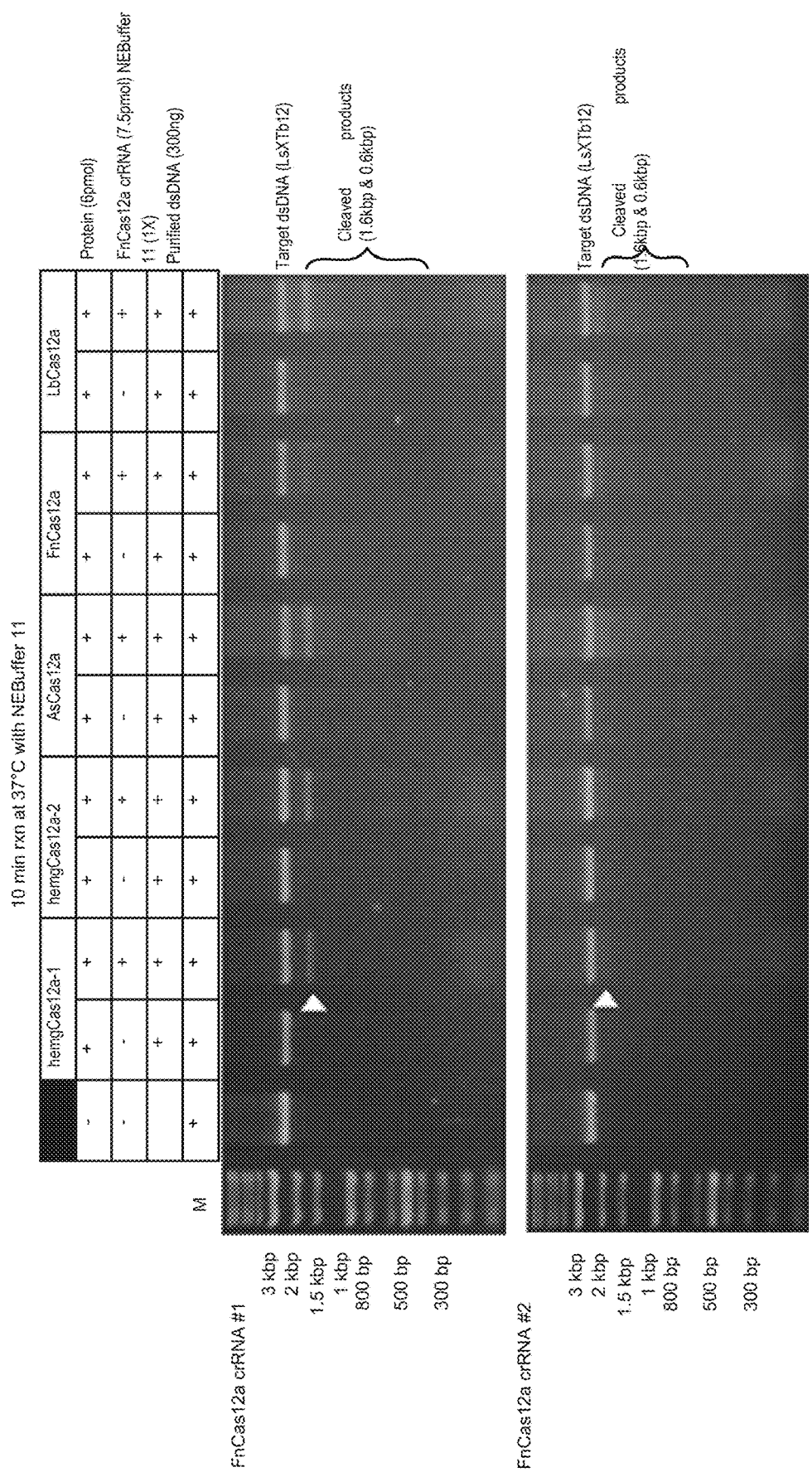
FIG. 12 shows gel electrophoresis of target dsDNA after exposure to mgCas12a-1 (SEQ ID NO: 1), mgCas12a-2 (SEQ ID NO: 3), AsCas12a, FnCas12a, and LbCas12a complexed with crRNA.

FIG. 12 shows gel electrophoresis of target dsDNA after exposure to Cas12a proteins including mgCas12a-1, mgCas12a-2, AsCas12a, FnCas12a, and LbCas12a complexed with crRNA in NEBuffer 1.1 for a 10 minute reaction run at 37° C. Cleaved products are indicated by an arrow. The target dsDNA (LsXTb12) resolves ~2.2 kbp. For mgCas12a-1, mgCas12a-2, AsCas12a, FnCas12a, and LbCas12a, cleavage occurred in the presence of 6 pmol of mgCas12a-1 protein, 7.5 pmol FnCas12a crRNA #1, and 300 ng of purified dsDNA. Cleaved products were detected at 1.6 kbp and 0.6 kbp. Additionally, during testing of mgCas12a-1, mgCas12a-2, AsCas12a, FnCas12a, or LbCas12a in the presence of 6 pmol of mgCas12a-1 protein, 7.5 pmol FnCas12a crRNA #2, and 300 ng of purified dsDNA, cleavage as best detected for mgCas12a-1. Cleaved products were detected at 1.8 kbp and 0.4 kbp.

Figure 13:
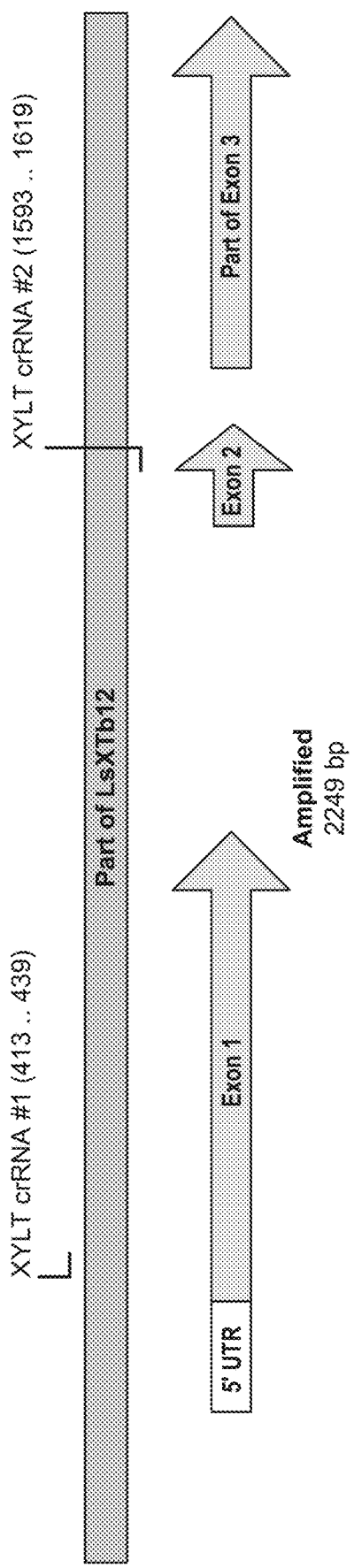
FIG. 13 shows a diagram of the target double stranded DNA LsXTb12 tested in the gel electrophoresis experiments of FIG. 10 to FIG. 12 and the corresponding binding regions of crRNA.

FIG. 13 shows the target double stranded DNA LsXTb12 tested in the gel electrophoresis experiments of FIG. 10 to FIG. 12 and the corresponding binding regions of crRNA #1 and crRNA #2, including in exon 1 and exon 2, respectively. FIG. 13 shows a solid top bar indicated to be "part of LsXTb12" and is shown from its 5' end to its 3' end. Indicated below the target dsDNA LsXTb12 to the left is an arrow running from left to right showing the 5' UTR and Exon 1. XYLT crRNA #1 (413 to 439) is shown above the solid top bar of the target dsDNA and is shown as binding to a region above Exon 1 in the target dsDNA. Indicated below the target dsDNA LsXTb12 to the right is two arrows running from left to right including Exon 2 followed by part of Exon 3. XYLT crRNA #2 (1593 to 1619) is shown above the solid top bar of the target dsDNA and is shown as binding to a region above Exon 2 in the target dsDNA.

Figure 14:
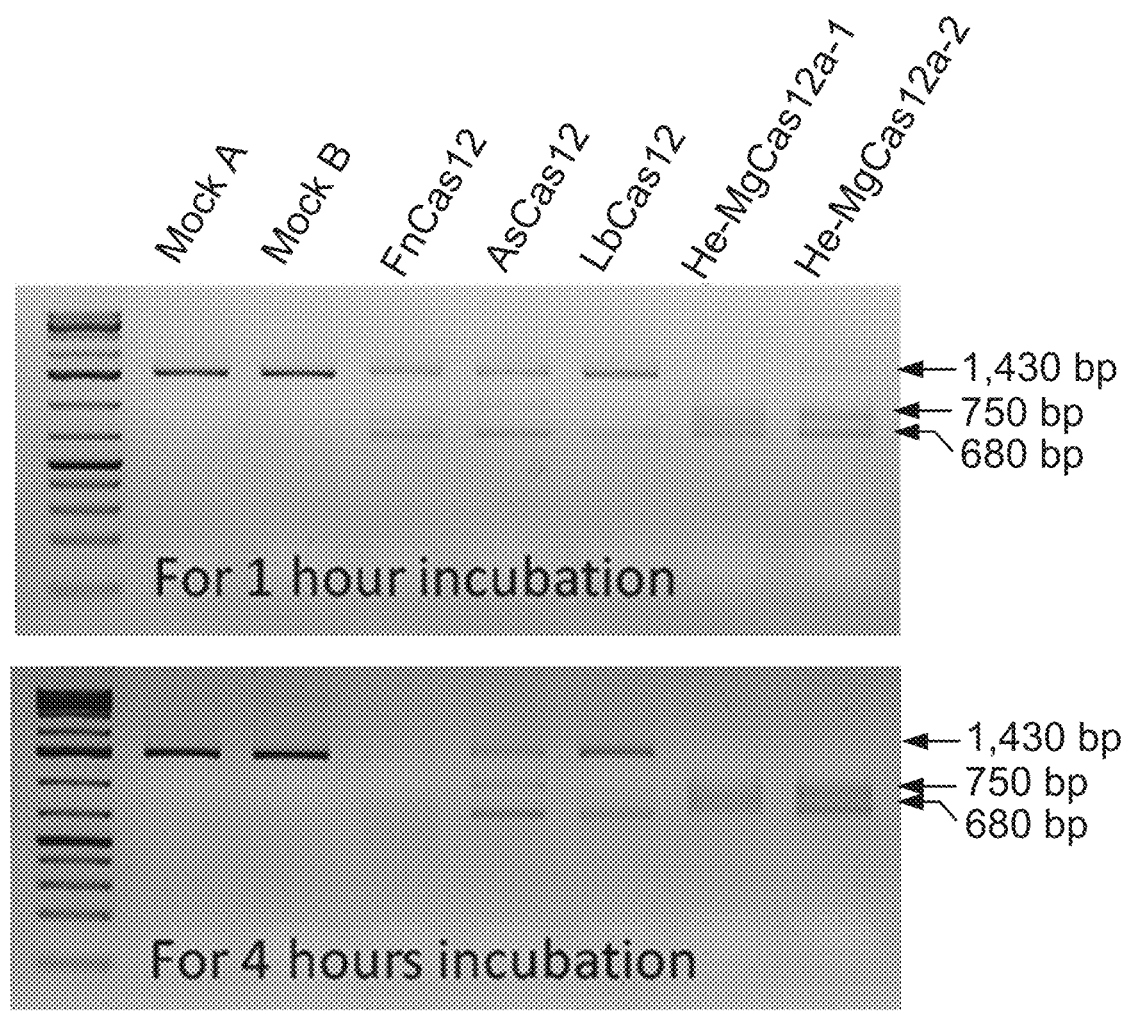
FIG. 14 shows the results of an in vitro cleavage assay using various nucleases including, FnCas12, AsCas12, LbCas12, He-MgCas12a-1 (humanized and engineered mgCas12a-1), and He-MgCas12a-2 (humanized and engineered mgCas12a-2), 1 hour after incubation of the target with the nucleases and 4 hours after incubation of the target with the nucleases.

FIG. 14 illustrates gel electrophoresis of a target DNA after incubation with a Cas12a nuclease of the present disclosure. The left most lane shows a DNA ladder and the Mock A and Mock B lane shows controls. The Mock A lane shows a reaction lacking gRNA and protein. Mock B indicates a reaction lacking protein. As expected, the target DNA remains uncut in the Mock A and Mock B lanes and resolves at a size of 1430 base pairs (bp). Cas12a proteins tested for cleavage of the target DNA includes FnCas12, AsCas12, LbCas12, He-MgCas12a-1 (humanized and engineered mgCas12a-1), and He-MgCas12a-2 (humanized and engineered mgCas12a-2). He-MgCas12a-1 and He-MgCas12a-2 both cleaved the DNA template (1,430 bp) into two pieces of 750 bp and 680 bp. He-MgCas12a-1 cleaved all the DNA template within 1 hour of incubation as evidenced by the lack of a band at the intact DNA template size. He-MgCas12a-2 cleaved all the DNA template within 4 hours of incubation as evidenced by the lack of a band at the intact DNA template size. Although FnCas12, AsCas12, and LbCas12 cleaved the target DNA, uncleaved DNA template remained even after 4 hours as evidenced by a band at the intact DNA template size.

Figure 15A:
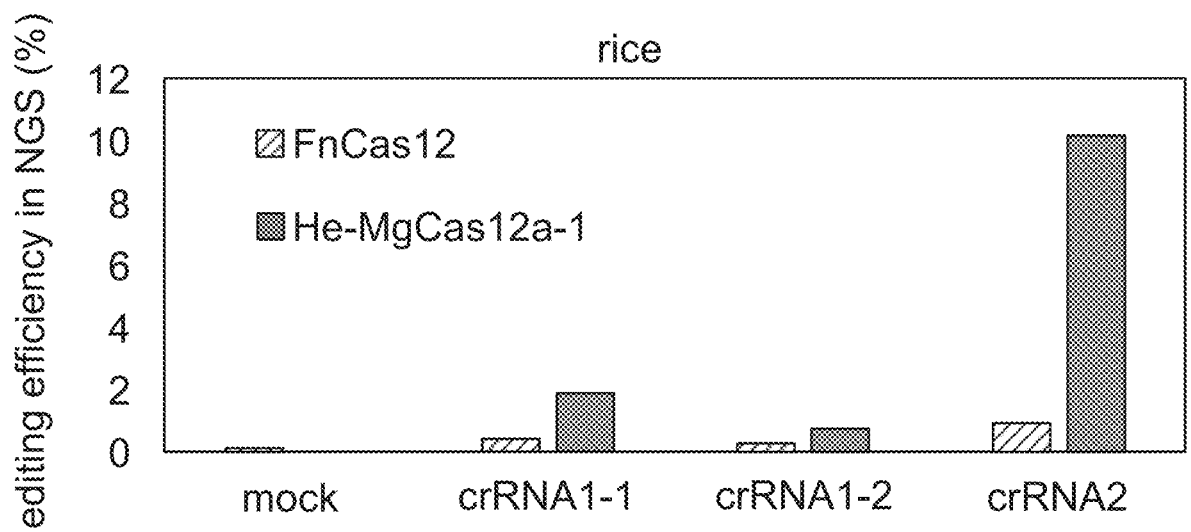
FIGS. 15A-15B illustrate genome editing efficiencies of FnCas12a and He-MgCas12a-1 in rice and *N. benthamiana*.
Figure 15B:
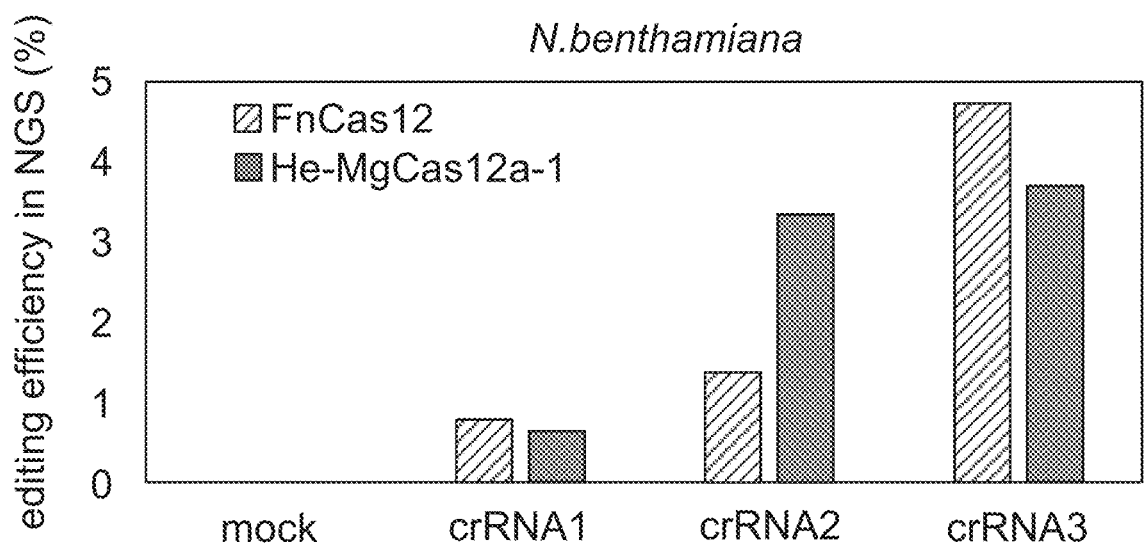

FIG. 15A-B shows two graphs illustrating genome editing efficiencies of FnCas12 versus He-MgCas12a-1 in rice (FIG. 15A) and in N. benthamiana (FIG. 15B). Genome editing efficiencies were measured by next generation sequencing techniques and the y-axis shows percent editing efficiency. Mock indicates a negative control sample. For genome editing in rice, two crRNAs were evaluated and for genome editing in N. benthamiana, three crRNAs were evaluated. He-MgCas12a-1 exhibited higher editing efficiency in rice with crRNA 1 and crRNA 2 as compared to FnCas12. He-MgCas12a-1 exhibited higher editing efficiency in N. benthamiana with crRNA 2 than FnCas12.

Figure 16:
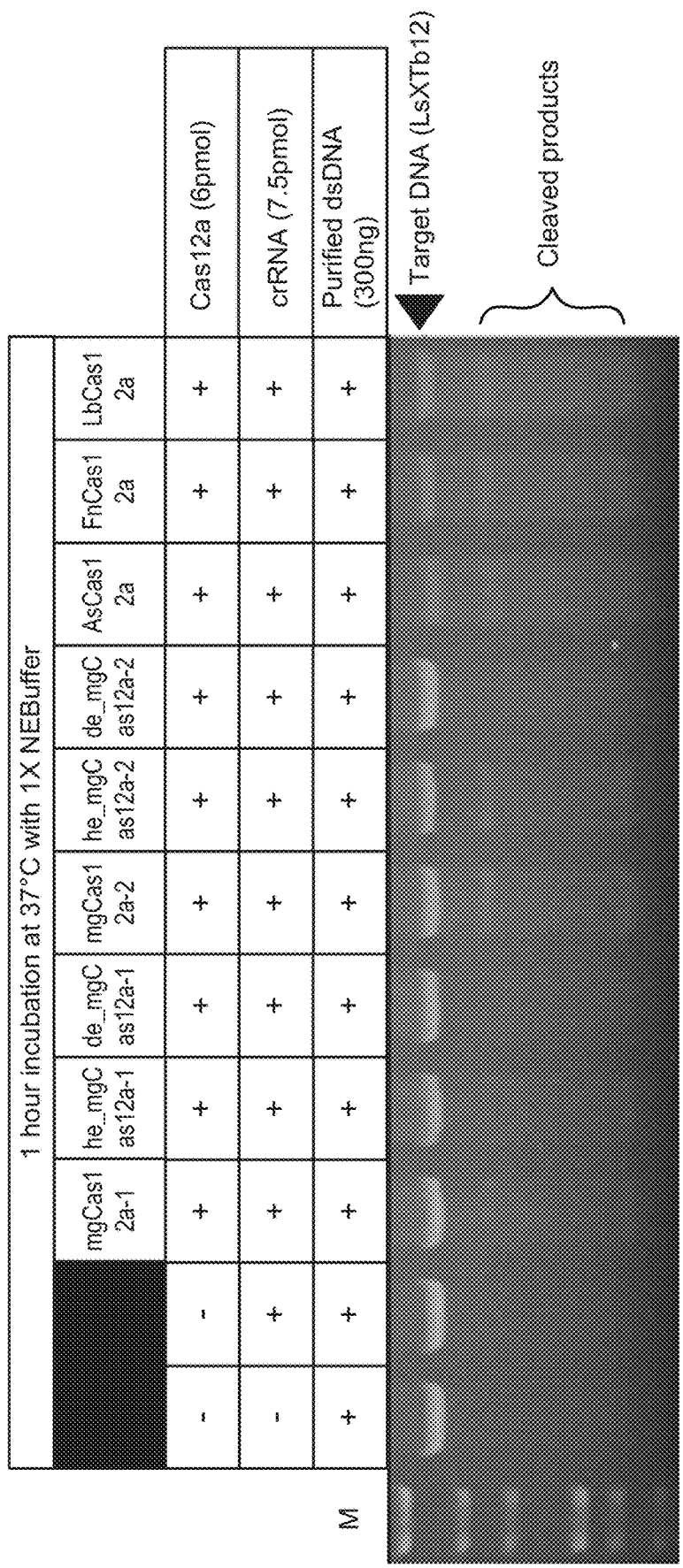

FIG. 16 illustrates a gel electrophoresis of 300 ng target DNA (LsXTb12) incubated with Cas12a(6 pmol)/crRNA (7.5 pmol) complexes for 1 hour at 370 in 1×NEBuffer. Each lane of the gel electrophoresis shows various conditions. The lanes in the gel from left to right show: 1) the DNA ladder, 2) the purified dsDNA and without Cas12a or crRNA, 3) mgCas12a-1, crRNA and purified dsDNA, 4) he_mgCas12a-1, crRNA and purified dsDNA, 5) de_mgCas12a-1, crRNA and purified dsDNA, 6) mgCas12a-2, crRNA and purified dsDNA, 7) he_mgCas12a-2, crRNA and purified dsDNA, 8) de_mgCas12a-2, crRNA, and purified dsDNA, 9) AsCas12a, crRNA and purified dsDNA, 10) FnCas12a, crRNA and purified dsDNA, 11) LbCas12a, crRNA, and purified dsDNA. Cleaved products were observed in the mgCas12a lanes and the he-mgCas12a lanes as well as the AsCas12a, FnCas12a, and LbCas12a lanes. Cleaved template DNA was seen at 1.8 kB and 0.65 kB.

Figure 17A:
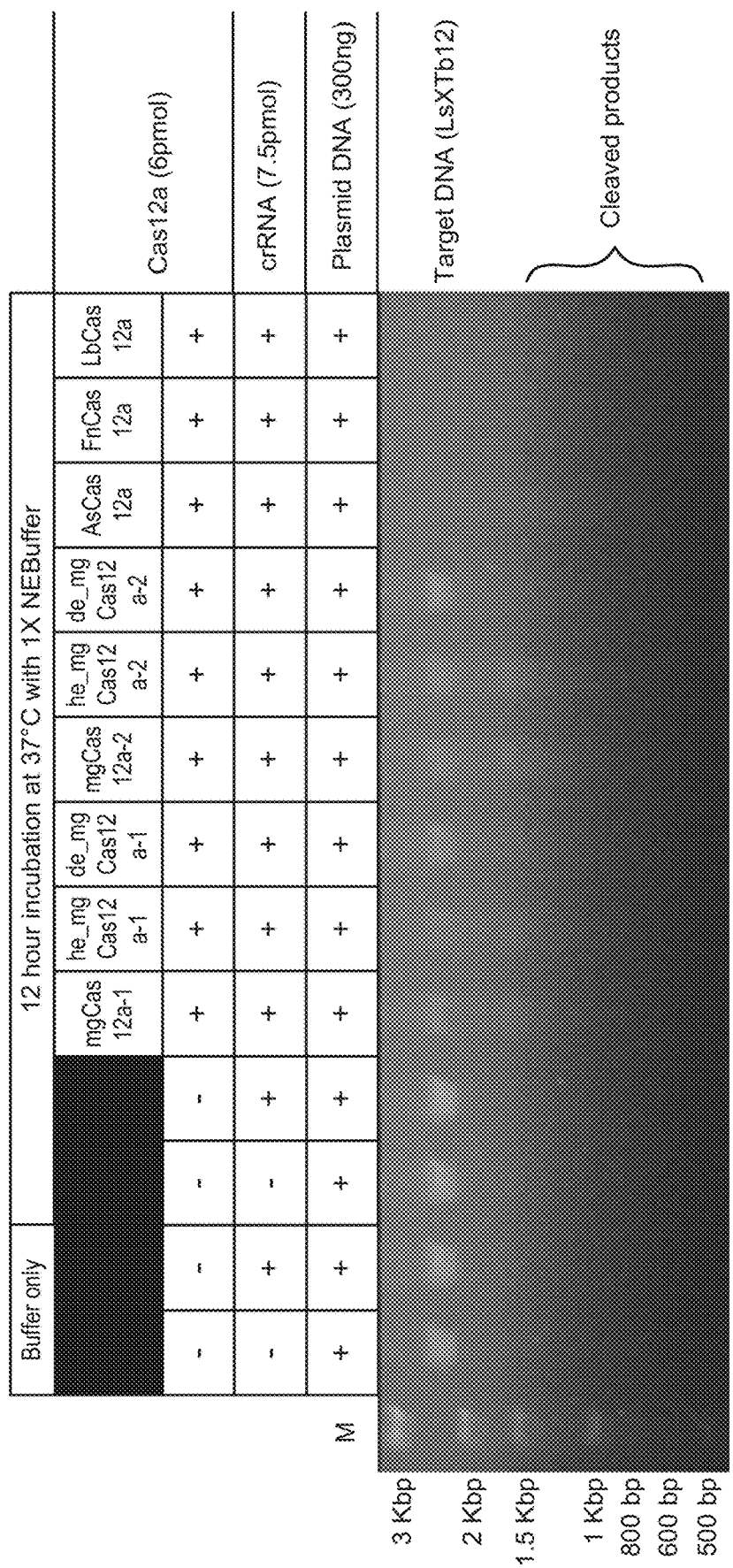
FIGS. 17A-17B show an in vitro cleavage assay of Cas12a nucleases including mgCas12a-1 (wild-type), he_mgCas12a-1 (humanized and engineered mgCas12a-1), de_mgCas12a-1 (dead and engineered mgCas12a), mg Cas12a-2, he_mgCas12a-2, de_mgCas12a-2, AsCas12a, FnCas12a, and LbCas12a after reaction times of 12 h (FIG. 17A) and 24 h (FIG. 17B).

FIG. 17A shows a gel electrophoresis of 300 ng of target DNA (LsXTb12) incubated with Cas12a (6 pmol) and crRNA (7.5 pmol) for 12 hour at 370 in 1×NEBuffer. The lanes in the gel from left to right show: 1) purified dsDNA alone, 2) crRNA and purified dsDNA, 3) purified dsDNA only at 37° C., 4) crRNA and purified dsDNA at 37° C., 5) mgCas12a-1, crRNA and purified dsDNA, 6) he_mgCas12a-1, crRNA and purified dsDNA, 7) de_mgCas12a-1, crRNA and purified dsDNA, 8) mgCas12a-2, crRNA and purified dsDNA, 9) he_mgCas12a-2, crRNA and purified dsDNA, 10) de_mgCas12a-2, crRNA and purified dsDNA, 11) AsCas12a, crRNA and purified dsDNA, 12) FnCas12a, crRNA and purified dsDNA, and 13) LbCas12a, crRNA, and purified dsDNA. While AsCas12a, FnCas12a, and LbCas12a fully degraded template DNA, as evidenced by a lack in a band at the target DNA size, intact template DNA was observed in the case of the mgCas12a, he_mgCas12a, and de_mgCas12a proteins. Cleaved products of the template DNA were observed for mgCas12a and he_mgCas12a proteins, which resolved at 1.8 kb and 0.65 kb.

Figure 17B:
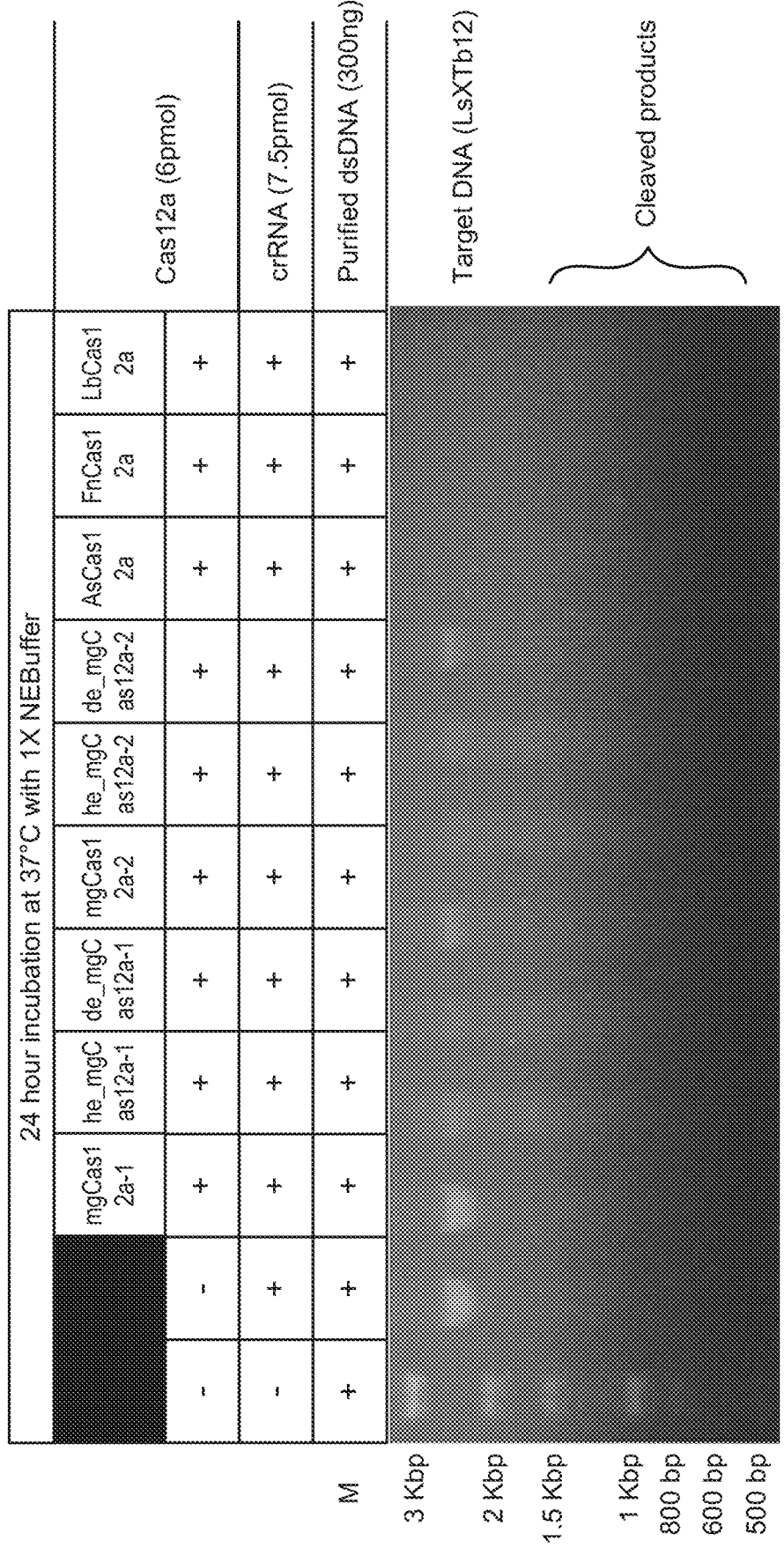

FIG. 17B shows a gel electrophoresis of 300 ng of target DNA (LsXTb12) incubated with Cas12a (6 pmol) and crRNA (7.5 pmol) for 24 hours at 37° in 1×NEBuffer. The lanes in the gel from left to right show: 1) the DNA ladder, 2) the purified dsDNA and without Cas12a or crRNA, 3) mgCas12a-1, crRNA and purified dsDNA, 4) he_mgCas12a-1, crRNA and purified dsDNA, 5) de_mgCas12a-1, crRNA and purified dsDNA, 6) mgCas12a-2, crRNA and purified dsDNA, 7) he_mgCas12a-2, crRNA and purified dsDNA, 8) de_mgCas12a-2, crRNA, and purified dsDNA, 9) AsCas12a, crRNA and purified dsDNA, 10) FnCas12a, crRNA and purified dsDNA, 11) LbCas12a, crRNA, and purified dsDNA. Template DNA was observed in the mgCas12a lanes after 24 hours. In contrast, no target DNA was observed in the AsCas12a, FnCas12a, and LbCas12a lanes.

Figure 18:
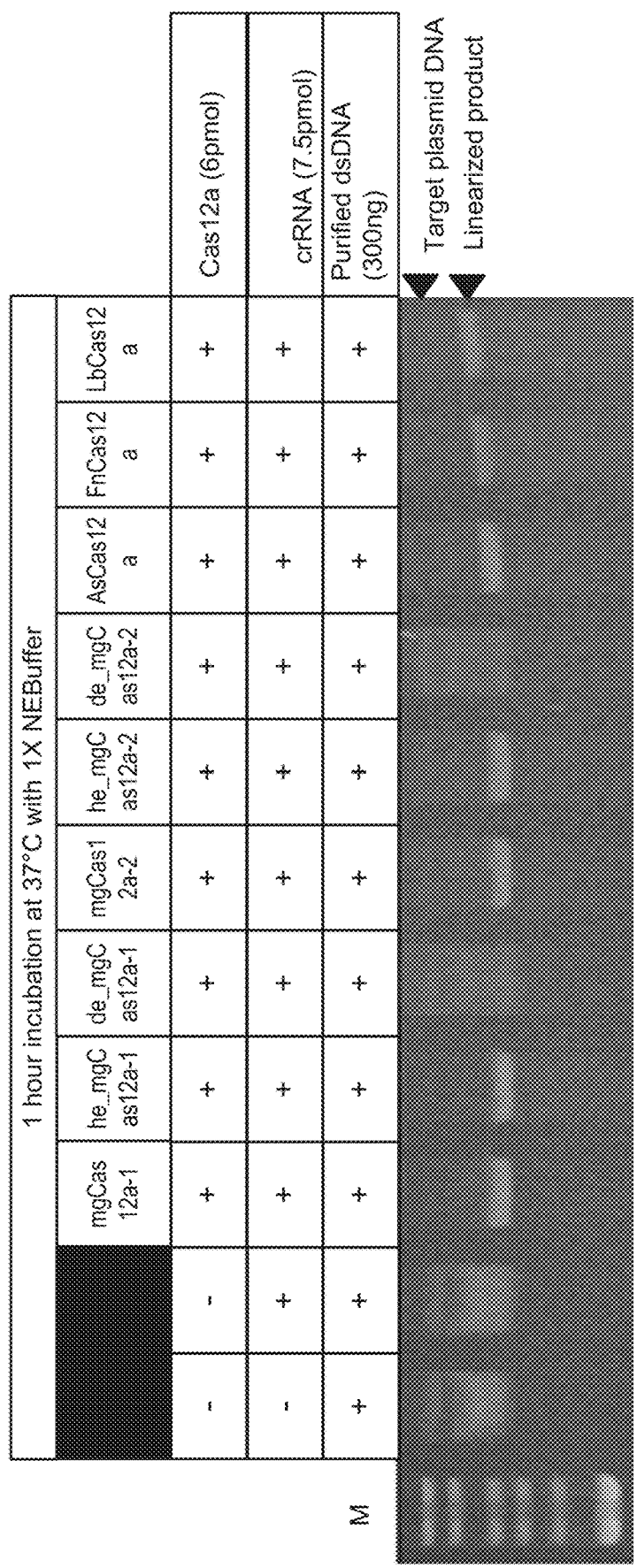

FIG. 18 shows a gel electrophoresis of 300 ng of target plasmid DNA (~10 kbp) incubated with Cas12a (6 pmol) and crRNA (7.5 pmol) for 1 hour at 37° in 1×NEBuffer. The lanes in the gel from left to right show: 1) the DNA ladder, 2) the purified dsDNA and without Cas12a or crRNA, 3) mgCas12a-1, crRNA and purified dsDNA, 4) he_mgCas12a-1, crRNA and purified dsDNA, 5) de_mgCas12a-1, crRNA and purified dsDNA, 6) mgCas12a-2, crRNA and purified dsDNA, 7) he_mgCas12a-2, crRNA and purified dsDNA, 8) de_mgCas12a-2, crRNA, and purified dsDNA, 9) AsCas12a, crRNA and purified dsDNA, 10) FnCas12a, crRNA and purified dsDNA, 11) LbCas12a, crRNA, and purified dsDNA. Target plasmid DNA was evidenced by a band at 10 kbp and cleaved products were observed at 6 kbp. All Cas12a proteins, with the exception of the de_mgCas12a proteins cleaved the target plasmid DNA to a linearized piece of DNA at 6 kbp in size.

Figure 19A:
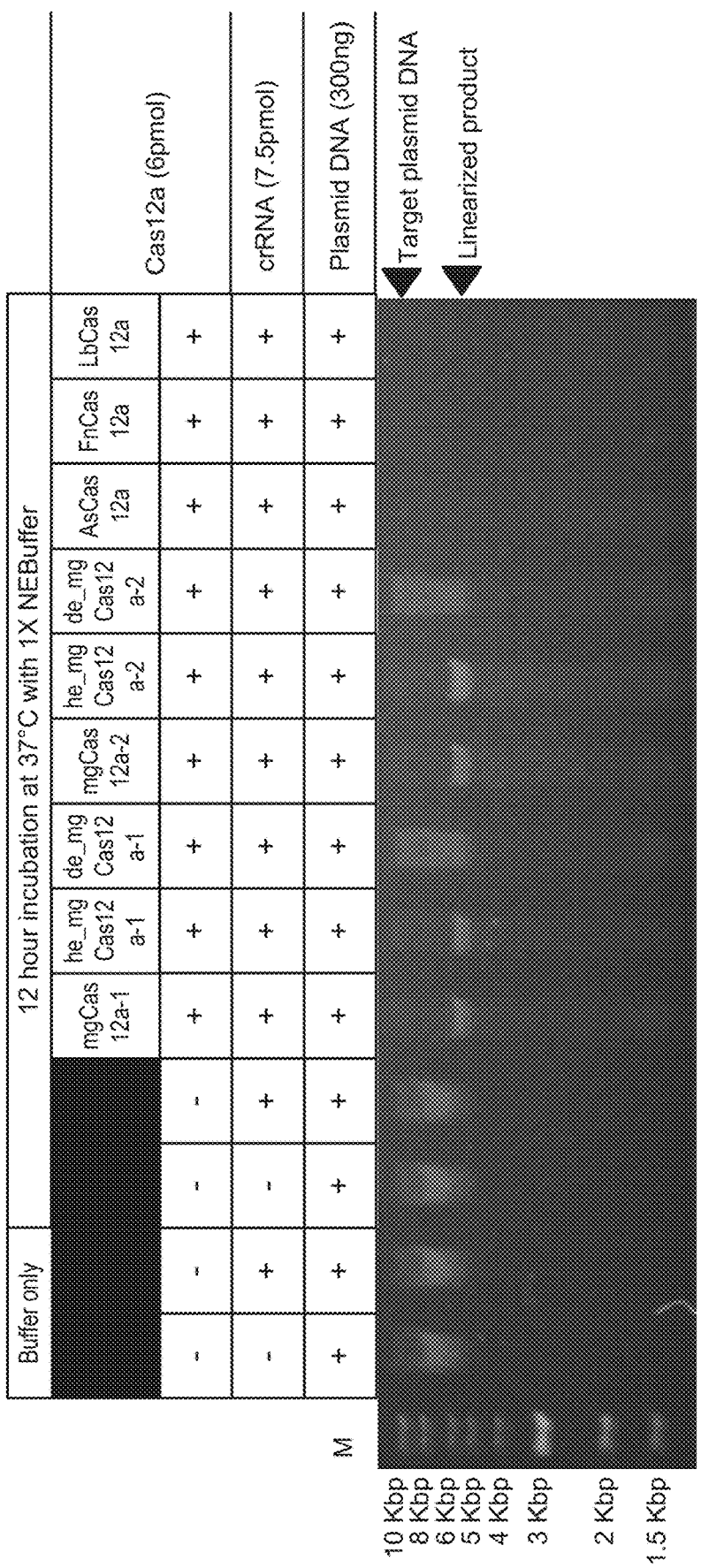
FIGS. 19A-19B shows an in vitro cleavage assay of target plasmid DNA with Cas12a nucleases including mgCas12a-1 (wild-type), he_mgCas12a-1 (humanized and engineered mgCas12a-1), de_mgCas12a-1 (dead and engineered mgCas12a), mg Cas12a-2, he_mgCas12a-2, de_mgCas12a-2, AsCas12a, FnCas12a, and LbCas12a after reaction times of 12 h (FIG. 19A) and 24 h (FIG. 19B).

FIG. 19A shows gel electrophoresis of 300 ng of target plasmid DNA incubated with Cas12a nucleases including mgCas12a-1 (wild-type), he_mgCas12a-1 (humanized and engineered mgCas12a-1), de_mgCas12a-1 (dead and engineered mgCas12a), mg Cas12a-2, he_mgCas12a-2, de_mgCas12a-2, AsCas12a, FnCas12a, and LbCas12a after a reaction time of 12 h in 1×NEBuffer at 37° C. The lanes in the gel from left to right show: 1) purified dsDNA alone, 2) crRNA and purified dsDNA, 3) purified dsDNA only at 37° C., 4) crRNA and purified dsDNA at 37° C., 5) mgCas12a-1, crRNA and purified dsDNA, 6) he_mgCas12a-1, crRNA and purified dsDNA, 7) de_mgCas12a-1, crRNA and purified dsDNA, 8) mgCas12a-2, crRNA and purified dsDNA, 9) he_mgCas12a-2, crRNA and purified dsDNA, 10) de_mgCas12a-2, crRNA, and purified dsDNA, 11) AsCas12a, crRNA and purified dsDNA, 12) FnCas12a, crRNA and purified dsDNA, and 13) LbCas12a, crRNA, and purified dsDNA. AsCa12a, FnCas12a, and LbCas12a degraded all template plasmid DNA within 12 hours as evidenced by the lack of any bands. mgCas12a proteins and he_mgCas12a proteins both exhibited linearized cleaved products and some target plasmid DNA as evidenced by bands at their respective expected sizes.

Figure 19B:
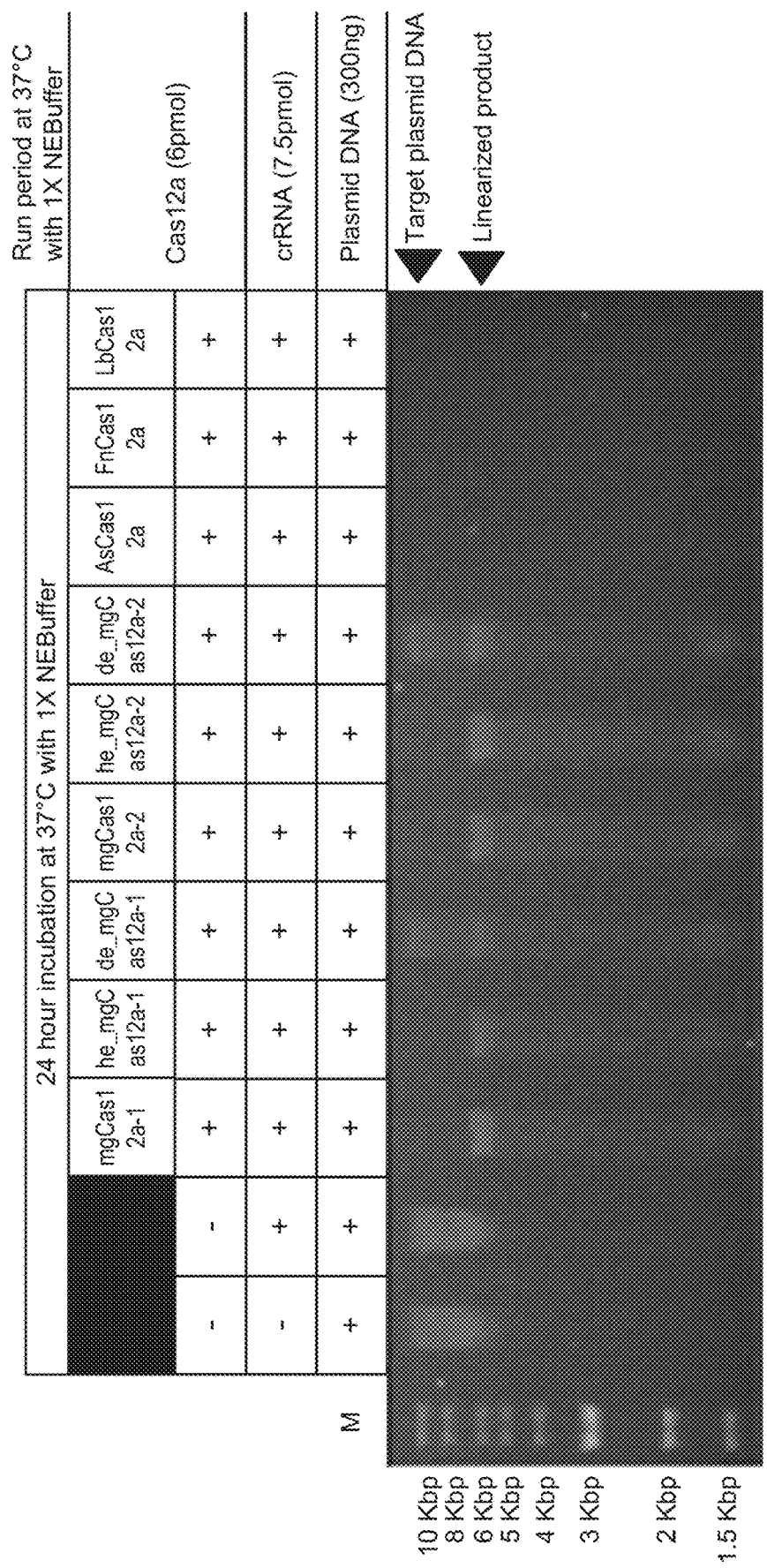

FIG. 19B shows gel electrophoresis of 300 ng of target plasmid DNA incubated with Cas12a nucleases including mgCas12a-1 (wild-type), he_mgCas12a-1 (humanized and engineered mgCas12a-1), de_mgCas12a-1 (dead and engineered mgCas12a), mg Cas12a-2, he_mgCas12a-2, de_mgCas12a-2, AsCas12a, FnCas12a, and LbCas12a after a reaction time of 24 h in 1×NEBuffer at 37° C. The lanes in the gel from left to right show: 1) the DNA ladder, 2) the purified dsDNA and without Cas12a or crRNA, 3) mgCas12a-1, crRNA and purified dsDNA, 4) he_mgCas12a-1, crRNA and purified dsDNA, 5) de_mgCas12a-1, crRNA and purified dsDNA, 6) mgCas12a-2, crRNA and purified dsDNA, 7) he_mgCas12a-2, crRNA and purified dsDNA, 8) de_mgCas12a-2, crRNA, and purified dsDNA, 9) AsCas12a, crRNA and purified dsDNA, 10) FnCas12a, crRNA and purified dsDNA, 11) LbCas12a, crRNA, and purified dsDNA. AsCa12a, FnCas12a, and LbCas12a degraded all template plasmid DNA within 24 hours as evidenced by the lack of any bands. mgCas12a proteins and he_mgCas12a proteins both exhibited linearized cleaved products and as evidenced by bands at the expected size.

Figure 20A:
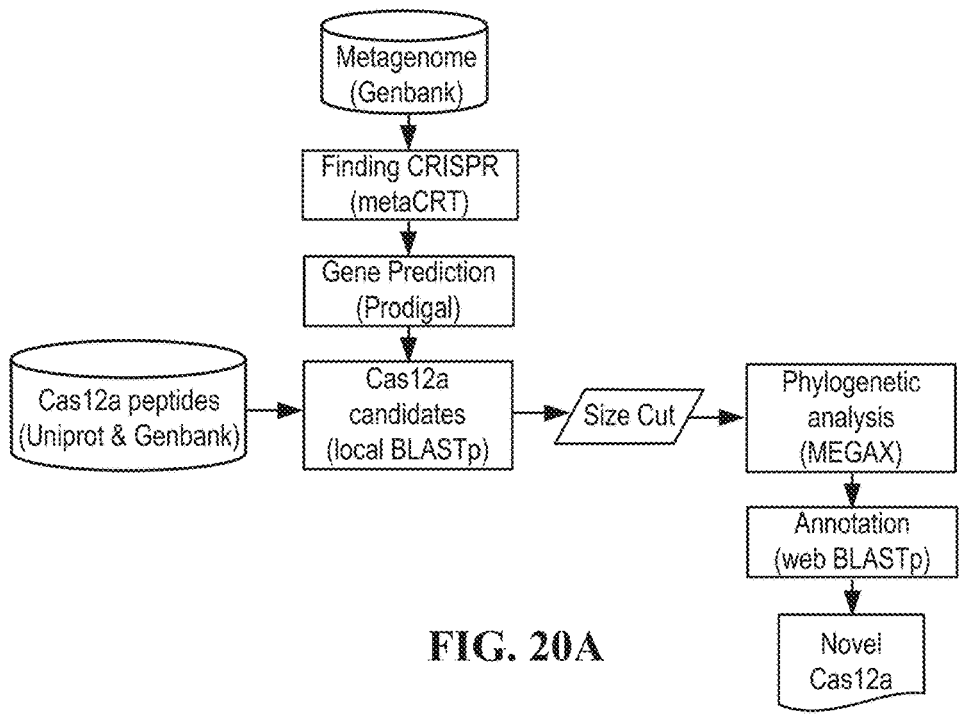
FIGS. 20A-20C show schematics of the mgCas12a proteins of the present disclosure.

FIG. 20A shows a flowchart for mining novel Cas12a proteins from the metagenome database. Metagenome sequence data can be obtained from Genbank and CRISPR sequences can be found using metaCRT and gene prediction (Prodigal). Cas12a candidate proteins are identified using local BLASTp of Cas12a sequences from Uniprot and Genbank. Such identified Cas12a candidate proteins are then analyzed to generate phylogenetic tree using MEGAX, which information is annotated using web BALSTp.

Figure 20B:
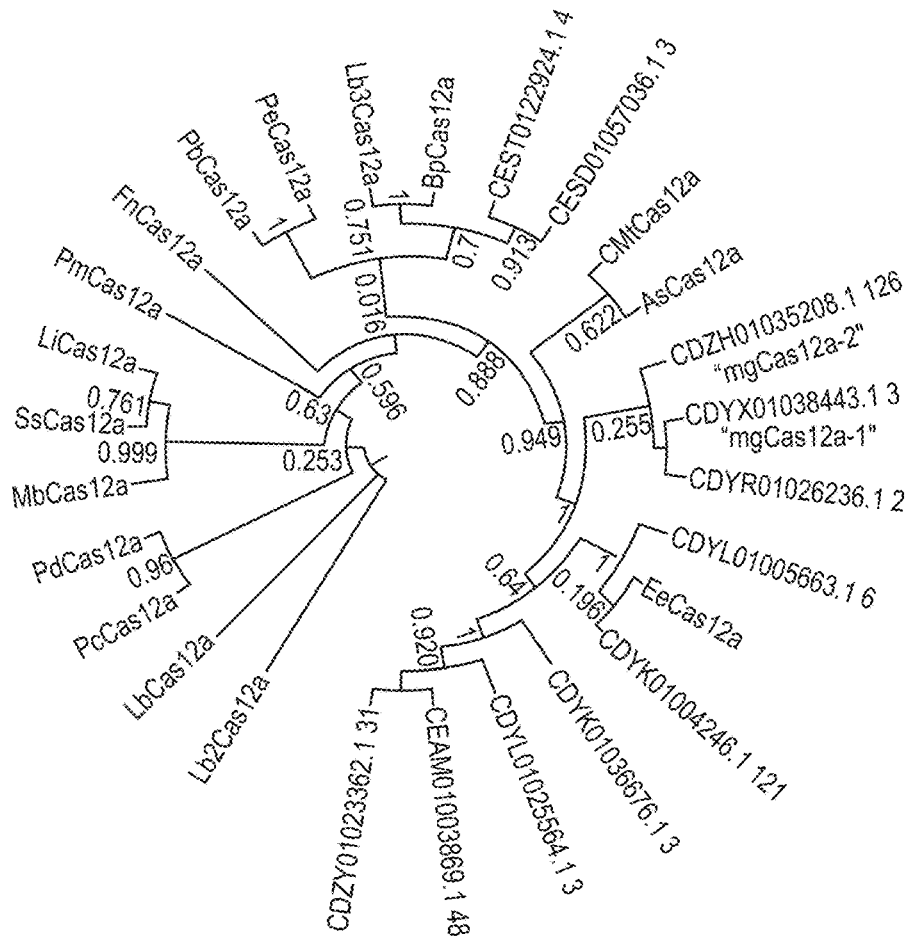

FIG. 20B shows a phylogenetic tree of various Cas12a orthologs. The metagenomically mined Cas12a proteins of the present disclosure, including mgCas12a-2 and mgCas12a-1 resolve at the right. The tree additionally shows the relationship between other Cas12a proteins using bootstrap values.

Figure 20C:
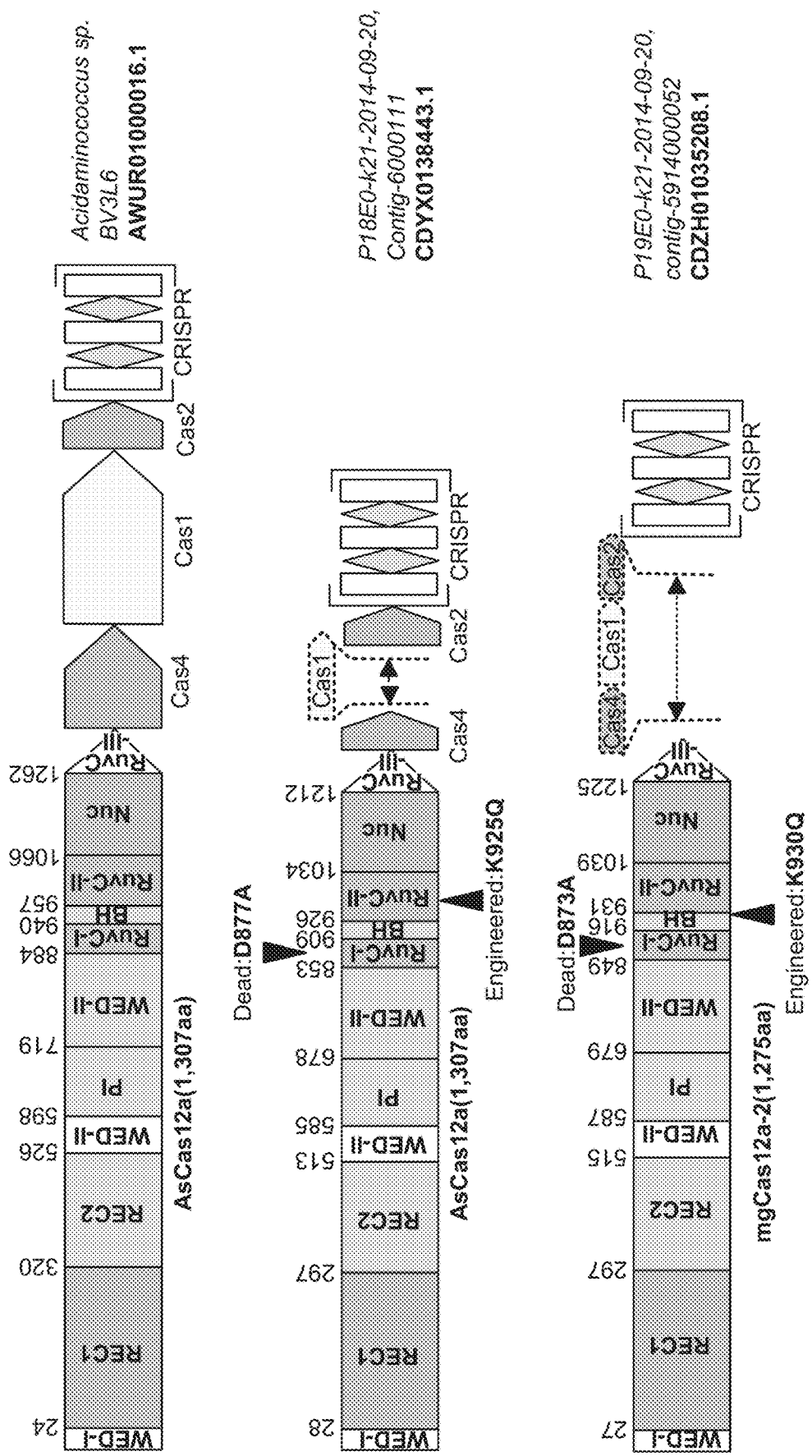

FIG. 20C shows a schematics of the various domains in AsCas12a, mgCas12a-1, and mgCas12a-2, which includes WED-I, REC1, REC2, WED-II, PI, WED-II, RuvC-I, BH, RuvC-II, Nuc, RuvC-III. Note that AsCas12a includes Cas4, Cas1, Cas2, CRISPR domains while Cas1 is absent in mgCas12a-1, and Cas4, Cas1, Cas2 are absent in mgCas12a-2. Further noted is that mgCas12a-1 comprises mutations of D877A and K925Q, and mgCas12a-2 comprises mutations of D873A and K925Q, in RuvC-I and RuvC-II domains, respectively.

Figure 21:
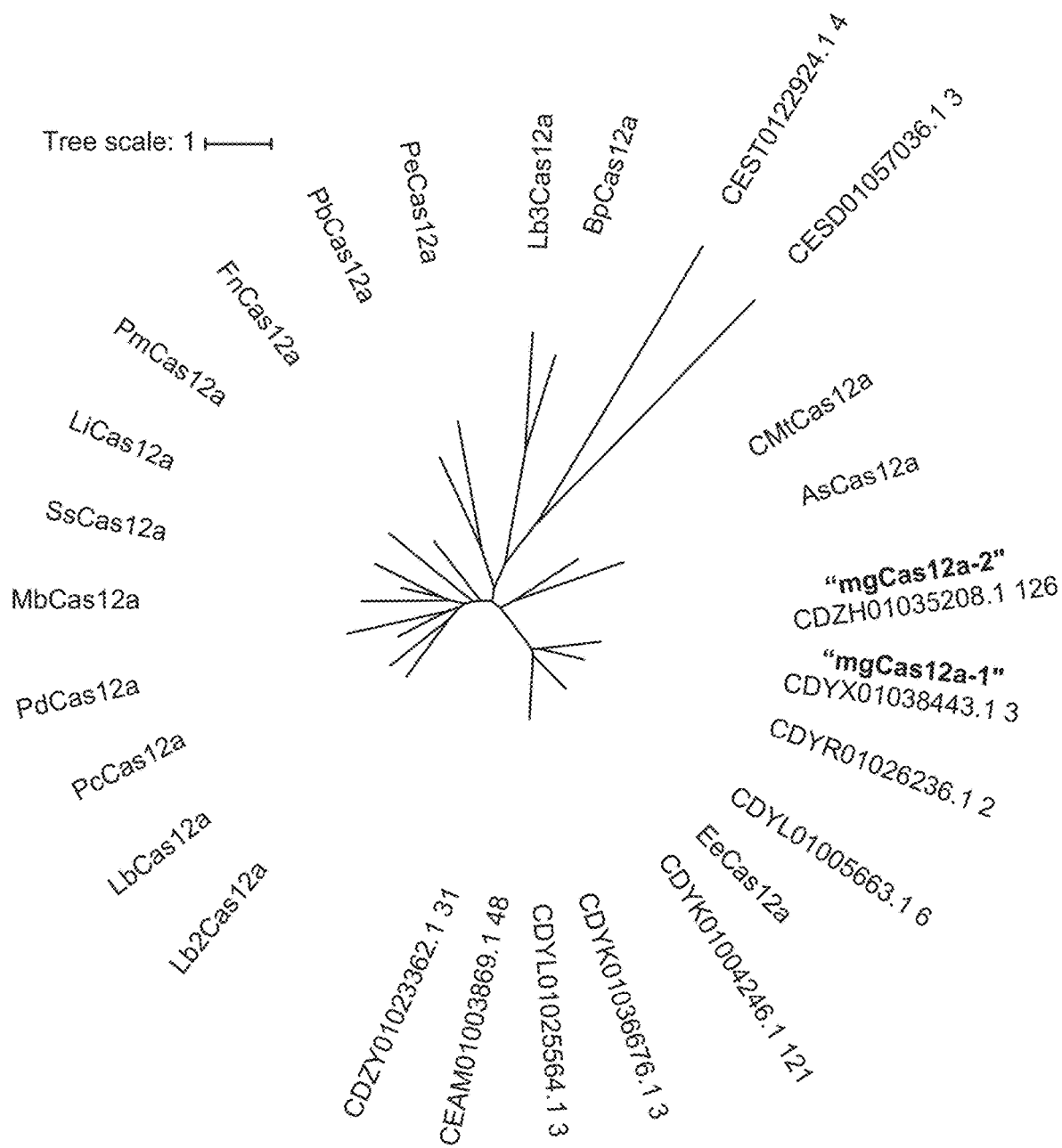
FIG. 21 shows an unrooted and evolutionary distance-based phylogenetic tree of metagenome-derived Cas12a of the present disclosure and other orthologs.

FIG. 21 shows an unrooted and evolutionary distance-based phylogenetic tree of metagenome-derived Cas12a, including mgCas12a-2 and mgCas12a-1, which resolve at right. Other Cas12 orthologs are also indicated, which clockwise from the bottom left are Lb2Cas12a, LbCas12a, PcCas12a, PdCas12a, MbCas12a, SsCas12a, LiCas12a, PmCas12a, FnCas12a, PbCas12a, PeCas12a, Lb3Cas12a, BpCas12a, CEST01022924.1 4, CESD01057036.1 3, CMtCas12a, AsCas12a, mgCas12a-2, mgCas12a-1, CDYR01026036.1 2, CDYL01005663.1 6, EeCas12a, CDYK01004246.1 121, CDYK01036676.1 3, CDYL01025564.1 3, CEAM01003869.1 48, and CDZY01023362.1 31.

Figure 22A:
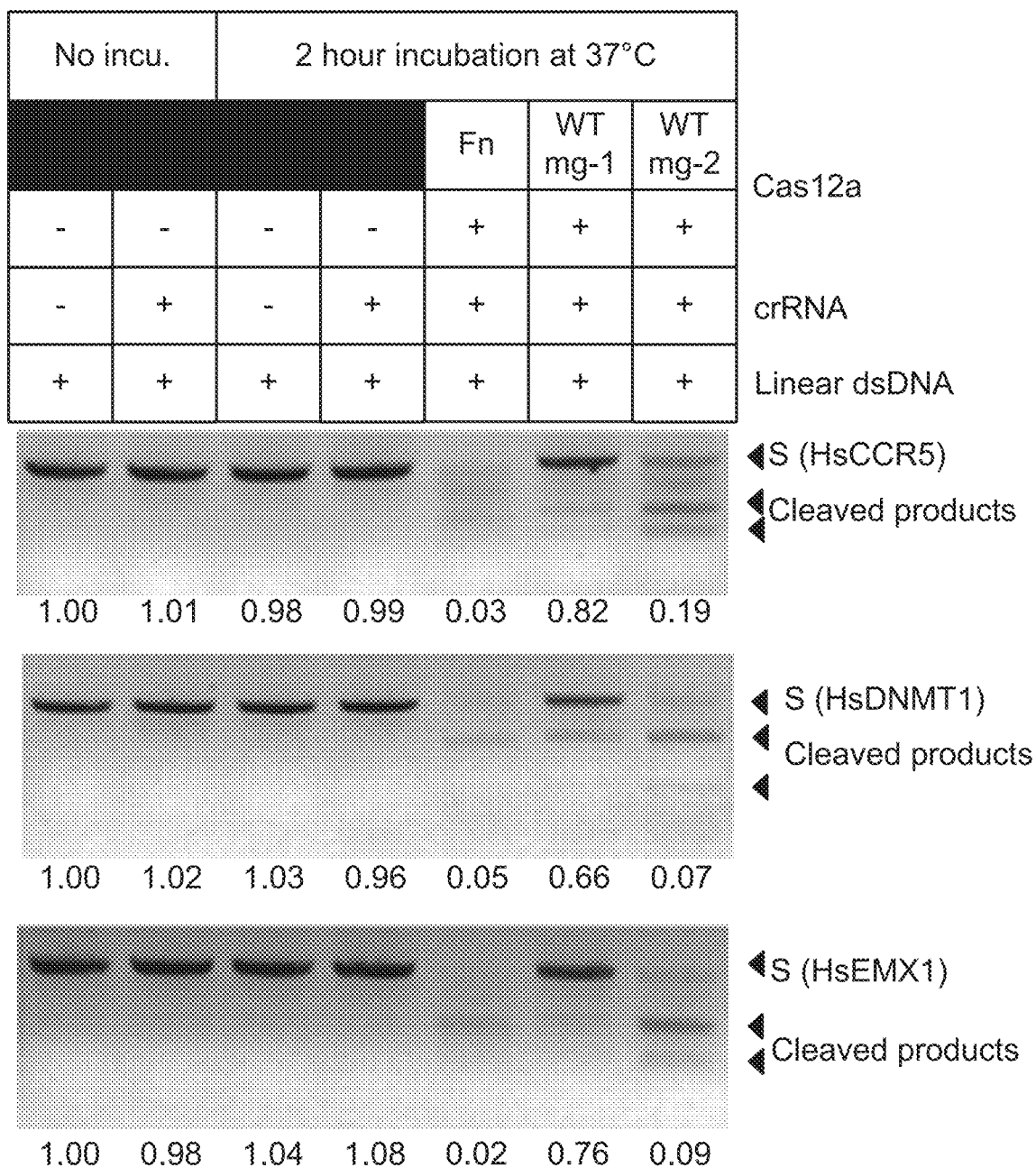
FIGS. 22A-22B show sequence-specific cleavage of dsDNA by crRNA guided-mgCas12a proteins of the present disclosure.

FIG. 22A shows at the top left a table. The first row, from left to right, shows no incubation and 2 hour incubation at 37° C. The second row, from left to right, shows 4 blank cells followed by Fn, WT mg-1, and WT mg-2. The third row indicates the presence or absence of Cas12a in the reaction. The fourth row indicates the presence or absence of crRNA in the reaction. The bottom row indicates the presence or absence of linear dsDNA. The gel immediately below shows each reaction in the table, where the linear dsDNA targets HsCCR5 and is indicated as "S" for substrate. Bands appearing by the arrow indicated as S shows uncleaved linear dsDNA. Cleaved products are also indicated by arrows and bands appearing by the arrows indicating the position of cleaved products show cleaved pieces of the target linear dsDNA. The gel immediately below shows each reaction in the table, where the linear dsDNA targets HsDNMT1 and is indicated as "S" for substrate. Bands appearing by the arrow indicated as S shows uncleaved linear dsDNA. Cleaved products are also indicated by arrows and bands appearing by the arrows indicating the position of cleaved products show cleaved pieces of the target linear dsDNA. The gel immediately below shows each reaction in the table, where the linear dsDNA targets HsEMX1 and is indicated as "S" for substrate. Bands appearing by the arrow indicated as S shows uncleaved linear dsDNA. Cleaved products are also indicated by arrows and bands appearing by the arrows indicating the position of cleaved products show cleaved pieces of the target linear dsDNA.

Figure 22B:
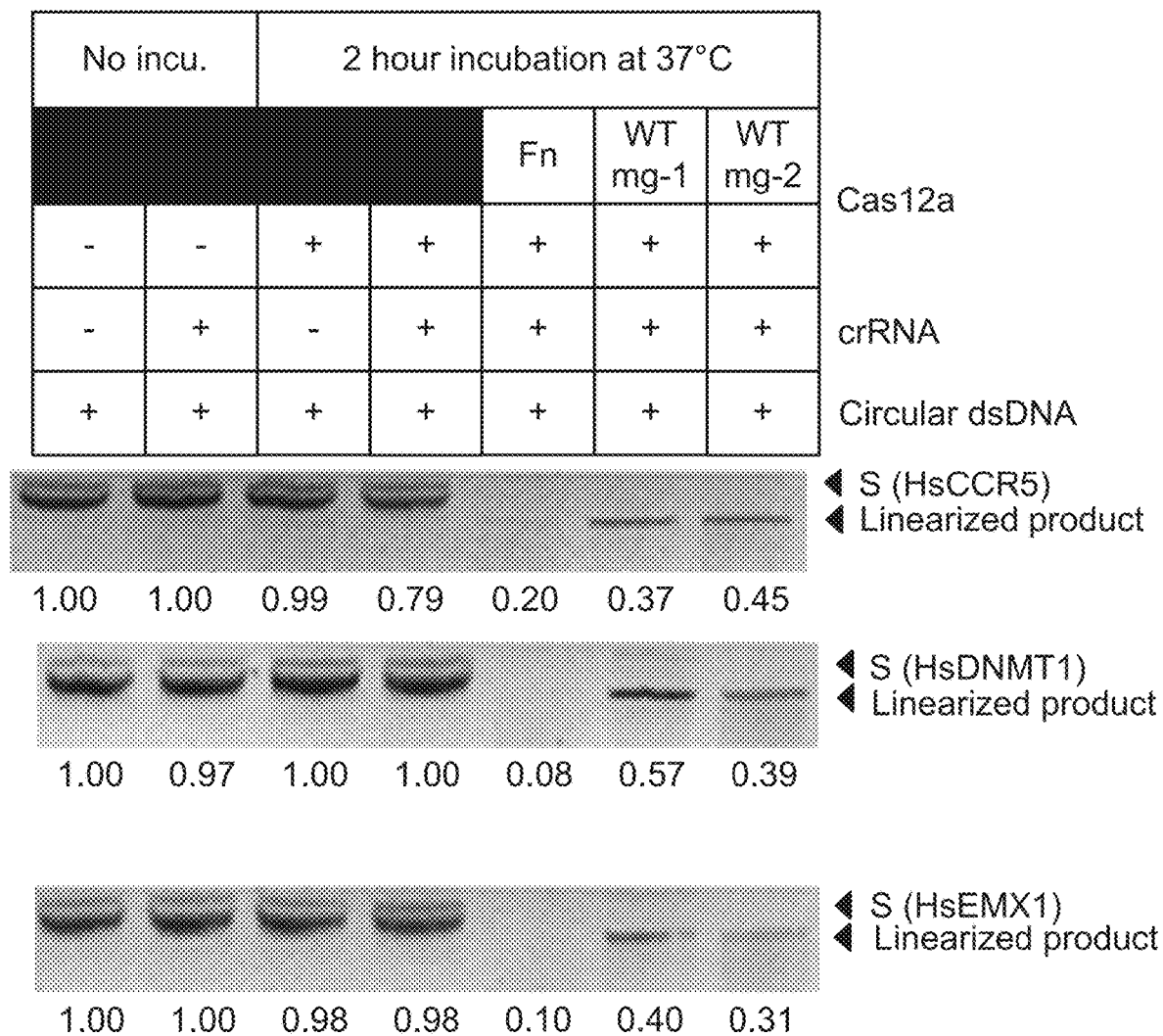

FIG. 22B shows at the top left a table. The first row, from left to right, shows no incubation and 2 hour incubation at 37° C. The second row, from left to right, shows 4 blank cells followed by Fn, WT mg-1, and WT mg-2. The third row indicates the presence or absence of Cas12a in the reaction. The fourth row indicates the presence or absence of crRNA in the reaction. The bottom row indicates the presence or absence of circular dsDNA. The gel immediately below shows each reaction in the table, where the circular dsDNA targets HsCCR5 and is indicated as "S" for substrate. Bands appearing by the arrow indicated as S shows uncleaved linear dsDNA. Linearized products are also indicated by arrows and bands appearing by the arrows indicating the position of linearized products show cleaved pieces of the target circular dsDNA. The gel immediately below shows each reaction in the table, where the circular dsDNA targets HsDNMT1 and is indicated as "S" for substrate. Bands appearing by the arrow indicated as S shows uncleaved circular dsDNA. Cleaved products are also indicated by arrows and bands appearing by the arrows indicating the position of cleaved products show cleaved pieces of the target circular dsDNA. The gel immediately below shows each reaction in the table, where the circular dsDNA targets HsEMX1 and is indicated as "S" for substrate. Bands appearing by the arrow indicated as S shows uncleaved circular dsDNA. Cleaved products are also indicated by arrows and bands appearing by the arrows indicating the position of cleaved products show cleaved pieces of the circular linear dsDNA.

Figure 23A:
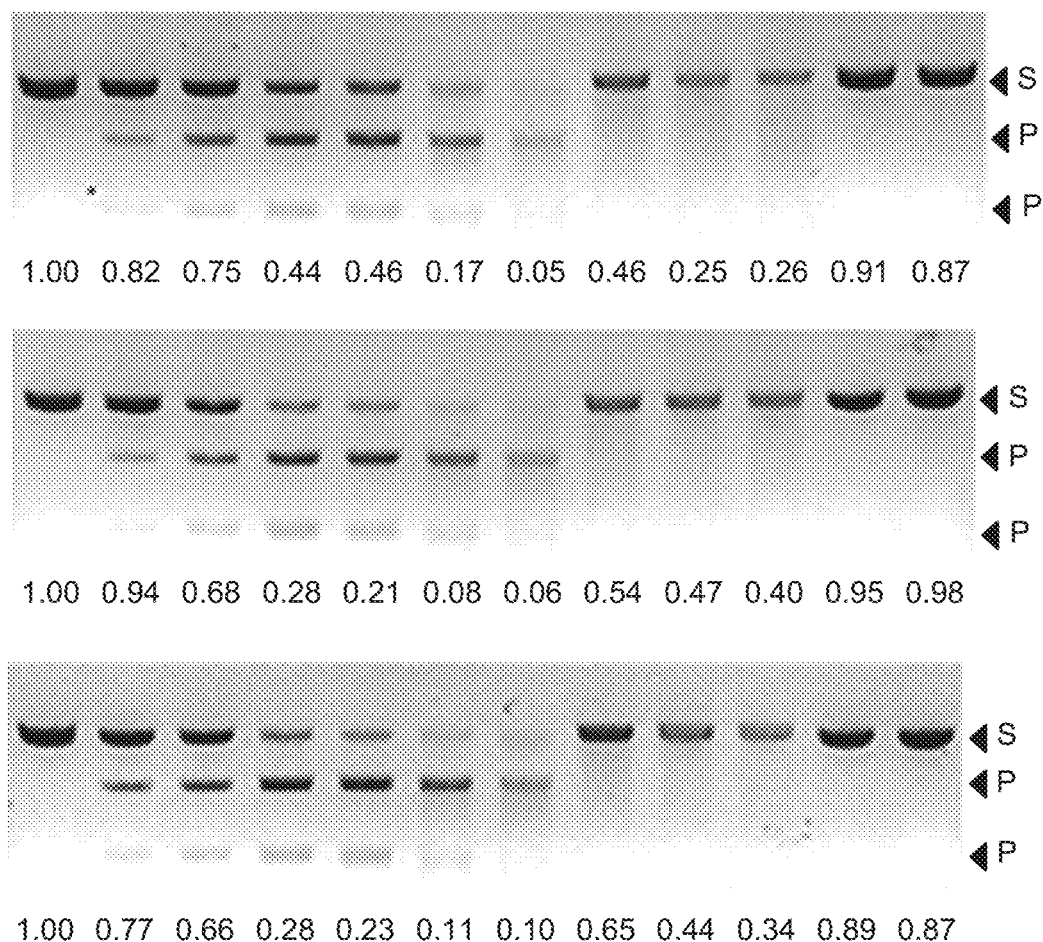
FIGS. 23A-23B shows that the mgCas12a proteins of the present disclosure can utilize three different types of Cas12a handles.

FIG. 23A shows a table of reaction conditions. The first row shows, from left to right, 0, 1 m, 10 m, 30 m, 1 h, 6 h, and 12 h. The second row indicates the presence or absence of d_mgCas12a, The third row indicates the presence or absence of WT mgCas12. The fourth row indicates the presence or absence of crRNA. The fifth row indicates the presence or absence of linear dsDNA. The gel immediately below shows each reaction in the table, where the mgCas12a-1 is complexed with a crRNA having a 5' handle from AsCas12a (the crRNA, from 5' to 3' is UAAUUUC-UACUCUUGUAGAU (SEQ ID NO: 64)). Linear dsDNA is indicated by an "S" for substrate and bands appearing at this position show uncleaved target linear dsDNA. Cleaved products are indicated by "P" for product and bands appearing at this position show cleaved segments of the target linear dsDNA. The gel immediately below shows each reaction in the table, where the mgCas12a-1 is complexed with a crRNA having a 5' handle from FnCas12a (the crRNA, from 5' to 3' is AAUUUCUACUGUUGUAGAU (SEQ ID NO: 65)). Linear dsDNA is indicated by an "S" for substrate and bands appearing at this position show uncleaved target linear dsDNA. Cleaved products are indicated by "P" for product and bands appearing at this position show cleaved segments of the target linear dsDNA. The gel immediately below shows each reaction in the table, where the mgCas12a-1 is complexed with a crRNA having a 5' handle from LbCas12a (the crRNA, from 5' to 3' is AAUUUCUACUAAGUGUAGAU (SEQ ID NO: 66)). Linear dsDNA is indicated by an "S" for substrate and bands appearing at this position show uncleaved target linear dsDNA. Cleaved products are indicated by "P" for product and bands appearing at this position show cleaved segments of the target linear dsDNA.

Figure 23B:
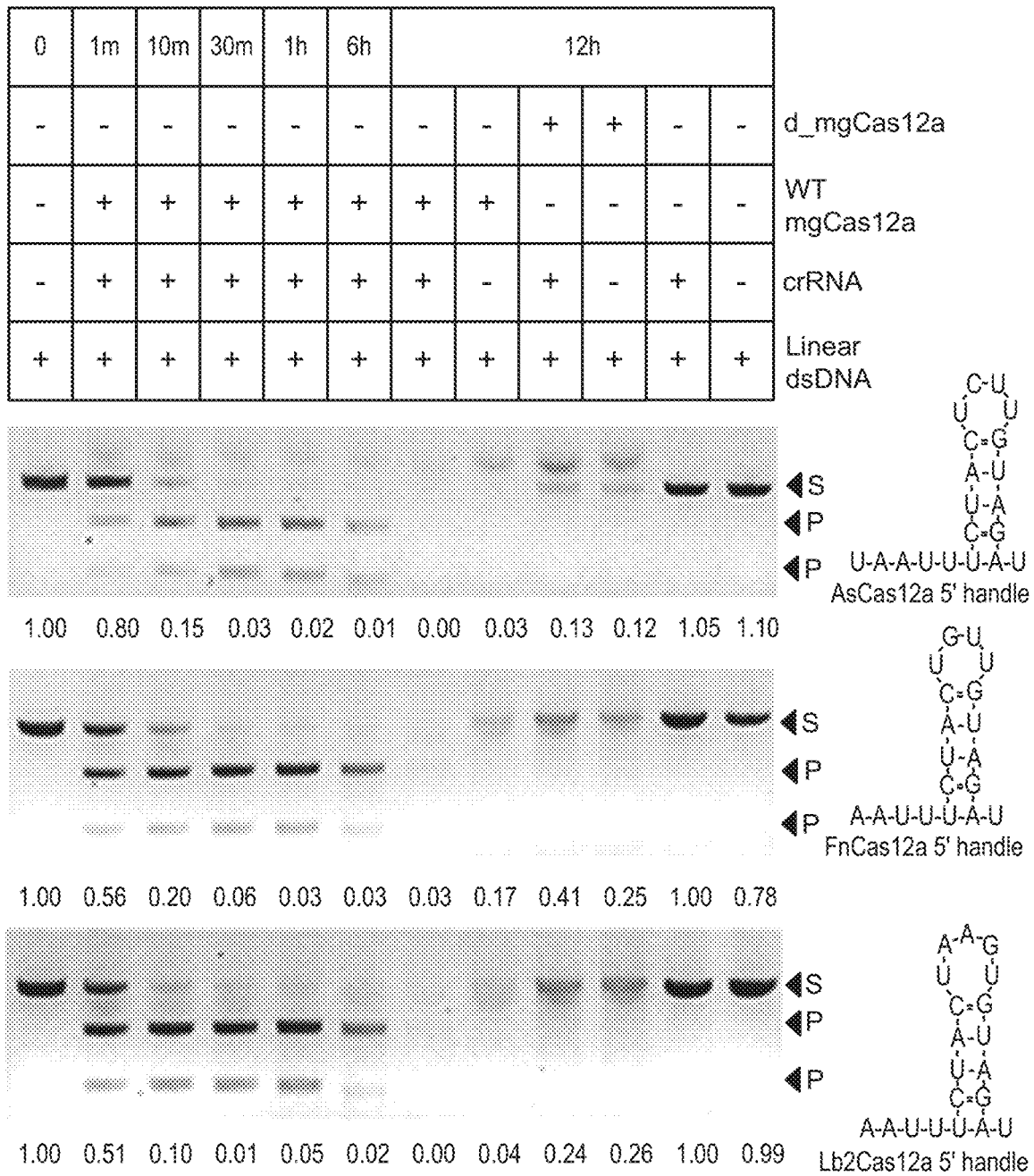

FIG. 23B shows a table of reaction conditions. The first row shows, from left to right, 0, 1 m, 10 m, 30 m, 1 h, 6 h, and 12 h. The second row indicates the presence or absence of d_mgCas12a, The third row indicates the presence or absence of WT mgCas12. The fourth row indicates the presence or absence of crRNA. The fifth row indicates the presence or absence of linear dsDNA. The gel immediately below shows each reaction in the table, where the mgCas12a-2 is complexed with a crRNA having a 5' handle from AsCas12a (the crRNA, from 5' to 3' is UAAUUUC-UACUCUUGUAGAU (SEQ ID NO: 64)). Linear dsDNA is indicated by an "S" for substrate and bands appearing at this position show uncleaved target linear dsDNA. Cleaved products are indicated by "P" for product and bands appearing at this position show cleaved segments of the target linear dsDNA. The gel immediately below shows each reaction in the table, where the mgCas12a-2 is complexed with a crRNA having a 5' handle from FnCas12a (the crRNA, from 5' to 3' is AAUUUCUACUGUUGUAGAU (SEQ ID NO: 65)). Linear dsDNA is indicated by an "S" for substrate and bands appearing at this position show uncleaved target linear dsDNA. Cleaved products are indicated by "P" for product and bands appearing at this position show cleaved segments of the target linear dsDNA. The gel immediately below shows each reaction in the table, where the mgCas12a-2 is complexed with a crRNA having a 5' handle from LbCas12a (the crRNA, from 5' to 3' is AAUUUCUACUAAGUGUAGAU (SEQ ID NO: 66)). Linear dsDNA is indicated by an "S" for substrate and bands appearing at this position show uncleaved target linear dsDNA. Cleaved products are indicated by "P" for product and bands appearing at this position show cleaved segments of the target linear dsDNA.

FIG. 24 shows a table at top, which from left to right summarizes reaction conditions. The top row from left to right indicates time points of 0 for two columns, 12 hour incubation at 37° C. for nine columns, and 24 hour incubation at 37° C. for nine columns. The second row indicates the Cas12a in each reaction and shows, from left to right, 4 blank cells, followed by WT mg-1, d_mg-1, WT mg-2, d_mg-2, As, Fn, Lb, 2 blank cells, followed by WT mg-1, d_mg-1, WT mg-2, d_mg-2, As, Fn, and Lb. The third row indicates the presence or absence of Cas12a. The fourth row indicates the presence or absence of crRNA. The fifth row indicates the presence or absence of linear dsDNA. The gel immediately below shows each reaction in the table, where each tested Cas12a is complexed with a crRNA targeted to HsCCR5 linear dsDNA. Linear dsDNA is indicated by an "S" for substrate and bands appearing at this position show uncleaved target linear dsDNA. Cleaved products are indicated by "P" for product and bands appearing at this position show cleaved segments of the target linear dsDNA. The gel immediately below shows each reaction in the table, where each tested Cas12a is complexed with a crRNA targeted to HsDNMT1 linear dsDNA. Linear dsDNA is indicated by an "S" for substrate and bands appearing at this position show uncleaved target linear dsDNA. Cleaved products are indicated by "P" for product and bands appearing at this position show cleaved segments of the target linear dsDNA. The gel immediately below shows each reaction in the table, where each tested Cas12a is complexed with a crRNA targeted to HsEMX1 linear dsDNA. Linear dsDNA is indicated by an "S" for substrate and bands appearing at this position show uncleaved target linear dsDNA. Cleaved products are indicated by "P" for product and bands appearing at this position show cleaved segments of the target linear dsDNA.

FIG. 25A shows a table at top summarizing reaction conditions for each reaction. The first row shows, from left to right, 0, 1m, 10m, 30m, 1h, 2h, 6h, 12h, 24h, and 48h for the last two columns. The second row indicates the presence or absence of Cas12a in each reaction. The third row indicates the presence or absence of linear dsDNA in each reaction. The gel immediately below shows each reaction in the table, where FnCas12a is complexed with a crRNA targeted to linear dsDNA. Linear dsDNA is indicated by an "S" for substrate and bands appearing at this position show uncleaved target linear dsDNA. The gel immediately below shows each reaction in the table, where WT mgCas12a-1 is complexed with a crRNA targeted to linear dsDNA. Linear dsDNA is indicated by an "S" for substrate and bands appearing at this position show uncleaved target linear dsDNA. The gel immediately below shows each reaction in the table, where WT mgCas12a-2 is complexed with a crRNA targeted to linear dsDNA. Linear dsDNA is indicated by an "S" for substrate and bands appearing at this position show uncleaved target linear dsDNA.

FIG. 25B shows a graph of incubation period versus cleaved target dsDNA. The x-axis shows incubation period, which from left to right is, dsDNA only, 1m, 10m, 30m, 1h, 2h, 6h, 12h, 24h, and 48h. The y-axis shows cleaved target dsDNA which ranges from 0.00 to 1.00 in increments of 0.20. The solid line shows data for FnCas12a. The dashed line shows data for WT mgCas12a-1. The dotted line shows data for WT mgCas12a-2.

Figure 26A:
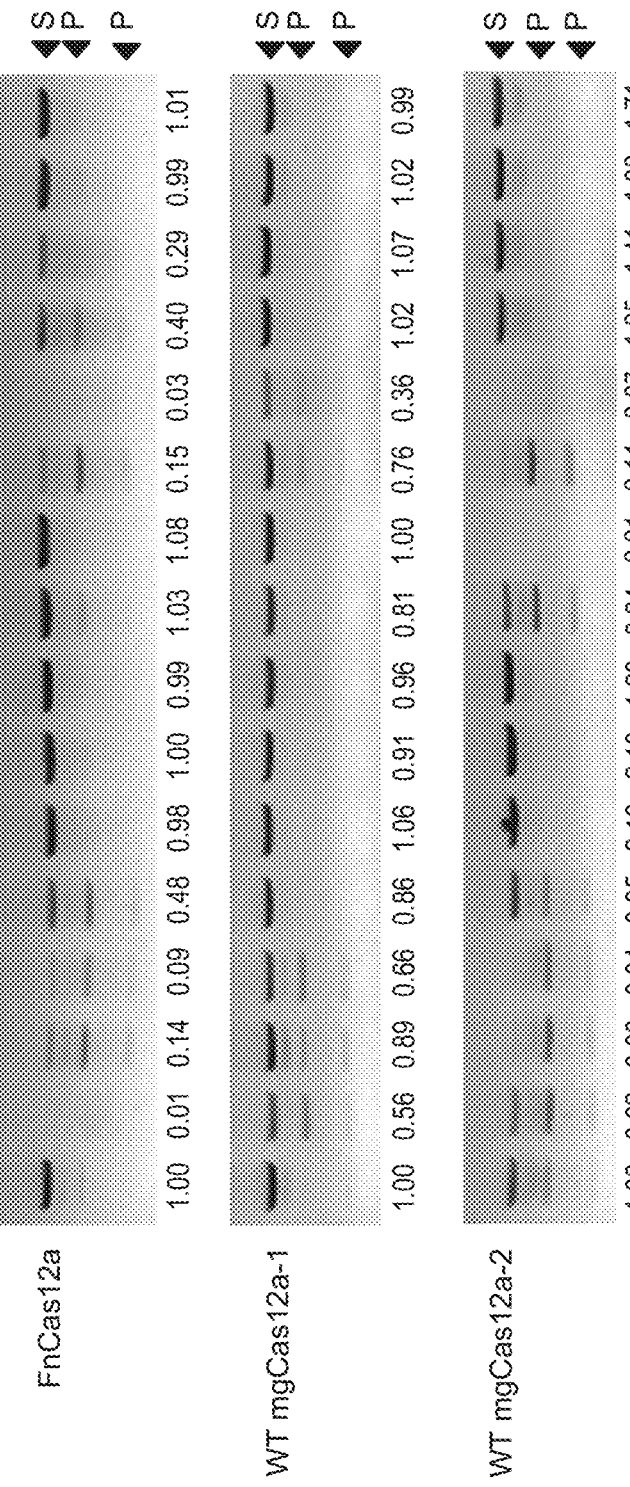
FIGS. 26A-26D show the activity of each Cas12a-RNP in the presence of different divalent cation.

FIG. 26A shows a table at top summarizing reaction conditions for each reaction. The first two rows show the divalent cations which, from left to right, DW, Control, $CaCl_2$) at 10 and 100, $CoCl_2$ at 10 and 100, $CuSO_4$ at 10 and 100, $FeCl_2$ at 10 and 100, $MnSO_4$ at 10 and 100, $NiSO_4$ at 10 and 100, and $ZnSO_4$ at 10 and 100. The third row shows the presence or absence of Cas12a in each reaction. The fourth row shows the presence or absence of crRNA in each reaction. The fifth row shows the presence or absence of linear dsDNA in each reaction. The gel immediately below shows each reaction in the table, where FnCas12a is complexed with a crRNA targeted to linear dsDNA. Linear dsDNA is indicated by an "S" for substrate and bands appearing at this position show uncleaved target linear dsDNA. Cleaved products are indicated by "P" for product and bands appearing at this position show cleaved segments of the target linear dsDNA. The gel immediately below shows each reaction in the table, where WT mgCas12a-1 is complexed with a crRNA targeted to linear dsDNA. Linear dsDNA is indicated by an "S" for substrate and bands appearing at this position show uncleaved target linear dsDNA. Cleaved products are indicated by "P" for product and bands appearing at this position show cleaved segments of the target linear dsDNA. The gel immediately below shows each reaction in the table, where WT mgCas12a-2 is complexed with a crRNA targeted to linear dsDNA. Linear dsDNA is indicated by an "S" for substrate and bands appearing at this position show uncleaved target linear dsDNA. Cleaved products are indicated by "P" for product and bands appearing at this position show cleaved segments of the target linear dsDNA.

Figure 26B:
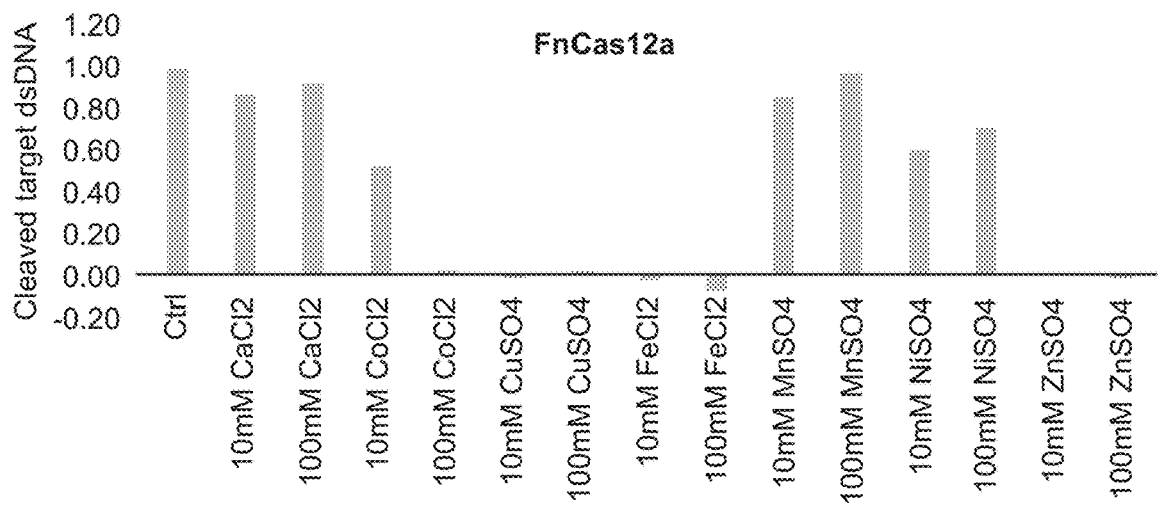

FIG. 26B shows a graph of cleaved target dsDNA versus various reaction conditions with divalent cations for FnCas12a complexed with crRNA targeting linear dsDNA. The x-axis shows reaction conditions, which from left to right are, Ctrl, 10 mM $CaCl_2$), 100 mM $CaCl_2$), 10 mM $CoCl_2$, 100 mM $CoCl_2$, 10 mM $CuSO_4$, 100 mM $CuSO_4$, 10 mM $FeCl_2$, 100 mM $FeCl_2$, 10 mM $MnSO_4$, 100 mM $MnSO_4$, 10 mM $NiSO_4$, 100 mM $NiSO_4$, 10 mM $ZnSO_4$, and 100 mM $ZnSO_4$. The y-axis shows cleaved target dsDNA ranging from −0.20 to 1.20 in increments of 0.20.

Figure 26C:
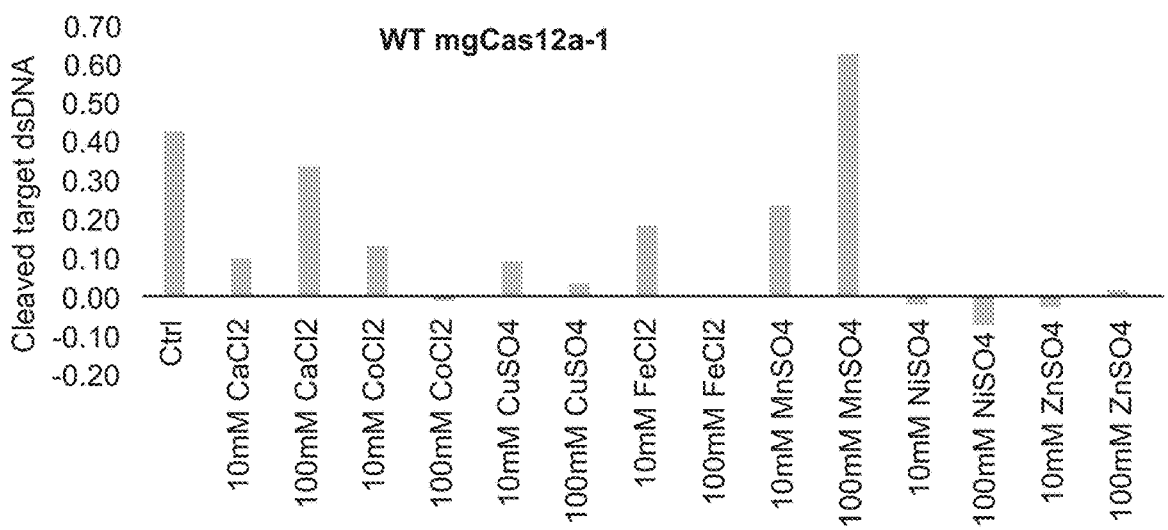

FIG. 26C shows a graph of cleaved target dsDNA versus various reaction conditions with divalent cations for WT mgCas12a-1 complexed with crRNA targeting linear dsDNA. The x-axis shows reaction conditions, which from left to right are, Ctrl, 10 mM $CaCl_2$), 100 mM $CaCl_2$), 10 mM $CoCl_2$, 100 mM $CoCl_2$, 10 mM $CuSO_4$, 100 mM $CuSO_4$, 10 mM $FeCl_2$, 100 mM $FeCl_2$, 10 mM $MnSO_4$, 100 mM $MnSO_4$, 10 mM $NiSO_4$, 100 mM $NiSO_4$, 10 mM $ZnSO_4$, and 100 mM $ZnSO_4$. The y-axis shows cleaved target dsDNA ranging from −0.20 to 0.70 in increments of 0.10.

Figure 26D:
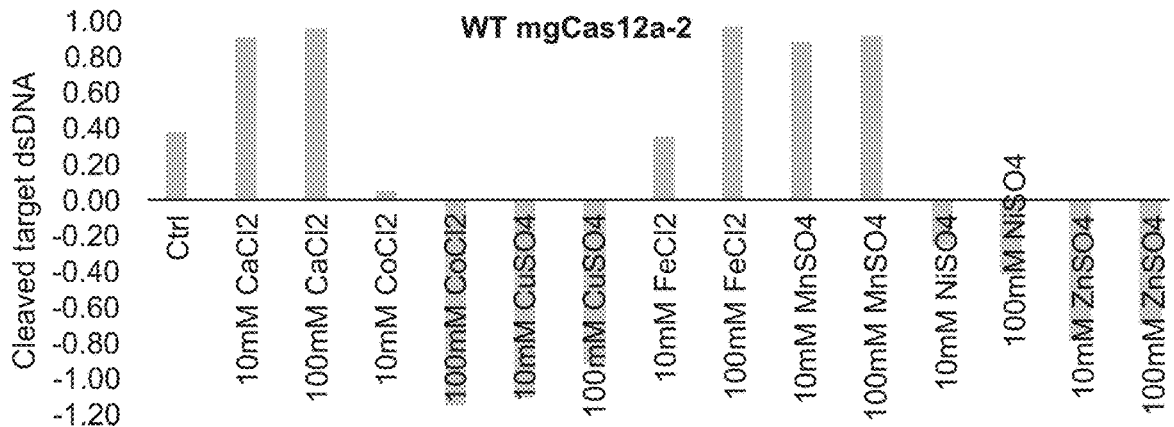

FIG. 26D shows a graph of cleaved target dsDNA versus various reaction conditions with divalent cations for WT mgCas12a-2 complexed with crRNA targeting linear dsDNA. The x-axis shows reaction conditions, which from left to right are, Ctrl, 10 mM $CaCl_2$), 100 mM $CaCl_2$), 10 mM $CoCl_2$, 100 mM $CoCl_2$, 10 mM $CuSO_4$, 100 mM $CuSO_4$, 10 mM $FeCl_2$, 100 mM $FeCl_2$, 10 mM $MnSO_4$, 100 mM $MnSO_4$, 10 mM $NiSO_4$, 100 mM $NiSO_4$, 10 mM $ZnSO_4$, and 100 mM $ZnSO_4$. The y-axis shows cleaved target dsDNA ranging from −1.20 to 1.00 in increments of 0.20.

Figure 27:
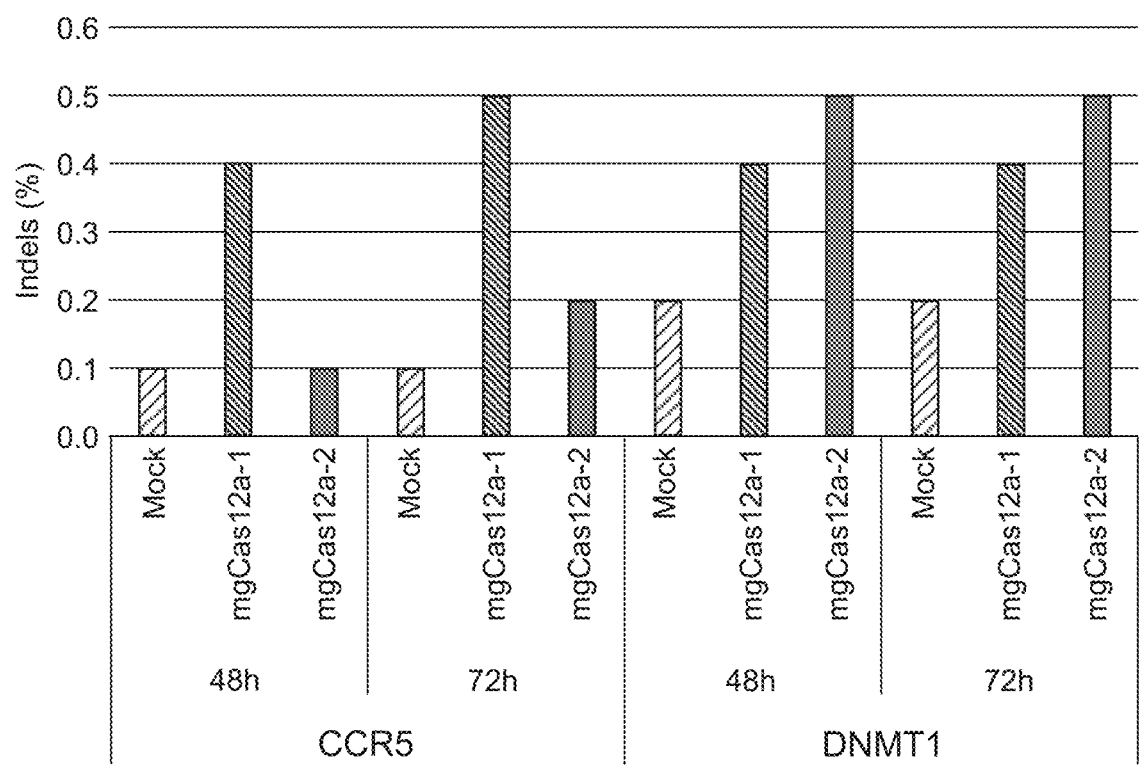
FIG. 27 shows a graph of editing efficiencies of mgCas12a-1, mgCas12a-2, and mock (negative control).

FIG. 27 shows a graph of reaction conditions versus indels (%). The x-axis shows, from left to right, Mock at 48 h targeting CCR5, mgCas12a-1 at 48 h targeting CCR5, mgCas12a-2 at 48 h targeting CCR5, Mock at 72 h targeting CCR5, mgCas12a-1 at 72 h targeting CCR5, mgCas12a-2 at 72 h targeting CCR5, Mock at 48 h targeting DNMT1, mgCas12a-1 at 48 h targeting DNMT1, mgCas12a-2 at 48 h targeting DNMT1, Mock at 72 h targeting DNMT1, mgCas12a-1 at 72 h targeting DNMT1, and mgCas12a-2 at 72 h targeting DNMT1. The y-axis shows indels (%) ranging from 0.0 to 0.6 in increments of 0.1.

Figure 28:
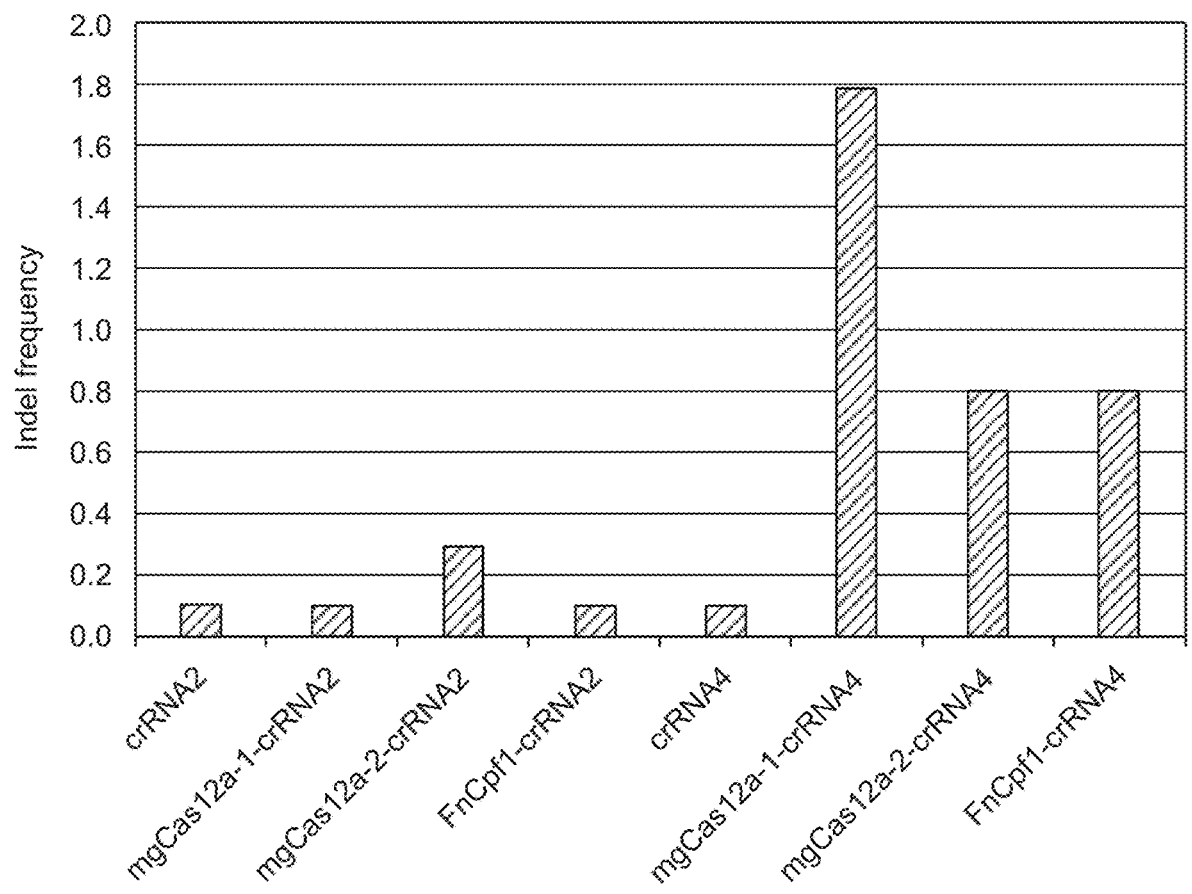
FIG. 28 shows a graph of indel frequency targeting nuclease protein in Nicotiana benthamiana. The gene editing efficiency of mgCas12a-1 was twice that of FnCpf1.

FIG. 28 shows a graph of Cas12a tested versus indel frequency (%). The x-axis shows the Cas12a and crRNA tested, which from left to right is crRNA2, mgCas12a-1-crRNA2, mgCas12a-2-crRNA2, FnCpf1-crRNA2, crRNA4, mgCas12a-1-crRNA4, mgCas12a-2-crRNA4, and FnCpf1-crRNA4. The y-axis shows indel frequency (%) ranging from 0.0 to 2.0 in increments of 0.2.

A "functional domain" of a protein RNA guided endonuclease of the present disclosure may be a putative transposase DNA binding domain, such as residue 829 through residue 991 of SEQ ID NO: 1, or residue 825 through residue 996 of SEQ ID NO: 3.

"Sequence identity" as used herein may describe the number, the fraction, or the percentage of nucleobases or amino acid residues that share identity, or are common, between two sequences being compared. Percent (%) sequence identity with respect to a reference polypeptide sequence is the percentage of amino acid residues in a first sequence (e.g., a candidate sequence) that are identical with the amino acid residues in a second sequence (e.g., the reference polypeptide sequence), after aligning the sequences, optionally introducing gaps to achieve the maximum percent sequence identity, and, optionally, not accounting for conservative substitutions as part of the sequence identity. Similarly, percent (%) sequence identity with respect to a reference nucleobase sequence is the percentage of nucleobases in a first sequence (e.g., a candidate sequence) that are identical with the nucleobases in a second sequence (e.g., the nucleobase reference sequence), after aligning the sequences, optionally introducing gaps to achieve the maximum percent sequence identity, and, optionally, not accounting for conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, percent (%) amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

"Consecutive residues" as used herein may describe nucleobases or amino acid residues that are immediately adjacent to each other in a given sequence.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 92%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Sequence identity, such as for the purpose of assessing percent complementarity, may be measured by any suitable alignment algorithm, including but not limited to the Needleman-Wunsch algorithm, the BLAST algorithm, or the Smith-Waterman algorithm, optionally with default settings). Optimal alignment may be assessed using any suitable parameters of a chosen algorithm, including default parameters.

Nucleic acid and amino acid sequence homology is determined according to any suitable method known in the art, including but not limited to those described herein.

For example, alignments and searches for similar sequences can be performed using the U.S. National Center for Biotechnology Information (NCBI, Bethesda, Md.) program, MegaBLAST. Use of this program with options for percent identity set at, for example, 70% for amino acid sequences, or set at, for example, 90% for nucleotide sequences, will identify those sequences with 70%, or 90%, or greater sequence identity to the query sequence. Other software known in the art is also available for aligning and/or searching for similar sequences, e.g., sequences at least 70% or 90% identical to an information string containing a secretion signal sequence herein. For example, sequence alignments for comparison to identify sequences at least 70% or 90% identical to a query sequence is often performed by use of, e.g., the GAP, BESTFIT, BLAST, FASTA, and TFASTA programs available in the GCG Sequence Analysis Software Package (available from the Genetics Computer Group, University of Wisconsin Biotechnology Center, 1710 University Avenue, Madison, Wis. 53705), with the default parameters as specified therein, plus a parameter for the extent of sequence identity set at the desired percentage. Also, for example, the CLUSTAL program (available in the PC/Gene software package from Intelligenetics, Mountain View, Calif.) may be used.

These and other sequence alignment methods may be conducted by manual alignment, by visual inspection, or by manual or automatic application of a sequence alignment algorithm, such as any of those embodied by the above-described programs. Various useful algorithms include, e.g.: the similarity search method described in W. R. Pearson & D. J. Lipman, Proc. Natl. Acad. Sci. USA 85:2444-48 (April 1988); the local homology method described in T. F. Smith & M. S. Waterman, in Adv. Appl. Math. 2:482-89 (1981) and in J. Molec. Biol. 147:195-97 (1981); the homology alignment method described in S. B. Needleman & C. D. Wunsch, J. Molec. Biol. 48(3):443-53 (March 1970); and the various methods described, e.g., by W. R. Pearson, in Genomics 11(3):635-50 (November 1991); by W. R. Pearson, in Methods Molec. Biol. 24:307-31 and 25:365-89 (1994); and by D. G. Higgins & P. M. Sharp, in Comp. Appl'ns in Biosci. 5:151-53 (1989) and in Gene 73(1):237-44 (15 Dec. 1988).

GAP Version 10, which uses the algorithm of Needleman and Wunsch (1970) supra, can be used to determine sequence identity or similarity using the following parameters: percent (%) identity and percent (%) similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent or similar programs may also be used as will be understood by one of skill in the art. For example, a sequence comparison program can be used that, for any two sequences in question, generates an alignment having identical nucleotide residue matches and an identical percent sequence identity when compared to the corresponding alignment generated by GAP Version 10. In some embodiments, the sequence comparison is performed across the entirety of the query or the subject sequence, or both.

NUMBERED EMBODIMENTS

The following embodiments recite non-limiting permutations of combinations of features disclosed herein. Other permutations of combinations of features are also contemplated. In particular, each of these numbered embodiments is contemplated as depending from or relating to every previous or subsequent numbered embodiment, independent of their order as listed. 1. A composition comprising: a protein having at least 80% sequence identity with residue 829 through residue 991 of SEQ ID NO: 1, wherein the protein comprises a Lysine at position 925; and a guide RNA comprising a sequence that is reverse complementary to a eukaryotic nucleic acid sequence comprising from 6 to 60 bases. 2. A composition comprising: a protein having at least 80% sequence identity with residue 825 through residue 996 of SEQ ID NO: 3, wherein the protein comprises a Lysine at position 930; and a guide RNA comprising a sequence that is reverse complementary to a eukaryotic nucleic acid sequence comprising from 6 to 60 bases. 3. A composition comprising: a protein having at least 80% sequence identity with SEQ ID NO: 1, wherein the protein comprises a Lysine at position 925; and a guide RNA comprising a sequence that is reverse complementary to a eukaryotic nucleic acid sequence comprising from 6 to 60 bases. 4. A composition comprising: a protein having at least 80% sequence identity with SEQ ID NO: 3, wherein the protein comprises a Lysine at position 930; and a guide RNA comprising a sequence that is reverse complementary to a eukaryotic nucleic acid sequence comprising from 6 to 60 bases. 5. The composition of any one of embodiments 1-4, wherein the eukaryotic nucleic acid sequence is a human nucleic acid sequence. 6. The composition of any one of embodiments 1-4, wherein the eukaryotic nucleic acid sequence is a plant nucleic acid sequence. 7. The composition of any one of embodiments 1 or 3, wherein a nucleotide sequence encoding for SEQ ID NO: 1 comprises at least 80% sequence identity to SEQ ID NO: 2. 8. The composition of any one of embodiments 2 or 4, wherein a nucleotide sequence encoding for SEQ ID NO: 3 comprises at least 80% sequence identity to SEQ ID NO: 4. 9. The composition of any one of embodiments 1-8, wherein the protein is from the Eubacteriaceae family. 10. The composition of any one of embodiments 1-9, wherein the protein comprises a nuclease. 11. The composition of embodiment 10, wherein the nuclease comprises a type V CRISPR-associated protein. 12. The composition of embodiment 11, the type V CRISPR-associated protein comprises a Cas12a protein. 13. The composition of embodiment 12, wherein the Cas12a protein is metagenomically mined. 14. The composition of any one of embodiment 5-13, wherein the human nucleic acid sequence is implicated in cancer. 15. The composition of any one of embodiments 1-14, wherein the composition comprises a pH of from 7 to 7.9. 16. The composition of any one of embodiments 1-15, wherein the composition comprises a pH of 7. 17. The composition of any one of embodiments 1-16, wherein the composition is formulated in a buffer. 18. The composition of embodiment 17, wherein the buffer comprises Bis-Tris Propane-HCl. 19. The composition of any one of embodiments 17-18, wherein the buffer comprises $MgCl_2$. 20. The composition of any one of embodiments 17-19, wherein the buffer comprises bovine serum albumin. 21. The composition of any one of embodiments 17-20, wherein the buffer comprises from 0.1 to 50 mM Bis-Tris Propane-HCl. 22. The composition of any one of embodiments 17-21, wherein the buffer comprises from 0.1 to 50 mM $MgCl_2$. 23. The composition of any one of embodiments 17-22, wherein the buffer comprises from 1 to 500 µg/ml bovine serum albumin, 24. The composition of any one of embodiments 17-23, wherein the buffer comprises 10 mM Bis-Tris Propane-HCl. 25. The composition of any one of embodiments 17-24, wherein the buffer comprises 10 mM $MgCl_2$. 26. The composition of any one of embodiments 17-25, wherein the buffer comprises 100 µg/ml of bovine serum albumin. 27. The composition of any one of embodiments 1-26, wherein the protein comprises a purification tag. 28. The composition of embodiment 27, wherein the purification tag comprises at least one tag selected from the group consisting of a His tag, a FLAG tag, an AU1 epitope tag, an AU5 epitope tag, a bacteriophage T7 tag, a bacteriophage V5 epitope tag, a Bluetongue virus tag (B-tag), a Glu-Glu tag (EE-tag), an HSV epitope tag, a KT3 epitope tag, a Myc epitope tag, a PDZ ligand tag, a polyarginine tag, a polyaspartate tag, a polycysteine tag, a polyphenylalanine tag, a protein C tag, an S1-tag, an S-tag, a Step-tag, and a VSV-G tag. 29. The composition of any one of embodiments 1-28, wherein the guide RNA comprises an A-rich protospacer adjacent motif (PAM) sequence, a G-rich PAM sequence, a T-rich PAM sequence, or a C-rich PAM sequence. 30. The composition of any one of embodiments 1-29, wherein the guide RNA comprises a T-rich PAM sequence. 31. The composition of any one of embodiments 29-30, wherein the PAM sequence comprises 3 T nucleobases, 2 T nucleobases, or 1 T nucleobase. 32. The composition of any one of embodiments 29-31, wherein the PAM sequence comprises TTTN. 33. The composition of any one of embodiments 5-32, wherein the human nucleic acid sequence comprises a region in KRAS, HER2/neu, PD-1, TCR, p53, CCR5, DNMT1, EMX1, and LKB1. 34. The composition of any one of embodiments 14-33, wherein the cancer comprises a bladder cancer, a bone cancer, a blood cancer, a breast cancer, a black colored tumor, a thyroid cancer, a parathyroid cancer, a bone marrow cancer, a laryngopharyngeal cancer, a laryngeal cancer, a lung cancer, an esophagus cancer, a pancreatic cancer, a colorectal cancer, a gastric cancer, a tongue cancer, a skin cancer, a brain tumor, a uterine cancer, a head or neck cancer, a gallbladder cancer, an oral cancer, a central nervous system tumor, or a liver cancer. 35. The composition of any one of embodiments 1-34, wherein the guide RNA sequence comprises from 1 to 100 nucleotides. 36. The composition of any one of embodiments 1-35, wherein the composition exhibits at least 2-fold than AsCas12a, FnCas12a, or LbCas12a. 37. The composition of any one of embodiments 1-36, wherein the guide RNA comprises a crRNA and a tracrRNA. 38. The composition of embodiment 37, wherein the crRNA comprises a 5' repeat recognition sequence of AAUU. 39. The composition of any one of embodiments 1-38, wherein protein exhibits cleavage activity in the presence of $CaCl2$, $CoCl2$, $FeCl2$, $MnSO_4$, or any combination thereof 40. A method of gene editing, wherein the method comprises contacting a cell with the composition of any one of embodiments 1-39; binding the guide RNA to the eukaryotic nucleic acid sequence; and cleaving the eukaryotic nucleic acid sequence. 41. A method of gene editing, wherein the method comprises providing a composition comprising a protein having at least 80% sequence identity with residue 829 through residue 991 of SEQ ID NO: 1, wherein the protein comprises a Lysine at position 925; and a guide RNA comprising a sequence that is reverse complementary to a nucleic acid sequence comprising from 6 to 60 bases; contacting a cell with the composition; binding the guide RNA to a eukaryotic nucleic acid sequence; and cleaving the nucleic acid sequence. 42. A method of gene editing, wherein the method comprises providing a composition comprising a protein having at least 80% sequence identity with residue 825 through residue 996 of SEQ ID NO: 3, wherein the protein comprises a Lysine at position 930; and a guide RNA comprising a sequence that is reverse complementary to a nucleic acid sequence comprising from 6 to 60 bases; contacting a cell with the composition; binding the guide RNA to a eukaryotic nucleic acid sequence; and cleaving the nucleic acid sequence. 43. A method of gene editing, wherein the method comprises providing a composition comprising a protein having at least 80% sequence identity with SEQ ID NO: 1, wherein the protein comprises a Lysine at position 925; and a guide RNA comprising a sequence that is reverse complementary to a nucleic acid sequence comprising from 6 to 60 bases; contacting a cell with the composition; binding the guide RNA to a eukaryotic nucleic acid sequence; and cleaving the nucleic acid sequence. 44. A method of gene editing, wherein the method comprises providing a composition comprising a protein having at least 80% sequence identity with SEQ ID NO: 3, wherein the protein comprises a Lysine at position 930; and a guide RNA comprising a sequence that is reverse complementary to a nucleic acid sequence comprising from 6 to 60 bases; contacting a cell with the composition; binding the guide RNA to a eukaryotic nucleic acid sequence; and cleaving the nucleic acid sequence. 45. The method of any one of embodiments 41-44, wherein the eukaryotic nucleic acid sequence is a human nucleic acid sequence. 46. The method of any one of embodiments 41-44, wherein the eukaryotic nucleic acid sequence is a plant nucleic acid sequence. 47. The method of any one of embodiments 41 or 43, wherein a nucleotide sequence encoding for SEQ ID NO: 1 comprises at least 80% sequence identity to SEQ ID NO: 2. 48. The composition of any one of embodiments 42 or 44, wherein a nucleotide sequence encoding for SEQ ID NO: 3 comprises at least 80% sequence identity to SEQ ID NO: 4. 49. The method of any one of embodiments 36-48, wherein the cell comprises a cancer cell. 50. The method of any one of embodiments 36-49, wherein the contacting the cell with the composition comprises administering the composition to a subject in need thereof 51. The method of embodiment 50, wherein the administering comprises intravenous, subcutaneous, intramuscular, oral, or mucosal administration. 52. The method of any one of embodiments 36-51, wherein the contacting the cell with the composition comprises administering the composition to the cell ex vivo. 53. The method of any one of embodiments 41-52, wherein the protein is from the Eubacteriaceae family. 54. The method of any one of embodiments 41-53, wherein the protein comprises a nuclease. 55. The method of embodiment 54, wherein the nuclease comprises a type V CRISPR-associated protein. 56. The method of embodiment 55, the type V CRISPR-associated protein comprises a Cas12a protein. 57. The method of embodiment 56, wherein the Cas12a protein is metagenomically mined. 58. The method of any one of embodiment 45-57, wherein the human nucleic acid sequence is implicated in cancer. 59. The method of any one of embodiments 41-58, wherein the method comprises cleaving the nucleic acid sequence at a pH of from 7 to 7.9. 60. The method of any one of embodiments 41-59, wherein the method comprises cleaving the nucleic acid sequence at a pH of 7. 61. The method of any one of embodiments 41-60, wherein the composition is formulated in a buffer. 62. The method of embodiment 61, wherein the buffer comprises Bis-Tris Propane-HCl. 63. The method of any one of embodiments 61-62, wherein the buffer comprises MgCl2. 64. The method of any one of embodiments 61-63, wherein the buffer comprises bovine serum albumin. 65. The method of any one of embodiments 61-64, wherein the buffer comprises from 0.1 to 50 mM Bis-Tris Propane-HCl. 66. The method of any one of embodiments 61-65, wherein the buffer comprises from 0.1 to 50 mM MgCl2. 67. The method of any one of embodiments 61-66, wherein the buffer comprises from 1 to 500 µg/ml bovine serum albumin, 68. The method of any one of embodiments 61-67, wherein the buffer comprises 10 mM Bis-Tris Propane-HCl. 69. The method of any one of embodiments 61-68, wherein the buffer comprises 10 mM MgCl2. 70. The method of any one of embodiments 61-69, wherein the buffer comprises 100 µg/ml of bovine serum albumin. 71. The method of any one of embodiments 41-70, wherein the protein comprises a purification tag. 72. The method of embodiment 71, wherein the purification tag comprises at least one tag selected from the group consisting of a His tag, a FLAG tag, an AU1 epitope tag, an AU5 epitope tag, a bacteriophage T7 tag, a bacteriophage V5 epitope tag, a Bluetongue virus tag (B-tag), a Glu-Glu tag (EE-tag), an HSV epitope tag, a KT3 epitope tag, a Myc epitope tag, a PDZ ligand tag, a polyarginine tag, a polyaspartate tag, a polycysteine tag, a polyphenylalanine tag, a protein C tag, an S1-tag, an S-tag, a Step-tag, and a VSV-G tag. 73. The composition of any one of embodiments 41-72, wherein the guide RNA comprises an A-rich protospacer adjacent motif (PAM) sequence, a G-rich PAM sequence, a T-rich PAM sequence, or a C-rich PAM sequence. 74. The method of any one of embodiments 41-73, wherein the guide RNA comprises a T-rich PAM sequence. 75. The composition of any one of embodiments 73-74, wherein the PAM sequence comprises 3 T nucleobases, 2 T nucleobases, or 1 T nucleobase. 76. The method of any one of embodiments 73-75, wherein the PAM sequence comprises TTTN. 77. The method of any one of embodiments 45-76, wherein the human nucleic acid sequence comprises a region in KRAS, HER2/neu, PD-1, TCR, p53, CCR5, DNMT1, EMX1, and LKB1. 78. The method of any one of embodiments 49-77, wherein the cancer cell comprises a bladder cancer cell, a bone cancer cell, a blood cancer cell, a breast cancer cell, a black colored tumor cell, a thyroid cancer cell, a parathyroid cancer cell, a bone marrow cancer cell, a laryngopharyngeal cancer cell, a laryngeal cancer cell, a lung cancer cell, an esophagus cancer cell, a pancreatic cancer cell, a colorectal cancer cell, a gastric cancer cell, a tongue cancer cell, a skin cancer cell, a brain tumor cell, a uterine cancer cell, a head or neck cancer cell, a gallbladder cancer cell, an oral cancer cell, a central nervous system tumor cell, or a liver cancer cell. 79. The method of any one of embodiments 45-78, wherein the composition exhibits at least 2-fold than AsCas12a, FnCas12a, or LbCas12a. 80. The method of any one of embodiments 45-79, wherein the guide RNA comprises a crRNA and a tracrRNA. 81. The method of embodiment 80, wherein the crRNA comprises a 5' repeat recognition sequence of AAUU. 82. The method of any one of embodiments 45-81, wherein protein exhibits cleavage activity in the presence of CaCl2, CoCl2, FeCl2, MnSO4, or any combination thereof. 83. The method of any one of embodiments 41-82, wherein the guide RNA sequence comprises from 1 to 100 nucleotides. 84. A method of improving cleaving efficiency of a type V CRISPR-associated protein, the method comprising providing the type V CRISPR-associated protein; identifying a residue at position 925 or 930; and mutating the residue at position 925 or 930 to Lysine, thereby improving cleaving efficiency of the type V CRISPR-associated protein.

EXAMPLES

These examples are provided for illustrative purposes only and not to necessarily limit the scope of the inventive subject matter provided herein.

Example 1

Discovery of Cas12a Proteins by Excavation of the Metagenome

This example illustrates discovery of Cas12a proteins by excavation of the metagenome. FIG. 1 shows a schematic of the Cas12a excavation process from the metagenome. Metagenome base sequences were downloaded from the NCBI Genbank BLAST database and were established as a local BLASTp database. Next, 16 Cas12a protein sequences and various CRISPR associated protein 1 (Cas1) amino acid sequences were downloaded from the Uniprot database. MetaCRT was used to identify CRISPR repeat and spacer sequence in the metagenome base sequences. Metagenome sequence having CRISPR sequences were extracted and genes were predicted using the Prodigal program.

A taxonomic hierarchy was built based on the predicted genes within a 10 kilobase scope of a CRISPR sequence and the Cas12a amino acid sequence was used to predict homologs for Cas12a proteins from the predicted genes. Using the Cas1 gene, it was predicted whether the taxonomic hierarchy of Cas12a homolog has Cas1 homolog, and Cas12a genes that are within 800 amino acids (aa) to 1500 aa scope of Cas1 were selected.

Non-broken Cas12a proteins aligned using the MAFFT (multiple alignment using fast fourier transform) program to align sequences, run neighbor joining (NJ) methods, and dendrograms were constructed with 100× bootstrap using MEGA7. A maximum-likelihood 1000× bootstrap dendrogram using MEGA7 was constructed using the Cas12a amino acid sequence discovered herein and by selecting genes that form a monophyletic group with known Cas12a genes, to identify any evolutionary relationship.

FIGS. 20A-C show schematics of the mgCas12a proteins of the present disclosure. FIG. 20A shows a condensed schematic relative to FIG. 1, showing the pipeline for mining Cas12a proteins from metagenome data. FIG. 20B shows a phylogenetic tree of metagenome-derived Cas12a proteins of the disclosure and other Cas12a orthologs. Bootstrap values are displayed at each node. Orthologs used in the present disclosure include FnCas12a, LbCas12a, AsCas12a, mgCas12a-1, and mgCas12a-2. FIG. 20C shows schematics of functionally-characterized novel Cas12a's and AsCas12a (Yamano et al. 2016). Protein domains were predicted using structure-based alignments with AsCas12a amino acid sequence. Absence of Cas elements in mgCas12a-1 and mgCas12a-2 are shown by dotted lines. Site-directed mutagenesis residues are marked with a black wedge. Sequence identifiers including contig title and GenBank accession number are at the right of each schematic. Acronyms in the schematics include: Cas (CRISPR-associated genes), WED (wedge domain), REC (recognition domain), PI (PAM interaction domain), RuvC (RuvC nuclease domain), BH (bridge helix domain), and Nuc (Nuclease domain). FIG. 2 shows a dendrogram of Cas12a, demonstrating that the metagenomics mining methods disclosed herein were successful. FIG. 21 shows an unrooted and evolutionary distance-based phylogenetic tree of metagenome-derived Cas12a of the present disclosure and other orthologs. Orthologs used in this paper include FnCas12a, LbCas12a, AsCas12a, mgCas12a-1, and mgCas12a-2.

Example 2

Synthesis of Gene and Guide RNA

This example illustrates synthesis of gene and guide RNA (gRNA). Structure-based alignment of novel Cas12aproteins, AsCas12a proteins, and LbCas12a proteins was performed with the ESPript program. Novel Cas12a proteins that displayed homology to AsCas12a were selected and were substituted with an amino acid residue yielding critical functional loss, as with AsCas12a amino acid residues at the same position. Sequences that exhibited critical functional loss included a K925Q mutant of SEQ ID NO: 1 (mgCas12a-1) and K930Q mutant of SEQ ID NO: 3 (mgCas12a-2).

Codon usage for humans, *Arabidopsis*, and colon *bacillus* was considered and codon optimization was performed. The base sequence of SEQ ID NO: 1 (mgCas12a-1) and SEQ ID NO: 3 (mgCas12a-2) that have been human codon optimized are shown in SEQ ID NO: 7 and SEQ ID NO: 8, respectively. FIG. 3-FIG. 8 shows an alignment of Cas12a proteins of the present disclosure, including SEQ ID NO: 1 (mgCas12a-1), SEQ ID NO: 3 (mgCas12a-2), SEQ ID NO: 9 (AsCas12a), SEQ ID NO: 67 (LbCas12a), and SEQ ID NO: 11 (FnCas12a). FIG. 9A shows a chart of characteristics of Cas12a proteins of the present disclosure, including Cas12a proteins discovered by metagenomics mining (e.g., SEQ ID NO: 1 (mgCas12a-1) and SEQ ID NO: 3 (mgCas12a-2), AsCas12a, LbCas12a, and FnCas12a. FIG. 9B shows a chart of amino acid sequence identities (%) between Cas12a orthologs. AsCas12 has less than 40% sequence identity to all other orthologs in the table. LbCas12a and FnCas12a have less than 40% sequence identity to mgCas12a-1 and mgCas12a-2. LbCas12a has between 40% and 50% sequence identity to FnCas12a. mgCas12a-1 has greater than 50% sequence identity to mgCas12a-2.

T4 ligation on pET28a-KanR-6×His-BPNLS ("6×His" disclosed as SEQ ID NO: 63) vectors was performed with a gene cloned to the pUC57 vector. Restriction cloning was also performed. Cloned vectors were transformed to colon *bacillus* DH5a and the Rosetta strain. The 5'-handle sequence of crRNA was extracted from the metagenome CRISPR repeat sequence, the RNA structure was modeled and synthesized with DNA oligonucleotides, sequences were transcribed, and concentration was confirmed using FLUOstar Omega and MEGAshortscript T7 RNA transcriptase.

Example 3

Protein Expression and Refinement

This example illustrates protein expression and refinement. Using Rosetta (DE3), 5 mL of colon *bacillus* was cultivated overnight. Inoculation was carried out using 500 mL of Terrific Broth (TB) and 100 mg/ml kanamycin. Cultures were cultivated in 37° C. culture medium until an OD600 of 0.6 was measured and additionally assayed for protein expression at 16 to 18 hours in 22° C. after processing with 0.4 µM IPTG (Isopropyl β-D-1-thiogalactopyranoside). After centrifuging, the cells were dissolved in 10 mL of buffer (20 mM HEPES pH 7.5, 100 mM KCl, 20 mM imidazole, 10% glycerol and EDTA-free protease inhibitor cocktail) and cells were redispersed by sonication. Cells were centrifuged three times for 20 minutes at 6000 rpm and filtered using a 0.22 micron filter.

Using nickel column (HisTrap FF 5 ml) and 300 mM imidazole buffer, the protein was cleaned, eluted, and purified by affinity-chromatography. Protein size was confirmed by SDS-PAGE electrophoresis and was dialyzed overnight using 20 mM HEPES pH 7.5, 100 mM KCl, 1 mM DTT, 10% glycerol. Based on the size of the protein, selective filtering and condensation (Amicon Ultra Centrifugal Filter 100,000 MWCO) was performed. Using the Bradford Protein Assay, protein concentration was measured and protein was stored at −80° C.

Example 4

In Vitro Cleavage Analysis

This example illustrates in vitro cleavage analysis. Xylosyltransferase of *Lactuca sativa* was amplified by PCR, the PAM (protospacer adjacent motif) sequence was predicted, and guide RNA was designed. RNP (ribonucleoprotein)

compounds of mgCas12a-1 (SEQ ID NO: 1) and mgCas12a-2 (SEQ ID NO: 3) were brought to room temperature for 20 minutes and protein and RNA were at a molar ratio of 1:1.25. After processing the refined xylosyltransferase PCR product, RNPs were resuspended in various buffers including NEBuffer 1.1 (1× buffer components, 10 mM Bis-Tris-Propane-HCl, 10 mM $MgCl_2$ and 100 μg/ml BSA), NEBuffer 2.1 (1× buffer components, 50 mM NaCl, 10 mM Tris-HCl, 10 mM $MgCl_2$ and 100 μg/ml BSA) and NEBuffer 3.1 (1× buffer components, 100 mM NaCl, 50 mM Tris-HCl, 10 mM $MgCl_2$ and 100 μg/ml BSA) and in vitro cleavage analysis was performed at 37° C. NEBuffer 1.1, NEBuffer 2.1 and NEBuffer 3.1 had pH values of 7.0, pH 7.9 and pH 7.9 at 25° C., respectively. Reactions were run until completion and stopped after 10 minutes of incubation at 65° C. The reaction products were confirmed via 1.5% agarose gel electrophoresis. FIGS. 10-12 show gel electrophoresis results.

As described in FIGS. 10-12, when mgCas12a-1 and crRNA was formulated in the NEBuffer 1.1 buffer, target dsDNA was cut. Moreover, if mgCas12a-2 and crRNA was formulated in the NEBuffer 1.1, the target dsDNA was cut. Thus, mgCas12a-1 and mgCas12a-2 were active at a pH of 7.0.

FIG. 16 shows an in vitro cleavage assay of Cas12a nucleases including mgCas12a-1 (wild-type), he_mgCas12a-1 (humanized and engineered mgCas12a-1), de_mgCas12a-1 (dead and engineered mgCas12a), mg Cas12a-2, he_mgCas12a-2, de_mgCas12a-2, AsCas12a, FnCas12a, and LbCas12a. The concentration of each RNP was 300 nM, the curly brace indicates the cleaved templates in the gel electrophoresis, which resolved at 1.8 kb and 0.65 kb. The samples of RNPs were incubated for 1 h at 37° C. with 1×NEBuffer. mgCas12a and de_mgCas12a were also humanized. Materials and methods used in the in vitro cleavage assay included a protein to gRNA molar ratio of 1:1.25. In a 20 μL reaction, 300 nM (911.4 ng) of protein (FnCas12a-BPNLS, 158.82 kDa) was used. In a 20 μL reaction, 375 nM (102.5 ng) of crRNA (LsXTb12) was used. Reactions were run for 1 hour. 300 ng of template DNA was used and incubation was carried out for 1 h at 37° C. All Cas12a nucleases cleaved the template DNA (2.45 kB) into two pieces of 1.8 kB and 0.65 kB. mgCas12a-1, he_mgCas12a-1, mgCas12a-2, he_mgCas12a-2, AsCas12a, FnCas12a and LbCas12a cut the template DNA in two, while template DNA mixed with de_mgCas12a-1 and de_mgCas12a-2 resolved at the uncut size.

FIG. 17A-B shows an in vitro cleavage assay of Cas12a nucleases including mgCas12a-1 (wild-type), he_mgCas12a-1 (humanized and engineered mgCas12a-1), de_mgCas12a-1 (dead and engineered mgCas12a), mg Cas12a-2, he_mgCas12a-2, de_mgCas12a-2, AsCas12a, FnCas12a, and LbCas12a after reaction times of 12 h (FIG. 17A) and 24 h (FIG. 17B). The concentration of each RNP was 300 nM, the curly brace indicates the cleaved templates in the gel electrophoresis, which resolved at 1.8 kb and 0.65 kb. The samples of RNPs were incubated for 12 h and 24 h at 37° C. with 1×NEBuffer. mgCas12a and de_mgCas12a were also humanized. Materials and methods used in the in vitro cleavage assay included a protein to gRNA molar ratio of 1:1.25. In a 20 μL reaction, 300 nM (911.4 ng) of protein (FnCas12a-BPNLS, 158.82 kDa) was used. In a 20 μL reaction, 375 nM (102.5 ng) of crRNA (LsXTb12) was used. Reactions were run for 12 h and 24 h at 37° C. and 300 ng of template DNA was used. Samples were incubated for 12 h and 24 h at 37° C. AsCas12a, FnCas12a, and LbCas12a fully degraded template DNA in 12 h, indicating that they have interminable dsDNase activity. mgCas12a-1, he_mgCas12a-1, mgCas12a-2, and he_mgCas12a-2 exhibited less interminable dsDNase activity and template DNA remained after a 24 h reaction. Samples incubated with de_mgCas12a-1 and de_mgCas12a-2 also lost interminable dsDNase activity.

FIG. 18 shows an in vitro cleavage assay of target plasmid DNA with Cas12a nucleases including mgCas12a-1 (wild-type), he_mgCas12a-1 (humanized and engineered mgCas12a-1), de_mgCas12a-1 (dead and engineered mgCas12a), mg Cas12a-2, he_mgCas12a-2, de_mgCas12a-2, AsCas12a, FnCas12a, and LbCas12a. The concentration of each RNP was 300 nM, an arrow shows cleaved templates, which are 6 kb of the linearized product. The samples of RNPs were incubated for 1 at 37° C. with 1×NEBuffer. mgCas12a and de_mgCas12a were also humanized. Materials and methods used in the in vitro cleavage assay included a protein to gRNA molar ratio of 1:1.25. In a 20 μL reaction, 300 nM (911.4 ng) of protein (FnCas12a-BPNLS, 158.82 kDa) was used. In a 20 μL reaction, 375 nM (102.5 ng) of crRNA (LsXTb12) was used. Reactions were run for 1 h at 37° C. 300 ng of template plasmid DNA was used and samples were incubated for 1 h at 37° C. All Cas12a nucleases cleaved template DNA, from 10 kb to its linearized form of 6 kb in size. mgCas12a-1, he_mgCas12a-1, mgCas12a-2, he_mgCas12a-2, AsCas12a, FnCas12a, and LbCas12a cut and linearized the target plasmid DNA, while target plasmid DNA incubated with de_mgCas12a-1 and de_mgCas12a-2 remained at the uncut size.

FIG. 19A-B shows an in vitro cleavage assay of target plasmid DNA with Cas12a nucleases including mgCas12a-1 (wild-type), he_mgCas12a-1 (humanized and engineered mgCas12a-1), de_mgCas12a-1 (dead and engineered mgCas12a), mg Cas12a-2, he_mgCas12a-2, de_mgCas12a-2, AsCas12a, FnCas12a, and LbCas12a after reaction times of 12 h (FIG. 19A) and 24 h (FIG. 19B). The concentration of each RNP was 300 nM, an arrow shows cleaved templates, which are 6 kb of the linearized product. The samples of RNPs were incubated for 12 h and 24 h at 37° C. with 1×NEBuffer. mgCas12a and de_mgCas12a were also humanized. Materials and methods used in the in vitro cleavage assay included a protein to gRNA molar ratio of 1:1.25. In a 20 μL reaction, 300 nM (911.4 ng) of protein (FnCas12a-BPNLS, 158.82 kDa) was used. In a 20 μL reaction, 375 nM (102.5 ng) of crRNA (LsXTb12) was used. Reactions were run for 12 h and 24 h at 37° C. and the amount of template DNA used was 300 ng. Samples were incubated for 12 h and 24 h at 37° C. AsCa12a, FnCas12a, and LbCas12a degraded all template plasmid DNA within 12 hours, indicating that these nucleases exhibited interminable dsDNase activity. mgCas12a-1, he_mgCas12a-1, mgCas12a-2 and he_mgCas12a-2 exhibited less interminable dsDNase activity and template plasmid DNA remained after a 24 h reaction. mgCas12a-1 and de_mgCas12a-2 also lost interminable dsDNase activity.

Example 5

Genome Editing with the Cas12a Protein of SEQ ID NO: 1

This example illustrates genome editing with the Cas12a protein of SEQ ID NO: 1. SEQ ID NO: 1 is recombinantly expressed or chemically synthesized. If recombinantly expressed, a Cas12a protein of SEQ ID NO: 1 comprises a purification tag used to purify the protein by affinity chromatography. The Cas12a protein of SEQ ID NO: 1 is coupled with a guide RNA (also referred to as crRNA) having a sequence that is reverse complementary to a nucleic acid sequence of interest. The nucleic acid sequence of interest is double stranded DNA (dsDNA) and is from a human. The guide RNA and the Cas12a protein of SEQ ID NO: 1 are administered to a subject. The subject is a human. The guide RNA guides the Cas12a protein of SEQ ID NO: 1 to the nucleic acid sequence if interest and the Cas12a protein of SEQ ID NO: 1 cleaves the dsDNA.

Example 6

Genome Editing with the Cas12a Protein of SEQ ID NO: 3

This example illustrates genome editing with the Cas12a protein of SEQ ID NO: 3. A Cas12a protein of SEQ ID NO: 3 is recombinantly expressed or chemically synthesized. If recombinantly expressed, the Cas12a protein of SEQ ID NO: 3 comprises a purification tag used to purify the protein by affinity chromatography. The Cas12a protein of SEQ ID NO: 3 is coupled with a guide RNA (also referred to as crRNA) having a sequence that is reverse complementary to a nucleic acid sequence of interest. The nucleic acid sequence of interest is double stranded DNA (dsDNA) and is from a human. The guide RNA and the Cas12a protein of SEQ ID NO: 3 are administered to a subject. The subject is a human. The guide RNA guides SEQ ID NO: 3 to the nucleic acid sequence if interest and the Cas12a protein of SEQ ID NO: 3 cleaves the dsDNA.

Example 7

Engineering Cells with the Cas12a Protein of SEQ ID NO: 1

This example illustrates engineering cells ex vivo with the Cas12a protein of SEQ ID NO: 1. A Cas12a protein of SEQ ID NO: 1 is recombinantly expressed or chemically synthesized. If recombinantly expressed, the Cas12a protein of SEQ ID NO: 1 comprises a purification tag used to purify the protein by affinity chromatography. The Cas12a protein of SEQ ID NO: 1 is coupled with a guide RNA (also referred to as crRNA) having a sequence that is reverse complementary to a nucleic acid sequence of interest. The nucleic acid sequence of interest is double stranded DNA (dsDNA) and is from a human. The guide RNA and the Cas12a protein of SEQ ID NO: 1 are administered to a plurality of cells. The guide RNA guides the Cas12a protein of SEQ ID NO: 1 to the nucleic acid sequence if interest and the Cas12a protein of SEQ ID NO: 1 cleaves the dsDNA, thereby editing the plurality of cells. The cells are edited to knock out an aberrant gene or to introduce a functional gene. The edited cells are administered to a subject in need thereof. The subject is a human and has cancer. The cancer is gastric cancer, colorectal cancer, liver cancer, lung cancer, or breast cancer.

Example 8

Engineering Cells with the Cas12a Protein of SEQ ID NO: 3

This example illustrates engineering cells ex vivo with the Cas12a protein of SEQ ID NO: 3. A Cas12a protein of SEQ ID NO: 3 is recombinantly expressed or chemically synthesized. If recombinantly expressed, the Cas12a protein of SEQ ID NO: 3 comprises a purification tag used to purify the protein by affinity chromatography. The Cas12a protein of SEQ ID NO: 3 is coupled with a guide RNA (also referred to as crRNA) having a sequence that is reverse complementary to a nucleic acid sequence of interest. The nucleic acid sequence of interest is double stranded DNA (dsDNA) and is from a human. The guide RNA and the Cas12a protein of SEQ ID NO: 3 are administered to a plurality of cells. The guide RNA guides the Cas12a protein of SEQ ID NO: 3 to the nucleic acid sequence if interest and the Cas12a protein of SEQ ID NO: 3 cleaves the dsDNA, thereby editing the plurality of cells. The cells are edited to knock out an aberrant gene or to introduce a functional gene. The edited cells are administered to a subject in need thereof. The subject is a human and has cancer. The cancer is gastric cancer, colorectal cancer, liver cancer, lung cancer, or breast cancer.

Example 9

In Vitro Cleavage Analysis of Cpf1 Proteins

This example illustrates in vitro cleavage analysis of Cpf1 proteins. Proteins and gRNA were co-incubated at a 1:1.2 molar ratio. In the case of 20 µl reactions, 100 nM (320 ng) of the protein FnCas12a-BPNLS (159.81 kDa) was used. In the case of 20 µl reactions, 120 nM (80 ng) of the crRNA DHCR7 was used. Reaction times of 1 hour and 4 hours at 37° C. were tested and 200 ng of template DNA was used. FIG. 14 shows the results of an in vitro cleavage assay using various nucleases including, FnCas12, AsCas12, LbCas12, He-MgCas12a-1 (humanized and engineered mgCas12a-1), and He-MgCas12a-2 (humanized and engineered mgCas12a-2), 1 hour after incubation of the target with the nucleases and 4 hours after incubation of the target with the nucleases. The concentration of each RNP was 100 nM. Arrows indicate the cleaved fragments of the template, which were resolved at 680 base pairs (bps) and 750 bps. Mock A indicates a sample in which neither gRNA or protein were used in the cleavage assay. Mock B indicates a sample in which no protein was used in the cleavage assay. He-MgCas12a-1 and He-MgCas12a-2 both cleaved the DNA template (1,430 bp) into two pieces of 750 bp and 680 bp.

By 1 h, He-MgCas12a-1 had completely cut the template DNA in two while some remaining template DNA at the uncut size was evident when incubated with He-MgCas12a-2. By 4 h, He-MgCas12a-2 had also completely cut the template DNA. The cleavage efficiencies of He-MgCas12a-1 and He-MgCas12a-2 were higher than the other three Cas12 nucleases, as uncut template DNA remained after incubation with the other three Cas12 nucleases (FnCas12, AsCas12, and LbCas12) at 1 hour. Additionally, the FnCas12 lane indicated that both template and cleaved products were degraded over time, while neither the He-MgCas12a-1 nor the He-MgCas12a-2 lanes indicated any further DNA degradation.

Example 10

Genome Editing of Rice and *N. benthamiana*

This example illustrates genome editing of rice and *N. benthamiana*. Two crRNAs in rice and three crRNAs in *N. benthamiana* were used to evaluate genome editing efficiencies of He-MgCas12a-1 versus FnCas12. Genome editing efficiency values were measured using amplicon targeted deep sequencing. Plants and other materials used in these assays include 20-30 seeds of lettuce (*Lactuca sativa* var. *Chungchima*), MS salt with vitamins (M0222, Duchefa, RV Haarlem, Netherlands), razor blades (NO. 10, FEATHER SAFETY RAZOR, Osaka, Japan), forceps (Cat. 3-SA, Jonostick by regine Switzerland Standard, China), cell strainer (Cat. 93100, SPL, Korea), 1000 μl wide-bore tip (T-205-WB-C-R-S, Axygen, NY), growth chamber 24° C. (HB103M, HanBaek Scientific Co., Korea), pH meter (STARA2115, ThermoFisher scientific, Waltham, Mass., USA), and a sterilizer (Cat.BF-60AC, BioFree, Korea). PEG transfection was carried out using 1) an enzyme solution, which included mannitol (M0803, Duchefa, RV Haarlem, Netherlands), KCl (P5405, Sigma-Aldrich, USA), MES (M1503, Duchefa, RV Haarlem, Netherlands), $CaCl_2$ (C3881, Sigma-Aldrich, Japan), BSA (A9056, Sigma-Aldrich, USA), cellulase R-10 (Yakurt Pharmaceutical Inc., Tokyo, Japan), and macerozyme R-10 (Yakurt Pharmaceutical Inc., Tokyo, Japan), 2) a PEG solution, which included NaCl (7548-4405, Daejung chemicals and metals, Korea), KCl (P5405, Sigma-Aldrich, USA), $CaCl_2$(C3881, Sigma-Aldrich, Japan), and MES (M1503, Duchefa, RV Haarlem, Netherlands), and 3) a MMG solution, which included mannitol (M0803, Duchefa, RV Haarlem, Netherlands), $MgCl_2$ (M0533, Duchefa, RV Haarlem, Netherlands), and MES (M1503, Duchefa, RV Haarlem, Netherlands).

Plant transformation and regeneration was carried out as follows. Plants and reagents for protoplast transformation included first sterilizing lettuce seeds with a 2% sodium hypochlorite (Clorox) for 10 min, washing seeds 5 times with sterile $dH_2O$, and planting the sterile seeds on ½ MS media. Lettuce leaves were harvested 5 days after germination for protoplast preparation. 40 mL of enzyme solution was made with 0.4 M mannitol, 20 mM KCl, 20 mM MES (pH 5.7), 1.5% Cellulase R-10 (Yakurt), and 0.3% Macerozyme R-10 (Yakurt). Incubations were carried out at 55° C. for 10 min, 10 mM $CaCl_2$) and 0.1% BSA was added, and enzyme solution was filtered through a 0.45 m syringe filter.

Protoplast preparation included cutting ten to fifteen leaves from rice or *N. benthamiana* plantlets with a razor, piling two or three leaves on a droplet of sterile water, and slicing piled leaves together. 20 mL of the enzyme solution was poured into a 90 mm diameter plate and fifteen sliced leaves were transferred into the 20 mL enzyme solution. The solution was covered with aluminum foil. The 90 mm plate was placed on a gyratory shaker at 50 rev/min and the plate was incubated for four to five hours. The enzyme solution with protoplasts were poured into a round tube and the same volume of W5 solution was added to the 20 mL enzyme solution. W5 solution included 154 mM NaCl, 125 mM $CaCl_2$), 5 mM KCl, and 2 mM MES (pH 5.7). 40 mL of enzyme solution containing protoplasts were flown through a 100 m cell strainer into a 50 mL round tube. The cell strainer was removed and the 50 mL tube was centrifuged at 100 g (or 80 g in Hanil) for 5 min. The supernatant was removed using a 20 mL long pipette. 1 mL of MMG solution was added. 5 mL of MMG solution was made by mixing 2.5 mL of 0.8 M mannitol, 0.25 mL of 300 mM $MgCl_2$, and 0.1 mL of 200 mM MES (pH 5.7). 10 mL of MMG solution was made by mixing 5 mL of 0.8 M mannitol, 0.5 mL of 300 mM $MgCl_2$, and 0.2 mL of 200 mM MES (pH 5.7). Protoplasts were counted with a hematocytometer, cell numbers were adjusted up to $2\times10^6$ cells/mL by adding MMG solution. 200 μl containing $2\times10^5$/mL of protoplasts were aliquoted into 1.5 mL tubes.

Protoplasts were transformed with CRISPR RNPs. A 20 μl transformation reaction was set up in a 1.5 mL tube as shown below in TABLE 3.

TABLE 3

| Transformation Reaction | |
| --- | --- |
| RNP | $2 \times 10^5$/mL Protoplasts |
| sgRNA | 5 μg |
| Cas9 protein | 10 μg |
| Plus reagent ™ | 2 μl |
| Lipofectamine ™ 3000 | 2 μl |
| NEB Buffer 3.1 | 2 μl |
| $dH_2O$ up to | 20 μl |

Both Lipofectamine™ 3000 and Plus Reagent™ transfection reagents were utilized for RNP deliver with PEG 4000. RNP can be replaced with Cpf1 or other Cas proteins. GFP-Cas9 was employed to help trace Cas9 localization instead of Cas9.

The RNP transformation mixture was incubated for 10 min at room temperature. 200 μl of the protoplast solution was aliquoted with a 1,000 μl wide bore tip into a clean 1.5 mL tube. The RNP mixture was added to the 200 μl protoplast solution and mixed gently. The same volume (200 l) of 40% PEG solution (shown below in TABLE 4) into the RNP-protoplast solution.

TABLE 4

| PEG Solution | | |
| --- | --- | --- |
| 40% PEG Solution Ingredients | 5 ml | 10 ml |
| 0.8M Mannitol | 1.25 ml | 2.5 ml |
| 1M $CaCl_2$ | 0.5 ml | 1 ml |
| PEG 4000 | 2 g | 4 g |
| $dH_2O$ up to | 5 ml | 10 ml |

The RNP-protoplast-PEG solution was gently pipetted five to ten times. The RNP-protoplast-PEG solution was placed at room temperature for 10 min. 800 μl of W5 solution was added to the RNP-protoplast-PEG solution and inverted four to five times. The tubes were centrifuged at 100 g for 1 min in a large tabletop centrifuge and the supernatant was discarded. 200 μl of W5 solution was added to samples and the samples were incubated for 4 hours at 28° C. Protoplasts were harvested and the genomic DNA was extracted. The target DNA region was amplified and amplicon targeted sequencing was performed.

The amplicon setup was carried out as follows. Working on ice, primers were added using a multichannel pipettes by adding 4 μl from the vertical i5(S5XX) primer strip to the columns of the plate and 4 μl from the horizontal i7(N7XX) primer strip to the rows of the plate. 10 μl of polymerase was added from the 8-well strip into each well, 2 μl of 0.5 ng/μl DNA was transferred into the corresponding wells. Plates were sealed, vortexed, and spun in a plate centrifuge for 2 mins at 2000 g. PCR was carried out using the cycling conditions outlined in TABLE 5. Either a qPCR machine or a standard PCR machine can be used to when using the KAPA HiFi mix. qPCR had the advantage of monitoring how each sample was amplified in real time, since each contained SYBR green.

TABLE 5

PCR Cycling Conditions

| | Temperature | Time | Cycles |
|---|---|---|---|
| Denaturation | 98 | 2 mins | 1X |
| Denaturation | 98 | 30 | |
| Annealing | 60 | 30 | 10-12 cycles |
| Extension | 72 | 30 | |
| Final | 72 | 5 mins | 1X |
| Hold | 4 | | |

The second round PCR products were cleaned as follows. 30 µl of H$_2$O was added to each well of the PCR plate to bring the total volume per well to 50 µl, 50 µl of AmpureXP beads was added to each well of a 96-well round bottom plate, and 50 µl of PCR product was transferred to the 96-well plate containing 50 µl AmpureXP mix and the solution was pipetted up and down 10× to mix. The samples were incubated for at least 10 minutes on the bench. The plate was placed on a 96-well plate magnet for 5 mins until the liquid appears clear. The supernatant was discarded by pipetting and aspirating. Samples were washed by adding 190 µl of 70-80% ethanol to each sample and left for 30 seconds. The ethanol was discarded by pipetting and aspiration. Washing samples with ethanol and discarding ethanol, as described above, was repeated for a total of two washes. Plates were removed from the magnet and allowed to air dry for 2-3 minutes and it was ensured that no ethanol was detected. The plate was taken off the magnet and the beads were resuspended in 22 µl of H$_2$O and mixed thoroughly by pipetting up and down 10 times. The plates were allowed to incubate for at least 10 mins on the bench. The plate was placed back on the magnet for 5 minutes and it was ensured that the liquid appeared clear. Finally, 20 µl of the supernatant was transferred to a new 96-well PCR plate.

PCR products were pooled and the library was quantified as follows. 10 µl of each second round PCR product was transferred from the plate into a single microcentrifuge tube. The concentration of DNA was determined using the Qubit. The DNA concentration was adjusted to 2 nM.

Sequencing was carried out using the MiSeq loading protocol as per Illumina instructions. Primer sequences are shown below in TABLE 6.

TABLE 6

Primer Sequences

| | Target Specific Primer Sequence | Adapter Primer Sequence |
|---|---|---|
| Rice DWF5 crRNA #1 | | |
| >NGS_OsDwarf5_F2 | ATTCCAGGGAATGGAACTAT (SEQ ID NO: 31) | TCGTCGGCAGCGTCAGATGTGTATAAGAGACAGATTCCAGGGAATGGAACTAT (SEQ ID NO: 32) |
| >NGS_OsDwarf5_R2 | TATTGGATAGCAACCAAAGC (SEQ ID NO: 33) | GTCTCGTGGGCTCGGAGATGTGTATAAGAGACAGTATTGGATAGCAACCAAAGC (SEQ ID NO: 34) |
| Rice DWF5 crRNA #2 | | |
| >1273 NGS OsDwarf5 F3 | GGTGAGCTTATTTATTAGGCTT (SEQ ID NO: 35) | TCGTCGGCAGCGTCAGATGTGTATAAGAGACAGGGTGAGCTTATTTATTAGGCTT (SEQ ID NO: 36) |
| >1274 NGS OsDwarf5 R3 | GGTGAAGAATGTCATCGCTAAT (SEQ ID NO: 37) | GTCTCGTGGGCTCGGAGATGTGTATAAGAGACAGGGTGAAGAATGTCATCGCTAAT (SEQ ID NO: 38) |
| Tobacco XTb12 crRNA #1 | | |
| >1267 NGS XTb12_1/2 F1 | AAATCCCCCCAAAACCACTTTT (SEQ ID NO: 39) | TCGTCGGCAGCGTCAGATGTGTATAAGAGACAGAAATCCCCCCAAAACCACTTTT (SEQ ID NO: 40) |
| >1268 NGS XTb12_1/2 R1 | CGGTGTTATCGCCGAATTTCCG (SEQ ID NO: 41) | GTCTCGTGGGCTCGGAGATGTGTATAAGAGACAGCGGTGTTATCGCCGAATTTCCG (SEQ ID NO: 42) |
| Tobacco XTb12 crRNA #2 | | |
| >1269 NGS NbXTb12_1/2 F2 | GGTTTACTCTCAAAGTTGACCT (SEQ ID NO: 43) | TCGTCGGCAGCGTCAGATGTGTATAAGAGACAGGGTTTACTCTCAAAGTTGACCT (SEQ ID NO: 44) |
| >1270 NGS NbXTb12_1/2 R2 | GGGCAGCTCATCATCTTCATTC (SEQ ID NO: 45) | GTCTCGTGGGCTCGGAGATGTGTATAAGAGACAGGGGCAGCTCATCATCTTCATTC (SEQ ID NO: 46) |

TABLE 6-continued

Primer Sequences

| | Target Specific Primer Sequence | Adapter Primer Sequence |
|---|---|---|
| Tobacco XTb12 crRNA #3 | | |
| >1271 NGS NbXTb12_1/2 F3 | CTCTGTACTAAGTAG TACACAC (SEQ ID NO: 47) | TCGTCGGCAGCGTCAGATGTGTATAA GAGACAG CTCTGTACTAAGTAGTACACAC (SEQ ID NO: 48) |
| >1272 NGS NbXTb12_1/2 R3 | GCTTGGAATATTGAG AAGTGAT (SEQ ID NO: 49) | GTCTCGTGGGCTCGGAGATGTGTATA AGAGACAG GCTTGGAATATTGAGAAGTGAT (SEQ ID NO: 50) |

FIG. 15A illustrates that FnCas12a exhibited genome editing efficiencies in rice of 0.5%0, 0.3%, and 0.9% in crRNA1-1, crRNA1-2, crRNA2, respectively and He-MgCas12a-1 exhibited genome editing efficiencies in rice of 1.9%, 0.7%, and 10.2% in crRNA1-1, crRNA1-2, crRNA2. FIG. 15B illustrates that FnCas12a exhibited genome editing efficiencies in N. benthamiana of 0.8%, 1.4%, and 4.8% in crRNA1, crRNA2, and crRNA3, respectively and He-MgCas12a-1 exhibited genome editing efficiencies in N. benthamiana of 0.7%, 3.7%, and 3.4% in crRNA1, crRNA2, and crRNA3, respectively.

Example 11

Genome Editing of CCR5 and DNMT1

This example illustrates genome editing of CCR5 and DNMT1.

Cell culture. ITEK293T cells were cultured in Dulbecco's modified Eagle's medium (DMVEM) supplemented with 10% fetal bovine serum, penicillin, and streptomycin.

crRNA sequences. Nucleotide sequences of synthetic crRNAs were obtained from TDT for CCR5 and DNMT1 and are listed below in TABLE 7.

TABLE 7 crRNA Sequences for Targeting CCR5 and DNMT1

| Genes | crRNA Sequence (5'-3') |
|---|---|
| CCR5 | CACCGAAUUUCUACUGUUGUAGAUGGAGUGAAGGGAGAGUUU GUCAAUUUUUUG (SEQ ID NO: 51) |
| DNMT1 | GGUCAAUUUCUACUGUUGUAGAUGCUCAGCAGGCACCUGCCU CUUUU (SEQ ID NO: 52) |

RNP preparation and electroporation. Before transfection of proteins in cells, purified mgCas12a-1 and mgCas12a-2 proteins (100 pmol) were incubated with CCR5 or DNMT1 crRNA (200 pmol) at room temperature for 20 minutes to form the RNP complex. Nucleofection of HEK293T cells was performed using Lonza. Each nucleofection reaction included mixing approximately $2\times10^5$ cells in 20 μl of nucleofection reagent with 10 μl of RNP.

Genomic DNA extraction. Cells were harvested at 48 and 72 hours after transfection. Genomic DNA extraction was performed using PureLink Genomic DNA kits (Invitrogen) following the manufacture's instruction.

Deep sequencing analysis of on-target sites. The genomic region flanking the target site for each gene was amplified using a two-step PCR method. First, the genomic DNA from the edited and control samples was isolated and PCR amplified for 35 cycles using Q5 High-fidelity DNA polymerase and adapter primers. Sequences of adapter primers are shown below in TABLE 8. The resulting amplicons were prepared using a QIAquick PCR Purification kit. These samples were subjected to eight cycles of PCR using KAPA HotStart DNA Polymerase for indexing, followed by AMPure bead purification. Purified DNA samples were quantified by Qubit 2.0 Fluorometer, size analyzed by Bio-Analyzer, and pooled in an equimolar ratio. Sequencing libraries were sequenced with the Illumina MiniSeq. Data was analyzed using the Cas-Analyzer program.

TABLE 8

Adapter Primer Sequences

| Genes | Adapter Primer Sequence (5'-3') |
|---|---|
| CCR5 | TCGTCGGCAGCGTCAGATGTGTATAAGAGACAGGGTATTTCT GTTCAGATCAC (SEQ ID NO: 53) |
| | GTCTCGTGGGCTCGGAGATGTGTATAAGAGACAGGCCCATCA ATTATAGAAAGCC (SEQ ID NO: 54) |
| DNMT1 | TCGTCGGCAGCGTAGATGTGTATAAGAGACAGCTGCACACAG CAGGCCTTTG (SEQ ID NO: 55) |
| | GTCTCGTGGGCTCGGAGATGTGTATAAGAGACAGCCCAATAA GTGGCAGAGTGC (SEQ ID NO: 56) |

FIG. 27 shows the resulting editing efficiencies of mgCas12a-1, mgCas12a-2, and mock (negative control). mgCas12a-1 exhibited more efficient editing efficiency when targeting CCR5, as indicated by the higher percent indels at 48h and 72h, in comparison to the negative control (mock) and mgCas12a-2. mgCas12a-2 exhibited percent indels over background when targeting CCR5 at 72 h. Both mgCas12a-1 and mgCas12a-2 exhibited percent indels over background when target DNMT1 at 48 h and 72 h, with mgCas12a-2 exhibiting slightly higher % indels than mgCas12a-1.

TABLE 9 below summarizes targeted deep sequencing data for indels of mgCas12a-1 and mgCas12a-2.

TABLE 9

Targeted Deep Sequencing Data for Indels of mgCas12a-1 and mgCas12a-2

| Samples | Gene | Time | Name | Total sequences | With both indicator sequences | Insertions | Deletions | Indel frequency | Indel frequency (%) |
|---|---|---|---|---|---|---|---|---|---|
| 1 | CCR5 | 48 h | Mock | 137952 | 137475 | 0 | 187 | 187 (0.1%) | 0.1 |
| 2 | | | mgCas12a-1 | 119684 | 119250 | 36 | 418 | 454 (0.4%) | 0.4 |
| 3 | | | mgCas12a-2 | 112387 | 112077 | 8 | 150 | 158 (0.1%) | 0.1 |
| 4 | | 72 h | Mock | 139323 | 138942 | 8 | 179 | 187 (0.1%) | 0.1 |
| 5 | | | mgCas12a-1 | 156705 | 156159 | 39 | 738 | 777 (0.5%) | 0.5 |
| 6 | | | mgCas12a-2 | 158717 | 158392 | 5 | 237 | 242 (0.2%) | 0.2 |
| 7 | DNMT1 | 48 h | Mock | 141182 | 136856 | 19 | 316 | 335 (0.2%) | 0.2 |
| 8 | | | mgCas12a-1 | 122368 | 120871 | 70 | 424 | 494 (0.4%) | 0.4 |
| 9 | | | mgCas12a-2 | 121928 | 120592 | 46 | 509 | 555 (0.5%) | 0.5 |
| 10 | | 72 h | Mock | 98480 | 96480 | 0 | 192 | 192 (0.2%) | 0.2 |
| 11 | | | mgCas12a-1 | 126317 | 123792 | 2 | 511 | 513 (0.4%) | 0.4 |
| 12 | | | mgCas12a-2 | 47398 | 47000 | 12 | 199 | 211 (0.5%) | 0.5 |

Example 12

Genome Editing of *Nicotiana benthamiana*

This example illustrates genome editing of CCR5 and DNMT1.

Plant growth condition. All plants were grown under a 150 E m$^{-2}$ s$^{-1}$ LED light under long-day (14-h light/10-h dark photoperiod) conditions at 25° C.

Protoplast transfection. Tobacco (*Nicotiana benthamiana*) and seeds were sterilized in a 0.4% hypochlorite solution for 1 min, washed three times in distilled water, and sown on a 0.5× Gamborg B5 solid medium supplemented with 2% sucrose. The 4-week-old leaves grown in B5 media were digested with enzymes (1.5% cellulose R10, 0.3% macerozyme R10, 0.5 M Mannitol, 8 mM CaCl$_2$, 5 mM MES [pH 5.7], 0.1% BSA) for 4 h at 25° C. in darkness. The mixture was filtered before protoplasts were collected by centrifugation at 100 g in a round-bottomed tube for 6 min. Re-suspended protoplasts were washed with W5 solution (154 mM NaCl, 125 mM CaCl2-2H$_2$O, 5 mM KCl, 2 mM MES [pH5.7]) and pelleted by centrifugation at 100 g for 6 min. Finally, protoplasts were re-suspended in MMG solution (0.4 M mannitol, 15 mM MgCl$_2$, 4 mM MES [pH 5.7]) and counted under a microscope using a hemocytometer. Protoplasts were diluted to a density of 1×10$^6$ protoplasts/ml of MMG solution and stabilized for at least for 30 min at 4° C. before PEG-mediated transfection. 2×10$^5$ protoplast cells were transfected with Nuclease protein (10 pg of mgCas12a-1, mgCas12a-2, or FnCpf1) pre-mixed with in vitro-transcribed crRNA (22 pg). Prior to transfection, Nuclease proteins were mixed with crRNA in 1×NEB buffer 1 and incubated for 10-20 min at room temperature. A mixture of protoplasts re-suspended in 200 μl MMG solution was gently mixed with 10-20 μl of RNP complex and 210-220 μl of freshly prepared PEG solution (0.2M mannitol, 40% W/V PEG-4000, 100 mM CaCl$_2$)) and incubated at 25° C. for 15 min. After a 15 min incubation at room temperature, transformation was stopped by adding 840-880 μL of W5 solution. Protoplasts were collected by centrifuging for 2 min at 100 g at room temperature and washed once with 1 ml of wash buffer by centrifugation for another 2 min at 100 g. Protoplasts were resuspended in 500 μL of W5 solution and incubated for 2 days in a growth chamber at 25° C.

Targeted deep sequencing. The on-target was amplified from genomic DNA. Indices and sequencing adaptors were added by additional PCR. High-throughput sequencing was performed using Illumina MiniSeq. TABLE 10 below shows the crRNA target region and sequence.

TABLE 10

| CRIPSR RNA (crRNA) target region and sequence | | |
|---|---|---|
| Target Gene | crRNA (primer name) | crRNA sequence (PAM site) |
| NbFucT14_1 NbFucT14_2 | NbFTa14_1/2-2 | TTTGGATAATTTGTACTCTTGT CGATGT (SEQ ID NO: 57) |
| | NbFTa14_1/2-4 | TTTAGTCCACAAACAGCTAAGC CCACAT (SEQ ID NO: 58) |

TABLE 11 below shows primers used for target region PCR analysis.

TABLE 11

| Primers For Target-Region PCR Analyses | | | |
|---|---|---|---|
| Target gene | Primer name | Sequence | Size (bp) |
| NbFucT14_1 | NGS_NbFTa14_1_F | TGAGCTGAAGATGGATTATG (SEQ ID NO: 59) | 216 |
| | NGS_NbFTa14_1_R | TCATGCTTAAGATAAAAGAG (SEQ ID NO: 60) | |
| NbFucT14_2 | NGS_NbFTa14_2_F | TCATGAGCTTAAGATGGATC (SEQ ID NO: 61) | 217 |
| | NGS_NbFTa14_2_R | GTTTAAGCTAAAAGAACTAC (SEQ ID NO: 62) | |

TABLE 12 below shows Cas12a editing efficiency, complexed with two crRNAs, for two FucT14 targets, as measured by MiniSeq.

TABLE 12

Cas12a Editing Efficiency

| Target gene | crRNA | Nuclease | Total Sequences | With both indicator sequences | More than minimum frequency | Insertions | Deletions | Indel frequency |
|---|---|---|---|---|---|---|---|---|
| FucT14-1 | 2 | none | 161551 | 161421 | 160896 | 4 | 180 | 184 (0.1%) |
|  |  | mgCas12a-1 | 124361 | 124255 | 123844 | 3 | 168 | 171 (0.1%) |
|  |  | mgCas12a-2 | 99154 | 99053 | 98734 | 0 | 131 | 131 (0.1%) |
|  |  | FnCpf1 | 50060 | 50022 | 49808 | 0 | 63 | 63 (0.1%) |
|  | 4 | none | 161551 | 161411 | 160899 | 4 | 178 | 182 (0.1%) |
|  |  | mgCas12a-1 | 106782 | 106706 | 106330 | 0 | 1877 | 1877 (1.8%) |
|  |  | mgCas12a-2 | 126665 | 126544 | 126057 | 79 | 885 | 964 (0.8%) |
|  |  | FnCpf1 | 64554 | 64501 | 64272 | 15 | 470 | 485 (0.8%) |
| FucT14-2 | 2 | none | 49459 | 49422 | 49192 | 2 | 49 | 51 (0.1%) |
|  |  | mgCas12a-1 | 81191 | 81101 | 80738 | 0 | 90 | 90 (0.1%) |
|  |  | mgCas12a-2 | 83694 | 83614 | 83286 | 0 | 99 | 99 (0.1%) |
|  |  | FnCpf1 | 108803 | 108682 | 108260 | 0 | 112 | 112 (0.1%) |
|  | 4 | none | 49459 | 49427 | 49199 | 2 | 49 | 51 (0.1%) |
|  |  | mgCas12a-1 | 54918 | 54854 | 54532 | 6 | 689 | 695 (1.3%) |
|  |  | mgCas12a-2 | 127825 | 127691 | 127213 | 2 | 143 | 145 (0.1%) |
|  |  | FnCpf1 | 64265 | 64168 | 63882 | 0 | 162 | 162 (0.3%) |

Example 13

Cas12a Cleavage of Linear dsDNA and Circular dsDNA

This example describes Cas12a cleavage of linear dsDNA and circular dsDNA. FnCa12a, mgCas12a-1, and mgCas12a-2 were complexed with crRNA targeting HsCCR5, HsDNMT1, and HsEMX1 (Hs standing for human). Cas12a nucleases were tested for their ability to target and cleave linear dsDNA and circular DNA. Purified PCR product was used to obtain target linear dsDNA and purified plasmid DNA was used to obtain circular dsDNA. Conditions tested include no incubation and 2 hours incubation at 37° C. The appropriate negative controls were also tested, as summarized in the tables.

FIG. 22A-B show sequence-specific cleavage of dsDNA by crRNA guided-mgCas12a proteins of the present disclosure. FIG. 22A shows sequence-specific cleavage of linear dsDNA by crRNA guided-Cas12a proteins including FnCas12a, WT mgCas12a-1 and WT mgCas12a-2. The substrate is indicated by an arrow and the letter S and cleaved products in the gel are also shown with arrows. Purified PCR product was used for linear dsDNA. The numbers below gel image indicate substrate DNA band intensity. FIG. 22B shows sequence-specific cleavage of circular dsDNA by crRNA guided-Cas12a proteins including FnCas12a, WT mgCas12a-1 and WT mgCas12a-2. The substrate is indicated by an arrow and the letter S and linearized product (from cleavage) in the gel are also shown with arrows. Purified plasmid DNA was used for circular dsDNA. The numbers below gel image indicate substrate DNA band intensity.

Example 14

Cas12a Cleavage of Target DNA Using Different 5' Handles

This example describes Cas12a cleavage of target DNA using different 5' handles. mgCas12a-1 and mgCas12a-2 were complexed with crRNA to target a specific nucleic acid. The crRNA for guiding mgCas12a-1 and mgCas12a-2 included the nucleotides at the 5' end prior to the step-loop region of the crRNA for AsCas12a, FnCas12a, and LbCas12a. Cleavage activity was monitored by running gels on the reaction of the Cas12a/crRNA complex with the target nucleic acid at various time points including 0 hr, 1 min, 10 min, 30 min, 1 h, 6 h, and 12 h.

FIG. 23A-B shows that the mgCas12a proteins of the present disclosure can utilize three different types of Cas12a handles. FIG. 23A shows cleavage of target linear dsDNA by WT mgCas12a-1 complexed with a crRNA having a 5' handle from AsCas12a, FnCas12a, and LbCas12a. FIG. 23B shows cleavage of target linear dsDNA by WT mgCas12a-2 complexed with a crRNA having a 5' handle from AsCas12a, FnCas12a, and LbCas12a. As seen in these gels, both mgCas12a proteins can utilize three types of 5' handles: AsCas12a, FnCas12a and LbCas12a, to sequence-specifically cleave dsDNA. The substrate ("S") indicates the target nucleic acid and the "P" indicates cleaved products. The numbers below gel image indicate substrate DNA band intensity. Controls included a catalytically inactive mgCas12a ("d_mgCas12a"), no Cas12a, or no crRNA. mgCas12a-1 and mgCas12a-2 exhibited cleavage of the target nucleic acid with all three crRNAs having the various 5' nucleotides found in crRNAs for AsCas12a, FnCas12a, and LbCas12a.

Example 15

Random dsDNase Activity of Cas12a-RNPs

This example describes random dsDNase activity of Cas12a_RNPs. mgCas12a-1, d_mgCas12a_1 (deactivated), mgCas12a_2, d_mgCas12a_2 (deactivated), AsCas12a, FnCas12a, and LbCas12a were complexed with crRNAs to target a linear dsDNA in HsCCR5, HsDNMT1, and HsEMX1. Cleavage was monitored over time.

As shown in FIG. 24, and FIG. 25A, seven different Cas12a-RNPs were incubated with target dsDNA for 12 or 24 hours. The target substrate dsDNA is indicated with an "S" for substrate and cleaved products are indicated with a "P" for products. The dsDNA substrate and resulting cleaved products were almost entirely degraded, which may be due to random DNase activity of some Cas12a orthologs, including FnCas12a and LbCas12a, after incubation of the reaction for 12 hours and 24 hours. Both substrate and cleaved products were detected in the 12 hour reaction with the metagenomically mined Cas12a proteins of the present disclosure, including WT mg-1 (SEQ ID NO: 1) and WT mg-2 (SEQ ID NO: 2). FIG. 25B shows a graph of time versus dsDNase activity of each Cas12a, demonstrating that target substrate dsDNA remains at later time points for mgCas12a-1 (SEQ ID NO: 1), indicating that mgCas12a-1 exhibits lower random DNase activity.

FIG. 25A-B show that Cas12a exhibits random dsDNase activity of target linear dsDNA (human DNMT1). FIG. 25A shows FnCas12a, WT mgCas12a-1, and mgCas12a-2, complexed with crRNA and incubated with linear dsDNA for different time periods. The numbers below gel image indicate substrate DNA band intensity. The band corresponding to the substrate linear dsDNA essentially disappeared over time for the FnCas12a, and was very faint for mgCas12a-2. Substrate bands were observed at the same later time points for mgCas12a-1. FIG. 25B shows a graph of time versus dsDNase activity of each Cas12a, demonstrating that the substrate target dsDNA remains at later time points for mgCas12a-1.

Example 16

Csa12a Activity in the Presence of Divalent Cations

This example describes Cas12a activity in the presence of divalent cations. Cas12a cleavage activity of linear dsDNA was tested for FnCas12a, WT mgCas12a-1, and WT mgCas12a-2. Cleavage of the target linear dsDNA was evaluated by running a gel for each of the divalent cations tested including CaCl2, CoCl2, $CuSO_4$, $FeCl_2$, $MnSO_4$, $NiSO_4$, and $ZnSO_4$. S indicates bands corresponding to the target linear dsDNA target substrate and P corresponds to cleavage products of the reactions.

FIG. 26A-D shows the activity of each Cas12a-RNP in the presence of different divalent cation. FIG. 26A shows the results from Cas12a-RNP cleavage of target, linear dsDNA in the presence of seven different divalent cations were given to each Cas12a-RNP. Abbreviations in the figure include DW for distilled water and Ctrl for 1×NEBuffer 1.1 (control). FIG. 26B shows sequence-specific dsDNA cleavage of FnCas12a-RNP under presence of different divalent cations. FIG. 26C shows sequence-specific dsDNA cleavage of each WT mgCas12a-1RNP under presence of different divalent cations. FIG. 26D shows sequence-specific dsDNA cleavage of each WT mgCas12a-2-RNP under presence of different divalent cations.

Cleaved products from targeting linear dsDNA was observed for all Cas12a orthologs tested. Linearized products from cleavage of circular dsDNA were clearly observed for mgCas12a-1 and mgCas12a-2. A light band was also observed for linearized products from cleavage of circular dsDNA by FnCas12a. However, the absence of a band at the circular dsDNA substrate (S) in all Cas12a orthologs tested indicates cleavage of the Cas12a by all orthologs, including FnCas12a.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising:
at least one of i)-ii):
   i) a polypeptide comprising at least 80% sequence identity with residue 825 through residue 996 of SEQ ID NO: 3, wherein the polypeptide comprises an amino acid sequence comprising a Lysine aligned to a Lysine at position 930 of SEQ ID NO: 3; or
   ii) a polypeptide comprising at least 80% sequence identity with SEQ ID NO: 3, wherein the polypeptide comprises an amino acid sequence comprising a Lysine aligned to a Lysine at position 930 of SEQ ID NO: 3; and
a guide RNA coupled to the at least one of i)-ii), wherein the guide RNA comprises a sequence that is reverse complementary to a eukaryotic nucleic acid sequence comprising from 6 to 60 bases.

2. The composition of claim 1, wherein the polypeptide is a type V CRISPR-associated protein, optionally wherein the type V CRISPR-associated protein is a Cas12a protein.

3. The composition of claim 1, wherein the polypeptide further comprises a purification tag.

4. The composition of claim 3, wherein the polypeptide comprises at least one tag selected from the group consisting of a His tag, a FLAG tag, an AU1 epitope tag, an AU5 epitope tag, a bacteriophage T7 tag, a bacteriophage V5 epitope tag, a Bluetongue virus tag (B-tag), a Glu-Glu tag (EE-tag), an HSV epitope tag, a KT3 epitope tag, a Myc epitope tag, a PDZ ligand tag, a polyarginine tag, a polyaspartate tag, a polycysteine tag, a polyphenylalanine tag, a protein C tag, an S1-tag, an S-tag, a Step-tag, and a VSV-G tag.

5. The composition of claim 1, wherein the guide RNA comprises an A-rich protospacer adjacent motif (PAM) sequence, a G-rich PAM sequence, a T-rich PAM sequence, or a C-rich PAM sequence.

6. The composition of claim 5, wherein the PAM sequence comprises 3 T nucleobases, 2 T nucleobases, 1 T nucleobase, or TTTN.

7. The composition of claim 1, wherein the composition exhibits at least 2-fold increased genome editing efficiency than AsCas12a, FnCas12a, or LbCas12a.

8. The composition of claim 1, wherein the composition comprises:
the polypeptide comprising at least 85% sequence identity with residue 825 through residue 996 of SEQ ID NO: 3, wherein the polypeptide comprises an amino acid sequence comprising a Lysine aligned to a Lysine at position 930 of SEQ ID NO: 3; or
the polypeptide comprising at least 85% sequence identity with SEQ ID NO: 3, wherein the polypeptide comprises an amino acid sequence comprising a Lysine aligned to a Lysine at position 930 of SEQ ID NO: 3.

9. The composition of claim 1, wherein the composition comprises:
a polypeptide comprising at least 90% sequence identity with residue 825 through residue 996 of SEQ ID NO: 3, wherein the polypeptide comprises an amino acid sequence comprising a Lysine aligned to a Lysine at position 930 of SEQ ID NO: 3; or
a polypeptide comprising at least 90% sequence identity with SEQ ID NO: 3, wherein the polypeptide comprises an amino acid sequence comprising a Lysine aligned to a Lysine at position 930 of SEQ ID NO: 3.

10. The composition of claim 1, wherein the composition comprises:
a polypeptide comprising at least 95% sequence identity with residue 825 through residue 996 of SEQ ID NO: 3, wherein the polypeptide comprises an amino acid sequence comprising a Lysine aligned to a Lysine at position 930 of SEQ ID NO: 3; or
a polypeptide comprising at least 95% sequence identity with SEQ ID NO: 3, wherein the polypeptide comprises an amino acid sequence comprising a Lysine aligned to a Lysine at position 930 of SEQ ID NO: 3.

11. A method of gene editing, wherein the method comprises:
providing a composition comprising: at least one of i)-ii):
   i) a polypeptide comprising at least 80% sequence identity with residue 825 through residue 996 of SEQ ID NO: 3, wherein the polypeptide comprises an amino acid sequence comprising a Lysine aligned to a Lysine at position 930 of SEQ ID NO: 3; or
   ii) a polypeptide comprising at least 80% sequence identity with SEQ ID NO: 3, wherein the polypeptide comprises an amino acid sequence comprising a Lysine aligned to a Lysine at position 930 of SEQ ID NO: 3; and
a guide RNA coupled to the at least one of i)-ii), wherein the guide RNA comprises a sequence that is reverse complementary to a eukaryotic nucleic acid sequence comprising from 6 to 60 bases; and
contacting a cell with the composition, thereby cleaving the eukaryotic nucleic acid sequence.

12. The method of claim 11, wherein the polypeptide comprises at least one tag selected from the group consisting of: a His tag, a FLAG tag, an AU1 epitope tag, an AU5 epitope tag, a bacteriophage T7 tag, a bacteriophage V5 epitope tag, a Bluetongue virus tag (B-tag), a Glu-Glu tag (EE-tag), an HSV epitope tag, a KT3 epitope tag, a Myc epitope tag, a PDZ ligand tag, a polyarginine tag, a polyaspartate tag, a polycysteine tag, a polyphenylalanine tag, a protein C tag, an S1-tag, an S-tag, a Step-tag, and a VSV-G tag.

13. The method of claim 11, wherein the guide RNA comprises an A-rich protospacer adjacent motif (PAM) sequence, a G-rich PAM sequence, a T-rich PAM sequence, or a C-rich PAM sequence.

14. The method of claim 11, wherein the PAM sequence comprises 3 T nucleobases, 2 T nucleobases, 1 T nucleobase, or TTTN.

15. The method of claim 11, wherein the composition exhibits at least 2-fold increased cleaving efficiency than AsCas12a, FnCas12a, or LbCas12a.

16. The method of claim 11, wherein the composition comprises:
the polypeptide comprising at least 85% sequence identity with residue 825 through residue 996 of SEQ ID NO: 3, wherein the polypeptide comprises an amino acid sequence comprising a Lysine aligned to a Lysine at position 930 of SEQ ID NO: 3; or
the polypeptide comprising at least 85% sequence identity with SEQ ID NO: 3, wherein the polypeptide comprises an amino acid sequence comprising a Lysine aligned to a Lysine at position 930 of SEQ ID NO: 3.

17. The method of claim 11, wherein the composition comprises:
a polypeptide comprising at least 90% sequence identity with residue 825 through residue 996 of SEQ ID NO: 3, wherein the polypeptide comprises an amino acid sequence comprising a Lysine aligned to a Lysine at position 930 of SEQ ID NO: 3; or a polypeptide comprising at least 90% sequence identity with SEQ ID NO: 3, wherein the polypeptide comprises an amino acid sequence comprising a Lysine aligned to a Lysine at position 930 of SEQ ID NO: 3.

18. The method of claim 11, wherein the composition comprises:

a polypeptide comprising at least 95% sequence identity with residue 825 through residue 996 of SEQ ID NO: 3, wherein the polypeptide comprises an amino acid sequence comprising a Lysine aligned to a Lysine at position 930 of SEQ ID NO: 3; or a polypeptide comprising at least 95% sequence identity with SEQ ID NO: 3, wherein the polypeptide comprises an amino acid sequence comprising a Lysine aligned to a Lysine at position 930 of SEQ ID NO: 3.

* * * * *

SEQUENCE LISTING

<160> NUMBER OF SEQ ID NOS: 67

<210> SEQ ID NO 1
<211> LENGTH: 1263
<212> TYPE: PRT
<213> ORGANISM: Unknown
<220> FEATURE:
<223> OTHER INFORMATION: Description of Unknown:
      mgCas12a-1 sequence

<400> SEQUENCE: 1

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

-continued

```
Thr Leu Ile Lys Glu Gln Ala Glu Lys Arg Lys Ala Ile Tyr Lys Lys
            100                 105                 110
Phe Ala Asp Asp Arg Phe Lys Asn Met Phe Ser Ala Lys Leu Ile
        115                 120                 125
Ser Asp Ile Leu Pro Glu Phe Val Ile His Asn Asn Tyr Ser Ala
    130                 135                 140
Ser Glu Lys Glu Lys Thr Gln Val Ile Lys Leu Phe Ser Arg Phe
145                 150                 155                 160
Ala Thr Ser Phe Lys Asp Tyr Phe Lys Asn Arg Ala Asn Cys Phe Ser
                165                 170                 175
Ala Asp Asp Ile Ser Ser Ser Cys His Arg Ile Val Asn Asp Asn
            180                 185                 190
Ala Glu Ile Phe Phe Ser Asn Ala Leu Val Tyr Arg Arg Ile Val Lys
        195                 200                 205
Asn Leu Ser Asn Asp Asp Ile Asn Lys Ile Ser Gly Asp Ile Lys Asp
        210                 215                 220
Ser Leu Lys Glu Met Ser Leu Glu Glu Ile Tyr Ser Tyr Glu Lys Tyr
225                 230                 235                 240
Gly Glu Phe Ile Thr Gln Glu Gly Ile Ser Phe Tyr Asn Asp Ile Cys
                245                 250                 255
Gly Lys Val Asn Ser Phe Met Asn Leu Tyr Cys Gln Lys Asn Lys Glu
            260                 265                 270
Asn Lys Asn Leu Tyr Lys Leu Arg Lys Leu His Lys Gln Ile Leu Cys
        275                 280                 285
Ile Ala Asp Thr Ser Tyr Glu Val Pro Tyr Lys Phe Glu Ser Asp Glu
        290                 295                 300
Glu Val Tyr Gln Ser Val Asn Gly Phe Leu Asp Asn Ile Ser Ser Lys
305                 310                 315                 320
His Ile Val Glu Arg Leu Arg Lys Ile Gly Asp Asn Tyr Asn Gly Tyr
                325                 330                 335
Asn Leu Asp Lys Ile Tyr Ile Val Ser Lys Phe Tyr Glu Ser Val Ser
            340                 345                 350
Gln Lys Thr Tyr Arg Asp Trp Glu Thr Ile Asn Thr Ala Leu Glu Ile
        355                 360                 365
His Tyr Asn Asn Ile Leu Pro Gly Asn Gly Lys Ser Lys Ala Asp Lys
        370                 375                 380
Val Lys Lys Ala Val Lys Asn Asp Leu Gln Lys Ser Ile Thr Glu Ile
385                 390                 395                 400
Asn Glu Leu Val Ser Asn Tyr Lys Leu Cys Pro Asp Asp Asn Ile Lys
                405                 410                 415
Ala Glu Thr Tyr Ile His Glu Ile Ser His Ile Leu Asn Asn Phe Glu
            420                 425                 430
Ala Gln Glu Leu Lys Tyr Asn Pro Glu Ile His Leu Val Glu Ser Glu
        435                 440                 445
Leu Lys Ala Ser Glu Leu Lys Asn Val Leu Asp Val Ile Met Asn Ala
        450                 455                 460
Phe His Trp Cys Ser Val Phe Met Thr Glu Glu Leu Val Asp Lys Asp
465                 470                 475                 480
Asn Asn Phe Tyr Ala Glu Leu Glu Glu Ile Tyr Asp Glu Ile Tyr Thr
                485                 490                 495
Val Ile Ser Leu Tyr Asn Leu Val Arg Asn Tyr Val Thr Gln Lys Pro
            500                 505                 510
```

-continued

```
Tyr Ser Thr Lys Lys Ile Lys Leu Asn Phe Gly Ile Pro Thr Leu Ala
            515                 520                 525

Asp Gly Trp Ser Lys Ser Lys Glu Tyr Ser Asn Asn Ala Ile Ile Leu
530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
            595                 600                 605

Ser Ala Tyr Ile Leu Glu Gly Tyr Lys Gln Asn Lys His Leu Lys Ser
        610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
        675                 680                 685

Asp Ile Asp Leu Leu Gln Glu Lys Gly Gln Leu Tyr Leu Phe Gln Ile
    690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
        755                 760                 765

Thr Tyr Glu Ala Glu Glu Lys Asp Gln Phe Gly Asn Ile Gln Ile Val
    770                 775                 780

Arg Lys Thr Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
        835                 840                 845

Phe Lys Ala Asn Lys Thr Ser Phe Ile Asn Asp Arg Ile Leu Gln Tyr
    850                 855                 860

Ile Ala Lys Glu Lys Asn Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
        915                 920                 925
```

Glu Ile Gly Lys Ile Lys Glu Ile Lys Glu Gly Tyr Leu Ser Leu Val
930                935              940

Ile His Glu Ile Ser Lys Met Val Ile Lys Tyr Asn Ala Ile Ile Ala
945                950              955              960

Met Glu Asp Leu Ser Tyr Gly Phe Lys Lys Gly Arg Phe Lys Val Glu
            965              970              975

Arg Gln Val Tyr Gln Lys Phe Glu Thr Met Leu Ile Asn Lys Leu Asn
        980              985              990

Tyr Leu Val Phe Lys Asp Ile Ser Ile Thr Glu Asn Gly Gly Leu Leu
        995              1000            1005

Lys Gly Tyr Gln Leu Thr Tyr Ile Pro Asp Lys Leu Lys Asn Val
    1010            1015            1020

Gly His Gln Cys Gly Cys Ile Phe Tyr Val Pro Ala Ala Tyr Thr
    1025            1030            1035

Ser Lys Ile Asp Pro Thr Thr Gly Phe Val Asn Ile Phe Lys Phe
    1040            1045            1050

Lys Asp Leu Thr Val Asp Ala Lys Arg Glu Phe Ile Lys Lys Phe
    1055            1060            1065

Asp Ser Ile Arg Tyr Asp Ser Glu Lys Lys Leu Phe Cys Phe Thr
    1070            1075            1080

Phe Asp Tyr Asn Asn Phe Ile Thr Gln Asn Thr Val Met Ser Lys
    1085            1090            1095

Ser Ser Trp Ser Val Tyr Thr Tyr Gly Val Arg Ile Lys Arg Arg
    1100            1105            1110

Phe Val Asn Gly Arg Phe Ser Asn Glu Ser Asp Thr Ile Asp Ile
    1115            1120            1125

Thr Lys Asp Met Glu Lys Thr Leu Glu Met Thr Asp Ile Asn Trp
    1130            1135            1140

Arg Asp Gly His Asp Leu Arg Gln Asp Ile Ile Asp Tyr Glu Ile
    1145            1150            1155

Val Gln His Ile Phe Glu Ile Phe Arg Leu Thr Val Gln Met Arg
    1160            1165            1170

Asn Ser Leu Ser Glu Leu Glu Asp Arg Asp Tyr Asp Arg Leu Ile
    1175            1180            1185

Ser Pro Val Leu Asn Glu Asn Asn Ile Phe Tyr Asp Ser Ala Lys
    1190            1195            1200

Ala Gly Asp Ala Leu Pro Lys Asp Ala Asp Ala Asn Gly Ala Tyr
    1205            1210            1215

Cys Ile Ala Leu Lys Gly Leu Tyr Glu Ile Lys Gln Ile Thr Glu
    1220            1225            1230

Asn Trp Lys Glu Asp Gly Lys Phe Ser Arg Asp Lys Leu Lys Ile
    1235            1240            1245

Ser Asn Lys Asp Trp Phe Asp Phe Ile Gln Asn Lys Arg Tyr Leu
    1250            1255            1260

<210> SEQ ID NO 2
<211> LENGTH: 3792
<212> TYPE: DNA
<213> ORGANISM: Unknown
<220> FEATURE:
<223> OTHER INFORMATION: Description of Unknown:
      mgCas12a-1 sequence

<400> SEQUENCE: 2

```
atgaataacg gaacaaataa ctttcagaac tttatcggaa tttcttcttt gcagaagact      60
cttaggaatg ctctcattcc aacagaaaca acacagcaat ttattgttaa aaatggaata     120
attaaagaag atgaactcag aggagaaaat cgtcagatac ttaaagatat catggatgat     180
tattacagag gtttcatttc agaaacttta tcgtcaattg atgatattga ctggacctct     240
ttatttgaga aaatggaaat tcagttaaaa aatggagata taaagacac tcttataaaa      300
gaacaggctg aaaacgtaa ggcaatctat aaaaaatttg cagatgatga tagatttaaa      360
aatatgttca gtgcaaaatt aatctcagat attcttcctg aatttgtcat tcataacaat     420
aattattctg catcagaaaa ggaagaaaaa acacaggtaa ttaaattatt ttccagattt     480
gcaacatcat tcaaggacta ttttaaaaac agggctaatt gttttctgc tgatgatata     540
tcttcttctt cttgtcatag aatagttaat gataatgcag aaatatttt tagtaatgca     600
ttggtgtata ggagaattgt aaaaaatctt tcaaatgatg atataaataa aatatccgga     660
gatattaagg attcattaaa ggaaatgtct ctggaggaaa tttattctta tgaaaaatat     720
ggggaattta ttacacagga aggtatatct ttttataatg atatatgcgg taaagtaaat     780
tcatttatga atttatattg ccagaaaaat aaagaaaaca aaatctcta taagctgcga     840
aagcttcata acagatact gtgcatagca gatacttctt atgaggtgcc gtataaattt     900
gaatcagatg aagaggttta tcaatcagtg aatggatttt tggacaatat tagttcaaaa     960
catatcgttg aaagattgcg taagattgga gacaactata acggctacaa tcttgataag    1020
atttatattg ttagtaaatt ctatgaatca gtttcacaaa agacatatag agattgggaa    1080
acaataaata ctgcattaga aattcattac aacaatatat acccggaaa tggtaaatct     1140
aaagctgaca aggtaaaaaa agcggtaaag aatgatctgc aaaaaagcat tactgaaatc    1200
aatgagcttg ttagcaatta taaattatgt ccggatgata tattaaagc agagacatat    1260
atacatgaaa tatcacatat tttgaataat tttgaagcac aggagcttaa gtataatcct    1320
gaaattcatc tggtggaaag tgaattgaaa gcatctgaat taaaaaatgt tctcgatgta    1380
ataatgaatg cttttcattg gtgttcggtt ttcatgacag aggagctggt agataaagat    1440
aataattttt atgcggagtt agaagagata tatgacgaaa tatatacggt aatttcattg    1500
tataatcttg tgcgtaatta tgtaacgcag aagccatata gtacaaaaaa aattaaattg    1560
aattttggta ttcctacact agcggatgga tggagtaaaa gtaaagaata tagtaataat    1620
gcaattattc tcatgcgtga taatttgtac tatttaggaa tatttaatgc aaaaaataag    1680
cctgacaaaa agataattga aggtaataca tcagaaaata aggggatta taagaagatg    1740
atttataatc ttctgccagg accaaataaa atgatcccca aggtattcct ctcttcaaaa    1800
accggagtgg aaacatataa gccgtctgcc tatatattgg agggctataa acaaaacaag    1860
catcttaaat cctctaagga ttttgatata acgttttgtc acgatttgat tgattatttt    1920
aagaactgta tagcaataca tcctgaatgg aagaattttg gctttgattt ttctgacacc    1980
tccacatatg aagatatcag cggatttac agagaagtcg aattgcaagg ttataaaatt    2040
gactggacat atatcagcga aaaggatatt gatttgttgc aggaaaaagg acagttatat    2100
ttatttcaaa tatataacaa agattttcc aagaaaagta ccggaaatga taatcttcat    2160
actatgtatt tgaagaattt gtttagcgaa gagaatttaa aggatattgt actgaaatta    2220
aacggtgagg cggaaatctt ctttagaaaa tcaagcataa agaatccaat aattcataaa    2280
```

| | | |
|---|---|---|
| aaaggctcta ttcttgttaa tagaacatat gaagcagagg aaaaagatca atttggaaat | 2340 | |
| atccagatag tcagaaaaac cataccggaa aatatatatc aggagcttta taaatatttc | 2400 | |
| aatgataaaa gtgataaaga actttcggat gaagcagcta agcttaagaa tgtagtaggt | 2460 | |
| catcatgagg ctgctacaaa catagtaaaa gattatagat atacatatga taaatatttt | 2520 | |
| cttcatatgc ctattacaat caattttaaa gccaataaga caagctttat taatgacaga | 2580 | |
| atattacaat atattgctaa agaaaagaat ttgcatgtaa taggcattga tcgtggtgaa | 2640 | |
| agaaacctga tatatgtttc agtaattgat acttgtggaa atattgttga acaaaaatcg | 2700 | |
| tttaacattg ttaatggata tgattatcag attaagctca agcagcagga gggggcgcga | 2760 | |
| caaatcgcac gaaaagaatg gaaagaaatc ggcaaaataa aagaaattaa agaaggctat | 2820 | |
| ttatctcttg taattcatga aatttcaaag atggttatta aatataatgc cataattgca | 2880 | |
| atggaggatt taagctacgg atttaaaaaa ggtcgtttca aggttgagcg acaggtttac | 2940 | |
| cagaagtttg agacaatgct tatcaacaaa ctcaactatc tggtatttaa agatatatcc | 3000 | |
| ataactgaaa acggtggtct tctaaaggga tatcagctta catatattcc agataaactg | 3060 | |
| aaaaatgtgg gtcatcaatg tggttgtata ttttacgtac ctgctgccta tacatcaaaa | 3120 | |
| atagatccta caaccggatt tgtaaatata ttcaaattta agatttaac agttgatgca | 3180 | |
| aagagagaat ttataaaaaa atttgacagt atcagatatg attcagaaaa aaaactgttt | 3240 | |
| tgttttacat ttgattataa taactttatt acgcaaaata ctgttatgtc aaagtcaagc | 3300 | |
| tggagtgtat atacgtacgg agttaggata aaaagaagat ttgtcaatgg caggttctca | 3360 | |
| aatgaatcgg atacaattga tataacaaaa gatatggaaa aaaccctcga atgacagat | 3420 | |
| ataaattgga gagatggtca tgatctgagg caggatatta ttgattatga aatcgtacaa | 3480 | |
| cacatatttg agattttag attgactgta caaatgagaa acagtttaag tgaattagaa | 3540 | |
| gacagggatt atgaccgttt gatttctccg gtgctcaatg aaaataatat atttttatgat | 3600 | |
| tcagctaaag caggagatgc gttacctaaa gacgcagatg ctaatggtgc atattgtata | 3660 | |
| gctctaaaag gcttgtatga aatcaaacaa attacagaga attggaaaga agacggtaag | 3720 | |
| ttttcaagag ataaacttaa aatttccaat aaggactggt tgactttat tcaaaataaa | 3780 | |
| aggtatttat aa | 3792 | |

<210> SEQ ID NO 3
<211> LENGTH: 1275
<212> TYPE: PRT
<213> ORGANISM: Unknown
<220> FEATURE:
<223> OTHER INFORMATION: Description of Unknown:
    mgCas12a-2 sequence

<400> SEQUENCE: 3

Met Gly Lys Asn Gln Asn Phe Gln Glu Phe Ile Gly Val Ser Pro Leu
1               5                   10                  15

Gln Lys Thr Leu Arg Asn Glu Leu Ile Pro Thr Glu Thr Thr Lys Lys
            20                  25                  30

Asn Ile Thr Gln Leu Asp Leu Leu Thr Glu Asp Glu Ile Arg Ala Gln
        35                  40                  45

Asn Arg Glu Lys Leu Lys Glu Met Met Asp Asp Tyr Tyr Arg Asn Val
    50                  55                  60

Ile Asp Ser Thr Leu His Val Gly Ile Ala Val Asp Trp Ser Tyr Leu
65                  70                  75                  80

-continued

Phe Ser Cys Met Arg Asn His Leu Arg Glu Asn Ser Lys Glu Ser Lys
                85                  90                  95

Arg Glu Leu Glu Arg Thr Gln Asp Ser Ile Arg Ser Gln Ile His Asn
            100                 105                 110

Lys Phe Ala Glu Arg Ala Asp Phe Lys Asp Met Phe Gly Ala Ser Ile
        115                 120                 125

Ile Thr Lys Leu Leu Pro Thr Tyr Ile Lys Gln Asn Ser Glu Tyr Ser
    130                 135                 140

Glu Arg Tyr Asp Glu Ser Met Glu Ile Leu Lys Leu Tyr Gly Lys Phe
145                 150                 155                 160

Thr Thr Ser Leu Thr Asp Tyr Phe Glu Thr Arg Lys Asn Ile Phe Ser
                165                 170                 175

Lys Glu Lys Ile Ser Ser Ala Val Gly Tyr Arg Ile Val Glu Glu Asn
            180                 185                 190

Ala Glu Ile Phe Leu Gln Asn Gln Asn Ala Tyr Asp Arg Ile Cys Lys
        195                 200                 205

Ile Ala Gly Leu Asp Leu His Gly Leu Asp Asn Glu Ile Thr Ala Tyr
    210                 215                 220

Val Asp Gly Lys Thr Leu Lys Glu Val Cys Ser Asp Glu Gly Phe Ala
225                 230                 235                 240

Lys Ala Ile Thr Gln Glu Gly Ile Asp Arg Tyr Asn Glu Ala Ile Gly
                245                 250                 255

Ala Val Asn Gln Tyr Met Asn Leu Leu Cys Gln Lys Asn Lys Ala Leu
            260                 265                 270

Lys Pro Gly Gln Phe Lys Met Lys Arg Leu His Lys Gln Ile Leu Cys
        275                 280                 285

Lys Gly Thr Thr Ser Phe Asp Ile Pro Lys Lys Phe Glu Asn Asp Lys
    290                 295                 300

Gln Val Tyr Asp Ala Val Asn Ser Phe Thr Glu Ile Val Thr Lys Asn
305                 310                 315                 320

Asn Asp Leu Lys Arg Leu Leu Asn Ile Thr Gln Asn Ala Asn Asp Tyr
                325                 330                 335

Asp Met Asn Lys Ile Tyr Val Val Ala Asp Ala Tyr Ser Met Ile Ser
            340                 345                 350

Gln Phe Ile Ser Lys Lys Trp Asn Leu Ile Glu Glu Cys Leu Leu Asp
        355                 360                 365

Tyr Tyr Ser Asp Asn Leu Pro Gly Lys Gly Asn Ala Lys Glu Asn Lys
    370                 375                 380

Val Lys Lys Ala Val Lys Glu Thr Tyr Arg Ser Val Ser Gln Leu
385                 390                 395                 400

Asn Glu Val Ile Glu Lys Tyr Tyr Val Glu Lys Thr Gly Gln Ser Val
                405                 410                 415

Trp Lys Val Glu Ser Tyr Ile Ser Ser Leu Ala Glu Met Ile Lys Leu
            420                 425                 430

Glu Leu Cys His Glu Ile Asp Asn Asp Glu Lys His Asn Leu Ile Glu
        435                 440                 445

Asp Asp Glu Lys Ile Ser Glu Ile Lys Glu Leu Leu Asp Met Tyr Met
    450                 455                 460

Asp Val Phe His Ile Ile Lys Val Phe Arg Val Asn Glu Val Leu Asn
465                 470                 475                 480

Phe Asp Glu Thr Phe Tyr Ser Glu Met Asp Glu Ile Tyr Gln Asp Met
                485                 490                 495

```
Gln Glu Ile Val Pro Leu Tyr Asn His Val Arg Asn Tyr Val Thr Gln
            500                 505                 510
Lys Pro Tyr Lys Gln Glu Lys Tyr Arg Leu Tyr Phe His Thr Pro Thr
        515                 520                 525
Leu Ala Asn Gly Trp Ser Lys Ser Lys Glu Tyr Asp Asn Asn Ala Ile
    530                 535                 540
Ile Leu Val Arg Glu Asp Lys Tyr Tyr Leu Gly Ile Leu Asn Ala Lys
545                 550                 555                 560
Lys Lys Pro Ser Lys Glu Ile Met Ala Gly Lys Glu Asp Cys Ser Glu
                565                 570                 575
His Ala Tyr Ala Lys Met Asn Tyr Tyr Leu Leu Pro Gly Ala Asn Lys
            580                 585                 590
Met Leu Pro Lys Val Phe Leu Ser Lys Gly Ile Gln Asp Tyr His
        595                 600                 605
Pro Ser Ser Tyr Ile Val Glu Gly Tyr Asn Glu Lys Lys His Ile Lys
    610                 615                 620
Gly Ser Lys Asn Phe Asp Ile Arg Phe Cys Arg Asp Leu Ile Asp Tyr
625                 630                 635                 640
Phe Lys Glu Cys Ile Lys Lys His Pro Asp Trp Asn Lys Phe Asn Phe
                645                 650                 655
Glu Phe Ser Ala Thr Glu Thr Tyr Glu Asp Ile Ser Val Phe Tyr Arg
            660                 665                 670
Glu Val Glu Lys Gln Gly Tyr Arg Val Glu Trp Thr Tyr Ile Asn Ser
        675                 680                 685
Glu Asp Ile Gln Lys Leu Glu Glu Asp Gly Gln Leu Phe Leu Phe Gln
    690                 695                 700
Ile Tyr Asn Lys Asp Phe Ala Val Gly Ser Thr Gly Lys Pro Asn Leu
705                 710                 715                 720
His Thr Leu Tyr Leu Lys Asn Leu Phe Ser Glu Glu Asn Leu Arg Asp
                725                 730                 735
Ile Val Leu Lys Leu Asn Gly Glu Ala Glu Ile Phe Phe Arg Lys Ser
            740                 745                 750
Ser Val Gln Lys Pro Val Ile His Lys Cys Gly Ser Ile Leu Val Asn
        755                 760                 765
Arg Thr Tyr Glu Ile Thr Glu Ser Gly Thr Thr Arg Val Gln Ser Ile
    770                 775                 780
Pro Glu Ser Glu Tyr Met Glu Leu Tyr Arg Tyr Phe Asn Ser Glu Lys
785                 790                 795                 800
Gln Ile Glu Leu Ser Asp Glu Ala Lys Lys Tyr Leu Asp Lys Val Gln
                805                 810                 815
Cys Asn Lys Ala Lys Thr Asp Ile Val Lys Asp Tyr Arg Tyr Thr Met
            820                 825                 830
Asp Lys Phe Phe Ile His Leu Pro Ile Thr Ile Asn Phe Lys Val Asp
        835                 840                 845
Lys Gly Asn Asn Val Asn Ala Ile Ala Gln Gln Tyr Ile Ala Gly Arg
    850                 855                 860
Lys Asp Leu His Val Ile Gly Ile Asp Arg Gly Glu Arg Asn Leu Ile
865                 870                 875                 880
Tyr Val Ser Val Ile Asp Met Tyr Gly Arg Ile Leu Glu Gln Lys Ser
                885                 890                 895
Phe Asn Leu Val Glu Gln Val Ser Ser Gln Gly Thr Lys Arg Tyr Tyr
            900                 905                 910
```

```
Asp Tyr Lys Glu Lys Leu Gln Asn Arg Glu Glu Arg Asp Lys Ala
        915                 920                 925

Arg Lys Ser Trp Lys Thr Ile Gly Lys Ile Lys Glu Leu Lys Glu Gly
930                 935                 940

Tyr Leu Ser Ser Val Ile His Glu Ile Ala Gln Met Val Val Lys Tyr
945                 950                 955                 960

Asn Ala Ile Ile Ala Met Glu Asp Leu Asn Tyr Gly Phe Lys Arg Gly
                965                 970                 975

Arg Phe Lys Val Glu Arg Gln Val Tyr Gln Lys Phe Glu Thr Met Leu
            980                 985                 990

Ile Ser Lys Leu Asn Tyr Leu Ala Asp Lys Ser Gln Ala Val Asp Glu
        995                 1000                1005

Pro Gly Gly Ile Leu Arg Gly Tyr Gln Met Thr Tyr Val Pro Asp
    1010                1015                1020

Asn Ile Lys Asn Val Gly Arg Gln Cys Gly Ile Ile Phe Tyr Val
    1025                1030                1035

Pro Ala Ala Tyr Thr Ser Lys Ile Asp Pro Thr Thr Gly Phe Ile
    1040                1045                1050

Asn Ala Phe Lys Arg Asp Val Val Ser Thr Asn Asp Ala Lys Glu
    1055                1060                1065

Asn Phe Leu Met Lys Phe Asp Ser Ile Gln Tyr Asp Ile Glu Lys
    1070                1075                1080

Gly Leu Phe Lys Phe Ser Phe Asp Tyr Lys Asn Phe Ala Thr His
    1085                1090                1095

Lys Leu Thr Leu Ala Lys Thr Lys Trp Asp Val Tyr Thr Asn Gly
    1100                1105                1110

Thr Arg Ile Gln Asn Met Lys Val Glu Gly His Trp Leu Ser Met
    1115                1120                1125

Glu Val Glu Leu Thr Thr Lys Met Lys Glu Leu Leu Asp Asp Ser
    1130                1135                1140

His Ile Pro Tyr Glu Glu Gly Gln Asn Ile Leu Asp Asp Leu Arg
    1145                1150                1155

Glu Met Lys Asp Ile Thr Thr Ile Val Asn Gly Ile Leu Glu Ile
    1160                1165                1170

Phe Trp Leu Thr Val Gln Leu Arg Asn Ser Arg Ile Asp Asn Pro
    1175                1180                1185

Asp Tyr Asp Arg Ile Ile Ser Pro Val Leu Asn Lys Asn Gly Glu
    1190                1195                1200

Phe Phe Asp Ser Asp Glu Tyr Asn Ser Tyr Ile Asp Ala Gln Lys
    1205                1210                1215

Ala Pro Leu Pro Ile Asp Ala Asp Ala Asn Gly Ala Phe Cys Ile
    1220                1225                1230

Ala Leu Lys Gly Met Tyr Thr Ala Asn Gln Ile Lys Glu Asn Trp
    1235                1240                1245

Val Glu Gly Glu Lys Leu Pro Ala Asp Cys Leu Lys Ile Glu His
    1250                1255                1260

Ala Ser Trp Leu Ala Phe Met Gln Gly Glu Arg Gly
    1265                1270                1275

<210> SEQ ID NO 4
<211> LENGTH: 3828
<212> TYPE: DNA
<213> ORGANISM: Unknown
<220> FEATURE:
```

<223> OTHER INFORMATION: Description of Unknown: mgCas12a-2 sequence

<400> SEQUENCE: 4

```
atgggtaaaa atcaaaattt tcaggaattt attggggtat caccacttca aaagacttta      60
agaaacgaat taatcccaac agaaacaaca aaaaagaata ttactcagct tgatcttttg     120
actgaggatg aaatccgcgc gcaaaatcga gagaagctga agagatgat ggatgactac      180
taccggaatg tgattgatag cactttgcat gtgggtatag ctgttgattg agctattta      240
ttttcgtgta tgcgaaatca tctaagggag aattccaaag agtcaaagcg ggaattggaa     300
cgaacacagg attctattcg ttcacaaatc cataataagt tgctgaacg agcggatttt      360
aaggatatgt ttggagcatc gataataaca aaattacttc cgacatatat aaaacagaat     420
tcagaatatt ccgagcggta tgacgagagc atggaaattt gaaactgta tggaaaattc      480
acaacatcgt tgaccgatta ctttgagaca agaaagaata tcttttctaa agagaaaata     540
tcttctgccg ttggatatcg aatcgtagag gaaaatgctg agatcttctt gcagaatcag     600
aatgcttacg acagaatctg taagatagcg ggactggatt tacatggatt ggataatgaa     660
ataacagcat atgttgatgg aaaaacatta aagaagtat gttcggatga aggatttgca      720
aaggctatta cacaagaagg gattgatcgc tacaacgagg caatcggtgc agtaaatcaa     780
tatatgaatc tgttatgcca gaagaataag gcattaaaac cgggacaatt taagatgaag     840
cggctacata acagattct tgcaaagga caacctctt tcgatattcc aaagaagttt        900
gaaaatgata acaggtgta tgacgcagtt aattcttta cagagatagt aacgaagaat       960
aatgatttga agcgactgtt aaatattaca cagaatgcaa atgattatga catgaataaa    1020
atctatgtag tagccgatgc atatagtatg atttcacagt ttatcagtaa aaaatggaat    1080
ctgattgaag aatgcttgct ggattattat agcgataatt tgccgggaaa aggaaatgcg    1140
aaagaaaaca aagttaaaaa ggcggtaaag gaagaaacgt atcgcagtgt tcacagttg     1200
aatgaagtta ttgagaaata ttatgtggaa aagaccggac agtcagtatg aaagtggaa     1260
agttatattt ctagtctggc agaaatgatt aagctggaat tgtgccacga gatagataac    1320
gatgagaagc ataatctgat tgaagatgat gagaagatat ccgagattaa ggaactgttg    1380
gatatgtaca tggatgtatt tcatattata aaagtgttcc gggtgaatga agtattgaat    1440
ttcgatgaaa cctttattc ggagatggat gagatctatc aggatatgca ggaaatcgtt     1500
ccattataca atcatgttcg aaactatgtt acacagaaac catataagca ggagaaatat    1560
cgtttatatt tccacactcc aacattggca atggctggt ccaagagtaa ggaatatgac      1620
aacaacgcaa ttatattggt gcgagaagat aaatattatt taggtattct gaatgcgaaa    1680
aagaaaccat cgaaagaaat tatggcgggc aagaggatt gttcagaaca tgcatatgca     1740
aagatgaatt attatttgtt gccgggcgcg aacaagatgc ttccaaaagt atttttatct    1800
aagaaaggaa tacaggacta tcacccatca tcatatattg ttgaaggata taatgaaaag    1860
aaacatatta aaggttccaa gaattttgat atccggtttt gtagggattt gattgactac    1920
ttcaaggaat gcattaaaaa acatccggat tggaataagt ttaactttga attttctgcg    1980
acagaaacat atgaggatat cagtgtctttt tatcgcgaag ttgaaaagca aggatatcgc    2040
gtagagtgga cgtatatcaa tagtgaagat attcagaaac tggaagaaga tggacagttg    2100
tttttatttc agatatataa caaagatttt gctgtgggaa gtacaggtaa accaaatctt    2160
catacattgt atctgaaaaa tctgttcagc gaagaaaatt tgcgggacat tgtattaaaa    2220
```

-continued

| | |
|---|---|
| ctaaatgggg aagcagaaat attcttccgt aaatcaagtg ttcaaaaacc ggtgattcat | 2280 |
| aagtgcggca gtattttagt caatcgtacc tatgagatta ccgagagtgg aacaacacgg | 2340 |
| gtacaatcaa ttccggaaag tgaatacatg gaattatatc gctactttaa tagtgaaaag | 2400 |
| cagatagaat tatcgatga ggcaaaaaaa tatttggaca aggtgcaatg taataaggca | 2460 |
| aagacagata ttgtgaaaga ctaccgatac accatggaca agttttttat tcatcttccg | 2520 |
| attacgatta attttaaggt tgataagggt aacaatgtta atgccattgc acagcaatat | 2580 |
| attgcagggc ggaaagattt acatgtgata ggaattgatc gaggagaacg gaatctgatt | 2640 |
| tacgtttctg taattgacat gtatggtaga attttagagc agaaatcctt taaccttgtg | 2700 |
| gaacaggtat cgtcgcaggg aacgaagcga tattacgatt acaaagaaaa attacagaac | 2760 |
| cgggaagagg aacgggataa agcaagaaag agttggaaga caatcggcaa gattaaggaa | 2820 |
| ttaaaagagg ggtatctgtc gtcagtaatt catgagattg cacagatggt cgtaaagtat | 2880 |
| aacgcaatca ttgcaatgga agatttgaat tatggattta gcggggaag attcaaagta | 2940 |
| gagcgccagg tatatcagaa atttgaaacg atgttgatca gtaagttgaa ttatctggca | 3000 |
| gataaatctc aggctgtgga tgaaccggga ggtatattac ggggatatca gatgacttat | 3060 |
| gtgccggata atattaagaa tgttggaaga caatgtggaa taatctttta tgtgccggca | 3120 |
| gcatataccg ccaagattga tccgacaacc ggatttatca atgcatttaa gcgggatgtg | 3180 |
| gtatcaacaa atgatgcaaa agagaatttc ctgatgaagt ttgattctat tcagtacgat | 3240 |
| atagaaaaag gcttatttaa gttttcattt gattacaaaa attttgccac acataaactt | 3300 |
| acacttgcga agacaaaatg ggacgtatat acaaatggaa ctcgaataca aaacatgaaa | 3360 |
| gttgaaggac attggctttc aatggaagtt gaacttacaa cgaaaatgaa agagttgctg | 3420 |
| gatgactcgc atattccata tgaagaagga cagaatatat tggatgattt gcggagatg | 3480 |
| aaagatataa caaccattgt gaatggtata ttggaaatct tctggttgac agtccagctt | 3540 |
| cggaatagca ggatagataa tccggattac gatagaatta tctcaccggt attgaataaa | 3600 |
| aatggagaat tttttgattc tgatgaatat aattcatata ttgatgcgca aaaggcaccg | 3660 |
| ttaccgatag atgccgatgc aaatggcgca ttttgcattg cattaaaagg aatgtatact | 3720 |
| gccaatcaga tcaaagaaaa ctgggttgaa ggggagaaac ttccggcgga ttgcttgaag | 3780 |
| atcgaacatg cgagttggtt agcatttatg caaggagaaa ggggatag | 3828 |

<210> SEQ ID NO 5
<211> LENGTH: 1263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Tyr Tyr Arg Gly
    50                  55                  60

Phe Ile Ser Glu Thr Leu Ser Ser Ile Asp Asp Ile Asp Trp Thr Ser
65                  70                  75                  80

-continued

```
Leu Phe Glu Lys Met Glu Ile Gln Leu Lys Asn Gly Asp Asn Lys Asp
                 85                  90                  95

Thr Leu Ile Lys Glu Gln Ala Glu Lys Arg Lys Ala Ile Tyr Lys Lys
                100                 105                 110

Phe Ala Asp Asp Asp Arg Phe Lys Asn Met Phe Ser Ala Lys Leu Ile
                115                 120                 125

Ser Asp Ile Leu Pro Glu Phe Val Ile His Asn Asn Tyr Ser Ala
130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
                180                 185                 190

Ala Glu Ile Phe Phe Ser Asn Ala Leu Val Tyr Arg Arg Ile Val Lys
                195                 200                 205

Asn Leu Ser Asn Asp Asp Ile Asn Lys Ile Ser Gly Asp Ile Lys Asp
210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
                260                 265                 270

Asn Lys Asn Leu Tyr Lys Leu Arg Lys Leu His Lys Gln Ile Leu Cys
                275                 280                 285

Ile Ala Asp Thr Ser Tyr Glu Val Pro Tyr Lys Phe Glu Ser Asp Glu
290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
                340                 345                 350

Gln Lys Thr Tyr Arg Asp Trp Glu Thr Ile Asn Thr Ala Leu Glu Ile
                355                 360                 365

His Tyr Asn Asn Ile Leu Pro Gly Asn Gly Lys Ser Lys Ala Asp Lys
                370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Pro Asp Asp Asn Ile Lys
                405                 410                 415

Ala Glu Thr Tyr Ile His Glu Ile Ser His Ile Leu Asn Asn Phe Glu
                420                 425                 430

Ala Gln Glu Leu Lys Tyr Asn Pro Glu Ile His Leu Val Glu Ser Glu
                435                 440                 445

Leu Lys Ala Ser Glu Leu Lys Asn Val Leu Asp Val Ile Met Asn Ala
450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Thr
                485                 490                 495
```

```
Val Ile Ser Leu Tyr Asn Leu Val Arg Asn Tyr Val Thr Gln Lys Pro
                500                 505                 510

Tyr Ser Thr Lys Lys Ile Lys Leu Asn Phe Gly Ile Pro Thr Leu Ala
                515                 520                 525

Asp Gly Trp Ser Lys Ser Lys Glu Tyr Ser Asn Asn Ala Ile Ile Leu
            530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
                580                 585                 590

Pro Lys Val Phe Leu Ser Ser Lys Thr Gly Val Glu Thr Tyr Lys Pro
                595                 600                 605

Ser Ala Tyr Ile Leu Glu Gly Tyr Lys Gln Asn Lys His Leu Lys Ser
                610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
                660                 665                 670

Val Glu Leu Gln Gly Tyr Lys Ile Asp Trp Thr Tyr Ile Ser Glu Lys
                675                 680                 685

Asp Ile Asp Leu Leu Gln Glu Lys Gly Gln Leu Tyr Leu Phe Gln Ile
                690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
                740                 745                 750

Ile Lys Asn Pro Ile Ile His Lys Lys Gly Ser Ile Leu Val Asn Arg
                755                 760                 765

Thr Tyr Glu Ala Glu Glu Lys Asp Gln Phe Gly Asn Ile Gln Ile Val
                770                 775                 780

Arg Lys Thr Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
                820                 825                 830

Arg Tyr Thr Tyr Asp Lys Tyr Phe Leu His Met Pro Ile Thr Ile Asn
                835                 840                 845

Phe Lys Ala Asn Lys Thr Ser Phe Ile Asn Asp Arg Ile Leu Gln Tyr
                850                 855                 860

Ile Ala Lys Glu Lys Asn Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
                900                 905                 910
```

Leu Lys Gln Gln Glu Gly Ala Arg Gln Ile Ala Arg Gln Glu Trp Lys
            915                 920                 925

Glu Ile Gly Lys Ile Lys Glu Ile Lys Glu Gly Tyr Leu Ser Leu Val
            930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Gly Arg Phe Lys Val Glu
                965                 970                 975

Arg Gln Val Tyr Gln Lys Phe Glu Thr Met Leu Ile Asn Lys Leu Asn
                980                 985                 990

Tyr Leu Val Phe Lys Asp Ile Ser Ile Thr Glu Asn Gly Gly Leu Leu
            995                 1000                1005

Lys Gly Tyr Gln Leu Thr Tyr Ile Pro Asp Lys Leu Lys Asn Val
        1010                1015                1020

Gly His Gln Cys Gly Cys Ile Phe Tyr Val Pro Ala Ala Tyr Thr
    1025                1030                1035

Ser Lys Ile Asp Pro Thr Thr Gly Phe Val Asn Ile Phe Lys Phe
        1040                1045                1050

Lys Asp Leu Thr Val Asp Ala Lys Arg Glu Phe Ile Lys Lys Phe
        1055                1060                1065

Asp Ser Ile Arg Tyr Asp Ser Glu Lys Lys Leu Phe Cys Phe Thr
        1070                1075                1080

Phe Asp Tyr Asn Asn Phe Ile Thr Gln Asn Thr Val Met Ser Lys
        1085                1090                1095

Ser Ser Trp Ser Val Tyr Thr Tyr Gly Val Arg Ile Lys Arg Arg
        1100                1105                1110

Phe Val Asn Gly Arg Phe Ser Asn Glu Ser Asp Thr Ile Asp Ile
        1115                1120                1125

Thr Lys Asp Met Glu Lys Thr Leu Glu Met Thr Asp Ile Asn Trp
        1130                1135                1140

Arg Asp Gly His Asp Leu Arg Gln Asp Ile Ile Asp Tyr Glu Ile
        1145                1150                1155

Val Gln His Ile Phe Glu Ile Phe Arg Leu Thr Val Gln Met Arg
        1160                1165                1170

Asn Ser Leu Ser Glu Leu Glu Asp Arg Asp Tyr Asp Arg Leu Ile
        1175                1180                1185

Ser Pro Val Leu Asn Glu Asn Asn Ile Phe Tyr Asp Ser Ala Lys
        1190                1195                1200

Ala Gly Asp Ala Leu Pro Lys Asp Ala Asp Ala Asn Gly Ala Tyr
        1205                1210                1215

Cys Ile Ala Leu Lys Gly Leu Tyr Glu Ile Lys Gln Ile Thr Glu
        1220                1225                1230

Asn Trp Lys Glu Asp Gly Lys Phe Ser Arg Asp Lys Leu Lys Ile
        1235                1240                1245

Ser Asn Lys Asp Trp Phe Asp Phe Ile Gln Asn Lys Arg Tyr Leu
        1250                1255                1260

<210> SEQ ID NO 6
<211> LENGTH: 1275
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 6

Met Gly Lys Asn Gln Asn Phe Gln Glu Phe Ile Gly Val Ser Pro Leu
1               5                   10                  15

Gln Lys Thr Leu Arg Asn Glu Leu Ile Pro Thr Glu Thr Thr Lys Lys
            20                  25                  30

Asn Ile Thr Gln Leu Asp Leu Leu Thr Glu Asp Ile Arg Ala Gln
        35                  40                  45

Asn Arg Glu Lys Leu Lys Glu Met Met Asp Asp Tyr Tyr Arg Asn Val
    50                  55                  60

Ile Asp Ser Thr Leu His Val Gly Ile Ala Val Asp Trp Ser Tyr Leu
65                  70                  75                  80

Phe Ser Cys Met Arg Asn His Leu Arg Glu Asn Ser Lys Glu Ser Lys
                85                  90                  95

Arg Glu Leu Glu Arg Thr Gln Asp Ser Ile Arg Ser Gln Ile His Asn
                100                 105                 110

Lys Phe Ala Glu Arg Ala Asp Phe Lys Asp Met Phe Gly Ala Ser Ile
        115                 120                 125

Ile Thr Lys Leu Leu Pro Thr Tyr Ile Lys Gln Asn Ser Glu Tyr Ser
130                 135                 140

Glu Arg Tyr Asp Glu Ser Met Glu Ile Leu Lys Leu Tyr Gly Lys Phe
145                 150                 155                 160

Thr Thr Ser Leu Thr Asp Tyr Phe Glu Thr Arg Lys Asn Ile Phe Ser
                165                 170                 175

Lys Glu Lys Ile Ser Ser Ala Val Gly Tyr Arg Ile Val Glu Glu Asn
            180                 185                 190

Ala Glu Ile Phe Leu Gln Asn Gln Asn Ala Tyr Asp Arg Ile Cys Lys
        195                 200                 205

Ile Ala Gly Leu Asp Leu His Gly Leu Asp Asn Glu Ile Thr Ala Tyr
210                 215                 220

Val Asp Gly Lys Thr Leu Lys Glu Val Cys Ser Asp Glu Gly Phe Ala
225                 230                 235                 240

Lys Ala Ile Thr Gln Glu Gly Ile Asp Arg Tyr Asn Glu Ala Ile Gly
            245                 250                 255

Ala Val Asn Gln Tyr Met Asn Leu Leu Cys Gln Lys Asn Lys Ala Leu
        260                 265                 270

Lys Pro Gly Gln Phe Lys Met Lys Arg Leu His Lys Gln Ile Leu Cys
    275                 280                 285

Lys Gly Thr Thr Ser Phe Asp Ile Pro Lys Lys Phe Glu Asn Asp Lys
290                 295                 300

Gln Val Tyr Asp Ala Val Asn Ser Phe Thr Glu Ile Val Thr Lys Asn
305                 310                 315                 320

Asn Asp Leu Lys Arg Leu Leu Asn Ile Thr Gln Asn Ala Asn Asp Tyr
                325                 330                 335

Asp Met Asn Lys Ile Tyr Val Val Ala Asp Ala Tyr Ser Met Ile Ser
            340                 345                 350

Gln Phe Ile Ser Lys Lys Trp Asn Leu Ile Glu Glu Cys Leu Leu Asp
        355                 360                 365

Tyr Tyr Ser Asp Asn Leu Pro Gly Lys Gly Asn Ala Lys Glu Asn Lys
370                 375                 380

Val Lys Lys Ala Val Lys Glu Glu Thr Tyr Arg Ser Val Ser Gln Leu
385                 390                 395                 400

Asn Glu Val Ile Glu Lys Tyr Tyr Val Glu Lys Thr Gly Gln Ser Val
                405                 410                 415
```

```
Trp Lys Val Glu Ser Tyr Ile Ser Ser Leu Ala Glu Met Ile Lys Leu
                420             425             430

Glu Leu Cys His Glu Ile Asp Asn Asp Glu Lys His Asn Leu Ile Glu
            435             440             445

Asp Asp Glu Lys Ile Ser Glu Ile Lys Glu Leu Leu Asp Met Tyr Met
450             455             460

Asp Val Phe His Ile Ile Lys Val Phe Arg Val Asn Glu Val Leu Asn
465             470             475             480

Phe Asp Glu Thr Phe Tyr Ser Glu Met Asp Glu Ile Tyr Gln Asp Met
            485             490             495

Gln Glu Ile Val Pro Leu Tyr Asn His Val Arg Asn Tyr Val Thr Gln
                500             505             510

Lys Pro Tyr Lys Gln Glu Lys Tyr Arg Leu Tyr Phe His Thr Pro Thr
            515             520             525

Leu Ala Asn Gly Trp Ser Lys Ser Lys Glu Tyr Asp Asn Asn Ala Ile
            530             535             540

Ile Leu Val Arg Glu Asp Lys Tyr Tyr Leu Gly Ile Leu Asn Ala Lys
545             550             555             560

Lys Lys Pro Ser Lys Glu Ile Met Ala Gly Lys Glu Asp Cys Ser Glu
                565             570             575

His Ala Tyr Ala Lys Met Asn Tyr Tyr Leu Leu Pro Gly Ala Asn Lys
            580             585             590

Met Leu Pro Lys Val Phe Leu Ser Lys Lys Gly Ile Gln Asp Tyr His
            595             600             605

Pro Ser Ser Tyr Ile Val Glu Gly Tyr Asn Glu Lys Lys His Ile Lys
            610             615             620

Gly Ser Lys Asn Phe Asp Ile Arg Phe Cys Arg Asp Leu Ile Asp Tyr
625             630             635             640

Phe Lys Glu Cys Ile Lys Lys His Pro Asp Trp Asn Lys Phe Asn Phe
                645             650             655

Glu Phe Ser Ala Thr Glu Thr Tyr Glu Asp Ile Ser Val Phe Tyr Arg
            660             665             670

Glu Val Glu Lys Gln Gly Tyr Arg Val Glu Trp Thr Tyr Ile Asn Ser
            675             680             685

Glu Asp Ile Gln Lys Leu Glu Glu Asp Gly Gln Leu Phe Leu Phe Gln
690             695             700

Ile Tyr Asn Lys Asp Phe Ala Val Gly Ser Thr Gly Lys Pro Asn Leu
705             710             715             720

His Thr Leu Tyr Leu Lys Asn Leu Phe Ser Glu Asn Leu Arg Asp
            725             730             735

Ile Val Leu Lys Leu Asn Gly Glu Ala Glu Ile Phe Phe Arg Lys Ser
            740             745             750

Ser Val Gln Lys Pro Val Ile His Lys Cys Gly Ser Ile Leu Val Asn
            755             760             765

Arg Thr Tyr Glu Ile Thr Glu Ser Gly Thr Thr Arg Val Gln Ser Ile
            770             775             780

Pro Glu Ser Glu Tyr Met Glu Leu Tyr Arg Tyr Phe Asn Ser Glu Lys
785             790             795             800

Gln Ile Glu Leu Ser Asp Glu Ala Lys Lys Tyr Leu Asp Lys Val Gln
                805             810             815

Cys Asn Lys Ala Lys Thr Asp Ile Val Lys Asp Tyr Arg Tyr Thr Met
            820             825             830
```

-continued

Asp Lys Phe Phe Ile His Leu Pro Ile Thr Ile Asn Phe Lys Val Asp
835                 840                 845

Lys Gly Asn Asn Val Asn Ala Ile Ala Gln Gln Tyr Ile Ala Gly Arg
850                 855                 860

Lys Asp Leu His Val Ile Gly Ile Asp Arg Gly Glu Arg Asn Leu Ile
865                 870                 875                 880

Tyr Val Ser Val Ile Asp Met Tyr Gly Arg Ile Leu Glu Gln Lys Ser
            885                 890                 895

Phe Asn Leu Val Glu Gln Val Ser Ser Gln Gly Thr Lys Arg Tyr Tyr
                900                 905                 910

Asp Tyr Lys Glu Lys Leu Gln Asn Arg Glu Glu Glu Arg Asp Lys Ala
            915                 920                 925

Arg Gln Ser Trp Lys Thr Ile Gly Lys Ile Lys Glu Leu Lys Glu Gly
930                 935                 940

Tyr Leu Ser Ser Val Ile His Glu Ile Ala Gln Met Val Val Lys Tyr
945                 950                 955                 960

Asn Ala Ile Ile Ala Met Glu Asp Leu Asn Tyr Gly Phe Lys Arg Gly
                965                 970                 975

Arg Phe Lys Val Glu Arg Gln Val Tyr Gln Lys Phe Glu Thr Met Leu
            980                 985                 990

Ile Ser Lys Leu Asn Tyr Leu Ala Asp Lys Ser Gln Ala Val Asp Glu
        995                 1000                1005

Pro Gly Gly Ile Leu Arg Gly Tyr Gln Met Thr Tyr Val Pro Asp
    1010            1015            1020

Asn Ile Lys Asn Val Gly Arg Gln Cys Gly Ile Ile Phe Tyr Val
    1025            1030            1035

Pro Ala Ala Tyr Thr Ser Lys Ile Asp Pro Thr Thr Gly Phe Ile
    1040            1045            1050

Asn Ala Phe Lys Arg Asp Val Val Ser Thr Asn Asp Ala Lys Glu
    1055            1060            1065

Asn Phe Leu Met Lys Phe Asp Ser Ile Gln Tyr Asp Ile Glu Lys
    1070            1075            1080

Gly Leu Phe Lys Phe Ser Phe Asp Tyr Lys Asn Phe Ala Thr His
    1085            1090            1095

Lys Leu Thr Leu Ala Lys Thr Lys Trp Asp Val Tyr Thr Asn Gly
    1100            1105            1110

Thr Arg Ile Gln Asn Met Lys Val Glu Gly His Trp Leu Ser Met
    1115            1120            1125

Glu Val Glu Leu Thr Thr Lys Met Lys Glu Leu Leu Asp Asp Ser
    1130            1135            1140

His Ile Pro Tyr Glu Glu Gly Gln Asn Ile Leu Asp Asp Leu Arg
    1145            1150            1155

Glu Met Lys Asp Ile Thr Thr Ile Val Asn Gly Ile Leu Glu Ile
    1160            1165            1170

Phe Trp Leu Thr Val Gln Leu Arg Asn Ser Arg Ile Asp Asn Pro
    1175            1180            1185

Asp Tyr Asp Arg Ile Ile Ser Pro Val Leu Asn Lys Asn Gly Glu
    1190            1195            1200

Phe Phe Asp Ser Asp Glu Tyr Asn Ser Tyr Ile Asp Ala Gln Lys
    1205            1210            1215

Ala Pro Leu Pro Ile Asp Ala Asp Ala Asn Gly Ala Phe Cys Ile
    1220            1225            1230

| Ala | Leu | Lys | Gly | Met | Tyr | Thr | Ala | Asn | Gln | Ile | Lys | Glu | Asn | Trp |
|---|---|---|---|---|---|---|---|---|---|---|---|---|---|---|
| 1235 | | | | 1240 | | | | | 1245 | | | | | |

| Val | Glu | Gly | Glu | Lys | Leu | Pro | Ala | Asp | Cys | Leu | Lys | Ile | Glu | His |
|---|---|---|---|---|---|---|---|---|---|---|---|---|---|---|
| 1250 | | | | | 1255 | | | | | 1260 | | | | |

| Ala | Ser | Trp | Leu | Ala | Phe | Met | Gln | Gly | Glu | Arg | Gly |
|---|---|---|---|---|---|---|---|---|---|---|---|
| 1265 | | | | | 1270 | | | | | 1275 | |

<210> SEQ ID NO 7
<211> LENGTH: 3789
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
atgaacaatg gcaccaacaa tttccagaac tttatcggaa ttagcagtct gcaaaagact      60
ctccggaatg cccttatacc caccgagaca acccagcagt tcatcgtgaa aacgggatt     120
atcaaggaag acgagctgcg cggcgaaaat cggcaaattt tgaaagatat aatggacgat    180
tattaccgcg gttttatctc tgagactctg agctccattg acgatatcga ctggacctca    240
ctcttcgaaa agatggagat tcagcttaaa acggcgata ataaggacac actgataaaa     300
gaacaggctg agaagcggaa agccatctat aagaaatttg cagatgacga tcgcttcaag    360
aacatgtta gcgccaaatt gattagtgac atcctgccgg aattcgttat tcacaataac     420
aattactctg ctagcgagaa ggaagagaaa acccaagtca taaagctctt ttcccggttc    480
gccacttcat ttaaagatta tttcaagaac cgcgcaaatt gctttagcgc cgacgatatc    540
agttctagct cctgtcatcg gattgtgaac gacaatgctg aaatcttctt ttcaaacgcc    600
cttgtatacc gccggattgt gaaaaatctg agcaacgatg acataaataa gatcagtgga    660
gatattaaag actctttgaa ggagatgagc ctggaagaga tctattccta cgaaaaatat    720
ggggagttca tacccagga aggcatatca ttttacaacg atatctgcgg taaggttaat    780
agcttcatga acctctattg tcagaaaaat aaggagaaca aaaatcttta caagctgcgc    840
aaattgcaca agcaaattct gtgcatcgca gacacaagtt atgaagtccc ttacaaattt    900
gagtctgatg aagaggtgta tcagagcgta aacggcttcc tcgacaatat ttcctcaaag    960
catatagtgg aacggcttcg caaaatcgga gataactaca atgggtataa cctggacaag   1020
atttacatcg ttagcaaatt ttatgagagt gtctctcaga agacctaccg ggattgggaa   1080
actattaata ccgccttgga gatacactat aacaatatcc tgcccggcaa cggtaaaagc   1140
aaggctgaca agtgaagaa agccgtaaag aatgatctcc aaaaatccat tacagaaatc   1200
aacgagcttg tgtcaaatta caagctgtgt ccggacgata acattaaagc agaaacctat   1260
atacatgaga tcagccacat tttgaataac ttcgaagccc aggagctgaa gtacaatcca   1320
gaaatccatc tcgttgagag tgaacttaaa gcttctgagc tgaagaacgt cttggacgtg   1380
attatgaatg cctttcactg gtgcagcgta ttcatgactg aagagctggt ggataaagac   1440
aacaattttt atgcagaact cgaggaaata tacgatgaga tctataccgt tatttccctt   1500
tacaacctgg tccgcaatta tgtgacacag aagcccacct caaccaaaaa gatcaaattg   1560
aacttcggca ttccgactct ggccgacgga tggagcaaga gtaaagaata ttctaataac   1620
gctataatcc tcatgcggga taatctttac tatctgggga ttttaacgc caagaataaa   1680
cctgacaaga aaatcattga gggcaacacc agcgaaaata agggtgatta caaaagatg   1740
```

```
atatataact tgctgcccgg cccgaataaa atgatcccaa aggtattcct ctcctcaaaa    1800
acaggagtgg agacctacaa gcccagcgca tatattcttg aagggtacaa acaaaacaag    1860
catctgaaaa gttctaagga ctttgatatc actttctgtc acgacttgat tgattatttt    1920
aaaaattgca tagccatcca tccggagtgg aagaacttcg gctttgactt cagcgatacc    1980
tccacatacg aagacatttc aggtttttat cgcgaggttg aactgcaggg ctacaaaatc    2040
gattggacct atattagcga aaggacata gatctccttc aggaaaaagg acaactgtac    2100
ttgttccaga tctataataa ggactttagt aaaaagtcta ctgggaacga taatctgcac    2160
accatgtacc tcaaaaacct tttcagcgag gaaaatctga aggacattgt cttgaaactg    2220
aacggcgagg ctgaaatctt tttccggaag tcctcaatta aaaatcctat aatccataag    2280
aaaggtagca ttctcgtgaa ccgcacatat gaggccgaag agaaggatca gtttggcaat    2340
atccaaattg tacggaaaac catacccgaa acatctacc aggagcttta taagtacttc    2400
aatgacaaaa gtgataagga actgtctgac gaggcagcca aattgaagaa cgtggttgga    2460
caccatgaag ctgccactaa tattgtcaaa gattatcgct acacctatga caagtacttt    2520
ctgcacatgc cgatcacaat taacttcaaa gcaaataaga ccagctttat aaacgatcgg    2580
attctccagt atattgccaa agagaagaat cttcatgtga tcgggattga ccgcggcgaa    2640
cggaacctga tatacgtatc cgtgatcgat acttgtggta atattgttga gcaaaaatca    2700
ttcaacatcg tcaatggcta tgactaccag attaagttga acagcaaga aggagctcgc    2760 cagatagccc ggcaggagtg gaaggaaatc gggaaaatta aggagatcaa agaaggctat    2820
ctgagcctcg tgattcacga gataagtaag atggtaatca aatacaacgc aattatcgcc    2880
atggaagatc tttcttatgg ttttaagaaa ggccgcttca aggtggagcg gcaagtttac    2940
cagaaatttg aaaccatgct gattaataag ttgaactatc tggtcttcaa agacataagc    3000
atcacagaga atggagggct ccttaagggc taccagctga cctatattcc agataaattg    3060
aagaacgtgg gtcatcaatg cggctgtatc ttttacgtac ccgctgccta tacttccaaa    3120
attgacccga ccacaggatt cgtgaatata tttaagttca agatctgac cgttgacgca    3180 aagcgcgaat ttatcaaaaa gttcgattca attcggtacg acagcgagaa aaagctcttt    3240
tgcttcactt ttgattataa caatttcatc acccagaaca cagtcatgag taaatctagc    3300
tggtccgtgt acacctatgg ggtacgcatt aagcggcgct ttgtgaatgg ccggttctca    3360
aacgaaagcg acactataga tatcaccaaa gacatggaga agacacttga aatgaccgat    3420
attaattggc gcgacggtca cgatctgcgg caggacatca ttgattacga gatagttcaa    3480
catatctttg aaattttccg cttgactgtc cagatgcgga acagtctgtc tgagctcgaa    3540
gaccgcgatt atgaccggct tatcagcccct gtgctgaatg agaacaatat tttttacgat    3600
tccgccaaag ctggcgacgc cttgcccaag gatgcagacg ccaacggagc ttattgtata    3660
gccctgaaag ggctctacga aatcaagcag attaccgaga attggaaaga agatggcaag    3720
ttctcacgcg acaaacttaa gatcagcaac aaagattggt tgacttcat tcaaaataag    3780 cggtatctg                                                            3789

<210> SEQ ID NO 8
<211> LENGTH: 3825
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 8

```
atgggcaaaa accaaaattt ccaagaattt atcggagtga gccccctgca gaagaccctc      60
cggaacgagc ttattccgac tgagaccaca agaaaaata  taacccagct ggacttgctg     120
actgaagatg agatccgcgc ccagaaccgg gaaaagctca agagatgat  ggacgattat     180
taccgcaatg ttattgacag tacccttcac gtcgggatcg ctgtggattg gtcttatctg     240
ttcagctgca tgcggaacca tttgcgcgaa aattccaagg agtcaaaacg ggaactggag     300
cgcacacagg acagcattcg gagtcagata cacaacaagt ttgccgaacg cgcagatttc     360
aaagacatgt ttggcgcctc tatcattacc aagctccttc ctacttacat caaacaaaat     420
agcgagtatt ccgaacggta cgatgagtca atggaaattc tgaagttgta tggtaaattc     480
accacaagcc tgaccgacta ctttgagact cgcaagaaca tattcagtaa agaaaagatc     540
tctagcgctg taggctatcg gattgtggag gaaaatgccg agatctttct ccagaaccag     600
aatgcatacg atcgcatttg taaaatagcc ggacttgacc tgcatgggtt ggataacgaa     660
atcaccgctt atgttgacgg caagacactg aaagaggtct gctccgatga aggtttcgcc     720
aaggcaatta cccaagaggg catcgaccgg tacaatgaag ccattggagc tgtgaaccag     780
tatatgaatc tcctttgtca gaaaaacaag gccctgaaac ccgggcaatt aagatgaaa     840
cgcttgcaca agcagatact gtgcaaaggc actacctcat cgatatccc  gaagaaattt     900
gagaatgaca agcaggtata cgatgcagtg aacagcttca cagaaattgt taccaaaaat     960
aacgacctca gcggcttct  gaatatcact caaaacgcca atgattatga catgaacaaa    1020
atttacgtcg tggctgatgc ctatagtatg atatctcagt ttatcagcaa gaaatggaat    1080
ttgattgagg aatgtctgct cgactactat tccgataacc ttccaggtaa gggcaatgca    1140
aaagagaaca aggtaaaaaa ggccgtgaaa gaagagacct accgctcagt tagccagctg    1200
aatgaagtca tcgagaagta ttacgtggaa aaaacaggac aaagtgtatg gaaggtggag    1260
tcttatatta gctccttggc tgaaatgata aaactggagc tctgccatga aatcgacaac    1320
gatgagaagc acaatcttat tgaagacgat gagaaaatct cagaaattaa ggagctgttg    1380
gacatgtaca tggatgtttt ccatataatc aaagtctttc gggtgaacga agtactgaat    1440
ttcgacgaga ccttttatag cgaaatggat gagatttacc aggacatgca ggaaatcgtg    1500
cccctctata accacgttcg caattacgtc actcaaaagc cgtataaaca ggagaagtac    1560
cggctttatt tccatacccc tacactggcc aacgggtgga gtaaatctaa ggaatacgat    1620
aataacgcaa ttatattggt gcgcgaggac aaatattacc tgggcatcct caatgccaag    1680
aaaaagccca gcaaagaaat tatggctggt aaggaggatt gttccgaaca cgcctatgca    1740
aaaatgaact actatcttct gccgggcgcc aataagatgt tgccaaaagt atttctgtca    1800
aagaaaggaa tccaggacta ccatcccagc agttatattg tggagggta  caacgaaaag    1860
aaacacataa agggctctaa aaatttcgat atccggtttt gccgcgacct cattgattat    1920
ttcaaggagt gtatcaaaaa gcatccggac tggaacaaat ttaatttcga atttagcgct    1980
accgagactt acgaagatat ttccgttttc tatcgggagg tcgaaaagca aggttaccgc    2040
gtggagtgga cctatataaa ctcagaagac atccagaaac ttgaggaaga tggccagctg    2100
ttttttgttcc aaatttacaa taaggacttt gccgtaggaa gcacagggaa acctaacctg    2160
cacacccttct atcttaagaa tctgttcagt gaggaaaact tgcgggatat cgtgctgaaa    2220
ctcaatggcg aggcagaaat ttttttccgc aagtctagcg ttcagaaacc cgtcatacat    2280
aagtgcggtt ccatccttgt gaaccggact tacgagatta ccgaatcagg cacaacccgc    2340
```

```
gtacagagca tcccggagag tgaatatatg gagctgtacc ggtattttaa ttctgaaaaa      2400
caaattgagt tgagcgacga agccaagaaa tacctggata aggtgcagtg taacaaagct      2460
aagactgaca tagttaaaga ttatcgctac accatggaca agttctttat ccacctccca      2520
attacaatca atttcaaagt cgataaggga acaatgtga acgccattgc acagcaatat      2580
atagccgggc ggaaagacct tcatgtaatc ggcattgatc gcggtgagcg aatctgatc      2640 tacgtgtccg ttattgacat gtatggccgc atattggaac agaagtcatt taacctggtc      2700
gagcaggtga gcagtcaagg aaccaaacgg tactatgatt acaaggaaaa actccagaat      2760
cgcgaggaag agcgggacaa ggctcgccag tcttggaaaa ctatcgggaa gattaaagaa      2820
cttaaggagg gctatctgag ctccgtaatc cacgaaattg cccaaatggt ggttaaatac      2880
aacgcaataa tcgccatgga ggatttgaat tatggtttca gcgggggccg ctttaaagtc      2940
gaacggcagg tgtaccagaa gttcgagacc atgctgattt caaaactcaa ctatcttgct      3000
gacaagagcc aagccgtaga tgaacccgga gggattctgc gcggctacca gatgacatat      3060
gtgccggaca atattaaaaa cgttggtcgg cagtgcggca taatctttta cgtccctgca      3120
gcctatacca gtaagattga tcccactacc ggattcatca atgcttttaa acgcgacgtg      3180
gtatctacaa cgatgccaa ggagaatttc ttgatgaaat ttgacagcat tcaatacgat      3240
atagaaaagg ggctgttcaa attttccttc gactataaga actttgcaac ccataaactc      3300
actcttgcca agaccaaatg ggatgtgtac acaaatggca cccggattca gaacatgaag      3360
gttgagggtc actggctgtc aatggaagtc gagttgacta ccaaaatgaa ggaactgctc      3420
gacgatagcc atattccgta tgaggaaggc cagaatatcc ttgacgatct gcgcgagatg      3480
aaagacatta caaccatagt gaacggaatc ttggaaattt tctggctgac tgtacaactc      3540
cggaatagtc gcatcgataa cccagactac gatcggatta tatctcccgt gcttaataag      3600
aacggggagt ttttcgacag cgatgaatat aattcctaca tcgacgctca gaaagccccg      3660
ctgcctattg atgcagacgc caacggcgct ttttgtatcg ccttgaaggg tatgtatacc      3720
gcaaatcaga ttaaagagaa ctgggttgaa ggcgagaagc tgcccgccga ttgcctcaaa      3780
atagaacacg cttcatggct tgccttcatg caaggagagc gcggg                      3825
```

<210> SEQ ID NO 9
<211> LENGTH: 1307
<212> TYPE: PRT
<213> ORGANISM: Acidaminococcus sp.

<400> SEQUENCE: 9

```
Met Thr Gln Phe Glu Gly Phe Thr Asn Leu Tyr Gln Val Ser Lys Thr
1               5                  10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110
```

```
Arg Thr Asp Asn Leu Thr Asp Ala Ile Asn Lys Arg His Ala Glu Ile
            115                 120                 125

Tyr Lys Gly Leu Phe Lys Ala Glu Leu Phe Asn Gly Lys Val Leu Lys
        130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
                180                 185                 190

Ile Val Gln Asp Asn Phe Pro Lys Phe Lys Glu Asn Cys His Ile Phe
            195                 200                 205

Thr Arg Leu Ile Thr Ala Val Pro Ser Leu Arg Glu His Phe Glu Asn
        210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
            290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525
```

-continued

```
Glu Lys Phe Lys Leu Asn Phe Gln Met Pro Thr Leu Ala Ser Gly Trp
            530                 535                 540
Asp Val Asn Lys Glu Lys Asn Asn Gly Ala Ile Leu Phe Val Lys Asn
545                 550                 555                 560
Gly Leu Tyr Tyr Leu Gly Ile Met Pro Lys Gln Lys Gly Arg Tyr Lys
                565                 570                 575
Ala Leu Ser Phe Glu Pro Thr Glu Lys Thr Ser Glu Gly Phe Asp Lys
            580                 585                 590
Met Tyr Tyr Asp Tyr Phe Pro Asp Ala Ala Lys Met Ile Pro Lys Cys
                595                 600                 605
Ser Thr Gln Leu Lys Ala Val Thr Ala His Phe Gln Thr His Thr Thr
            610                 615                 620
Pro Ile Leu Leu Ser Asn Asn Phe Ile Glu Pro Leu Glu Ile Thr Lys
625                 630                 635                 640
Glu Ile Tyr Asp Leu Asn Asn Pro Glu Lys Glu Pro Lys Lys Phe Gln
                645                 650                 655
Thr Ala Tyr Ala Lys Lys Thr Gly Asp Gln Lys Gly Tyr Arg Glu Ala
            660                 665                 670
Leu Cys Lys Trp Ile Asp Phe Thr Arg Asp Phe Leu Ser Lys Tyr Thr
            675                 680                 685
Lys Thr Thr Ser Ile Asp Leu Ser Ser Leu Arg Pro Ser Ser Gln Tyr
690                 695                 700
Lys Asp Leu Gly Glu Tyr Tyr Ala Glu Leu Asn Pro Leu Leu Tyr His
705                 710                 715                 720
Ile Ser Phe Gln Arg Ile Ala Glu Lys Glu Ile Met Asp Ala Val Glu
                725                 730                 735
Thr Gly Lys Leu Tyr Leu Phe Gln Ile Tyr Asn Lys Asp Phe Ala Lys
            740                 745                 750
Gly His His Gly Lys Pro Asn Leu His Thr Leu Tyr Trp Thr Gly Leu
            755                 760                 765
Phe Ser Pro Glu Asn Leu Ala Lys Thr Ser Ile Lys Leu Asn Gly Gln
770                 775                 780
Ala Glu Leu Phe Tyr Arg Pro Lys Ser Arg Met Lys Arg Met Ala His
785                 790                 795                 800
Arg Leu Gly Glu Lys Met Leu Asn Lys Lys Leu Lys Asp Gln Lys Thr
                805                 810                 815
Pro Ile Pro Asp Thr Leu Tyr Gln Glu Leu Tyr Asp Tyr Val Asn His
                820                 825                 830
Arg Leu Ser His Asp Leu Ser Asp Glu Ala Arg Ala Leu Leu Pro Asn
            835                 840                 845
Val Ile Thr Lys Glu Val Ser His Glu Ile Ile Lys Asp Arg Arg Phe
            850                 855                 860
Thr Ser Asp Lys Phe Phe Phe His Val Pro Ile Thr Leu Asn Tyr Gln
865                 870                 875                 880
Ala Ala Asn Ser Pro Ser Lys Phe Asn Gln Arg Val Asn Ala Tyr Leu
                885                 890                 895
Lys Glu His Pro Glu Thr Pro Ile Ile Gly Ile Asp Arg Gly Glu Arg
                900                 905                 910
Asn Leu Ile Tyr Ile Thr Val Ile Asp Ser Thr Gly Lys Ile Leu Glu
            915                 920                 925
Gln Arg Ser Leu Asn Thr Ile Gln Gln Phe Asp Tyr Gln Lys Lys Leu
            930                 935                 940
```

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
            965                 970                 975

His Glu Ile Val Asp Leu Met Ile His Tyr Gln Ala Val Val Leu
        980                 985                 990

Glu Asn Leu Asn Phe Gly Phe Lys Ser Lys Arg Thr Gly Ile Ala Glu
        995                 1000                1005

Lys Ala Val Tyr Gln Gln Phe Glu Lys Met Leu Ile Asp Lys Leu
1010                1015                1020

Asn Cys Leu Val Leu Lys Asp Tyr Pro Ala Glu Lys Val Gly Gly
1025                1030                1035

Val Leu Asn Pro Tyr Gln Leu Thr Asp Gln Phe Thr Ser Phe Ala
1040                1045                1050

Lys Met Gly Thr Gln Ser Gly Phe Leu Phe Tyr Val Pro Ala Pro
1055                1060                1065

Tyr Thr Ser Lys Ile Asp Pro Leu Thr Gly Phe Val Asp Pro Phe
1070                1075                1080

Val Trp Lys Thr Ile Lys Asn His Glu Ser Arg Lys His Phe Leu
1085                1090                1095

Glu Gly Phe Asp Phe Leu His Tyr Asp Val Lys Thr Gly Asp Phe
1100                1105                1110

Ile Leu His Phe Lys Met Asn Arg Asn Leu Ser Phe Gln Arg Gly
1115                1120                1125

Leu Pro Gly Phe Met Pro Ala Trp Asp Ile Val Phe Glu Lys Asn
1130                1135                1140

Glu Thr Gln Phe Asp Ala Lys Gly Thr Pro Phe Ile Ala Gly Lys
1145                1150                1155

Arg Ile Val Pro Val Ile Glu Asn His Arg Phe Thr Gly Arg Tyr
1160                1165                1170

Arg Asp Leu Tyr Pro Ala Asn Glu Leu Ile Ala Leu Leu Glu Glu
1175                1180                1185

Lys Gly Ile Val Phe Arg Asp Gly Ser Asn Ile Leu Pro Lys Leu
1190                1195                1200

Leu Glu Asn Asp Asp Ser His Ala Ile Asp Thr Met Val Ala Leu
1205                1210                1215

Ile Arg Ser Val Leu Gln Met Arg Asn Ser Asn Ala Ala Thr Gly
1220                1225                1230

Glu Asp Tyr Ile Asn Ser Pro Val Arg Asp Leu Asn Gly Val Cys
1235                1240                1245

Phe Asp Ser Arg Phe Gln Asn Pro Glu Trp Pro Met Asp Ala Asp
1250                1255                1260

Ala Asn Gly Ala Tyr His Ile Ala Leu Lys Gly Gln Leu Leu Leu
1265                1270                1275

Asn His Leu Lys Glu Ser Lys Asp Leu Lys Leu Gln Asn Gly Ile
1280                1285                1290

Ser Asn Gln Asp Trp Leu Ala Tyr Ile Gln Glu Leu Arg Asn
1295                1300                1305

<210> SEQ ID NO 10
<211> LENGTH: 1228
<212> TYPE: PRT
<213> ORGANISM: Unknown
<220> FEATURE:

-continued

```
<223> OTHER INFORMATION: Description of Unknown:
      Lachnospiraceae sequence
<220> FEATURE:
<221> NAME/KEY: MOD_RES
<222> LOCATION: (162)..(162)
<223> OTHER INFORMATION: Any amino acid
<220> FEATURE:
<221> NAME/KEY: MOD_RES
<222> LOCATION: (188)..(188)
<223> OTHER INFORMATION: Any amino acid
<220> FEATURE:
<221> NAME/KEY: MOD_RES
<222> LOCATION: (457)..(457)
<223> OTHER INFORMATION: Any amino acid
<220> FEATURE:
<221> NAME/KEY: MOD_RES
<222> LOCATION: (532)..(532)
<223> OTHER INFORMATION: Any amino acid
<220> FEATURE:
<221> NAME/KEY: MOD_RES
<222> LOCATION: (559)..(559)
<223> OTHER INFORMATION: Any amino acid
<220> FEATURE:
<221> NAME/KEY: MOD_RES
<222> LOCATION: (593)..(593)
<223> OTHER INFORMATION: Any amino acid
<220> FEATURE:
<221> NAME/KEY: MOD_RES
<222> LOCATION: (604)..(604)
<223> OTHER INFORMATION: Any amino acid
<220> FEATURE:
<221> NAME/KEY: MOD_RES
<222> LOCATION: (627)..(627)
<223> OTHER INFORMATION: Any amino acid
<220> FEATURE:
<221> NAME/KEY: MOD_RES
<222> LOCATION: (702)..(702)
<223> OTHER INFORMATION: Any amino acid
<220> FEATURE:
<221> NAME/KEY: MOD_RES
<222> LOCATION: (723)..(723)
<223> OTHER INFORMATION: Any amino acid
<220> FEATURE:
<221> NAME/KEY: MOD_RES
<222> LOCATION: (747)..(747)
<223> OTHER INFORMATION: Any amino acid
<220> FEATURE:
<221> NAME/KEY: MOD_RES
<222> LOCATION: (950)..(950)
<223> OTHER INFORMATION: Any amino acid
<220> FEATURE:
<221> NAME/KEY: MOD_RES
<222> LOCATION: (958)..(958)
<223> OTHER INFORMATION: Any amino acid
<220> FEATURE:
<221> NAME/KEY: MOD_RES
<222> LOCATION: (987)..(987)
<223> OTHER INFORMATION: Any amino acid
<220> FEATURE:
<221> NAME/KEY: MOD_RES
<222> LOCATION: (1036)..(1036)
<223> OTHER INFORMATION: Any amino acid
<220> FEATURE:
<221> NAME/KEY: MOD_RES
<222> LOCATION: (1129)..(1129)
<223> OTHER INFORMATION: Any amino acid
<220> FEATURE:
<221> NAME/KEY: MOD_RES
<222> LOCATION: (1132)..(1132)
<223> OTHER INFORMATION: Any amino acid
<220> FEATURE:
<221> NAME/KEY: MOD_RES
<222> LOCATION: (1135)..(1135)
<223> OTHER INFORMATION: Any amino acid
<220> FEATURE:
<221> NAME/KEY: MOD_RES
<222> LOCATION: (1138)..(1138)
<223> OTHER INFORMATION: Any amino acid
```

```
<400> SEQUENCE: 10

Ala Ala Ser Lys Leu Glu Lys Phe Thr Asn Cys Tyr Ser Leu Ser Lys
1               5                   10                  15

Thr Leu Arg Phe Lys Ala Ile Pro Val Gly Lys Thr Gln Glu Asn Ile
            20                  25                  30

Asp Asn Lys Arg Leu Leu Val Glu Asp Glu Lys Arg Ala Glu Asp Tyr
        35                  40                  45

Lys Gly Val Lys Lys Leu Leu Asp Arg Tyr Tyr Leu Ser Phe Ile Asn
    50                  55                  60

Asp Val Leu His Ser Ile Lys Leu Lys Asn Leu Asn Asn Tyr Ile Ser
65                  70                  75                  80

Leu Phe Arg Lys Lys Thr Arg Thr Glu Lys Glu Asn Lys Glu Leu Glu
                85                  90                  95

Asn Leu Glu Ile Asn Leu Arg Lys Glu Ile Ala Lys Ala Phe Lys Gly
            100                 105                 110

Ala Ala Gly Tyr Lys Ser Leu Phe Lys Lys Asp Ile Ile Glu Thr Ile
        115                 120                 125

Leu Pro Glu Ala Ala Asp Asp Lys Asp Glu Ile Ala Leu Val Asn Ser
    130                 135                 140

Phe Asn Gly Phe Thr Thr Ala Phe Thr Gly Phe Phe Asp Asn Arg Glu
145                 150                 155                 160

Asn Xaa Phe Ser Glu Glu Ala Lys Ser Thr Ser Ile Ala Phe Arg Cys
                165                 170                 175

Ile Asn Glu Asn Leu Thr Arg Tyr Ile Ser Asn Xaa Asp Ile Phe Glu
            180                 185                 190

Lys Val Asp Ala Ile Phe Asp Lys His Glu Val Gln Glu Ile Lys Glu
        195                 200                 205

Lys Ile Leu Asn Ser Asp Tyr Asp Val Glu Asp Phe Phe Glu Gly Glu
    210                 215                 220

Phe Phe Asn Phe Val Leu Thr Gln Glu Gly Ile Asp Val Tyr Asn Ala
225                 230                 235                 240

Ile Ile Gly Gly Phe Val Thr Glu Ser Gly Glu Lys Ile Lys Gly Leu
                245                 250                 255

Asn Glu Tyr Ile Asn Leu Tyr Asn Ala Lys Thr Lys Gln Ala Leu Pro
            260                 265                 270

Lys Phe Lys Pro Leu Tyr Lys Gln Val Leu Ser Asp Arg Glu Ser Leu
        275                 280                 285

Ser Phe Tyr Gly Glu Gly Tyr Thr Ser Asp Glu Glu Val Leu Glu Val
    290                 295                 300

Phe Arg Asn Thr Leu Asn Lys Asn Ser Glu Ile Phe Ser Ser Ile Lys
305                 310                 315                 320

Lys Leu Glu Lys Leu Phe Lys Asn Phe Asp Glu Tyr Ser Ser Ala Gly
                325                 330                 335

Ile Phe Val Lys Asn Gly Pro Ala Ile Ser Thr Ile Ser Lys Asp Ile
            340                 345                 350

Phe Gly Glu Trp Asn Leu Ile Arg Asp Lys Trp Asn Ala Glu Tyr Asp
        355                 360                 365

Asp Ile His Leu Lys Lys Ala Val Val Thr Glu Lys Tyr Glu Asp
370                 375                 380

Asp Arg Arg Lys Ser Phe Lys Lys Ile Gly Ser Phe Ser Leu Glu Gln
385                 390                 395                 400

Leu Gln Glu Tyr Ala Asp Ala Asp Leu Ser Val Val Glu Lys Leu Lys
                405                 410                 415
```

```
Glu Ile Ile Ile Gln Lys Val Asp Glu Ile Tyr Lys Val Tyr Gly Ser
                420                 425                 430

Ser Glu Lys Leu Phe Asp Ala Asp Phe Val Leu Glu Lys Ser Leu Lys
            435                 440                 445

Lys Asn Asp Ala Val Val Ala Ile Xaa Lys Asp Leu Leu Asp Ser Val
        450                 455                 460

Lys Ser Phe Glu Asn Tyr Ile Lys Ala Phe Phe Gly Glu Gly Lys Glu
465                 470                 475                 480

Thr Asn Arg Asp Glu Ser Phe Tyr Gly Asp Phe Val Leu Ala Tyr Asp
                485                 490                 495

Ile Leu Leu Lys Val Asp His Ile Tyr Asp Ala Ile Arg Asn Tyr Val
            500                 505                 510

Thr Gln Lys Pro Tyr Ser Lys Asp Lys Phe Lys Leu Tyr Phe Gln Asn
        515                 520                 525

Pro Gln Phe Xaa Gly Gly Trp Asp Lys Asp Lys Glu Thr Asp Tyr Arg
530                 535                 540

Ala Thr Ile Leu Arg Tyr Gly Ser Lys Tyr Tyr Leu Ala Ile Xaa Asp
545                 550                 555                 560

Lys Lys Tyr Ala Lys Cys Leu Gln Lys Ile Asp Lys Asp Val Asn
                565                 570                 575

Gly Asn Tyr Glu Lys Ile Asn Tyr Lys Leu Leu Pro Gly Pro Asn Lys
            580                 585                 590

Xaa Leu Pro Lys Val Phe Phe Ser Lys Lys Trp Xaa Ala Tyr Tyr Asn
        595                 600                 605

Pro Ser Glu Asp Ile Gln Lys Ile Tyr Lys Asn Gly Thr Phe Lys Lys
            610                 615                 620

Gly Asp Xaa Phe Asn Leu Asn Asp Cys His Lys Leu Ile Asp Phe Phe
625                 630                 635                 640

Lys Asp Ser Ile Ser Arg Tyr Pro Lys Trp Ser Asn Ala Tyr Asp Phe
                645                 650                 655

Asn Phe Ser Glu Thr Glu Lys Tyr Lys Asp Ile Ala Gly Phe Tyr Arg
            660                 665                 670

Glu Val Glu Glu Gln Gly Tyr Lys Val Ser Phe Glu Ser Ala Ser Lys
        675                 680                 685

Lys Glu Val Asp Lys Leu Val Glu Glu Gly Lys Leu Tyr Xaa Phe Gln
        690                 695                 700

Ile Tyr Asn Lys Asp Phe Ser Asp Lys Ser His Gly Thr Pro Asn Leu
705                 710                 715                 720

His Thr Xaa Tyr Phe Lys Leu Leu Phe Asp Glu Asn Asn His Gly Gln
                725                 730                 735

Ile Arg Leu Ser Gly Gly Ala Glu Leu Phe Xaa Arg Arg Ala Ser Leu
            740                 745                 750

Lys Lys Glu Glu Leu Val Val His Pro Ala Asn Ser Pro Ile Ala Asn
        755                 760                 765

Lys Asn Pro Asp Asn Pro Lys Lys Thr Thr Thr Leu Ser Tyr Asp Val
        770                 775                 780

Tyr Lys Asp Lys Arg Phe Ser Glu Asp Gln Tyr Glu Leu His Ile Pro
785                 790                 795                 800

Ile Ala Ile Asn Lys Cys Pro Lys Asn Ile Phe Lys Ile Asn Thr Glu
                805                 810                 815

Val Arg Val Leu Leu Lys His Asp Asp Asn Pro Tyr Val Ile Gly Ile
            820                 825                 830
```

```
Asp Arg Gly Glu Arg Asn Leu Leu Tyr Ile Val Val Asp Gly Lys
        835                 840                 845
Gly Asn Ile Val Glu Gln Tyr Ser Leu Asn Glu Ile Ile Asn Asn Phe
850                 855                 860
Asn Gly Ile Arg Ile Lys Thr Asp Tyr His Ser Leu Leu Asp Lys Lys
865                 870                 875                 880
Glu Lys Glu Arg Phe Glu Ala Arg Gln Asn Trp Thr Ser Ile Glu Asn
                    885                 890                 895
Ile Lys Glu Leu Lys Ala Gly Tyr Ile Ser Gln Val Val His Lys Ile
                900                 905                 910
Cys Glu Leu Val Glu Lys Tyr Asp Ala Val Ile Ala Leu Glu Asp Leu
                915                 920                 925
Asn Ser Gly Phe Lys Asn Ser Arg Val Lys Val Glu Lys Gln Val Tyr
        930                 935                 940
Gln Lys Phe Glu Lys Xaa Leu Ile Asp Lys Leu Asn Tyr Xaa Val Asp
945                 950                 955                 960
Lys Lys Ser Asn Pro Cys Ala Thr Gly Gly Ala Leu Lys Gly Tyr Gln
                965                 970                 975
Ile Thr Asn Lys Phe Glu Ser Phe Lys Ser Xaa Ser Thr Gln Asn Gly
                980                 985                 990
Phe Ile Phe Tyr Ile Pro Ala Trp Leu Thr Ser Lys Ile Asp Pro Ser
        995                 1000                1005
Thr Gly Phe Val Asn Leu Leu Lys Thr Lys Tyr Thr Ser Ile Ala
        1010                1015                1020
Asp Ser Lys Lys Phe Ile Ser Ser Phe Asp Arg Ile Xaa Tyr Val
        1025                1030                1035
Pro Glu Glu Asp Leu Phe Glu Phe Ala Leu Asp Tyr Lys Asn Phe
        1040                1045                1050
Ser Arg Thr Asp Ala Asp Tyr Ile Lys Lys Trp Lys Leu Tyr Ser
        1055                1060                1065
Tyr Gly Asn Arg Ile Arg Ile Phe Ala Ala Ala Lys Lys Asn Asn
        1070                1075                1080
Val Phe Ala Trp Glu Glu Val Cys Leu Thr Ser Ala Tyr Lys Glu
        1085                1090                1095
Leu Phe Asn Lys Tyr Gly Ile Asn Tyr Gln Gln Gly Asp Ile Arg
        1100                1105                1110
Ala Leu Leu Cys Glu Gln Ser Asp Lys Ala Phe Tyr Ser Ser Phe
        1115                1120                1125
Xaa Ala Leu Xaa Ser Leu Xaa Leu Gln Xaa Arg Asn Ser Ile Thr
        1130                1135                1140
Gly Arg Thr Asp Val Asp Phe Leu Ile Ser Pro Val Lys Asn Ser
        1145                1150                1155
Asp Gly Ile Phe Tyr Asp Ser Arg Asn Tyr Glu Ala Gln Glu Asn
        1160                1165                1170
Ala Ile Leu Pro Lys Asn Ala Asp Ala Asn Gly Ala Tyr Asn Ile
        1175                1180                1185
Ala Arg Lys Val Leu Trp Ala Ile Gly Gln Phe Lys Lys Ala Glu
        1190                1195                1200
Asp Glu Lys Leu Asp Lys Val Lys Ile Ala Ile Ser Asn Lys Glu
        1205                1210                1215
Trp Leu Glu Tyr Ala Gln Thr Ser Val Lys
        1220                1225
```

```
<210> SEQ ID NO 11
<211> LENGTH: 1300
<212> TYPE: PRT
<213> ORGANISM: Francisella tularensis

<400> SEQUENCE: 11
```

| | | | | | | | | | | | | | | |
|---|---|---|---|---|---|---|---|---|---|---|---|---|---|---|
| Met | Ser | Ile | Tyr | Gln | Glu | Phe | Val | Asn | Lys | Tyr | Ser | Leu | Ser | Lys | Thr |
| 1 | | | | 5 | | | | | 10 | | | | | 15 | |
| Leu | Arg | Phe | Glu | Leu | Ile | Pro | Gln | Gly | Lys | Thr | Leu | Glu | Asn | Ile | Lys |
| | | | 20 | | | | | 25 | | | | | 30 | | |
| Ala | Arg | Gly | Leu | Ile | Leu | Asp | Asp | Glu | Lys | Arg | Ala | Lys | Asp | Tyr | Lys |
| | | 35 | | | | | 40 | | | | | 45 | | | |
| Lys | Ala | Lys | Gln | Ile | Ile | Asp | Lys | Tyr | His | Gln | Phe | Phe | Ile | Glu | Glu |
| | 50 | | | | | 55 | | | | | 60 | | | | |
| Ile | Leu | Ser | Ser | Val | Cys | Ile | Ser | Glu | Asp | Leu | Leu | Gln | Asn | Tyr | Ser |
| 65 | | | | | 70 | | | | | 75 | | | | | 80 |
| Asp | Val | Tyr | Phe | Lys | Leu | Lys | Lys | Ser | Asp | Asp | Asn | Leu | Gln | Lys |
| | | | | 85 | | | | | 90 | | | | | 95 |
| Asp | Phe | Lys | Ser | Ala | Lys | Asp | Thr | Ile | Lys | Lys | Gln | Ile | Ser | Glu | Tyr |
| | | | 100 | | | | | 105 | | | | | 110 | | |
| Ile | Lys | Asp | Ser | Glu | Lys | Phe | Lys | Asn | Leu | Phe | Asn | Gln | Asn | Leu | Ile |
| | | 115 | | | | | 120 | | | | | 125 | | | |
| Asp | Ala | Lys | Lys | Gly | Gln | Glu | Ser | Asp | Leu | Ile | Leu | Trp | Leu | Lys | Gln |
| | 130 | | | | | 135 | | | | | 140 | | | | |
| Ser | Lys | Asp | Asn | Gly | Ile | Glu | Leu | Phe | Lys | Ala | Asn | Ser | Asp | Ile | Thr |
| 145 | | | | | 150 | | | | | 155 | | | | | 160 |
| Asp | Ile | Asp | Glu | Ala | Leu | Glu | Ile | Ile | Lys | Ser | Phe | Lys | Gly | Trp | Thr |
| | | | | 165 | | | | | 170 | | | | | 175 | |
| Thr | Tyr | Phe | Lys | Gly | Phe | His | Glu | Asn | Arg | Lys | Asn | Val | Tyr | Ser | Ser |
| | | | 180 | | | | | 185 | | | | | 190 | | |
| Asn | Asp | Ile | Pro | Thr | Ser | Ile | Ile | Tyr | Arg | Ile | Val | Asp | Asp | Asn | Leu |
| | | 195 | | | | | 200 | | | | | 205 | | | |
| Pro | Lys | Phe | Leu | Glu | Asn | Lys | Ala | Lys | Tyr | Glu | Ser | Leu | Lys | Asp | Lys |
| | 210 | | | | | 215 | | | | | 220 | | | | |
| Ala | Pro | Glu | Ala | Ile | Asn | Tyr | Glu | Gln | Ile | Lys | Lys | Asp | Leu | Ala | Glu |
| 225 | | | | | 230 | | | | | 235 | | | | | 240 |
| Glu | Leu | Thr | Phe | Asp | Ile | Asp | Tyr | Lys | Thr | Ser | Glu | Val | Asn | Gln | Arg |
| | | | | 245 | | | | | 250 | | | | | 255 | |
| Val | Phe | Ser | Leu | Asp | Glu | Val | Phe | Glu | Ile | Ala | Asn | Phe | Asn | Asn | Tyr |
| | | | 260 | | | | | 265 | | | | | 270 | | |
| Leu | Asn | Gln | Ser | Gly | Ile | Thr | Lys | Phe | Asn | Thr | Ile | Ile | Gly | Gly | Lys |
| | | 275 | | | | | 280 | | | | | 285 | | | |
| Phe | Val | Asn | Gly | Glu | Asn | Thr | Lys | Arg | Lys | Gly | Ile | Asn | Glu | Tyr | Ile |
| | 290 | | | | | 295 | | | | | 300 | | | | |
| Asn | Leu | Tyr | Ser | Gln | Gln | Ile | Asn | Asp | Lys | Thr | Leu | Lys | Lys | Tyr | Lys |
| 305 | | | | | 310 | | | | | 315 | | | | | 320 |
| Met | Ser | Val | Leu | Phe | Lys | Gln | Ile | Leu | Ser | Asp | Thr | Glu | Ser | Lys | Ser |
| | | | | 325 | | | | | 330 | | | | | 335 | |
| Phe | Val | Ile | Asp | Lys | Leu | Glu | Asp | Asp | Ser | Asp | Val | Val | Thr | Thr | Met |
| | | | 340 | | | | | 345 | | | | | 350 | | |
| Gln | Ser | Phe | Tyr | Glu | Gln | Ile | Ala | Ala | Phe | Lys | Thr | Val | Glu | Glu | Lys |
| | | 355 | | | | | 360 | | | | | 365 | | | |
| Ser | Ile | Lys | Glu | Thr | Leu | Ser | Leu | Leu | Phe | Asp | Asp | Leu | Lys | Ala | Gln |
| | 370 | | | | | 375 | | | | | 380 | | | | |

-continued

```
Lys Leu Asp Leu Ser Lys Ile Tyr Phe Lys Asn Asp Lys Ser Leu Thr
385                 390                 395                 400

Asp Leu Ser Gln Gln Val Phe Asp Tyr Ser Val Ile Gly Thr Ala
        405                 410                 415

Val Leu Glu Tyr Ile Thr Gln Gln Ile Ala Pro Lys Asn Leu Asp Asn
            420                 425                 430

Pro Ser Lys Lys Glu Gln Leu Ile Ala Lys Lys Thr Glu Lys Ala
        435                 440                 445

Lys Tyr Leu Ser Leu Glu Thr Ile Lys Leu Ala Leu Glu Glu Phe Asn
450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Val Lys Ala Ile Lys Asp
        515                 520                 525

Leu Leu Asp Gln Thr Asn Asn Leu Leu His Lys Leu Lys Ile Phe His
530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800
```

-continued

Pro Asn Leu His Thr Leu Tyr Trp Lys Ala Leu Phe Asp Glu Arg Asn
                805                 810                 815
Leu Gln Asp Val Val Tyr Lys Leu Asn Gly Glu Ala Glu Leu Phe Tyr
            820                 825                 830
Arg Lys Gln Ser Ile Pro Lys Lys Ile Thr His Pro Ala Lys Glu Ala
        835                 840                 845
Ile Ala Asn Lys Asn Lys Asp Asn Pro Lys Lys Glu Ser Val Phe Glu
    850                 855                 860
Tyr Asp Leu Ile Lys Asp Lys Arg Phe Thr Glu Asp Lys Phe Phe Phe
865                 870                 875                 880
His Cys Pro Ile Thr Ile Asn Phe Lys Ser Ser Gly Ala Asn Lys Phe
                885                 890                 895
Asn Asp Glu Ile Asn Leu Leu Leu Lys Glu Lys Ala Asn Asp Val His
            900                 905                 910
Ile Leu Ser Ile Asp Arg Gly Glu Arg His Leu Ala Tyr Tyr Thr Leu
        915                 920                 925
Val Asp Gly Lys Gly Asn Ile Ile Lys Gln Asp Thr Phe Asn Ile Ile
    930                 935                 940
Gly Asn Asp Arg Met Lys Thr Asn Tyr His Asp Lys Leu Ala Ala Ile
945                 950                 955                 960
Glu Lys Asp Arg Asp Ser Ala Arg Lys Asp Trp Lys Lys Ile Asn Asn
                965                 970                 975
Ile Lys Glu Met Lys Glu Gly Tyr Leu Ser Gln Val Val His Glu Ile
            980                 985                 990
Ala Lys Leu Val Ile Glu Tyr Asn Ala Ile Val Val Phe Glu Asp Leu
        995                 1000                1005
Asn Phe Gly Phe Lys Arg Gly Arg Phe Lys Val Glu Lys Gln Val
        1010                1015                1020
Tyr Gln Lys Leu Glu Lys Met Leu Ile Glu Lys Leu Asn Tyr Leu
        1025                1030                1035
Val Phe Lys Asp Asn Glu Phe Asp Lys Thr Gly Gly Val Leu Arg
        1040                1045                1050
Ala Tyr Gln Leu Thr Ala Pro Phe Glu Thr Phe Lys Lys Met Gly
        1055                1060                1065
Lys Gln Thr Gly Ile Ile Tyr Tyr Val Pro Ala Gly Phe Thr Ser
        1070                1075                1080
Lys Ile Cys Pro Val Thr Gly Phe Val Asn Gln Leu Tyr Pro Lys
        1085                1090                1095
Tyr Glu Ser Val Ser Lys Ser Gln Glu Phe Phe Ser Lys Phe Asp
        1100                1105                1110
Lys Ile Cys Tyr Asn Leu Asp Lys Gly Tyr Phe Glu Phe Ser Phe
        1115                1120                1125
Asp Tyr Lys Asn Phe Gly Asp Lys Ala Ala Lys Gly Lys Trp Thr
        1130                1135                1140
Ile Ala Ser Phe Gly Ser Arg Leu Ile Asn Phe Arg Asn Ser Asp
        1145                1150                1155
Lys Asn His Asn Trp Asp Thr Arg Glu Val Tyr Pro Thr Lys Glu
        1160                1165                1170
Leu Glu Lys Leu Leu Lys Asp Tyr Ser Ile Glu Tyr Gly His Gly
        1175                1180                1185
Glu Cys Ile Lys Ala Ala Ile Cys Gly Glu Ser Asp Lys Lys Phe
        1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230

Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
    1280                1285                1290

Phe Val Gln Asn Arg Asn Asn
    1295                1300

<210> SEQ ID NO 12
<211> LENGTH: 7
<212> TYPE: PRT
<213> ORGANISM: Unknown
<220> FEATURE:
<223> OTHER INFORMATION: Description of Unknown:
      Cas12a sequence

<400> SEQUENCE: 12

Leu Ile Pro Thr Glu Thr Thr
1               5

<210> SEQ ID NO 13
<211> LENGTH: 6
<212> TYPE: PRT
<213> ORGANISM: Unknown
<220> FEATURE:
<223> OTHER INFORMATION: Description of Unknown:
      Cas12a sequence

<400> SEQUENCE: 13

Met Asp Asp Tyr Tyr Arg
1               5

<210> SEQ ID NO 14
<211> LENGTH: 5
<212> TYPE: PRT
<213> ORGANISM: Unknown
<220> FEATURE:
<223> OTHER INFORMATION: Description of Unknown:
      Cas12a sequence

<400> SEQUENCE: 14

Asn Ala Glu Ile Phe
1               5

<210> SEQ ID NO 15
<211> LENGTH: 5
<212> TYPE: PRT
<213> ORGANISM: Unknown
<220> FEATURE:
<223> OTHER INFORMATION: Description of Unknown:
      Cas12a sequence

<400> SEQUENCE: 15

Cys Gln Lys Asn Lys
1               5

<210> SEQ ID NO 16

```
<211> LENGTH: 7
<212> TYPE: PRT
<213> ORGANISM: Unknown
<220> FEATURE:
<223> OTHER INFORMATION: Description of Unknown:
      Cas12a sequence

<400> SEQUENCE: 16

Leu His Lys Gln Ile Leu Cys
1               5

<210> SEQ ID NO 17
<211> LENGTH: 7
<212> TYPE: PRT
<213> ORGANISM: Unknown
<220> FEATURE:
<223> OTHER INFORMATION: Description of Unknown:
      Cas12a sequence

<400> SEQUENCE: 17

Lys Val Lys Lys Ala Val Lys
1               5

<210> SEQ ID NO 18
<211> LENGTH: 10
<212> TYPE: PRT
<213> ORGANISM: Unknown
<220> FEATURE:
<223> OTHER INFORMATION: Description of Unknown:
      Cas12a sequence

<400> SEQUENCE: 18

Val Arg Asn Tyr Val Thr Gln Lys Pro Tyr
1               5                   10

<210> SEQ ID NO 19
<211> LENGTH: 8
<212> TYPE: PRT
<213> ORGANISM: Unknown
<220> FEATURE:
<223> OTHER INFORMATION: Description of Unknown:
      Cas12a sequence

<400> SEQUENCE: 19

Gly Trp Ser Lys Ser Lys Glu Tyr
1               5

<210> SEQ ID NO 20
<211> LENGTH: 7
<212> TYPE: PRT
<213> ORGANISM: Unknown
<220> FEATURE:
<223> OTHER INFORMATION: Description of Unknown:
      Cas12a sequence

<400> SEQUENCE: 20

Asp Leu Ile Asp Tyr Phe Lys
1               5

<210> SEQ ID NO 21
<211> LENGTH: 18
<212> TYPE: PRT
<213> ORGANISM: Unknown
<220> FEATURE:
<223> OTHER INFORMATION: Description of Unknown:
      Cas12a sequence
```

<400> SEQUENCE: 21

Asp Ile Val Leu Lys Leu Asn Gly Glu Ala Glu Ile Phe Phe Arg Lys
1               5                   10                  15

Ser Ser

<210> SEQ ID NO 22
<211> LENGTH: 10
<212> TYPE: PRT
<213> ORGANISM: Unknown
<220> FEATURE:
<223> OTHER INFORMATION: Description of Unknown:
      Cas12a sequence

<400> SEQUENCE: 22

Gly Ser Ile Leu Val Asn Arg Thr Tyr Glu
1               5                   10

<210> SEQ ID NO 23
<211> LENGTH: 6
<212> TYPE: PRT
<213> ORGANISM: Unknown
<220> FEATURE:
<223> OTHER INFORMATION: Description of Unknown:
      Cas12a sequence

<400> SEQUENCE: 23

Glu Leu Ser Asp Glu Ala
1               5

<210> SEQ ID NO 24
<211> LENGTH: 8
<212> TYPE: PRT
<213> ORGANISM: Unknown
<220> FEATURE:
<223> OTHER INFORMATION: Description of Unknown:
      Cas12a sequence

<400> SEQUENCE: 24

Ile Val Lys Asp Tyr Arg Tyr Thr
1               5

<210> SEQ ID NO 25
<211> LENGTH: 20
<212> TYPE: PRT
<213> ORGANISM: Unknown
<220> FEATURE:
<223> OTHER INFORMATION: Description of Unknown:
      Cas12a sequence

<400> SEQUENCE: 25

Leu His Val Ile Gly Ile Asp Arg Gly Glu Arg Asn Leu Ile Tyr Val
1               5                   10                  15

Ser Val Ile Asp
            20

<210> SEQ ID NO 26
<211> LENGTH: 11
<212> TYPE: PRT
<213> ORGANISM: Unknown
<220> FEATURE:
<223> OTHER INFORMATION: Description of Unknown:
      Cas12a sequence

<400> SEQUENCE: 26

Lys Tyr Asn Ala Ile Ile Ala Met Glu Asp Leu
1               5                   10

<210> SEQ ID NO 27
<211> LENGTH: 18
<212> TYPE: PRT
<213> ORGANISM: Unknown
<220> FEATURE:
<223> OTHER INFORMATION: Description of Unknown:
      Cas12a sequence

<400> SEQUENCE: 27

Gly Arg Phe Lys Val Glu Arg Gln Val Tyr Gln Lys Phe Glu Thr Met
1               5                   10                  15

Leu Ile

<210> SEQ ID NO 28
<211> LENGTH: 18
<212> TYPE: PRT
<213> ORGANISM: Unknown
<220> FEATURE:
<223> OTHER INFORMATION: Description of Unknown:
      Cas12a sequence

<400> SEQUENCE: 28

Ile Phe Tyr Val Pro Ala Ala Tyr Thr Ser Lys Ile Asp Pro Thr Thr
1               5                   10                  15

Gly Phe

<210> SEQ ID NO 29
<211> LENGTH: 6
<212> TYPE: PRT
<213> ORGANISM: Unknown
<220> FEATURE:
<223> OTHER INFORMATION: Description of Unknown:
      Cas12a sequence

<400> SEQUENCE: 29

Ile Ser Pro Val Leu Asn
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Tyr Lys Asp Asp Asp Asp Lys
1               5

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
attccaggga atggaactat                                              20

<210> SEQ ID NO 32
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
tcgtcggcag cgtcagatgt gtataagaga cagattccag ggaatggaac tat        53

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
tattggatag caaccaaagc                                             20

<210> SEQ ID NO 34
<211> LENGTH: 54
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
gtctcgtggg ctcggagatg tgtataagag acagtattgg atagcaacca aagc        54

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
ggtgagctta tttattaggc tt                                          22

<210> SEQ ID NO 36
<211> LENGTH: 55
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
tcgtcggcag cgtcagatgt gtataagaga cagggtgagc ttatttatta ggctt       55

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
ggtgaagaat gtcatcgcta at                                          22

```
<210> SEQ ID NO 38
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtctcgtggg ctcggagatg tgtataagag acagggtgaa gaatgtcatc gctaat        56

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39 aaatccccc aaaaccactt tt                                              22

<210> SEQ ID NO 40
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tcgtcggcag cgtcagatgt gtataagaga cagaaatccc cccaaaacca ctttt          55

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cggtgttatc gccgaatttc cg                                             22

<210> SEQ ID NO 42
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gtctcgtggg ctcggagatg tgtataagag acagcggtgt tatcgccgaa tttccg        56

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ggtttactct caaagttgac ct                                             22

<210> SEQ ID NO 44
```

```
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tcgtcggcag cgtcagatgt gtataagaga cagggtttac tctcaaagtt gacct      55

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gggcagctca tcatcttcat tc                                          22

<210> SEQ ID NO 46
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gtctcgtggg ctcggagatg tgtataagag acagggggcag ctcatcatct tcattc     56

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ctctgtacta agtagtacac ac                                          22

<210> SEQ ID NO 48
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tcgtcggcag cgtcagatgt gtataagaga cagctctgta ctaagtagta cacac      55

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gcttggaata ttgagaagtg at                                          22

<210> SEQ ID NO 50
<211> LENGTH: 56
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gtctcgtggg ctcggagatg tgtataagag acaggcttgg aatattgaga agtgat         56

<210> SEQ ID NO 51
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
caccgaauuu cuacuguugu agauggagug aagggagagu uugucaauuu uuug           54

<210> SEQ ID NO 52
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
ggucaauuuc uacuguugua gaugcucagc aggcaccugc cucuuuu                   47

<210> SEQ ID NO 53
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tcgtcggcag cgtcagatgt gtataagaga cagggtattt ctgttcagat cac            53

<210> SEQ ID NO 54
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gtctcgtggg ctcggagatg tgtataagag acaggcccat caattataga aagcc          55

<210> SEQ ID NO 55
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tcgtcggcag cgtcagatgt gtataagaga cagctgcaca cagcaggcct ttg            53

<210> SEQ ID NO 56
<211> LENGTH: 54
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 56
gtctcgtggg ctcggagatg tgtataagag acagcccaat aagtggcaga gtgc        54

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
tttggataat ttgtactctt gtcgatgt                                     28

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tttagtccac aaacagctaa gcccacat                                     28

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tgagctgaag atggattatg                                              20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tcatgcttaa gataaaagag                                              20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tcatgagctt aagatggatc                                              20

<210> SEQ ID NO 62
<211> LENGTH: 20
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 62
gtttaagcta aaagaactac                                                     20

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 63

His His His His His His
1               5

<210> SEQ ID NO 64
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64 uaauucuac ucuuguagau                                                      20

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65 aauucuacu guuguagau                                                       19

<210> SEQ ID NO 66
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66 aauucuacu aaguguagau                                                      20

<210> SEQ ID NO 67
<211> LENGTH: 1228
<212> TYPE: PRT
<213> ORGANISM: Unknown
<220> FEATURE:
<223> OTHER INFORMATION: Description of Unknown:
      Lachnospiraceae sequence

<400> SEQUENCE: 67

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30
```

```
Asn Lys Arg Leu Leu Val Glu Asp Glu Lys Arg Ala Glu Asp Tyr Lys
        35                  40                  45
Gly Val Lys Lys Leu Leu Asp Arg Tyr Tyr Leu Ser Phe Ile Asn Asp
    50                  55                  60
Val Leu His Ser Ile Lys Leu Lys Asn Leu Asn Asn Tyr Ile Ser Leu
65                  70                  75                  80
Phe Arg Lys Lys Thr Arg Thr Glu Lys Glu Asn Lys Glu Leu Glu Asn
                85                  90                  95
Leu Glu Ile Asn Leu Arg Lys Glu Ile Ala Lys Ala Phe Lys Gly Asn
            100                 105                 110
Glu Gly Tyr Lys Ser Leu Phe Lys Lys Asp Ile Ile Glu Thr Ile Leu
                115                 120                 125
Pro Glu Phe Leu Asp Asp Lys Asp Glu Ile Ala Leu Val Asn Ser Phe
        130                 135                 140
Asn Gly Phe Thr Thr Ala Phe Thr Gly Phe Phe Asp Asn Arg Glu Asn
145                 150                 155                 160
Met Phe Ser Glu Glu Ala Lys Ser Thr Ser Ile Ala Phe Arg Cys Ile
                165                 170                 175
Asn Glu Asn Leu Thr Arg Tyr Ile Ser Asn Met Asp Ile Phe Glu Lys
            180                 185                 190
Val Asp Ala Ile Phe Asp Lys His Glu Val Gln Glu Ile Lys Glu Lys
                195                 200                 205
Ile Leu Asn Ser Asp Tyr Asp Val Glu Asp Phe Phe Glu Gly Glu Phe
        210                 215                 220
Phe Asn Phe Val Leu Thr Gln Glu Gly Ile Asp Val Tyr Asn Ala Ile
225                 230                 235                 240
Ile Gly Gly Phe Val Thr Glu Ser Gly Glu Lys Ile Lys Gly Leu Asn
                245                 250                 255
Glu Tyr Ile Asn Leu Tyr Asn Gln Lys Thr Lys Gln Lys Leu Pro Lys
            260                 265                 270
Phe Lys Pro Leu Tyr Lys Gln Val Leu Ser Asp Arg Glu Ser Leu Ser
        275                 280                 285
Phe Tyr Gly Glu Gly Tyr Thr Ser Asp Glu Glu Val Leu Glu Val Phe
        290                 295                 300
Arg Asn Thr Leu Asn Lys Asn Ser Glu Ile Phe Ser Ser Ile Lys Lys
305                 310                 315                 320
Leu Glu Lys Leu Phe Lys Asn Phe Asp Glu Tyr Ser Ser Ala Gly Ile
                325                 330                 335
Phe Val Lys Asn Gly Pro Ala Ile Ser Thr Ile Ser Lys Asp Ile Phe
            340                 345                 350
Gly Glu Trp Asn Val Ile Arg Asp Lys Trp Asn Ala Glu Tyr Asp Asp
        355                 360                 365
Ile His Leu Lys Lys Lys Ala Val Val Thr Glu Lys Tyr Glu Asp Asp
        370                 375                 380
Arg Arg Lys Ser Phe Lys Lys Ile Gly Ser Phe Ser Leu Glu Gln Leu
385                 390                 395                 400
Gln Glu Tyr Ala Asp Ala Asp Leu Ser Val Val Glu Lys Leu Lys Glu
                405                 410                 415
Ile Ile Ile Gln Lys Val Asp Glu Ile Tyr Lys Val Tyr Gly Ser Ser
            420                 425                 430
Glu Lys Leu Phe Asp Ala Asp Phe Val Leu Glu Lys Ser Leu Lys Lys
        435                 440                 445
```

Asn Asp Ala Val Val Ala Ile Met Lys Asp Leu Leu Asp Ser Val Lys
450                     455                     460

Ser Phe Glu Asn Tyr Ile Lys Ala Phe Phe Gly Glu Gly Lys Glu Thr
465                     470                     475                     480

Asn Arg Asp Glu Ser Phe Tyr Gly Asp Phe Val Leu Ala Tyr Asp Ile
                        485                     490                     495

Leu Leu Lys Val Asp His Ile Tyr Asp Ala Ile Arg Asn Tyr Val Thr
                500                     505                     510

Gln Lys Pro Tyr Ser Lys Asp Lys Phe Lys Leu Tyr Phe Gln Asn Pro
                515                     520                     525

Gln Phe Met Gly Gly Trp Asp Lys Asp Lys Glu Thr Asp Tyr Arg Ala
530                     535                     540

Thr Ile Leu Arg Tyr Gly Ser Lys Tyr Tyr Leu Ala Ile Met Asp Lys
545                     550                     555                     560

Lys Tyr Ala Lys Cys Leu Gln Lys Ile Asp Lys Asp Val Asn Gly
                565                     570                     575

Asn Tyr Glu Lys Ile Asn Tyr Lys Leu Leu Pro Gly Pro Asn Lys Met
                580                     585                     590

Leu Pro Lys Val Phe Phe Ser Lys Lys Trp Met Ala Tyr Tyr Asn Pro
                595                     600                     605

Ser Glu Asp Ile Gln Lys Ile Tyr Lys Asn Gly Thr Phe Lys Lys Gly
                610                     615                     620

Asp Met Phe Asn Leu Asn Asp Cys His Lys Leu Ile Asp Phe Phe Lys
625                     630                     635                     640

Asp Ser Ile Ser Arg Tyr Pro Lys Trp Ser Asn Ala Tyr Asp Phe Asn
                        645                     650                     655

Phe Ser Glu Thr Glu Lys Tyr Lys Asp Ile Ala Gly Phe Tyr Arg Glu
                660                     665                     670

Val Glu Glu Gln Gly Tyr Lys Val Ser Phe Glu Ser Ala Ser Lys Lys
                675                     680                     685

Glu Val Asp Lys Leu Val Glu Glu Gly Lys Leu Tyr Met Phe Gln Ile
690                     695                     700

Tyr Asn Lys Asp Phe Ser Asp Lys Ser His Gly Thr Pro Asn Leu His
705                     710                     715                     720

Thr Met Tyr Phe Lys Leu Leu Phe Asp Glu Asn Asn His Gly Gln Ile
                        725                     730                     735

Arg Leu Ser Gly Gly Ala Glu Leu Phe Met Arg Arg Ala Ser Leu Lys
                740                     745                     750

Lys Glu Glu Leu Val Val His Pro Ala Asn Ser Pro Ile Ala Asn Lys
                755                     760                     765

Asn Pro Asp Asn Pro Lys Lys Thr Thr Thr Leu Ser Tyr Asp Val Tyr
                770                     775                     780

Lys Asp Lys Arg Phe Ser Glu Asp Gln Tyr Glu Leu His Ile Pro Ile
785                     790                     795                     800

Ala Ile Asn Lys Cys Pro Lys Asn Ile Phe Lys Ile Asn Thr Glu Val
                        805                     810                     815

Arg Val Leu Leu Lys His Asp Asp Asn Pro Tyr Val Ile Gly Ile Asp
                820                     825                     830

Arg Gly Glu Arg Asn Leu Leu Tyr Ile Val Val Val Asp Gly Lys Gly
                835                     840                     845

Asn Ile Val Glu Gln Tyr Ser Leu Asn Glu Ile Ile Asn Asn Phe Asn
850                     855                     860

-continued

```
Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
                900                 905                 910

Glu Leu Val Glu Lys Tyr Asp Ala Val Ile Ala Leu Glu Asp Leu Asn
                915                 920                 925

Ser Gly Phe Lys Asn Ser Arg Val Lys Val Glu Lys Gln Val Tyr Gln
930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
                980                 985                 990

Ile Phe Tyr Ile Pro Ala Trp Leu Thr Ser Lys Ile Asp Pro Ser Thr
                995                 1000                1005

Gly Phe Val Asn Leu Leu Lys Thr Lys Tyr Thr Ser Ile Ala Asp
    1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His
    1220                1225
```